(12) United States Patent
Cipriano et al.

(10) Patent No.: US 12,201,629 B2
(45) Date of Patent: Jan. 21, 2025

(54) METHOD OF TREATMENT AND DOSAGE FORMS THEREOF

(71) Applicant: PURDUE PHARMA L.P., Stamford, CT (US)

(72) Inventors: Alessandra Cipriano, Eastchester, NY (US); Salvatore Colucci, Stamford, CT (US); Stephen Harris, Weston, CT (US); Michele Hummel, Marlton, NJ (US); Donald Kyle, Yardley, PA (US); Garth Whiteside, Yardley, PA (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 16/625,011

(22) PCT Filed: Jun. 29, 2018

(86) PCT No.: PCT/US2018/040460
§ 371 (c)(1),
(2) Date: Dec. 20, 2019

(87) PCT Pub. No.: WO2019/006404
PCT Pub. Date: Jan. 3, 2019

(65) Prior Publication Data
US 2020/0215052 A1    Jul. 9, 2020

Related U.S. Application Data

(60) Provisional application No. 62/527,337, filed on Jun. 30, 2017.

(51) Int. Cl.
*A61K 31/485* (2006.01)
*A61K 9/00* (2006.01)
*A61K 31/4468* (2006.01)

(52) U.S. Cl.
CPC .......... *A61K 31/485* (2013.01); *A61K 9/0019* (2013.01); *A61K 31/4468* (2013.01)

(58) Field of Classification Search
CPC .................................................. A61K 31/485
USPC ...................................................... 514/282
See application file for complete search history.

(56) References Cited

U.S. PATENT DOCUMENTS

| | | | |
|---|---|---|---|
| 3,965,256 A | 6/1976 | Leslie | |
| 4,235,870 A | 11/1980 | Leslie | |
| 4,443,428 A | 4/1984 | Oshlack et al. | |
| 4,588,580 A | 5/1986 | Gale et al. | |
| 4,769,372 A | 9/1988 | Kreek | |
| 4,785,000 A | 11/1988 | Kreek et al. | |
| 4,834,984 A | 5/1989 | Goldie et al. | |
| 4,844,909 A | 7/1989 | Goldie et al. | |
| 4,861,598 A | 8/1989 | Oshlack | |
| 4,970,075 A | 11/1990 | Oshlack | |
| 4,987,136 A | 1/1991 | Kreek et al. | |
| 4,990,341 A | 2/1991 | Goldie et al. | |
| 5,266,331 A | 11/1993 | Oshlack et al. | |
| 5,273,760 A | 12/1993 | Oshlack et al. | |
| 5,286,493 A | 2/1994 | Oshlack et al. | |
| 5,324,351 A | 6/1994 | Oshlack et al. | |
| 5,356,467 A | 10/1994 | Oshlack et al. | |
| 5,411,745 A | 5/1995 | Oshlack et al. | |
| 5,472,712 A | 12/1995 | Oshlack et al. | |
| 5,478,577 A | 12/1995 | Sackller et al. | |
| 5,500,227 A | 3/1996 | Oshlack et al. | |
| 5,508,042 A | 4/1996 | Oshlack et al. | |
| 5,549,912 A | 8/1996 | Oshlack et al. | |
| 5,580,578 A | 12/1996 | Oshlack et al. | |
| 5,639,476 A | 6/1997 | Oshlack et al. | |
| 5,656,295 A | 8/1997 | Oshlack et al. | |
| 5,672,360 A | 9/1997 | Sackler et al. | |
| 5,681,585 A | 10/1997 | Oshlack et al. | |
| 5,843,480 A | 12/1998 | Miller et al. | |
| 5,849,240 A | 12/1998 | Miller et al. | |

(Continued)

FOREIGN PATENT DOCUMENTS

| DE | 102010048883 | 4/2012 |
|---|---|---|
| EP | 1958621 | 8/2008 |

(Continued)

OTHER PUBLICATIONS

Nasser et al., J. Clin. Psychopharmacol. (Feb. 2016), vol. 36(1), pp. 18-26.*
Daniel Alford, Medication Assisted Treatment, Boston Univ. Sch. of Med., pp. 30.*
"Buprenorphine: A Guide for Nurses," Technical Assistance Publication (TAP) Series, Substance Abuse and Mental Health Services Administration, 2009, pp. 1-104, DHHS Publication No. (SMA) 09-4376.
"Clinical Guidelines for the Use of Buprenorphine in the Treatment of Opioid Addiction," Quick Guide for Physicians Based on TIP 40, 2005, pp. 1-35, U.S. Department of Health and Human Services, DHHS Publication No. (SMA) 05-4003.
Alhaddad, H., et al., "Respiratory toxicity of buprenorphine results from the blockage of Pglycoprotein-mediated efflux of norbuprenorphine at the blood-brain barrier in mice," Critical Care Medicine, vol. 40, No. 12, pp. 3215-3223, Dec. 2012.

(Continued)

*Primary Examiner* — Taofiq A Solola
(74) *Attorney, Agent, or Firm* — Purdue Pharma L.P.; Weiying Yang

(57) ABSTRACT

The invention provides an oral dosage form comprising (i) an amount of oxycodone and (ii) an amount of buprenorphine, wherein the weight ratio of the amount of buprenorphine to the amount of oxycodone is greater than 1:40 calculated with the amount of buprenorphine in the dosage form expressed as the equimolar amount of buprenorphine base (Mw=467.64 g/mol) in mg, and the amount of oxycodone in the dosage form expressed as the equimolar amount of oxycodone hydrochloride (Mw=351.82 g/mol) in mg. The invention also provides combinations of an opioid agonist and buprenorphine for use to treat pain, wherein the combination achieves a reduction of adverse pharmacodynamic responses (such as, respiratory depression), compared with a corresponding stand-alone opioid therapy. The invention also includes methods of treatment and dosage forms thereof comprising such combinations.

14 Claims, 41 Drawing Sheets

(56) References Cited

U.S. PATENT DOCUMENTS

| | | |
|---|---|---|
| 5,891,471 A | 4/1999 | Miller et al. |
| 5,914,131 A | 6/1999 | Merrill et al. |
| 5,958,452 A | 9/1999 | Oshlack et al. |
| 5,965,161 A | 10/1999 | Oshlack et al. |
| 5,965,163 A | 10/1999 | Miller et al. |
| 5,968,547 A | 10/1999 | Reder et al. |
| 5,968,551 A | 10/1999 | Oshlack et al. |
| 6,024,982 A | 2/2000 | Oshlack et al. |
| 6,143,322 A | 11/2000 | Sackler et al. |
| 6,162,467 A | 12/2000 | Mliller et al. |
| 6,210,714 B1 | 4/2001 | Oshlack et al. |
| 6,228,863 B1 | 5/2001 | Palermo et al. |
| 6,277,384 B1 | 8/2001 | Kaiko et al. |
| 6,344,212 B2 | 2/2002 | Reder et al. |
| 6,375,957 B1 | 3/2002 | Champlin |
| 6,572,885 B2 | 6/2003 | Oshlack et al. |
| 6,696,066 B2 | 2/2004 | Kaiko et al. |
| 6,696,088 B2 | 2/2004 | Oshlack et al. |
| 6,716,449 B2 | 4/2004 | Oshlack |
| 6,733,783 B2 | 5/2004 | Oshlack et al. |
| 7,141,250 B2 | 11/2006 | Oshlack et al. |
| 7,144,587 B2 | 12/2006 | Oshlack |
| 7,157,103 B2 | 1/2007 | Sackler |
| 7,332,182 B2 | 2/2008 | Sackler |
| 7,384,653 B2 | 6/2008 | Wright, IV |
| 7,514,100 B2 | 4/2009 | Oshlack |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,727,557 B2 | 6/2010 | Sackler |
| RE41,489 E | 8/2010 | Reder et al. |
| RE41,571 E | 8/2010 | Reder et al. |
| 7,842,307 B2 | 11/2010 | Oshlack |
| 7,842,311 B2 | 11/2010 | Oshlack et al. |
| 7,943,174 B2 | 5/2011 | Oshlack |
| 8,017,148 B2 | 9/2011 | Sackler |
| 8,337,888 B2 | 12/2012 | Wright et al. |
| 8,389,007 B2 | 3/2013 | Wright et al. |
| 8,524,275 B2 | 9/2013 | Oshlack et al. |
| 8,529,948 B1 | 9/2013 | Wright et al. |
| 8,551,520 B2 | 10/2013 | Oshlack et al. |
| 8,609,683 B2 | 12/2013 | Wright et al. |
| 8,647,667 B2 | 2/2014 | Oshlack et al. |
| 8,652,497 B2 | 2/2014 | Sackler |
| 8,652,515 B2 | 2/2014 | Sackler |
| 8,673,355 B2 | 3/2014 | Kaiko et al. |
| 8,808,740 B2 | 8/2014 | Huang |
| 8,822,487 B2 | 9/2014 | Kaiko et al. |
| 8,846,090 B2 | 9/2014 | Broegmann et al. |
| 8,846,091 B2 | 9/2014 | Broegmann et al. |
| 8,946,253 B2 * | 2/2015 | Hummel ............... A61P 1/04 514/282 |
| 8,969,369 B2 | 3/2015 | Caruso et al. |
| 8,980,291 B2 | 3/2015 | Oshlack |
| 9,211,293 B2 | 12/2015 | Deaver et al. |
| 9,233,073 B2 | 1/2016 | Sackler |
| 9,662,326 B2 | 5/2017 | Hummel |
| 9,849,124 B2 | 12/2017 | Hummel |
| 9,855,262 B2 | 1/2018 | Hummel |
| 9,867,817 B2 | 1/2018 | Hummel |
| 9,872,856 B2 | 1/2018 | Hummel |
| 9,931,337 B2 | 4/2018 | Hummel |
| 2001/0031278 A1 | 10/2001 | Oshlack et al. |
| 2003/0068375 A1 | 4/2003 | Wright et al. |
| 2003/0068392 A1 | 4/2003 | Sackler |
| 2003/0187010 A1 | 10/2003 | Foss et al. |
| 2007/0020339 A1 | 1/2007 | Bear |
| 2009/0246265 A1 | 10/2009 | Stinchcomb et al. |
| 2010/0152222 A1 | 6/2010 | Chapleo et al. |
| 2010/0227876 A1 | 9/2010 | Rech |
| 2010/0284960 A1 | 11/2010 | Riggs-Sauthier |
| 2011/0097395 A1 | 4/2011 | Babul et al. |
| 2011/0245287 A1 | 10/2011 | Holaday et al. |
| 2012/0178771 A1 | 7/2012 | Babul et al. |
| 2013/0281388 A1 | 10/2013 | Deaver et al. |
| 2014/0056979 A1 | 2/2014 | Huang |
| 2015/0196548 A1 | 7/2015 | Hummel |
| 2015/0196549 A1 | 7/2015 | Hummel |
| 2015/0196553 A1 | 7/2015 | Hummel |
| 2016/0074387 A1 | 3/2016 | Hummel |

FOREIGN PATENT DOCUMENTS

| | | |
|---|---|---|
| JP | 2015514743 A | 5/2015 |
| RU | 20120122945 | 10/2013 |
| WO | WO-1996/002251 | 2/1996 |
| WO | WO-2004/054554 | 7/2004 |
| WO | WO-2005/011579 | 2/2005 |
| WO | WO-2006/087160 | 8/2006 |
| WO | WO-2006/089973 | 8/2006 |
| WO | WO-2007/005716 | 1/2007 |
| WO | WO-2010/141505 | 12/2010 |
| WO | WO-2011/109743 | 9/2011 |
| WO | WO-2012/166998 | 6/2012 |
| WO | WO-2013156850 A1 | 10/2013 |

OTHER PUBLICATIONS

Aurilio, C., et al., "Transdermal buprenorphine combined with spinal morphine and naropine for pain relief in chronic peripheral vasculopathy," Minerva Anestesiologica, vol. 71, No. 7-8, pp. 445-449, Jul.-Aug. 2005.

Beltrutti, D., et al., "Late Antinociception and Lower Untoward Effects of Concomitant Intrathecal Morphine and Intravenous Buprenorphine in Humans," Journal of Clinical Anesthesia, vol. 14, No. 6, pp. 441-446, Sep. 2002.

Beltrutti, D., et al., "Pain relief after simultaneous administration of intravenous buprenorphine and intrathecal morphine in terminally ill patients; A report of two cases," The Pain Clinic, vol. 12, No. 2, pp. 121-123, Jun. 2000.

Ben-Abraham et al., "The benefit of combining spinal morphine and intravenous buprenorphine for perioperative pain," vol. 140, No. 8, pp. 709-712, Aug. 2001, Abstract.

Bickel, et al., "Buprenorphine: Dose-Related Blockade of Opioid Challenge Effects in Opioid Dependent Humans, The Journal of Pharmacology and Experimental Therapeutics", vol. 247, No. 1 : pp. 47-53, 1988.

Boysen, et al., Buprenorphine antagonism of ventilatory depression following fentanyl anaesthesia. Acta Anaesthesiol Scand, 1988; 32:490-2.

Bruzgin, V. V. "Treatment of Chronic Pain Syndrome in Patients with Generalized Forms of Breast Cancer," Tumors of the Female Reproductive System, vol. 3: pp. 6-10., 2007.

Chen, et. al., Interaction of combined intrathecal morphine with subcutaneous buprenorphine, Acta pharmacologica Sinica , 21 (8), 685-689, 2000.

Chung, et al., "Analgesic properties of loperamide differ following systemic and local administration to rats after spinal nerve injury," European Journal of Pain, vol. 16, No. 7, pp. 1021-1032, Aug. 2012.

Cowan, A., et al. "Basic Pharmacology of Buprenorphine." Buprenorphine: The Unique Opioid Analgesic. Eds. K. Budd and R. Raffa. New York, NY: Georg Thieme Verlag Stuttgart, 3-21, 2005.

Dahan et al. Incidence, Reversal, and Prevention of Opioid-induced respiratory depression, Anesthesiology, Jan. 2010, vol. 112, No. 1; 112:226-38.

Dahan, Opioid-induced respiratory effects: new data on buprenorphine , Palliative Medicine, vol. 20; s3-s8, 2006.

Dahan, et al., "Buprenorphine induces ceiling in respiratory depression but not in analgesia". British Journal of Anesthesia, , 96 (5): 627-632, Mar. 2017, 2006.

Davis, M.P., "Evidence from Basic Research for Opioid Combnations", Expert Opinion on Drug Discovery, 7:2, 165-178, (2012).

Elkader, et al., "Buprenorphine Clinical Pharmacokinetics in the Treatment of Opioid Dependence," Adis Data Information BV, Canada, vol. 44, No. 7, A: 661-680, 2005.

European Search Report, P15012WOEP/ES References, Appl No. 18823900.8-1112/3645000, PCT/US2018040460, Feb. 29, 2021.

(56) References Cited

OTHER PUBLICATIONS

Fickel, et al., "Opioid receptor expression in the rat gastrointestinal tract: a quantitative study with comparison to the brain," Molecular Brain Research, vol. 46, No. 1-2, pp. 1-8, Jun. 1997.

Huang, et al., "Comparison of Pharmacological Activities of Buprenorphine and Norbuprenorphine: Norbuprenorphine is a Potent Opioid Agonist," The Journal of Pharmacology and Experimental Therapeutics, vol. 297, No. 2, pp. 688-695, May 2001.

International Preliminary Report on Patentability dated Nov. 14, 2014 from PCT App. No. PCT/IB2013/000746 filed Apr. 17, 2013.

International Search Report and Written Opinion dated Jan. 16, 2016 for International Application No. PCT/US15/49948 filed Sep. 14, 2015, 9 pgs.

International Search Report dated Jul. 12, 2013 from PCT App. No. PCT/IB2013/000746 filed Apr. 17, 2013.

Jasiniski, et al., "Human Pharmacology and Abuse Potential of the Analgesic Buprenorphine", Arch Gen Psychiatry, vol. 35: pp. 501-516, Apr. 1978.

Jensen, et al., "Comparison of cerebral pharmacokinetics of buprenorphine and norbuprenorphine in an in vivo sheep model," Xenobiotica, vol. 37, No. 4, pp. 441-457, Apr. 2007.

Jones, et al., "The Subjective, Reinforcing, and Analgesic Effects of Oxycodone in Patients with Chronic, Non-Malignant Pain who are Maintained on Sublingual Buprenorphine/Naloxone, Neuropsychopharmacology", 2011, pp. 11-422, vol. 36, American College of Neuropsychopharmacology, United States.

Khanna, et al. "Buprenorphine—an Attractive Opioid with Underutilized Potential in Treatment of Chronic Pain." Journal of Pain Research 8: 859-70, 2015.

Kogel, B., et al., "Interaction of mu-Opioid Receptor Agonists and Antagonists with the Analgesic Effect of Buprenorphine in Mice," European Journal of Pain, vol. 9, pp. 599-611, Oct. 2005.

Kress, H. G. "Clinical Update on the Pharmacology, Efficacy and Safety of Transdermal Buprenorphine." European Journal of Pain (London, England) 13.3 (2009): 219-30.

Kwarcinski et al. , "The use of immeidate-release opioids as supplemental analgesia during the management of moderate to severe chronic pain with tansdermal buprenorphine , a partial mu-opioid receptor agonist" APhA2012 Abstracts, Journal of the American Pharmacists Association, Mar.-Apr. 2012, vol. 52, No. 2, pp. 284.

Liang Zhou et al., "Efficacy of combination of morphine sulfate controlled-release tablet and buprenorphine sublingual tablet in moderate to severe cancer pain patient." Intl. J. Anesth. Resus, 36(2): 113-116, Feb. 2015, and its English language translation thereof.

Megarbane, et al., "Buprenorphine is protective against the depressive effects of norbuprenorphine on ventilation," Toxicology and Applied Pharmacology, vol. 212, No. 3, pp. 256-267, May 2006.

Mendelson et al., "Bioavailability of Sublingual Buprenorphine", Journal Clinical Pharmacology, 1997, pp. 31-37, Vo. 37, SAGE Social Science Collections, United States.

Mercadante, et al., "Safety and Effectiveness of Intravenous Morphine for Episodic Breakthrough Pain in Patients Receiving Transdermal Buprenorphine," Journal of Pain and Symptom Management, vol. 32, No. 2, pp. 175-179, Aug. 2006.

Morgan, et al., "An Examination of the Interactions between the Antinociceptive Effects of Morphine and Various mu-Opioids: The Role of Intrinsic Efficacy and Stimulus Intensity," Anesthesia & Analgesia, vol. 88, No. 2, pp. 407-413, Feb. 1999.

Nemirovsky A et al., Antinociceptive effect of combined administration of spinal morphine and systemic buprenorphine, Anesthesiology (Hagerstown), (Sep. 1998) vol. 89, No. 3A, pp. A1087.

Nemirovsky A et al., Mutual antagonism of buprenorphine and morphine as evidenced in the nociceptive activity evoked in thalamus neurons of the rat, Anesthesiology, (Sep. 2000) vol. 93, No. 3A, Supp. [S], pp. U192-U192.

Nemirovsky et al., "Antinociceptive Effect of the Combinations of Spinal Morphine and Systemic Morphine or Buprenorphine." Faseb Journal, vol. 12, No. 4, pp. A156: (1998).

Niv, D., et al., "Antinociceptive Effect Induced by the Combined Administration of Spinal Morphine and Systemic Buprenorphine," Anesthesia & Analgesia, vol. 87, No. 3, pp. 583-586, Sep. 1998.

Parker, et al., "Patient-Controlled Epidural Analgesia: Interactions between Nalbuphine and Hydromorphone," Anesthesia & Analgesia, vol. 84, No. 4, pp. 757-763, Apr. 1997.

Pchelintcev, Ketamine influence on analgesic effect of the combination of fentanyl and buprenorphine in thermal nociceptive effect model in mice, Scientific notes of the Saint Petersburg State Medical University named after acad. Pavlov. vol. XVII No. 2, 2010.

Pergolizzi Joseph et al., Current knowledge of buprenorphine and its unique pharmacological profile, Pain practice : the official journal of World Institute of Pain, (Sep.-Oct. 2010) vol. 10, No. 5, pp. 428-450.

Pick, C.G., et al., "Pharmacological Characterization of Buprenorphine, a Mixed Agonist-Antagonist with kappa3 Analgesia," Brian Research, vol. 744, pp. 41-46, Jan. 1997.

Plosker, Greg L., "Buprenorphine 5, 10 and 20 micrograms/hour Transdermal Patch A Review of its Use in the Management of Chronic Non-Malignant Pain", ADIS Drug Evaluation: Transdermal Buprenorphine: A Review, 2011, p. 2492-2509, ADIS, A Walter Kluwer Business, Auckland, New Zealand.

Purdue Pharma LP, "Butrans—buprenorphine patch, extended release," available at http://app.purduepharma.com/xmlpublishing/pi.aspx?id=b, pp. 1-43, Jun. 2014.

Ramasubbu, et al., "Pharmacological Treatment of Opioid-Induced Hyperalgesia: A Review of the Evidence," Journal of Pain & Palliative Care Pharmacotherapy, vol. 25, No. 3, pp. 219-230, Aug. 2011.

Ravera E. et al., Controlled-release oxycodone tablets after transdermal-based opioid therapy in patients with cancer and non-cancer pain, Aging clinical and experimental research, (Oct.-Dec. 2011) vol. 23, No. 5-6, pp. 328-332.

Rosen, et al., "Buprenorphine: duration of blockade of effects of intramuscular hydromorphone", Drug and Alcohol Dependence 1994, pp. 141-149, vol. 35, Elsevier, Ireland.

Rosti, G., et al., "Opioid-Related Bowel Dysfunction: Prevalence and Identification of Predictive Factors in a Large Sample of Italian Patients on Chronic Treatment," European Review for Medical and Pharmacological Sciences, vol. 14, No. 12, pp. 1045-1050, Dec. 2010.

Stoller et al., "Effects of Buprenorphine/Naloxone in Opioid-Dependent Humans." Psychopharmacology, vol. 154, No. 3, pp. 230-242 (2001).

Strain EC et al, "The effects of buprenorphine in buprenorphine-maintained volunteers", Psychopharmacology (Berl) Feb. 1997; 129(4):329-38.

Strain, E. C., , et al., "Blockade of Hydromorphone Effects by buprenorphine/naloxone and Buprenorphine." Psychopharmacology 159.2 (2002): 161-166.

Strain, E. C., et al. "Effects of Buprenorphine Versus buprenorphine/naloxone Tablets in Non-Dependent Opioid Abusers." Psychopharmacology 148.4 (2000): 374-83.

Teoh, et al., "Buprenorphine Effects on Morphine- and Cocaine-Induced Subjective Responses by Drug-Dependent Men," Journal of Clinical Psychopharmacology, vol. 14, No. 1, pp. 15-27, Feb. 1994.

Troster, Andreas; Ihmsen, Harald; Singler, Boris; Filitz, Jorg; Koppert, Wolfgang, "Interaction of fentanyl and buprenorphine in an experimental model of pain and central sensitization in human volunteers.", The Clinical journal of pain, (Oct. 2012) vol. 28, No. 8, pp. 705-711.

Van der Shier, R. et al, Opoid-induced respritaroy depression: reversal by non-opioid drugs, F1000Prime Reports, Sep. 4, 2014, 6:79, pp. 1-8.

Vedig AE, Gibbs jM, Rutten Aj, Ilsley AH. The effect of buprenorphine on the analgesic and respiratory depressant effects of pethidine: A preliminary study. Pain. 1988;34:253-259.

Virk, et al., "Buprenorphine Is a Weak Partial Agonist That Inhibits Opioid Receptor Desensitization," The Journal of Neuroscience, vol. 29, No. 22, pp. 7341-7348, Jun. 2009.

(56) References Cited

OTHER PUBLICATIONS

Walker, et al., "Buprenorphine Antagonism of Mu Opioids in the Rhesus Tail-Withdrawal Procedure," Journal of Pharmacology and Experimental Therapeutics, vol. 273, No. 3, pp. 1345-1352, Jun. 1995.

Walsh, et al., "Acute Administration of Buprenorphine in Humans: Partial Agonist and Blockade Effects," The Journal of Pharmacology and Experimental Therapeutics, vol. 274, No. 1, pp. 361-372, Jul. 1995.

Walsh, Sharon L. et al., "Intranasal buprenorphine alone and in combination with naloxone: Abuse liability and reinforcing efficacy in physically dependent opioid abusers.", Drug and Alcohol Dependence, (May 1, 2016) vol. 162, pp. 190-198.

Written Opinion dated Jul. 12, 2013 from PCT App. No. PCT/IB2013/000746 filed Apr. 17, 2013.

Yassen et al., "Pharmacokinetic-Pharmacodynamic Modeling of the Respiratory Depressant Effect of Norbuprenorphine in Rats," The Journal of Pharmacology and Experimental Therapeutics, vol. 321, No. 2, pp. 598-607, May 2007.

Zanette G, Manani G, Giusti F, et al. Respiratory depression following administration of low dose buprenorphine as postoperative analgesic after fentanyl balanced anaesthesia. PaediatrAnaesth. 1996;6:419-422.

* cited by examiner

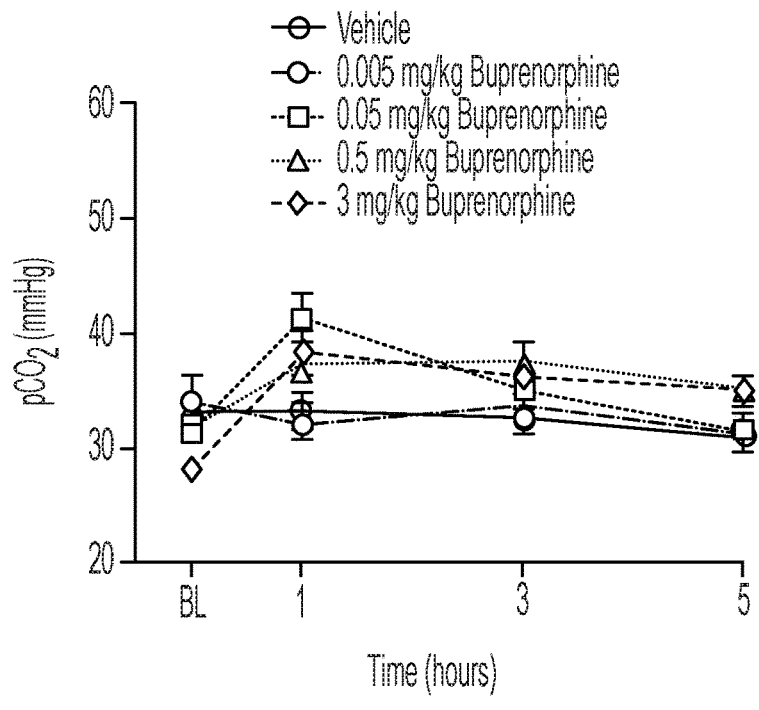
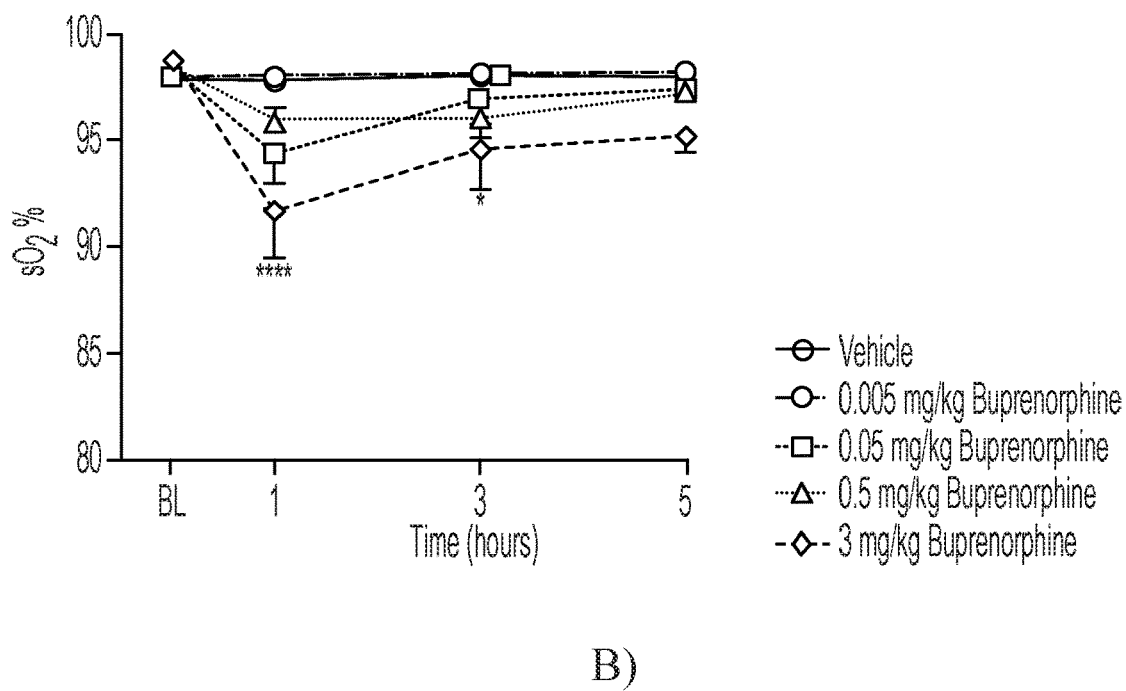
Figures 17A)-B)

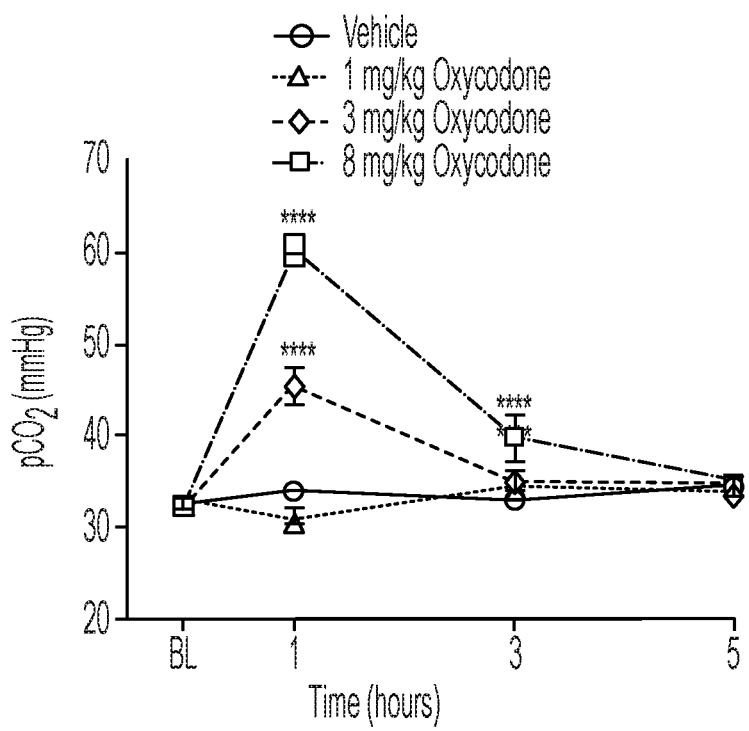
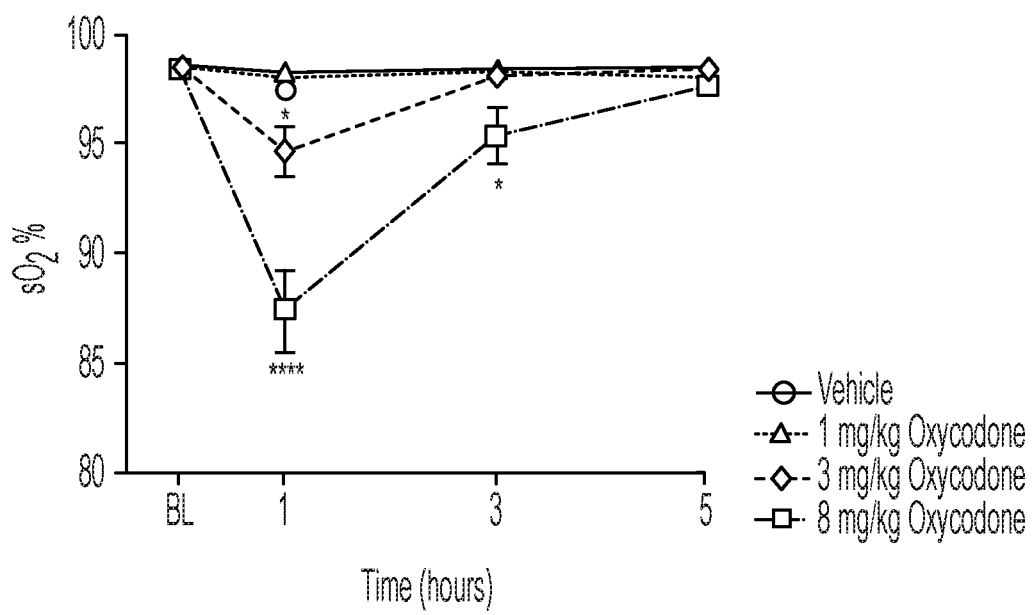
Figures 18 A)- B)

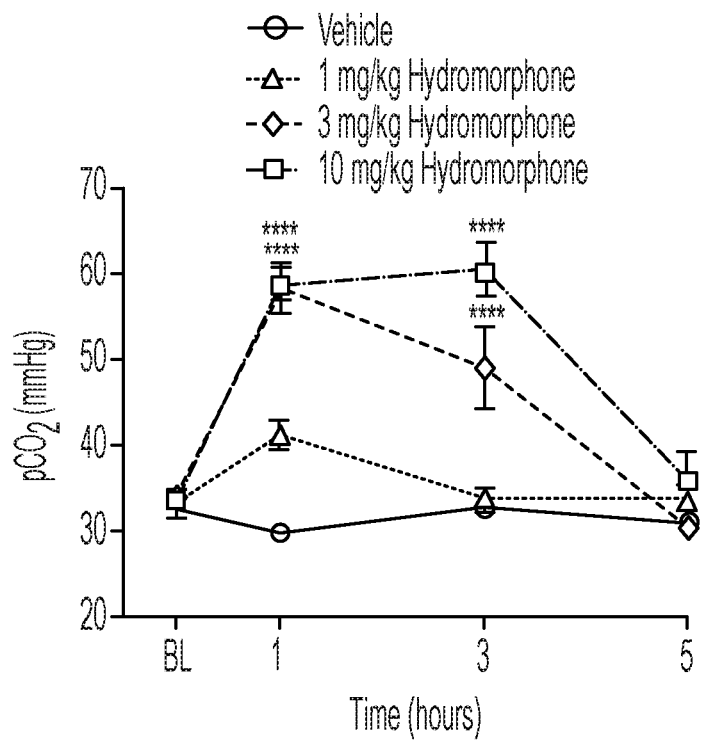
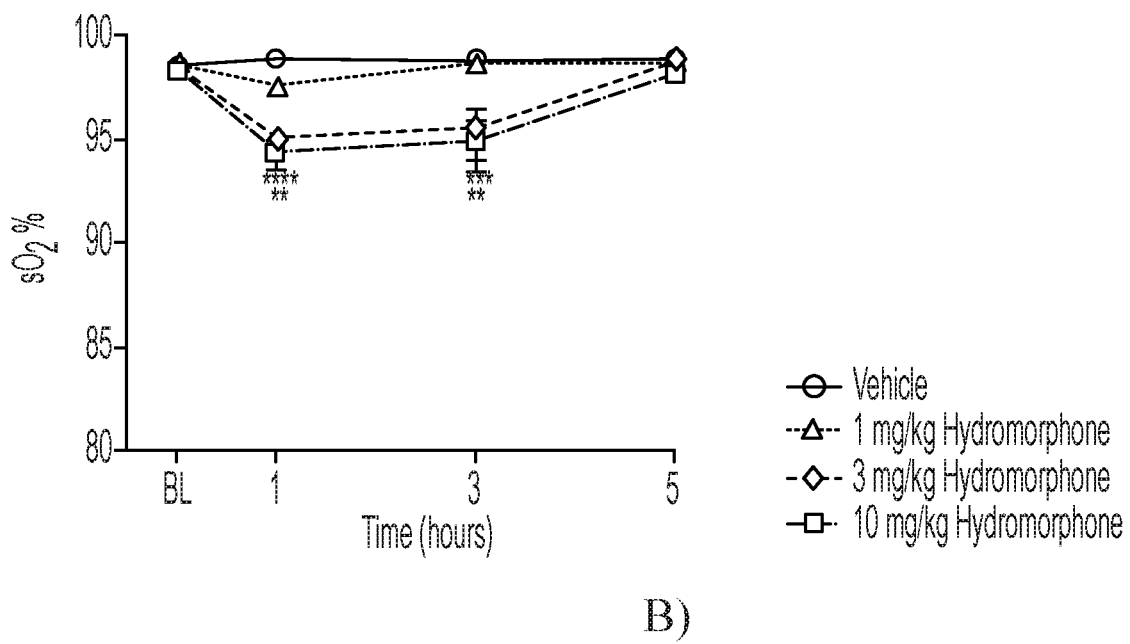
Figures 19 A)-B)

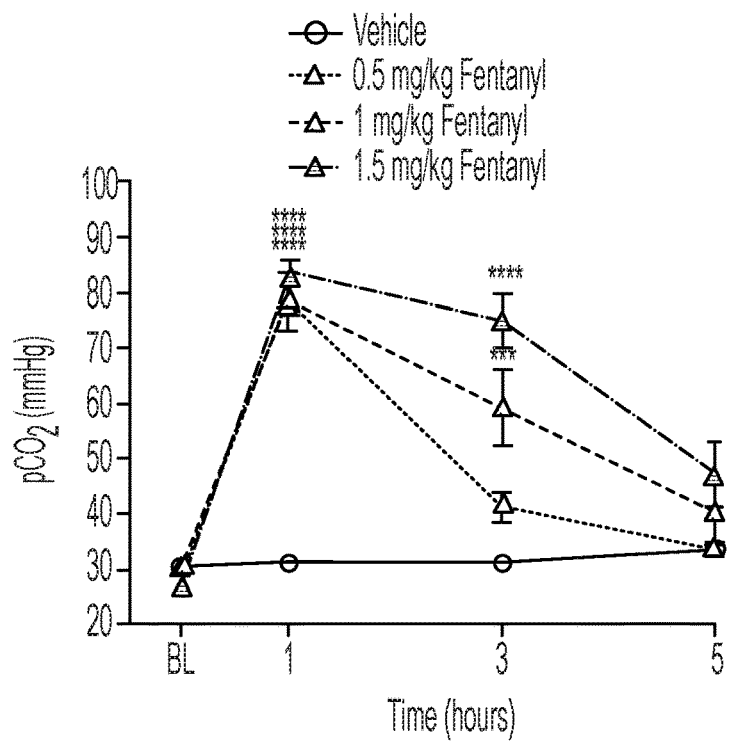
A)
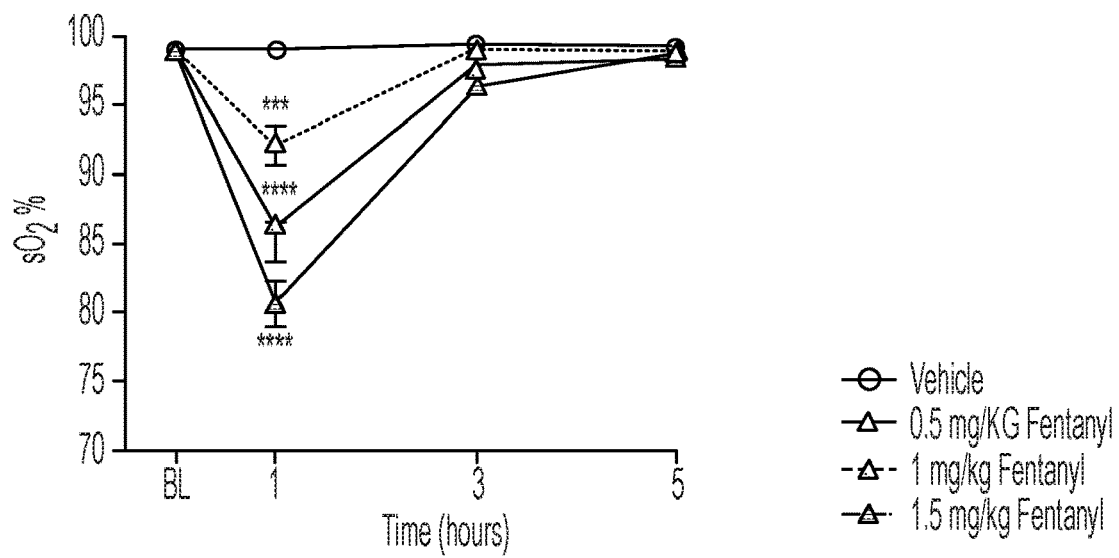
B)
Figures 20 A)-B)

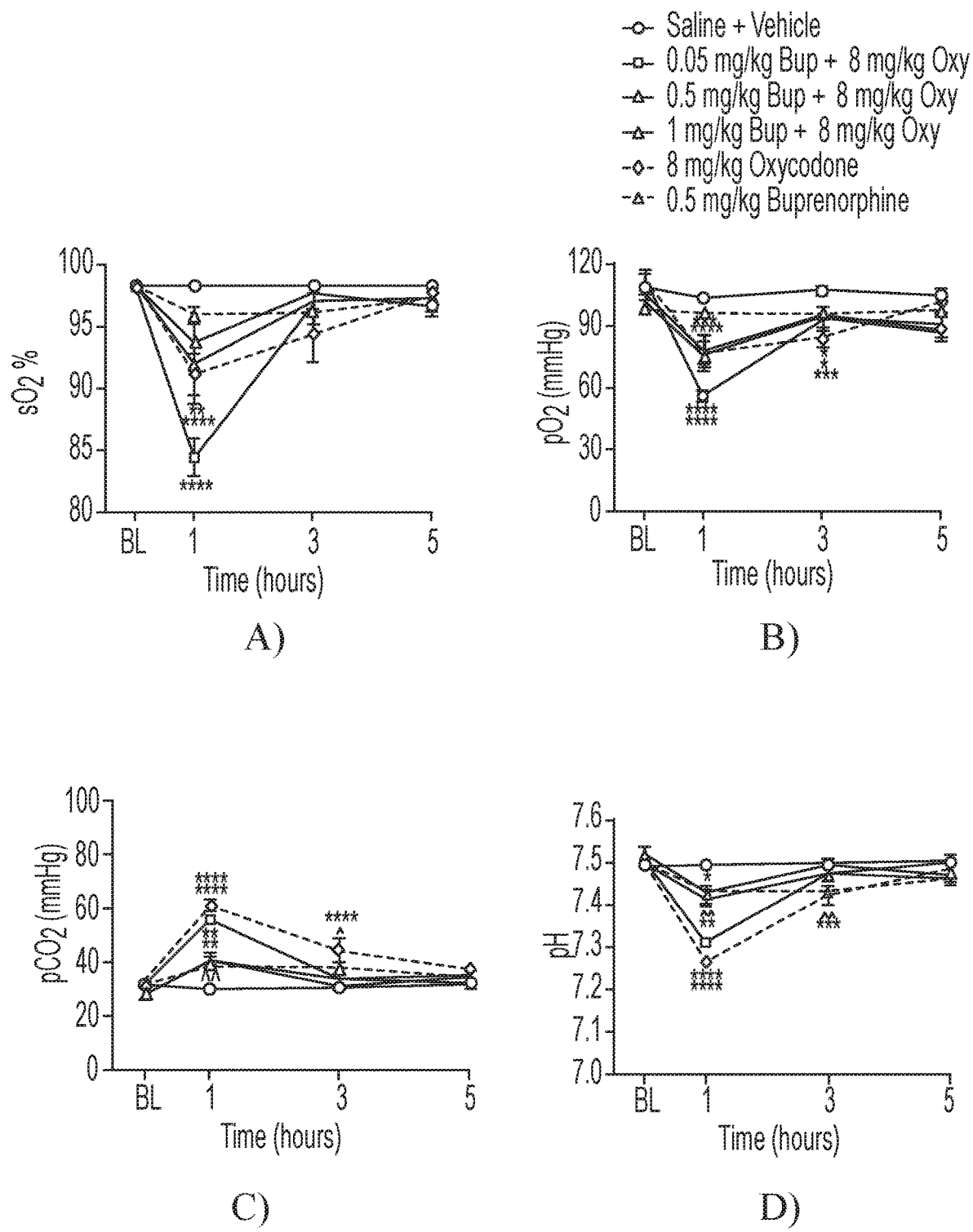
Figures 21 A)-D)

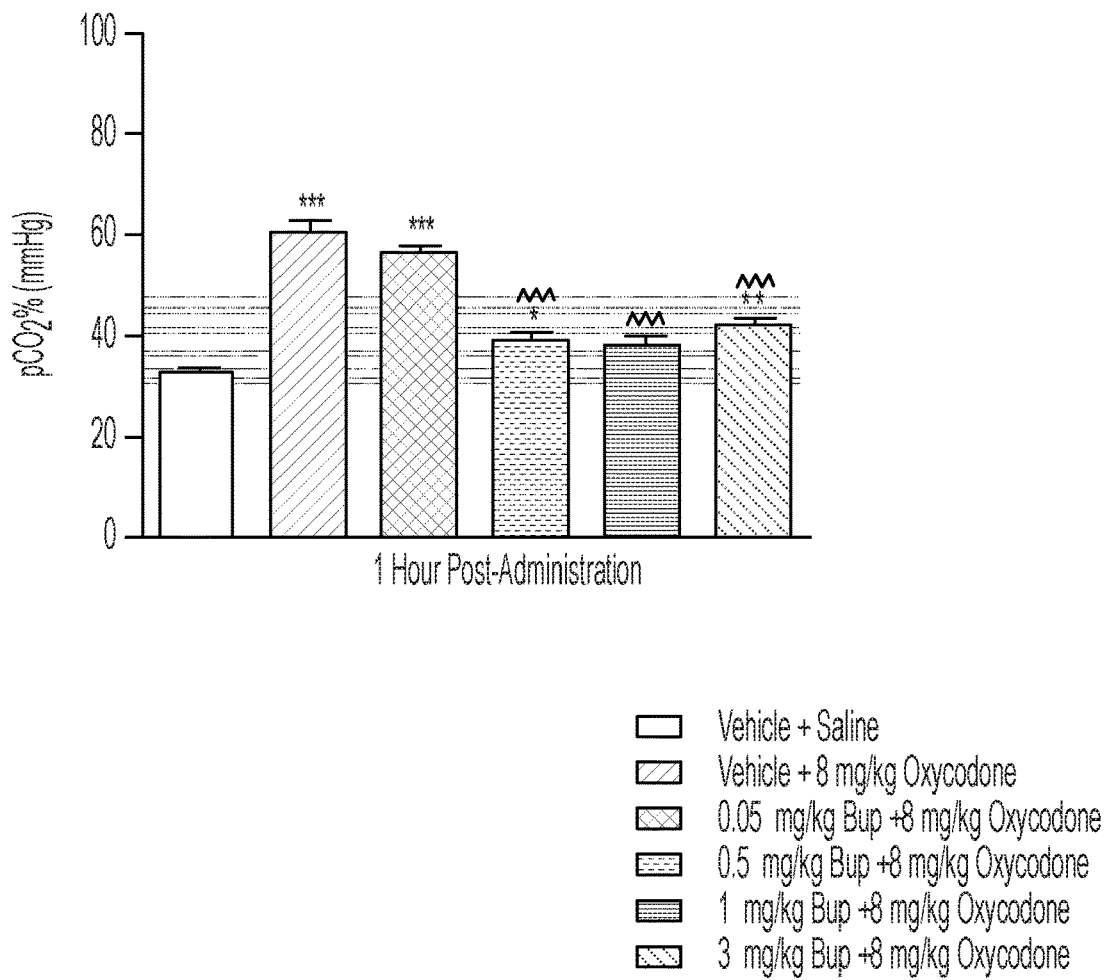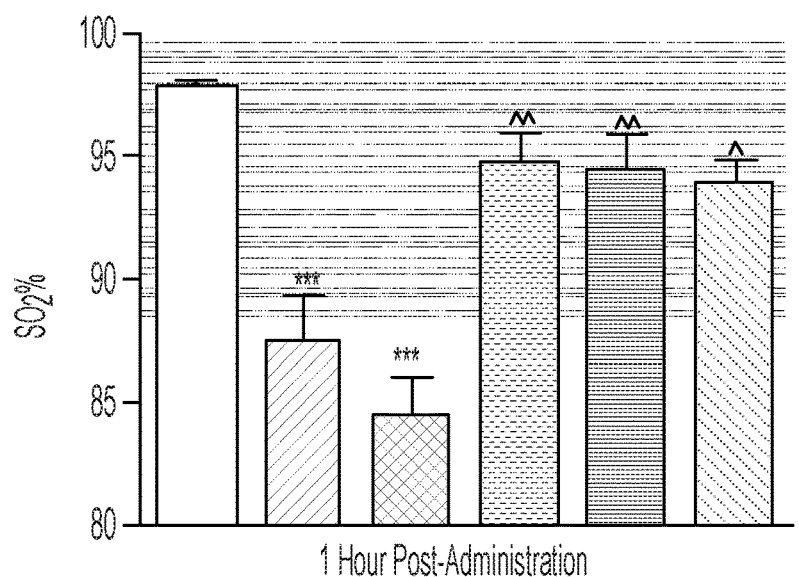
Figures 22 A)-B)

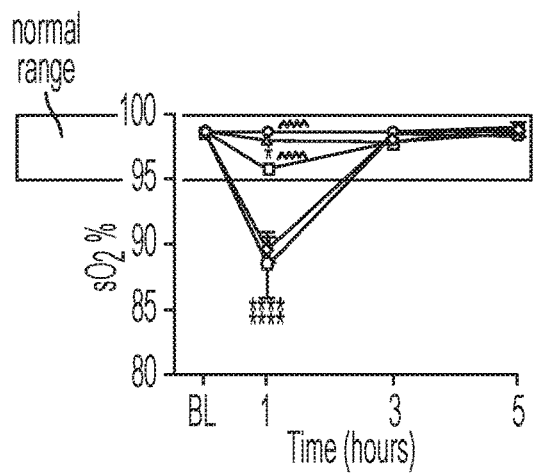
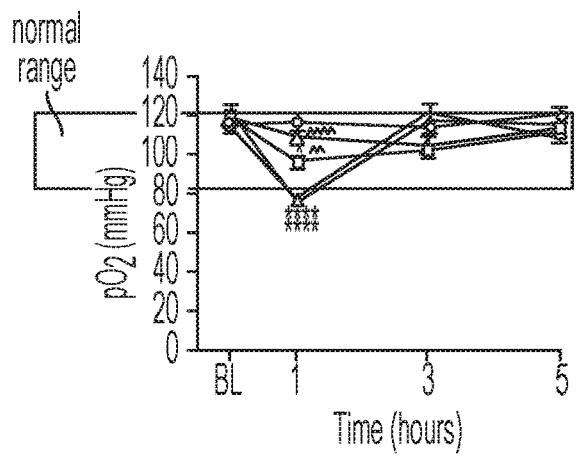
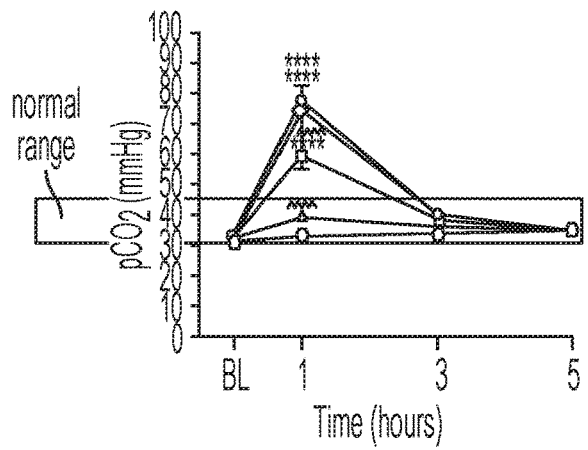
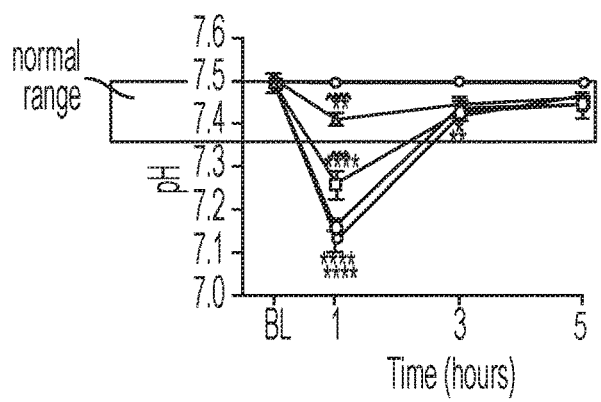
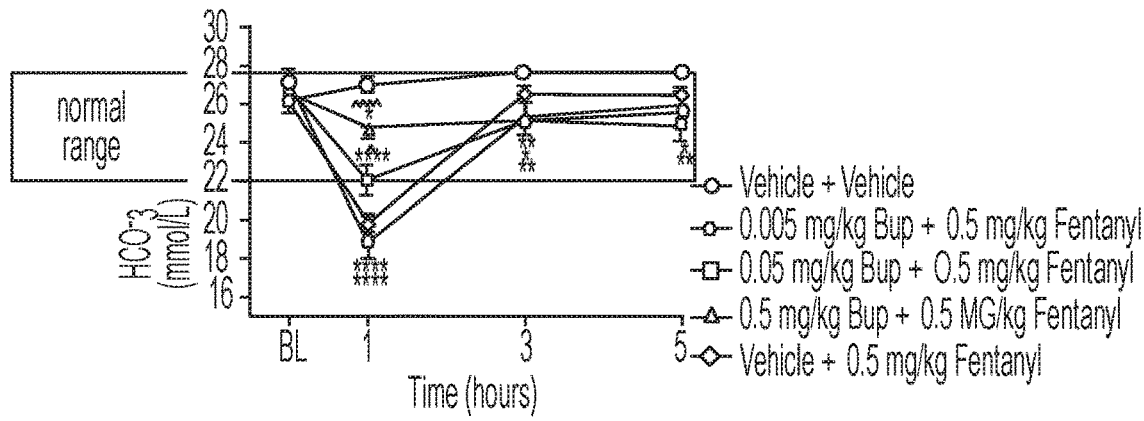
Figures 24 A)-E)

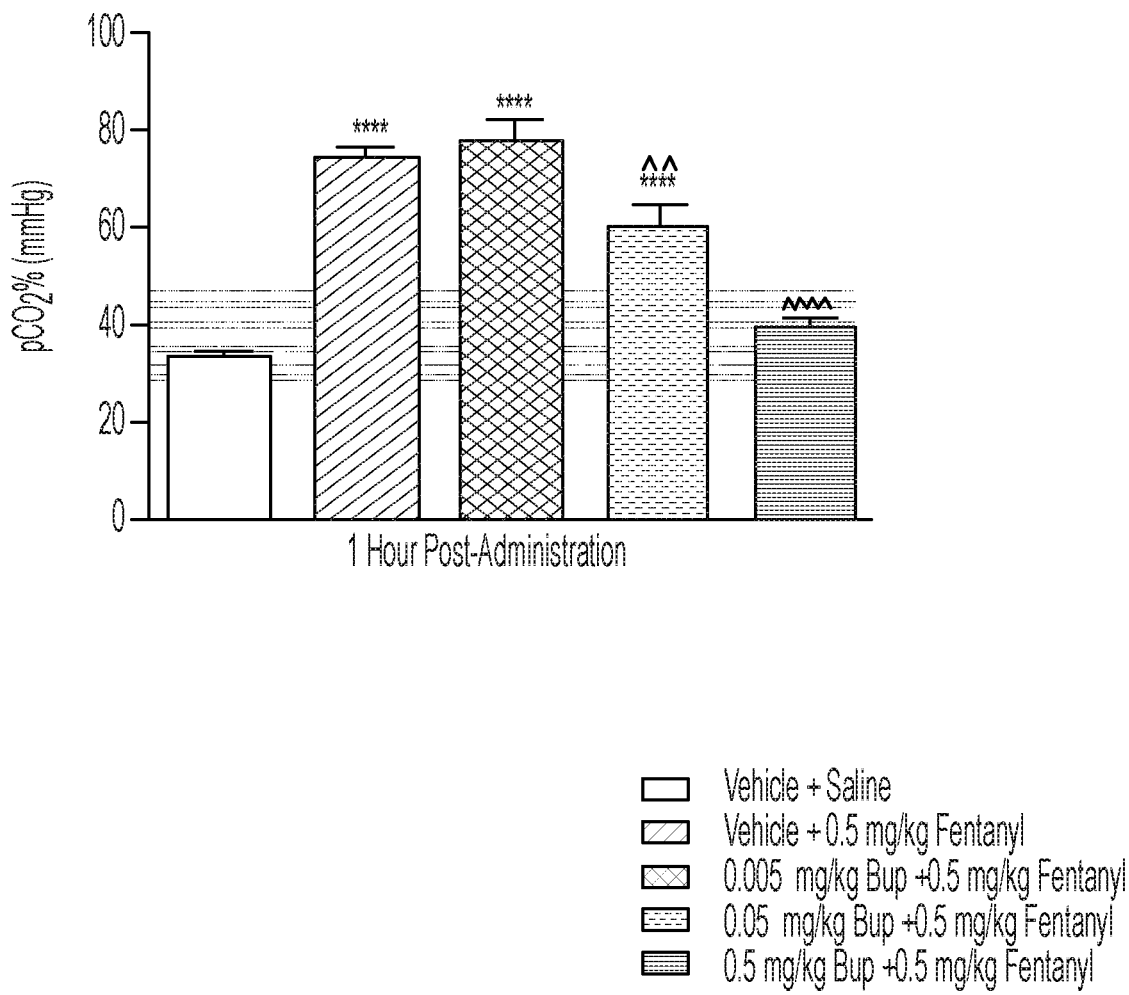
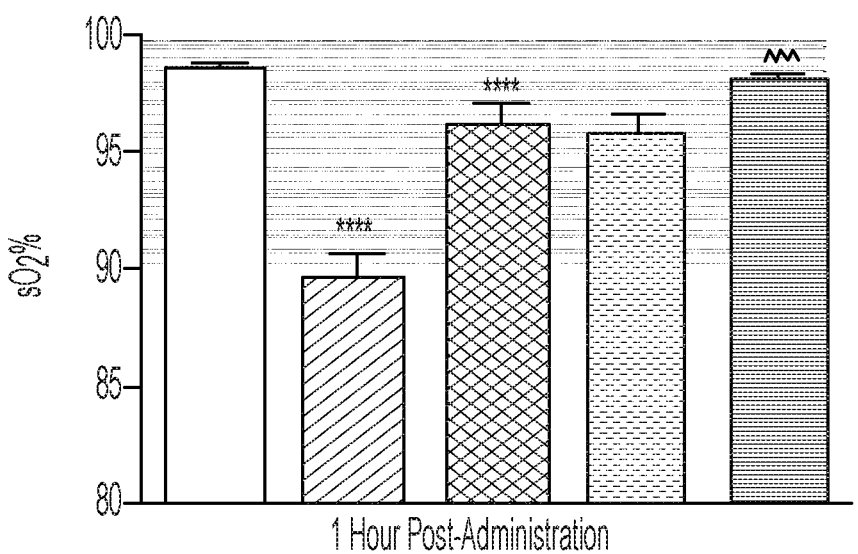
Figures 25A)-B)

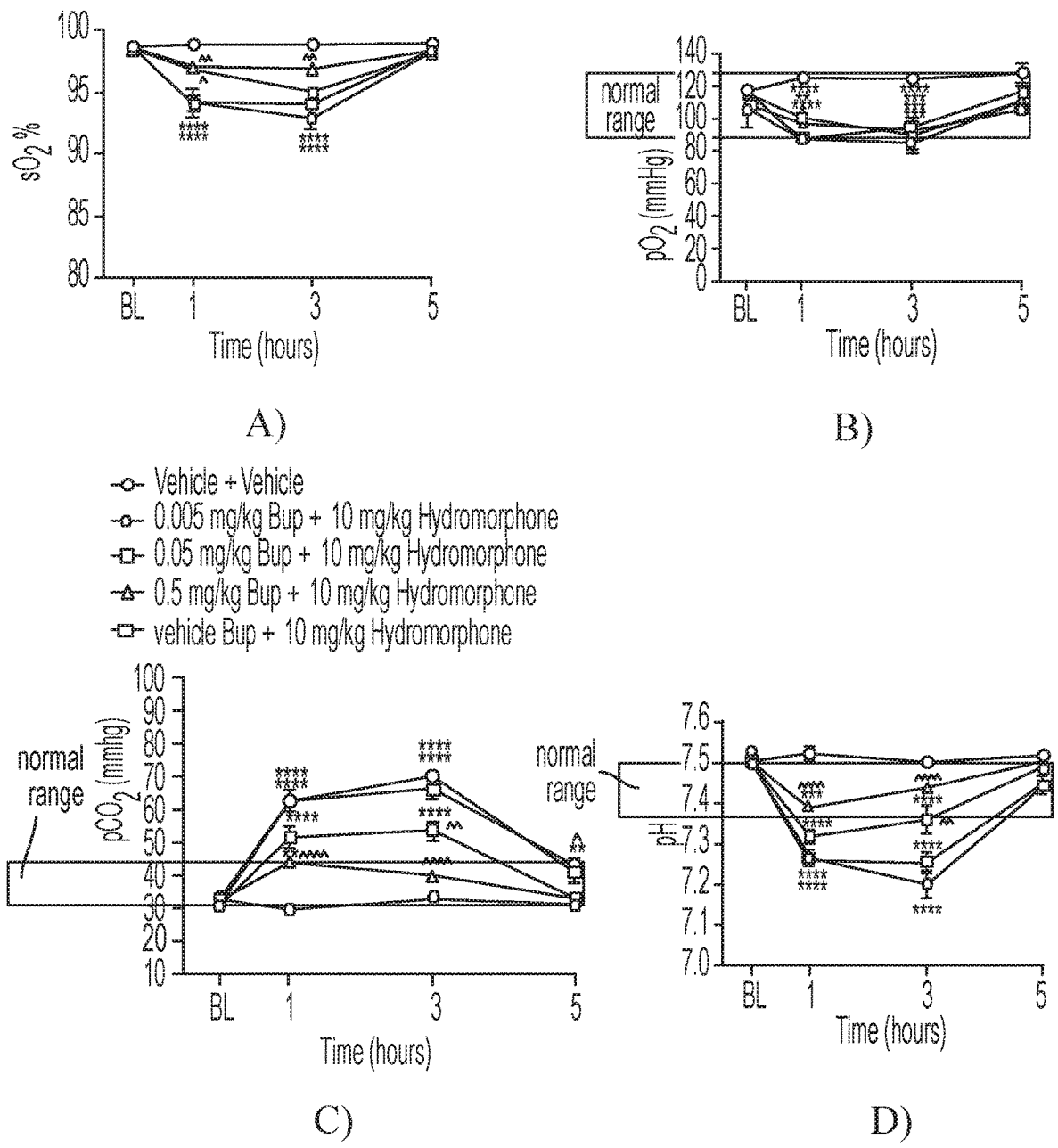
Figures 27 A)-D)

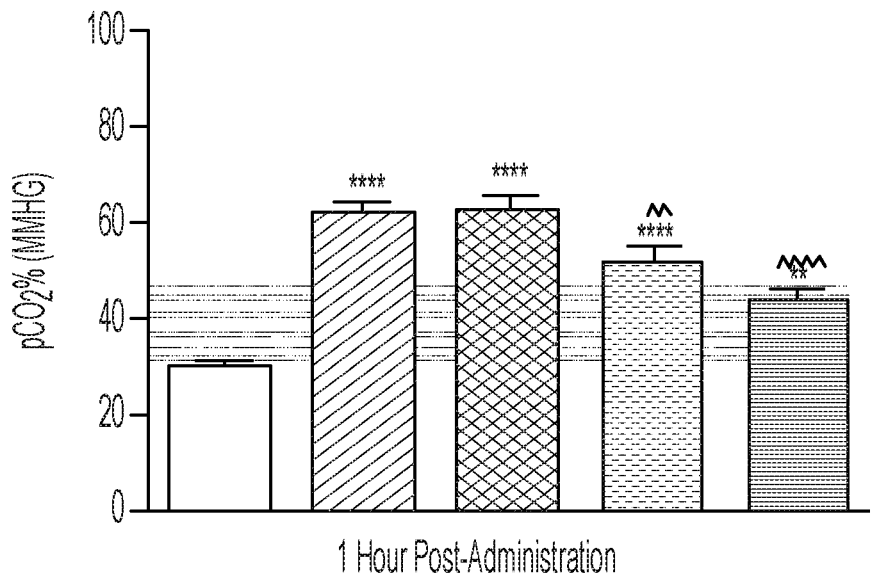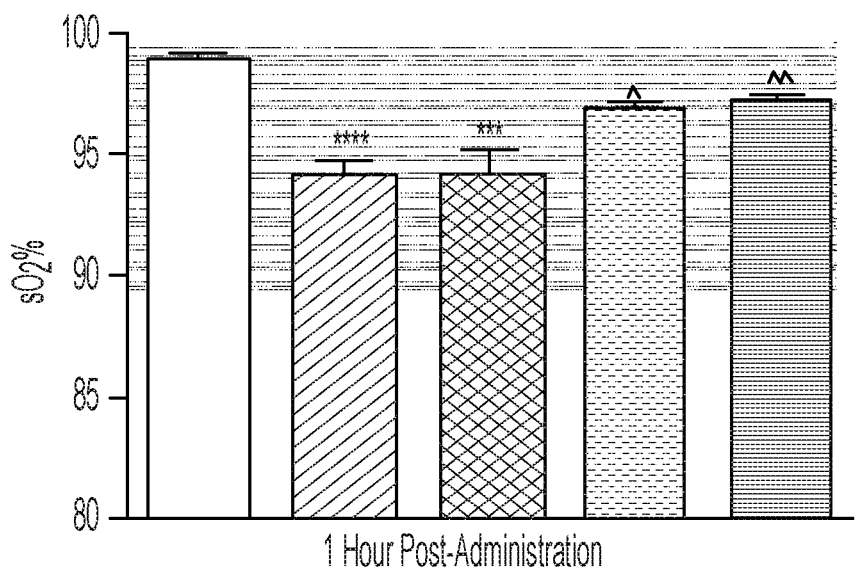
Figures 28A)-B)

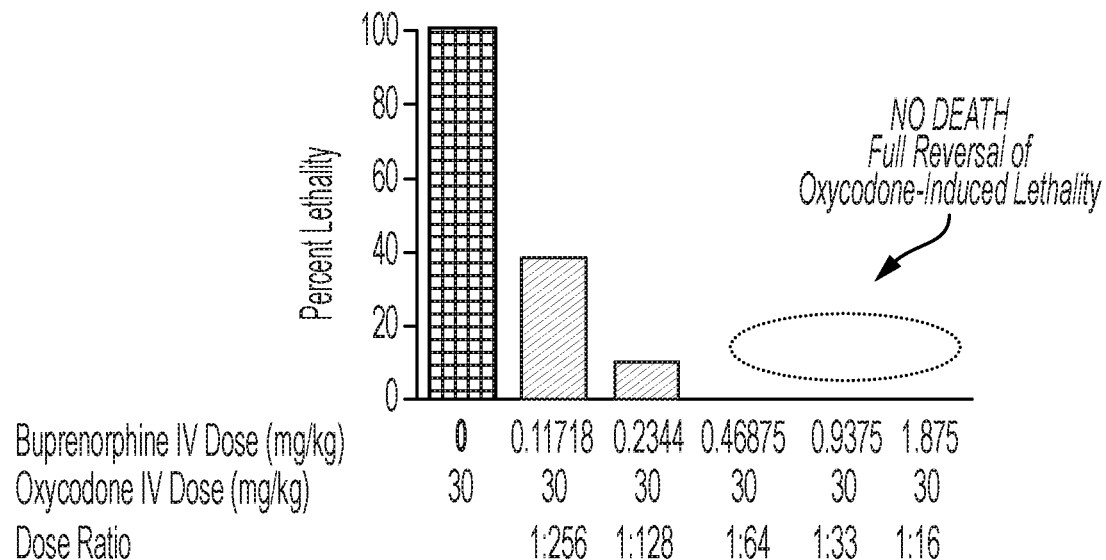
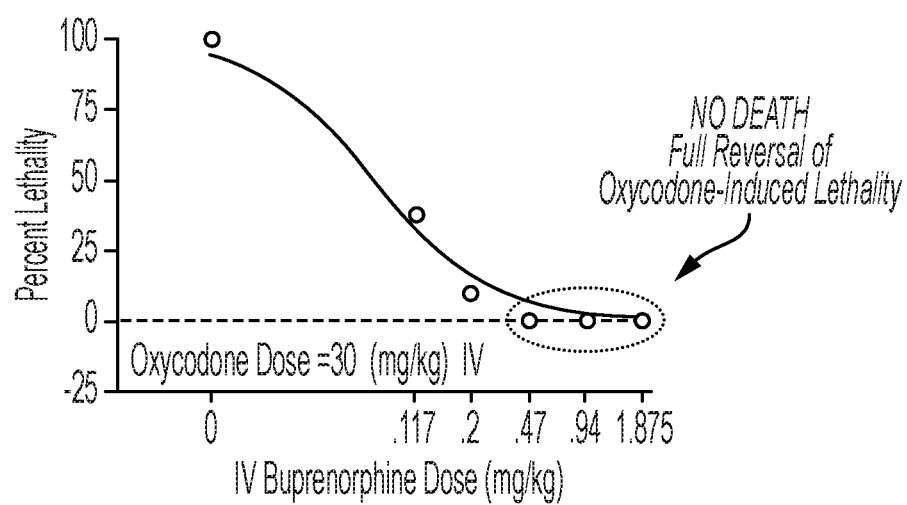
Figures 30A)-B)

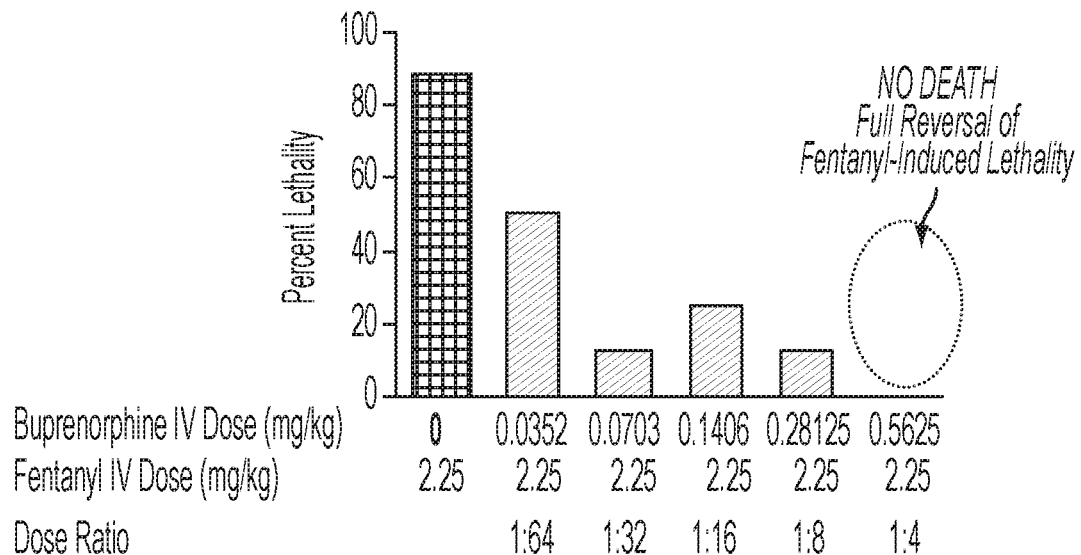
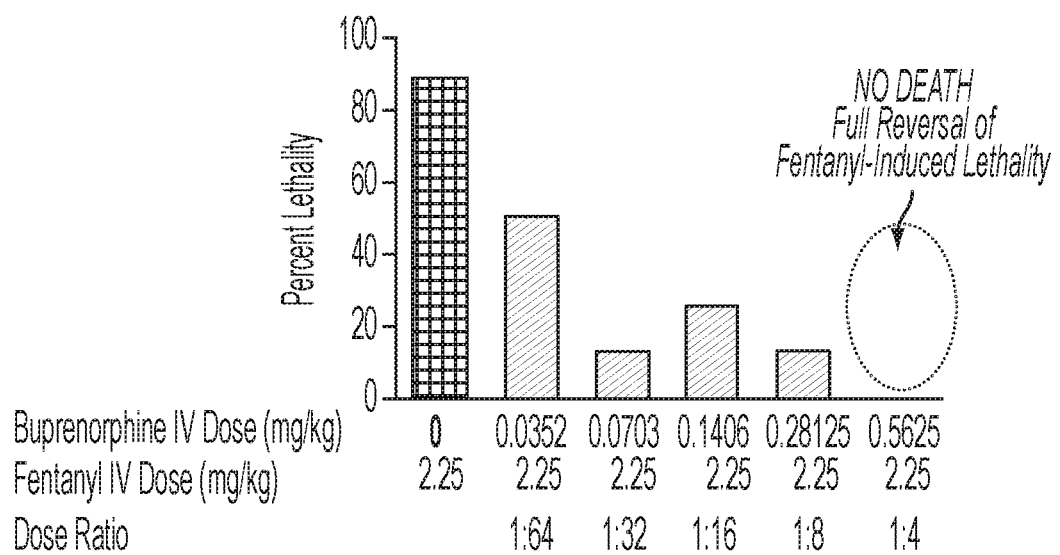
Figures 31A)-B)

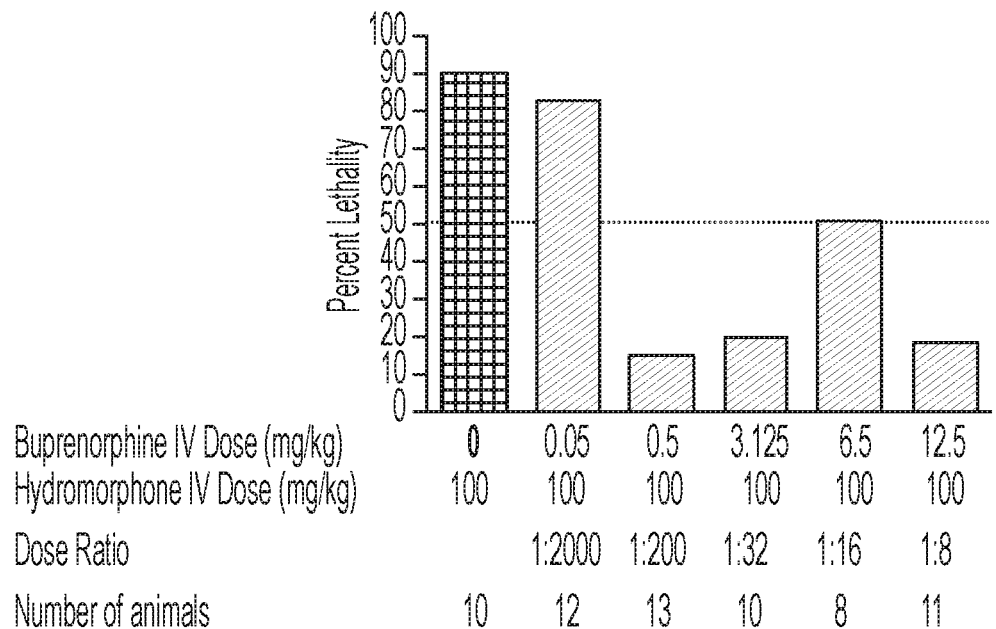
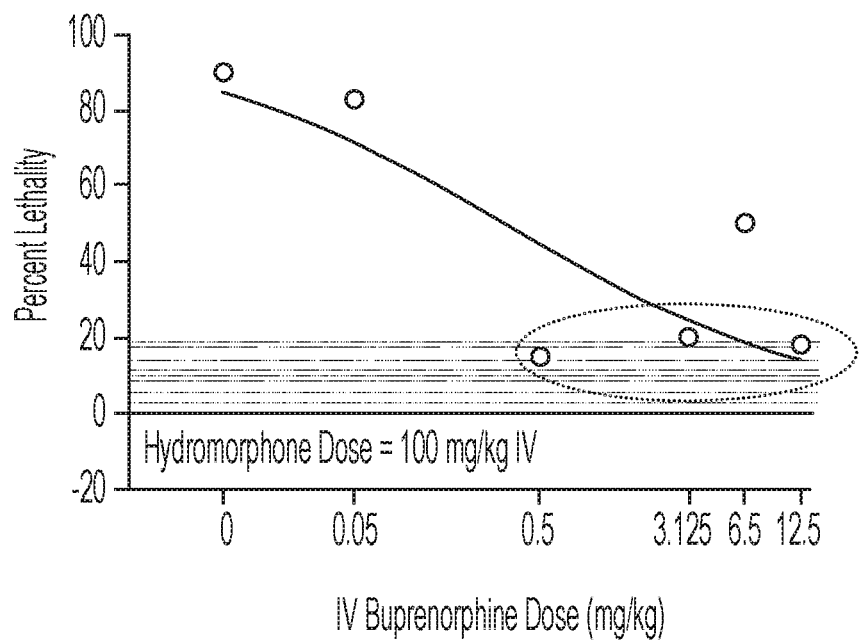
Figures 32A)-B)

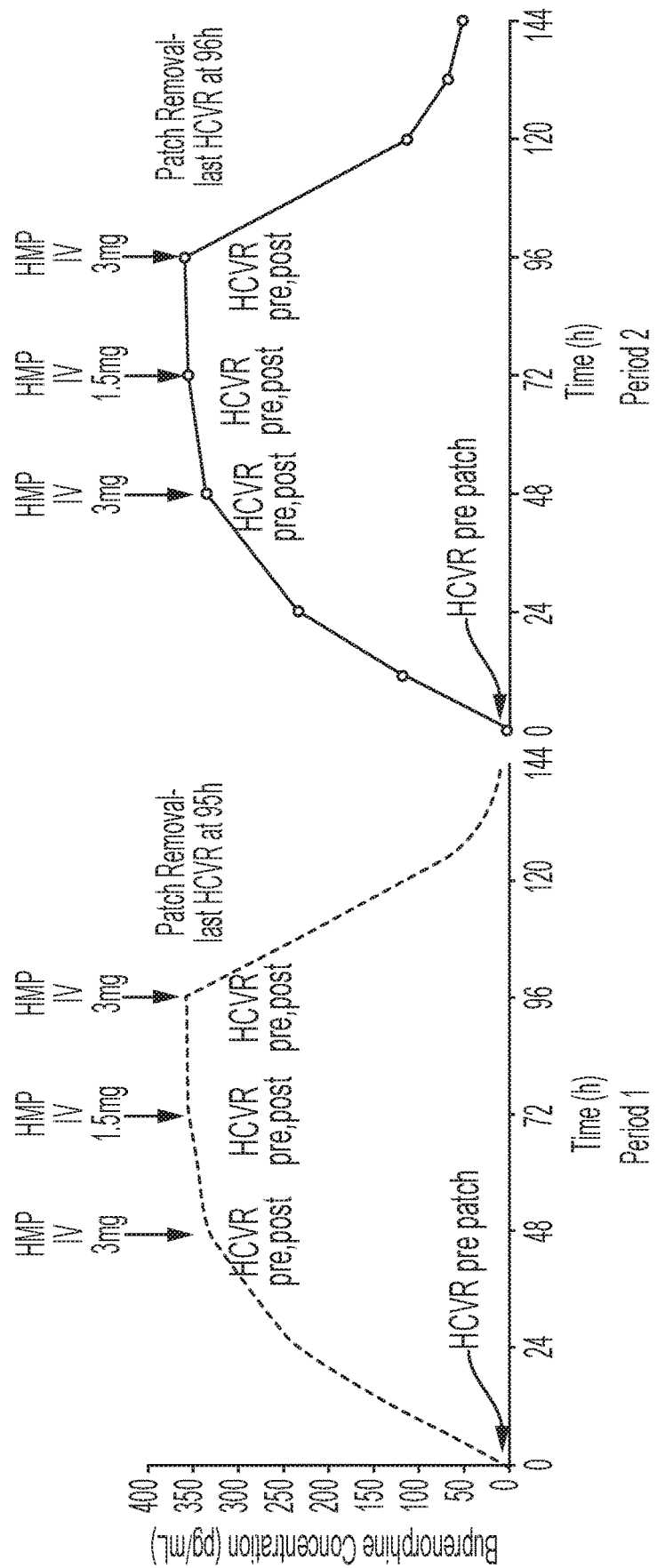
Figures 33 A)-B)

METHOD OF TREATMENT AND DOSAGE FORMS THEREOF

CROSS-REFERENCE TO RELATED APPLICATIONS

This application is the U.S. national phase, pursuant to 35 U.S.C. § 371, of PCT International Application Ser. No. PCT/US2018/040460, filed on Jun. 29, 2018 designating the United States and published in English on Jan. 3, 2019 as publication WO 2019/006404 A1, which claims priority to U.S. Provisional Application Ser. No. 62/527,337, filed on Jun. 30, 2017. The contents of the afore-mentioned patent applications are incorporated herein by their entirety.

TECHNICAL FIELD OF THE INVENTION

The present invention relates to methods for the treatment of pain and dosage forms thereof. The present invention relates, in particular, to methods for the treatment of pain with certain specific combinations of an opioid agonist and buprenorphine, and dosage forms containing such specific combinations thereof. In particular embodiments, the specific combination is a combination of oxycodone and buprenorphine, a combination of fentanyl and buprenorphine, or a combination of hydromorphone and buprenorphine. In certain embodiments, the combinations used herein offer improved characteristics, including such as, a reduction of adverse pharmacodynamic responses (such as, respiratory depression, bowel dysfunction, sedation, and drug liking) associated with stand-alone opioid agonist treatments, such as oxycodone, fentanyl and hydromorphone treatments. In particular, the combinations of the invention reduce potential toxicity associated with certain opioid agonists and reduce adverse side effects (e.g., respiratory depression), thus improving the overall safety profiles of certain opioid treatments. It is further believed that the methods of treatment and dosage forms thereof of the invention offer effective pain relief with reduced abuse potential compared with stand-alone opioid treatments.

BACKGROUND OF THE INVENTION

Opioid-induced adverse pharmacodynamic responses in patients receiving certain opioid therapies (e.g., fentanyl, hydromorphone, and oxycodone) for pain management can be troublesome, as these patients are already trying to manage pain, and the adverse side effects can add to their distress. Among potential opioid-induced adverse pharmacodynamic responses, respiratory depression is a particularly dangerous adverse pharmacodynamic response, since it may lead to respiratory arrest, which is potentially fatal. Unfortunately, it has been observed that certain opioids, when overdosed, can cause respiratory depression. Safety is thus a major concern in these opioid therapies.

There is therefore a long-felt need for improved methods and dosage forms thereof for effective pain treatment using opioid medication with reduced opioid-induced adverse pharmacodynamic responses (including such as, respiratory depression, excessive or unnecessary drug liking, and euphoria) and with a reduced likelihood to be illicitly used by non-patients. It remains a need in the art for opioid therapies and methods with effective analgesia and with much improved overall safety profiles.

OBJECTS AND SUMMARY OF THE INVENTION

It is an object of certain embodiments of the present invention to provide improved methods of treating pain.

It is an object of certain embodiments of the present invention to provide methods of treating pain with reduced adverse pharmacodynamic responses (such as, less potential for causing addiction and drug abuse, and improved safety).

It is an object of certain embodiments of the present invention to provide methods of treating pain with reduced public health risks associated with toxicity, respiratory depression, addiction and drug abuse.

It is an object of certain embodiments of the present invention to provide dosage forms for effective pain treatment with improved overall safety profiles.

It is an object of certain embodiments of the present invention to provide dosage forms for treating pain with less potential for causing respiratory depression, addiction, and drug abuse, and with an improved safety profile.

It is an object of certain embodiments of the present invention to provide dosage forms for treating pain with reduced public health risks associated with toxicity, respiratory depression, addiction, and drug abuse.

These objects are to be understood also to relate to use-limited products and uses in a method of treatment as stated herein.

The above objects can be achieved by certain embodiments of the invention, which are directed to a method of treating pain, comprising administering to a patient in need thereof a specific combination of an opioid agonist (e.g., hydromorphone, oxycodone, and fentanyl) and buprenorphine.

In a certain embodiment, the specific combination of an opioid agonist and buprenorphine is a combination of hydromorphone and buprenorphine, wherein the combination of hydromorphone and buprenorphine reduces hydromorphone-induced respiratory depression by about 20% or higher, compared to a corresponding hydromorphone-alone therapy. In one embodiment, the combination of hydromorphone and buprenorphine reduces hydromorphone-induced respiratory depression by about ⅓ or higher.

In another embodiment, the method for treating pain comprises administering to a patient in need thereof
   (i) an effective amount of hydromorphone during an administration period 1 at a mean input rate (in mg/h) of hydromorphone during said administration period 1, wherein said mean input rate of hydromorphone is expressed as the equimolar amount of hydromorphone free base administered during said administration period 1 divided by the duration of said administration period 1, and
   (ii) another effective amount of buprenorphine during an administration period 2 at a mean input rate (in mg/h) of buprenorphine during said administration period 2, wherein said mean input rate of buprenorphine is expressed as the equimolar amount of buprenorphine free base administered during said administration period 2 divided by the duration of said administration period 2,
   wherein the administration period 1 and the administration period 2 overlap by at least 75%, and wherein the ratio of said mean input rate of buprenorphine to said mean input rate of hydromorphone is from about 1:8000 to about 1:100.

In another embodiment, the specific combination of the invention is a combination of fentanyl and buprenorphine, wherein the combination of fentanyl and buprenorphine reduces fentanyl-induced respiratory depression by about 30% or higher, compared to a corresponding fentanyl-alone therapy.

In one embodiment, the invention is directed to a method of treating pain, comprising administering to a patient in need thereof
(i) an effective amount of fentanyl during an administration period 1 at a mean input rate (in mg/h) of fentanyl during said administration period 1, wherein said mean input rate of fentanyl is expressed as the equimolar amount of fentanyl free base administered during said administration period 1 divided by the duration of said administration period 1, and
(ii) another effective amount of buprenorphine during an administration period 2 at a mean input rate (in mg/h) of buprenorphine during said administration period 2, wherein said mean input rate of buprenorphine is expressed as the equimolar amount of buprenorphine free base administered during said administration period 2 divided by the duration of said administration period 2,
wherein the administration period 1 and the administration period 2 overlap by at least 75%, and wherein the ratio of said mean input rate of buprenorphine to said mean input rate of fentanyl is from about 1:80 to about 1:0.5.

In certain embodiments, the invention is directed to a pharmaceutical composition suitable to treat pain comprising hydromorphone and buprenorphine, wherein
(i) an effective amount of hydromorphone is administered during an administration period at a mean input rate (in mg/h) of hydromorphone during said administration period, wherein said mean input rate of hydromorphone is expressed as the equimolar amount of hydromorphone free base administered during said administration period divided by the duration of said administration period, and
(ii) another effective amount of buprenorphine is administered during the same administration period at a mean input rate (in mg/h) of buprenorphine during said administration period, wherein said mean input rate of buprenorphine is expressed as the equimolar amount of buprenorphine free base administered during said administration period divided by the duration of said administration period, wherein the ratio of said mean input rate of buprenorphine to said mean input rate of hydromorphone is from about 1:8000 to about 1:100.

In another embodiment, the invention is directed to a pharmaceutical composition suitable to treat pain comprising fentanyl and buprenorphine, wherein
(i) an effective amount of fentanyl is administered during an administration period at a mean input rate (in mg/h) of fentanyl during said administration period, wherein said mean input rate of fentanyl is expressed as the equimolar amount of fentanyl free base administered during said administration period divided by the duration of said administration period, and
(ii) another effective amount of buprenorphine is administered during the same administration period at a mean input rate (in mg/h) of buprenorphine during said administration period, wherein said mean input rate of buprenorphine is expressed as the equimolar amount of buprenorphine free base administered during said administration period divided by the duration of said administration period, wherein the ratio of said mean input rate of buprenorphine to said mean input rate of fentanyl is from about 1:80 to about 1:0.5.

In certain embodiments, the invention is directed to a method of treating pain comprising administering to a patient in need thereof
(i) an effective amount of an opioid selected from the group consisting of fentanyl, oxycodone, oxymorphone, hydrocodone, hydromorphone, and morphine, during an administration period 1 at a mean input rate (in mg/h) of the opioid during said administration period 1, wherein said mean input rate of the opioid is expressed as the equimolar amount of its free base form administered during said administration period 1 divided by the duration of said administration period 1, and
(ii) another effective amount of buprenorphine during an administration period 2 at a mean input rate (in mg/h) of buprenorphine during said administration period 2, wherein said mean input rate of buprenorphine is expressed as the equimolar amount of buprenorphine free base administered during said administration period 2 divided by the duration of said administration period 2,
wherein the administration period 1 and the administration period 2 overlap by at least 75%.

In one embodiment, buprenorphine is administered via a subdermal administration. In another embodiment, buprenorphine is administered via a transdermal administration The above objects and others can be further achieved by the invention, which, in certain embodiments, is directed to oral dosage forms comprising:
(i) an amount of oxycodone, and
(ii) an amount of buprenorphine,
wherein the weight ratio of the amount of buprenorphine to the amount of oxycodone is greater than 1:40 calculated with the amount of buprenorphine in the dosage form expressed as the equimolar amount of buprenorphine base (Mw=467.64 g/mol) in mg, and the amount of oxycodone in the dosage form expressed as the equimolar amount of oxycodone hydrochloride (Mw=351.82 g/mol) in mg.

The above objects and others can be achieved by the present invention, which in certain embodiments is directed to a method of treating pain comprising administering to a patient in need thereof an oral dosage form comprising:
(i) an amount of oxycodone and
(ii) an amount of buprenorphine,
wherein the weight ratio of the amount of buprenorphine to the amount of oxycodone is greater than 1:40 calculated with the amount of buprenorphine in the dosage form expressed as the equimolar amount of buprenorphine base (Mw=467.64 g/mol) in mg, and the amount of oxycodone in the dosage form expressed as the equimolar amount of oxycodone hydrochloride (Mw=351.82 g/mol) in mg.

The above objects and others can be achieved by the present invention, which in certain embodiments is directed to an oral dosage form comprising:
(i) an amount of oxycodone in immediate release form, and
(ii) an amount of buprenorphine in immediate release form,
wherein the weight ratio of the amount of buprenorphine to the amount of oxycodone is equal to or greater than about 1:100 calculated with the amount of buprenorphine in the dosage form expressed as the equimolar amount of buprenorphine base (Mw=467.64 g/mol) in mg, and the amount of oxycodone in the dosage form expressed as the equimolar amount of oxycodone hydrochloride (Mw=351.82 g/mol) in mg.

The above objects and others can be achieved by the present invention, which in certain embodiments is directed to a method of treating pain comprising administering to a patient in need thereof an oral dosage form comprising:
(i) an amount of oxycodone in immediate release form, and
(ii) an amount of buprenorphine in immediate release form, wherein the weight ratio of the amount of buprenorphine to the amount of oxycodone is equal to or greater than about 1:100 calculated with the amount of buprenorphine in the dosage form expressed as the equimolar amount of buprenorphine base (Mw=467.64 g/mol) in mg, and the amount of oxycodone in the dosage form expressed as the equimolar amount of oxycodone hydrochloride (Mw=351.82 g/mol) in mg.

The above objects and others can be achieved by the present invention, which in certain embodiments is directed to a dosage form comprising:
(i) an amount of oxycodone, and
(ii) an amount of buprenorphine,
wherein after single-dose administration, the dosage form provides in one group of subjects a ratio of the mean $C_{max}$ of buprenorphine to the mean $C_{max}$ of oxycodone of at least about 1:280.

The above objects and others can be achieved by the present invention, which in certain embodiments is directed to a method of treating pain comprising a concurrent administration to a patient in need thereof of:
(i) an amount of oxycodone, and
(ii) an amount of buprenorphine,
wherein said concurrent administration provides in one group of subjects a ratio of the mean $C_{max}$ of buprenorphine to the mean $C_{max}$ of oxycodone of at least about 1:280 after single-dose administration.

The above objects and others can be achieved by the present invention, which in certain embodiments is directed to a set of at least two oral dosage forms comprising oxycodone in different dosage strengths, wherein each of the dosage forms comprises
(i) an amount of oxycodone which is equimolar to
  a. about 10 mg of oxycodone hydrochloride (Mw=351.82 g/mol),
  b. about 15 mg of oxycodone hydrochloride (Mw=351.82 g/mol),
  c. about 20 mg of oxycodone hydrochloride (Mw=351.82 g/mol),
  d. about 30 mg of oxycodone hydrochloride (Mw=351.82 g/mol), or
  e. about 40 mg of oxycodone hydrochloride (Mw=351.82 g/mol); and
(ii) an amount of buprenorphine,
  wherein the weight ratio of the amount of buprenorphine to the amount of oxycodone
  is greater than 1:40 calculated with the amount of buprenorphine in the dosage form expressed as the equimolar amount of buprenorphine base (Mw=467.64 g/mol) in mg, and the amount of oxycodone in the dosage form expressed as the equimolar amount of oxycodone hydrochloride (Mw=351.82 g/mol) in mg, and
  has the same value for each dosage form of the set.

The above objects and others can be achieved by the present invention, which in certain embodiments is directed to a method of treating pain comprising administering to a patient in need thereof an oral dosage form comprising:
(i) an amount of oxycodone, and
(ii) an amount of buprenorphine,
wherein the mean $E_{max}$ of "feeling high VAS" is reduced by at least 15%, when measured in a comparison study, and/or
wherein the mean $E_{max}$ of "at the moment drug liking VAS" is reduced by at least 15%, when measured in a comparison study, and/or
wherein the mean $E_{max}$ of "overall drug liking VAS" is reduced by at least 15%, when measured in a comparison study, and/or
wherein the mean $E_{max}$ of "take drug again VAS" is reduced by at least 15%, when measured in a comparison study, and/or
wherein the mean "cold pain score VAS" measured in a cold pressor test at 1, 2, 3 and 4 hours after administration, does not increase more than 10% as compared to a comparative method of treatment when measured in a comparison study.

The above objects and others can be achieved by the present invention, which in certain embodiments is directed to a method of treating pain comprising a concurrent administration to a patient in need thereof of
(i) an amount of oxycodone, and
(ii) an amount of buprenorphine,
wherein the mean $E_{max}$ of "feeling high VAS" is reduced by at least 15%, when measured in a comparison study, and/or
wherein the mean $E_{max}$ of "at the moment drug liking VAS" is reduced by at least 15%, when measured in a comparison study, and/or
wherein the mean $E_{max}$ of "overall drug liking VAS" is reduced by at least 15%, when measured in a comparison study, and/or
wherein the mean $E_{max}$, of "take drug again VAS" is reduced by at least 15%, when measured in a comparison study, and/or
wherein the mean "cold pain score VAS" measured in a cold pressor test at 1, 2, 3 and 4 hours after administration, does not increase more than 10% as compared to a comparative method of treatment when measured in a comparison study.

According to certain embodiments of the invention the above pharmaceutical combination is for use in a method of treating pain. According to certain embodiments the invention is directed to the use of the above pharmaceutical combination in the manufacture of a medicament for the treatment of pain.

Definitions

In describing the present invention, the following terms are to be used as indicated below.

As used herein, the singular forms "a", "an", and "the" include plural references unless the context clearly indicates otherwise.

As used herein, the term "therapeutically effective" refers to the amount of drug or the rate of drug administration needed to produce a desired therapeutic result.

The term "pain" means moderate to severe, acute and chronic pain of malignant and non-malignant origin, in particular severe to most severe, acute and chronic pain of malignant and non-malignant origin, including but not limited to nociceptive pain, neuropathic pain, and visceral pain. Examples include but are not limited to severe pain resulting from diseases such as cancer, rheumatism and arthritis. Further examples are post-operative pain, cluster headaches, dental pain, surgical pain, pain resulting from severe burns, pain from third degree burns, back pain, lower back pain, herpes neuralgia, phantom limb pain, central pain, bone injury pain, and pain during labor and delivery.

The term "patient" means a subject, particularly a human, who has presented a clinical manifestation of a particular symptom or symptoms suggesting the need for treatment, who is treated preventatively or prophylactically for a condition, or who has been diagnosed with a condition to be treated. The term "subject" is inclusive of the definition of the term "patient" and does not exclude individuals who are entirely normal in all respects or with respect to a particular condition.

"Pharmaceutically acceptable salts" include, but are not limited to, inorganic acid salts such as hydrochloride, hydrobromide, sulfate, phosphate and the like; organic acid salts such as myristate, formate, acetate, trifluoroacetate, maleate, tartrate and the like; sulfonates such as methanesulfonate, benzenesulfonate, p-toluenesulfonate and the like; amino acid salts such as arginate, asparaginate, glutamate and the like; metal salts such as sodium salt, potassium salt, cesium salt and the like; alkaline earth metals such as calcium salt, magnesium salt and the like; and organic amine salts such as triethylamine salt, pyridine salt, picoline salt, ethanolamine salt, triethanolamine salt, discyclohexylamine salt, N,N'-dibenzylethyl-enediamine salt and the like. Preferred salts are the hydrochloride salts.

The term "buprenorphine" means buprenorphine base, and all pharmaceutically acceptable salts thereof. Suitable salts include, such as buprenorphine hydrochloride. The buprenorphine base and pharmaceutically acceptable salts thereof may be present in solvent free form (such as, the anhydrous form), as solvates (such as, the hydrates), as complexes, and in mixtures thereof.

The term "fentanyl" means fentanyl base, and all pharmaceutically acceptable salts thereof. Suitable salts include, such as, fentanyl citrate and fentanyl hydrochloride. The fentanyl base and pharmaceutically acceptable salts thereof may be present in solvent free form (such as, the anhydrous form), as solvates (such as, the hydrates), as complexes, and in mixtures thereof.

The term "hydromorphone" means hydromorphone base, and all pharmaceutically acceptable salts thereof. Suitable salts include, such as, hydromorphone hydrochloride. The hydromorphone base and pharmaceutically acceptable salts thereof may be present in solvent free form (such as, the anhydrous form), as solvates (such as, hydrates), as complexes, and in mixtures thereof.

The term "oxycodone" means oxycodone base, and all pharmaceutically acceptable salts thereof. Suitable salts include, such as, oxycodone hydrochloride and oxycodone terephthalate. The oxycodone base and pharmaceutically acceptable salts thereof may be present in solvent free form (such as, the anhydrous form), as solvates (such as, hydrates), as complexes, and in mixtures thereof.

Whenever the molecular weight of Mw=467.64 g/mol is added to the mention of buprenorphine base, the base free of solvents or complexing agents is referred to. Whenever the molecular weight of Mw=504.10 g/mol is added to the mention of buprenorphine hydrochloride, the buprenorphine hydrochloride free of solvents or complexing agents is referred to. Whenever the molecular weight of Mw=351.82 g/mol is added to the mention of oxycodone hydrochloride, the oxycodone hydrochloride free of solvents or complexing agents is referred to. When the term "free base" is used, it refers to the base in solvent free form.

PCT International Publication WO 2005/097801 A1, U.S. Pat. No. 7,129,248 B2, and U.S. Patent Application Publication 2006/0173029 A1, all of which are hereby incorporated by reference, describe a process for preparing oxycodone hydrochloride having a 14-hydroxycodeinone level of less than about 25 ppm, preferably of less than about 15 ppm, less than about 10 ppm, or less than about 5 ppm, more preferably of less than about 2 ppm, less than about 1 ppm, less than about 0.5 ppm or less than about 0.25 ppm.

The term "ppm" as used herein means "parts per million". Regarding 14-hydroxycodeinone, "ppm" means parts per million of 14-hydroxycodeinone in a particular sample product. The 14-hydroxycodeinone level can be determined by any method known in the art, preferably by HPLC analysis using UV detection.

In certain embodiments of the present invention, wherein the active agent is oxycodone hydrochloride, oxycodone hydrochloride is used having a 14-hydroxycodeinone level of less than about 25 ppm, preferably of less than about 15 ppm, less than about 10 ppm, or less than about 5 ppm, more preferably of less than about 2 ppm, less than about 1 ppm, less than about 0.5 ppm or less than about 0.25 ppm.

The term "$C_{max}$" denotes the maximum plasma concentration obtained during a dosing interval and/or an administration period.

The term "$C_{av}$" denotes the average plasma concentration obtained during a dosing interval and/or during an administration period. It is calculated as the total area under the plasma vs. time curve divided by the appropriate time duration.

The term "$T_{max}$" denotes the time to maximum plasma concentration ($C_{max}$).

The term "$E_{max}$" denotes the maximum effect during the period of testing.

Mean pharmacokinetic and pharmacodynamic values are arithmetic means.

The term "oral bioavailability" is defined for purposes of the present invention as the fraction (%) to which the drug (e.g., buprenorphine) is absorbed from the oral unit dosage form in comparison to intravenous administration dose normalized.

The term "opioid-induced adverse pharmacodynamic response" means an unintended side effect experienced by a patient receiving opioid therapy for an intended therapeutic effect. Typically, the intended effect is analgesia and the opioid an opioid analgesic. Unintended side effects associated with opioid therapy include, such as, euphoria, feeling high, bowel dysfunction, nausea, vomiting, somnolence, dizziness, respiratory depression, headache, dry mouth, sedation, sweats, asthenia, hypotension, dysphoria, delirium, miosis, pruritis, urticaria, urinary retention, hyperalgesia, allodynia, physical dependence and tolerance, in particular respiratory depression, euphoria, feeling high and bowel dysfunction.

The term "toxicity" refers to the potential of an overdose leading to death and may also be referred to as "lethality". In certain embodiments of the invention, toxicity is not considered an adverse pharmacodynamic response but is an effect of its own.

The term "opioid" or "opioid analgesic" means one or more compounds selected from opioid agonists, mixed opioid agonist-antagonists, partial opioid agonists. Opioid analgesics include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, and tramadol. The invention is in particular concerned with adverse pharmacodynamic responses and toxicity associated with the use of certain opioid agonists like oxycodone, fentanyl and hydromorphone.

The term "concurrent administration" means that a dose of buprenorphine is administered prior to the end of the dosing interval of oxycodone, such as, e.g., within a period starting 6 hours before the start of the dosing interval of oxycodone and ending 1 hour before the end of the dosing interval of oxycodone, or within a period starting 3 hours before the start of the dosing interval of oxycodone and ending 1 hour before the end of the dosing interval of oxycodone. A dose of oxycodone with a 6-hour dosing interval would be concurrently administered with a buprenorphine dose administered within the 6 hours of the oxycodone administration. In particular, a dose of buprenorphine would be concurrently administered with a dose of oxycodone if administered within 60 minutes, within 30 minutes, within 20 minutes, within 10 minutes, within 5 minutes, or within 1 minute of each other. Preferably the buprenorphine is administered not later than the oxycodone, preferably exactly at the same time point, such as when administered in the same dosage form. The above considerations particularly apply for embodiments wherein both oxycodone and buprenorphine are administered orally.

The term "administration period" refers to the period of time during which a drug (such as, buprenorphine, fentanyl, hydromorphone and oxycodone) is administered. The administration period of a transdermal therapeutic system starts with the application of the transdermal therapeutic system and ends with its removal. The administration period of a subdermal implant starts when the subdermal implant is implanted and ends with the removal of the subdermal implant or complete degradation of the same. The administration period of an intravenous administration like an infusion starts when the infusion is started and ends when the infusion ends. The administration period may be the same as or different from the dosing interval, which refers to a repeated administration and may encompass periods of non-administration. In most cases, the dosing interval and the administration period are the same, e.g. with transdermal systems and subdermal implants.

Further, the administration periods of two drugs, referred to above as "administration period 1" and "administration period 2", do not designate the order of the two administration periods. The administration periods of two drugs are considered to overlap by 100% when the administration periods are identical (i.e., have the identical starting points and endpoints), or when one of the administration periods is 100% within (i.e., falls entirely within) the other administration period. The administration periods of two drugs (for example, buprenorphine on the one hand, and hydromorphone, fentanyl, or oxycodone on the other hand) may overlap only to a certain extent; nonetheless, such an overlap is not less than 75%, not less than 90%, or not less than 95%. The percentage of overlap is calculated on the basis of the administration period of the opioid agonist (e.g., hydromorphone, fentanyl and oxycodone).

For example, an administration period of buprenorphine starting at 8:00 am and ending at 10:00 am of the same day, and an administration period of hydromorphone starting at 9:00 am of the same day and ending at 2:00 pm of the same day, would be considered to overlap by 20%. An administration period of buprenorphine starting at 8:00 am on day 1 and ending at 8:00 am on day 2, and an administration period of hydromorphone starting at 9:00 am on day 1 and ending at 10:00 am on day 1, would be considered to overlap by 100%.

In certain embodiments wherein said amount of oxycodone is administered orally and said amount of buprenorphine is administered transdermally, the dosing interval of buprenorphine will be considerably longer than the dosing interval of oxycodone (e.g., several days versus several times a day). In embodiments wherein said amount of oxycodone is administered orally and said amount of buprenorphine is administered subdermally (i.e., via a subdermal implant), the dosing interval of buprenorphine will also be considerably longer than the dosing interval of oxycodone, (e.g., several weeks or months versus several times a day). Thus, in embodiments wherein said amount of oxycodone is administered orally (e.g., in doses each having a dosing interval of several hours) and said amount of buprenorphine is administered transdermally or subdermally, the term "concurrent administration" means that the doses of oxycodone are administered within the dosing interval of buprenorphine. A dose of subdermally-administered buprenorphine with a six months dosing interval would be concurrently administered with oxycodone doses administered within the six months of the buprenorphine administration.

The term "subdermal/subdermally" refers to administration via a subdermal implant. A subdermal implant is a dosage form which is implanted subdermally (e.g., by insertion through a small subdermal incision) and delivers the active agent over extended time periods of several weeks or months, such as 1 to 6 months or even longer.

The term "mean input rate" is defined as the rate of supplying a drug, (such as, fentanyl, hydromorphone, oxycodone and buprenorphine) to the blood system. Such a mean input rate refers to rates of routes of administration wherein the first pass effect does not play a significant role and the rate of supplying to the blood system can be determined. In addition to transdermal, subdermal, and any kind of injections/infusions, this concept may also apply to sublingual and buccal administration. In the case of a patch/transdermal therapeutic system, the mean input rate is defined to be identical to the mean release rate as indicated in the package insert. The same is true for subdermal implants. The ratio of mean input rates can then be calculated. In cases when the buprenorphine and an opioid (hydromorphone, fentanyl or oxycodone) are administered by the same route of administration, and the route of administration is selected from all types of injections and infusions (such as, subcutaneous, intravenous or intramuscular injections/infusions) the administration periods are identical, and the ratio of mean input rates can be calculated by the amount of drugs administered. This is the case, e.g., with simultaneous subcutaneous injections.

The term "immediate release" formulation or form means wherein the dosage form releases at least about 70% of the active agent within 45 minutes as measured by in-vitro dissolution in a USP Apparatus 2 (paddle) at 50 rpm in 500 ml 0.1N HCl at 37° C.

The term "in one group of subjects" in the context of $C_{max}$ and/or $T_{max}$ values means that the respective $C_{max}$ and/or $T_{max}$ value is measured in the same clinical study in the same group of subjects.

The term "comparison study" in the context of measuring differences in "feeling high" and/or "drug liking" ("overall drug liking", "at the moment drug liking", and "take drug again") and/or "cold pain score" refers to a clinical study wherein the dosage form of the invention and/or the method of treatment of the invention and a comparative method of treatment are administered and/or applied to a group of subjects, preferably in a double-blind, placebo- and positive-controlled randomized, crossover study, and the results compared to each other. Preferably the subjects are healthy male and female recreational opioid users, which are preferably selected according to the selection criteria as used in Example 1. The rating of feeling high and of drug liking as well as pain scores are measured using Visual Analogue Scales (VAS).

The term "comparative method of treatment" in the context of measuring differences in "feeling high" and/or "drug liking" ("overall drug liking", "at the moment drug liking", and "take drug again") and/or "cold pain score" refers to a method of treatment comprising the administration of the same total combination of active agents as in the dosage form of the invention and/or the method of treatment of the invention, except for buprenorphine, and which is bioequivalent with respect to the administration of oxycodone.

In embodiments wherein the dosage form of the invention is an oral dosage form comprising oxycodone and buprenorphine, and/or the method of treatment of the invention comprises the administration of an oral dosage form comprising oxycodone and buprenorphine, the term "comparative method of treatment" in the context of measuring differences in "feeling high" and/or "drug liking" ("overall drug liking", "at the moment drug liking", and "take drug again") and/or "cold pain score" alternatively refers to a method of treatment comprising the administration of an oral dosage form comprising the same total combination of active agents as the dosage form according to the invention, except for buprenorphine, and in particular an equimolar amount of oxycodone, and which provides an in vitro dissolution rate of oxycodone that is substantially the same as the in vitro dissolution rate of oxycodone of the dosage form of the invention and/or of the dosage form administered in the method of treatment of the invention.

The term "an in vitro dissolution rate of oxycodone which is substantially the same" in the context of measuring differences in "feeling high" and/or "drug liking" ("overall drug liking", "at the moment drug liking", and "take drug again") and/or "cold pain score" refers to an in-vitro dissolution rate, which, when measured in a USP Apparatus 1 (basket) at 100 rpm in 900 ml simulated gastric fluid without enzymes (SGF) at 37° C., is characterized by the percent amount of oxycodone released at 1 hour of dissolution, preferably at 1 and 2 hours of dissolution, more preferably at 1, 2 and 3 hours of dissolution, that deviates no more than about 20% points, preferably no more than about 10% points, from the corresponding in-vitro dissolution rate of oxycodone of the dosage form of the present invention.

The term "bioequivalent/bioequivalence" is defined for the purposes of the present invention to refer to a dosage form that provides geometric mean values of $C_{max}$, $AUC_t$, and $AUC_{inf}$ for an active agent, wherein the 90% confidence intervals estimated for the ratio (test/reference) fall within the range of 80.00% to 125.00%. Preferably, the mean values $C_{max}$, $AUC_t$, and $AUC_{inf}$ fall within the range of 80.00% to 125.00% as determined in both the fed and the fasting states.

Within the meaning of the present invention, "cold pressor test (CPT)" in the context of measuring "cold pain score" refers to a test using a circulating water bath capable of sustaining water temperatures between 0-2° C. and accommodating an adult's hand submerged to the wrist. The temperature is set to within the range of 0-2° C., ideally 1° C. An excursion of more than 2 is avoided because that may affect the pain experienced by the subject. The test is conducted in that the subjects immerse their hand quickly into the water bath. Subjects are instructed to keep their hand open, relaxed, and immersed until the pain becomes excruciating. The initial maximum duration of hand immersion is 2 minutes, but can be extended to a maximum of 5 minutes. Subjects were instructed that they may remove their hand from the water at any time and that they should not keep their hand in the water if they find the pain intolerable. The duration of hand immersion is measured from the moment of complete immersion until the subject removes his or her hand from the water bath. The start time and the duration in seconds was recorded in the source documents.

The "weight ratio of the amount of buprenorphine to the amount of oxycodone, calculated with the amount of buprenorphine in the dosage form expressed as the equimolar amount of buprenorphine base (Mw=467.64 g/mol) in mg, and the amount of oxycodone in the dosage form expressed as the equimolar amount of oxycodone hydrochloride (Mw=351.82 g/mol) in mg" is calculated as exemplified in the following for the amounts used in Example 1:

Oxycodone HCl (Mw=351.82 g/mol): 40 mg,
Buprenorphine HCl (Mw=504.10 g/mol): 5.39 mg,
Buprenorphine HCl expressed as the equimolar amount of buprenorphine base (Mw=467.64 g/mol): 5 mg;
Weight ratio=5 mg: 40 mg=1:8;
wherein a weight ratio of 1:8 equals 0.125, and is thus e.g. greater than 1:40 which equals 0.025.

BRIEF DESCRIPTION OF THE DRAWINGS

FIGS. 17 A) and B) depict the effect of buprenorphine alone on blood gas parameters: A) $pCO_2$; and B) $sO_2$, in rats, respectively.

FIGS. 18 A) and B) depict the effect of oxycodone alone on blood gas parameters: A) $pCO_2$; and B) $sO_2$, in rats, respectively.

FIGS. 19 A) and B) depict the effect of hydromorphone alone on blood gas parameters: A) $pCO_2$; and B) $sO_2$, in rats, respectively.

FIGS. 20 A) and B) depict the effect of fentanyl alone on blood gas parameters: A) $pCO_2$; and B) $sO_2$, in rats, respectively.

FIGS. 21 A)-D) depict the effect of buprenorphine on oxycodone-induced deficits in arterial blood gas (ABG) parameters: A) $sO_2\%$, B) $pO_2$, C) $pCO_2$, and D) arterial blood pH, in rats.

FIGS. 22 A)-B) depict the effect of buprenorphine on oxycodone-induced deficits in arterial blood gas (ABG) parameters: A) $pCO_2$, and B) $sO_2\%$, in rats, at 1 hour post-administration.

FIGS. 24 A)-E) depict the effect of buprenorphine on fentanyl-induced deficits in arterial blood gas (ABG) parameters: A) $sO_2\%$, B) $pO_2$, C) $pCO_2$, D) arterial blood pH, and on E) Acid-Base status in rats.

FIGS. 25 A)-B) depict the effect of buprenorphine on fentanyl-induced deficits in arterial blood gas (ABG) parameters: A) $pCO_2$, and B) $sO_2\%$, in rats, at 1 hour post-administration.

FIGS. 27 A)-D) depict the effect of buprenorphine on hydromorphone-induced deficits in arterial blood gas (ABG) parameters: A) $sO_2\%$, B) $pO_2$, C) $pCO_2$, and D) arterial blood pH, in rats.

FIGS. 28 A)-B) depict the effect of buprenorphine on hydromorphone-induced deficits in arterial blood gas (ABG) parameters: A) $pCO_2$, and B) $sO_2\%$, in rats, at 1 hour post-administration.

FIGS. 30 A) and B) depict the effect of buprenorphine on oxycodone-induced lethality.

FIGS. 31 A) and B) depict the effect of buprenorphine on fentanyl-induced lethality.

FIGS. 32 A) and B) depict the effect of buprenorphine on hydromorphone-induced lethality.

FIGS. 33 A) and B) present the schematic views of three hydromorphone (HMP) infusions with placebo patch (A) and buprenorphine (BUP, 20 mcg/hr Butrans® patch) (B) in Study part 2a).

DETAILED DESCRIPTION

Figure 1:
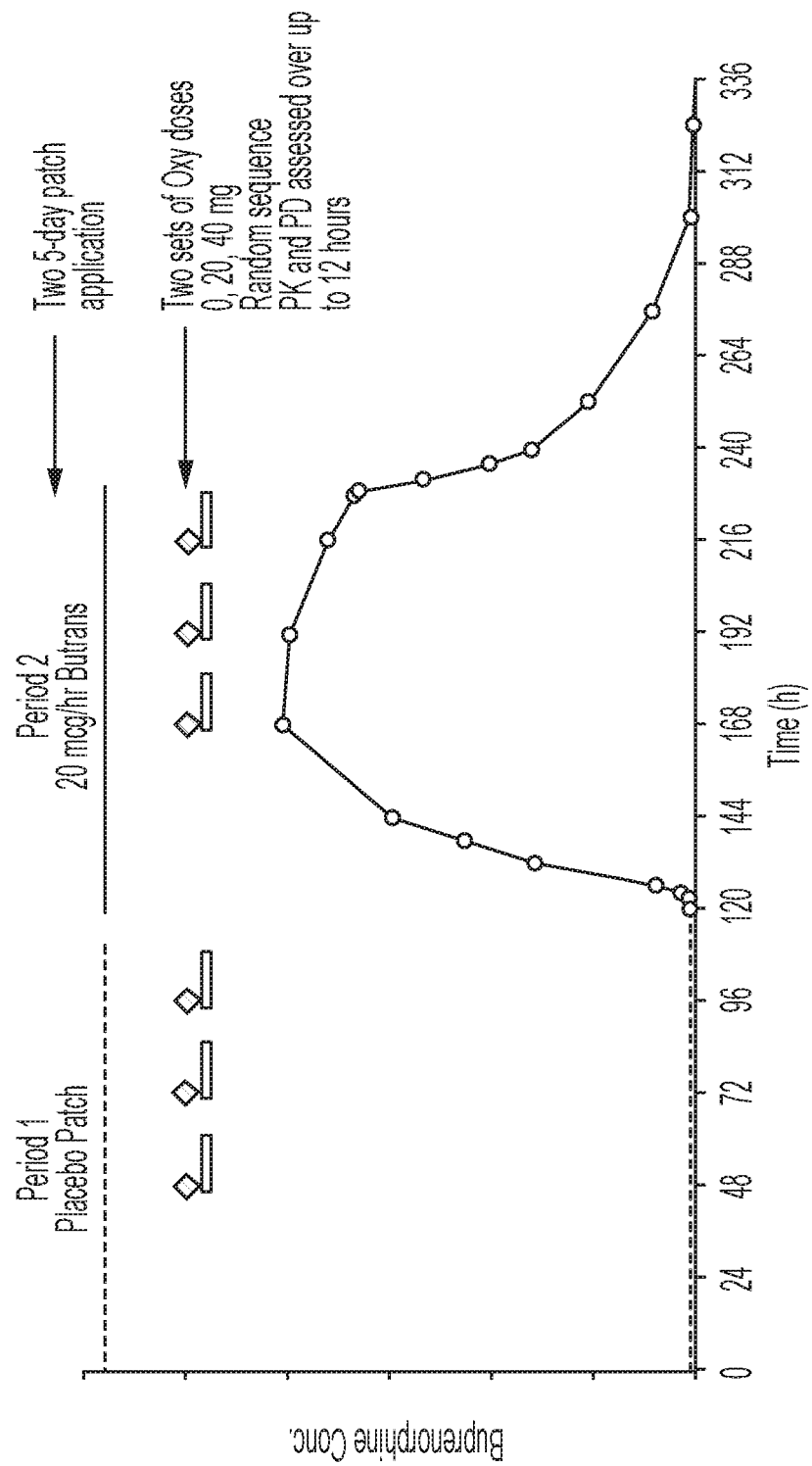
FIG. 1 is a graphical depiction of the study design of Example 1.

Oxycodone, fentanyl, hydromorphone and buprenorphine are all separately commonly used for their analgesic properties.

Fentanyl is formulated, for example, in a transdermal therapeutic system, for treating pain.

Hydromorphone is formulated, for example, in a composition for intravenous infusion, for treating pain.

Oxycodone is formulated, for example, in oral IR formulations, for treating pain. The rapid release of oxycodone in IR formulations is, in particular, suitable to promote euphoria and drug liking. It is known that oxycodone in certain circumstances promotes abuse and causes addiction.

Buprenorphine is formulated, for example, in a transdermal patch (transdermal therapeutic system), for treating pain. Sublingual buprenorphine is also used in substitution therapy where it is administered instead of the addiction creating opioid, e.g. oxycodone. A new subcutaneously administered depot product was recently approved by the USFDA under the name Sublocade@. The subcutaneous injection is administered once-monthly and provides an extended release of buprenorphine. Opioid substitution therapy supplies illicit drug users with a replacement drug, a prescribed medicine such as methadone or buprenorphine, which is usually administered in a supervised clinical setting. Buprenorphine is an opioid partial agonist. This means that, although buprenorphine is an opioid that can produce typical opioid effects and side effects, such as euphoria, its maximal effects are less than those of full agonists like oxycodone. At low doses, buprenorphine produces sufficient agonist effect to enable opioid-addicted individuals to discontinue the misuse of opioids without experiencing withdrawal symptoms. The agonist effects of buprenorphine increase linearly with increasing doses of the drug until it reaches a plateau and no longer continues to increase with further increases in dosage. This is called the "ceiling effect" Thus, buprenorphine carries a lower risk of abuse, addiction, and side effects compared to full opioid agonists, but is limited by the ceiling effect. In fact, buprenorphine is considered to actually block the effects of full opioid agonists and to be able to precipitate withdrawal symptoms if administered to an opioid-addicted individual while a full agonist is in the bloodstream. Buprenorphine is usually administered transdermally, bucally, sublingually and intravenously. Oral treatment is considered ineffective due to the extensive first pass metabolism.

It has now been found that certain combinations of opioid agonists (oxycodone, fentanyl, or hydromorphone) with buprenorphine provide an analgesic effect that is substantially the same compared to the same dose of oxycodone, fentanyl or hydromorphone when administered alone, but which provide an overall reduction in respiratory depression, euphoria, and drug liking, and with improved safety profiles. Reference is made to the examples provided below, and FIGS. 5 to 10 and further figures.

It has also been found that certain oral treatments and corresponding oral dosage forms making use of certain combinations of oxycodone and buprenorphine provide an analgesic effect that is substantially the same compared to the same dose of oxycodone administered alone, but which provide a reduction in euphoria and drug liking. Reference is made to Example 1 and FIGS. 11 to 15.

Figure 3:
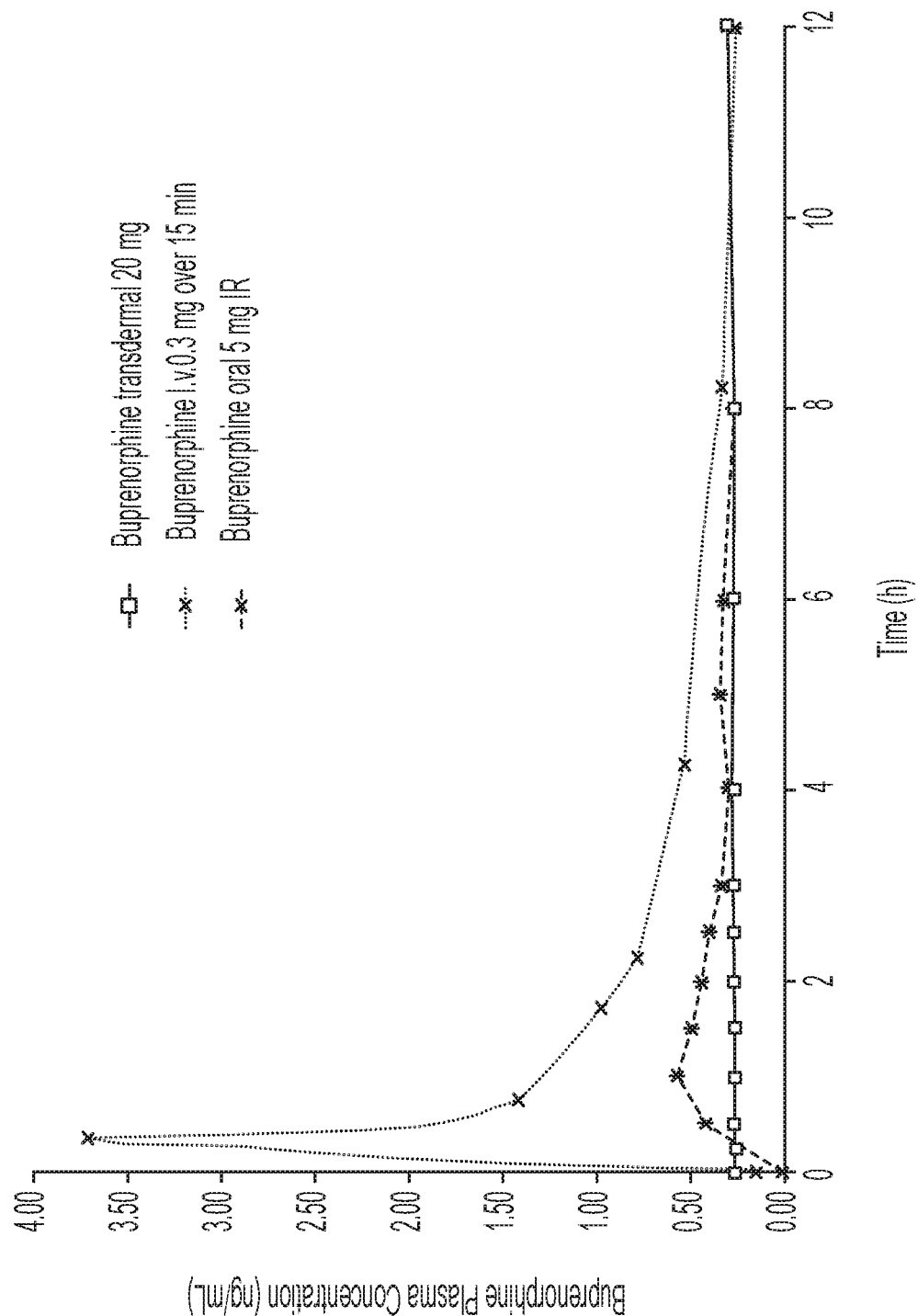
FIG. 3 depicts the results of combined Examples 1 and 2 (buprenorphine mean plasma concentration versus time following a transdermal, intravenous and oral administration wherein the result following transdermal administration is from Example 1 and the result following intravenous and oral administration is from Example 2).
Figure 16:
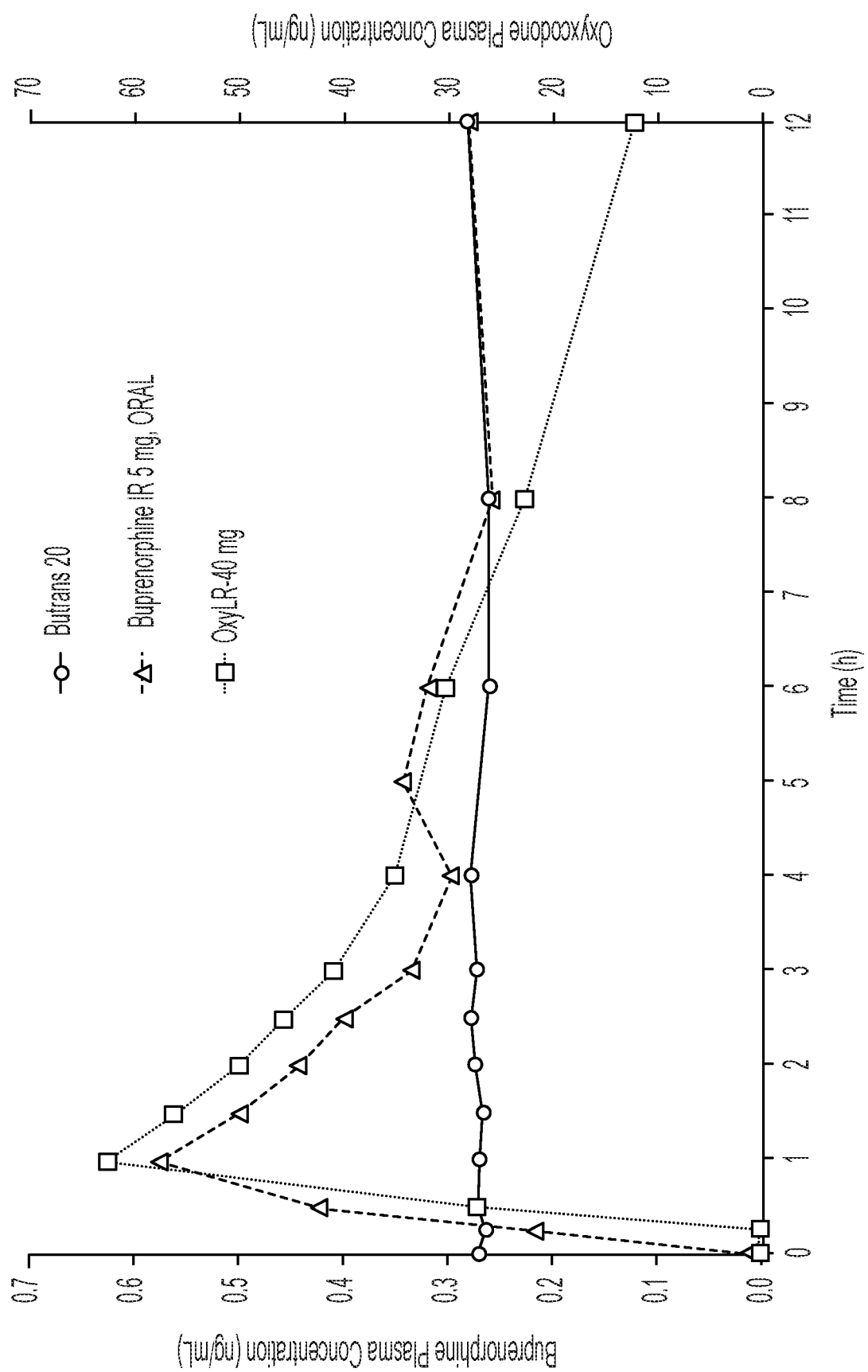
FIG. 16 depicts the results of combined Examples 1 and 2 (buprenorphine mean plasma concentration versus time following buprenorphine transdermal administration from Example 1 and following oral IR buprenorphine administration from Example 2 and oxycodone mean plasma concentration versus time following oral IR oxycodone administration from Example 1).

It has also been found that the oral administration of buprenorphine leads to blood levels on the level of the transdermal blood levels. Reference is made to FIG. 3. It has also been found that oral IR administration of buprenorphine and oxycodone leads to similar blood curve shapes wherein the absolute amounts of the two drugs differ by about a factor of 100. Reference is made to FIG. 16.

Modes of Administration for Fentanyl, Hydromorphone and Buprenorphine and Dosage Forms In certain embodiments, the invention provides a specific combination of hydromorphone and buprenorphine, wherein the combination of hydromorphone and buprenorphine reduces hydromorphone-induced respiratory depression by about 20% or higher, compared to a corresponding hydromorphone-alone therapy. In one embodiment, the combination of hydromorphone and buprenorphine reduces hydromorphone-induced respiratory depression by about ⅓ or higher.

In certain embodiments, the method of treating pain of the invention comprises administering to a patient in need thereof (i) an effective amount of hydromorphone during an administration period 1 at a mean input rate (in mg/h) of hydromorphone during said administration period 1 (in mg/h), wherein said mean input rate of hydromorphone is expressed as the equimolar amount of hydromorphone free base administered during said administration period 1 divided by the duration of said administration period 1, and (ii) another effective amount of buprenorphine during an administration period 2 at a mean input rate (in mg/h) of buprenorphine during said administration period 2, wherein said mean input rate of buprenorphine is expressed as the equimolar amount of buprenorphine free base administered during said administration period 2 divided by the duration of said administration period 2, wherein the administration period 1 and the administration period 2 overlap by at least 75%, and wherein the ratio of said mean input rate of buprenorphine to said mean input rate of hydromorphone is from about 1:8000 to about 1:100, or from about 1:8000 to about 1:200, or from about 1:8000 to about 1:400, or from about 1:8000 to about 1:600; or from about 1:8000 to about 1:800, or from about 1:4000 to about 1:800, or from about 1:3000 to about 1:1100.

In certain embodiments, the method of treating pain of the invention comprises administering to a patient in need thereof (i) an effective amount of fentanyl during an administration period 1 at a mean input rate (in mg/h) of fentanyl during said administration period 1, wherein said mean input rate of fentanyl is expressed as the equimolar amount of fentanyl free base administered during said administration period 1 divided by the duration of said administration period 1, and (ii) another effective amount of buprenorphine during an administration period 2 at a mean input rate (in mg/h) of buprenorphine during said administration period 2, wherein said mean input rate of buprenorphine is expressed as the equimolar amount of buprenorphine free base administered during said administration period 2 divided by the duration of said administration period 2, wherein the administration period 1 and the administration period 2 overlap by at least 75%, and wherein the ratio of said mean input rate of buprenorphine to said mean input rate of fentanyl from about 1:80 to about 1:0.5, or from about 1:80 to about 1:1, or from about 1:80 to about 1:2, or from about 1:80 to about 1:4, or from about 1:80 to about 1:6, or from about 1:80 to about 1:8, or from about 1:40 to about 1:8, or from about 1:30 to about 1:11.

In certain embodiments of the invention, fentanyl or hydromorphone and buprenorphine are administered by the same route of administration. In certain embodiments, hydromorphone is administered at a rate of about 1 mg/h to 10 mg/h, or at a rate of about 2 mg/h to about 8 mg/h, or at a rate of about 3 mg/h to about 7 mg/h, or at a rate of about 3 mg/h to about 5 mg/h, or at a rate of about 1 mg/h to about 3.5 mg/h, or at a rate of about 3.5 mg/h to about 10 mg/h. In a certain embodiment, hydromorphone is administered at a rate of about 1 mg/h, about 3.5 mg/h, about 4 mg/h, about 4.5 mg/h, or about 10 mg/h. In certain embodiments, fentanyl is administered at a rate of about 12.5 µg/h, 25 µg/h, 50 µg/h, 75 µg/h, 100 µg/h, 150 µg/h, or 200 µg/h.

In another embodiment of the invention, fentanyl or hydromorphone and buprenorphine are administered by different routes of administration. In certain embodiments, hydromorphone is administered at a rate of about 1 mg/h to 10 mg/h, or at a rate of about 2 mg/h to 8 mg/h, or at a rate of about 3 mg/h to 7 mg/h, or at a rate of about 3 mg/h to 5 mg/h. In a certain embodiment, hydromorphone is administered at a rate of about 1 mg/h, about 3.5 mg/h, about 4 mg/h, about 4.5 mg/h, or about 10 mg/h. In certain embodiments, fentanyl is administered at a rate of about 12.5 µg/h, 25 µg/h, 50 µg/h, 75 µg/h, 100 µg/h, 150 µg/h, or 200 µg/h.

In certain embodiments of the method of the invention, the routes of administration are selected from the group consisting of intravenous administration, intramuscular administration, subcutaneous administration, sublingual administration, buccal administration, subdermal administration, and transdermal administration. In a certain embodiment, fentanyl is administered transdermally. In another embodiment, hydromorphone is administered intravenously. In certain embodiments of the invention, fentanyl and buprenorphine are administered via transdermal administration; and in certain other embodiments of the invention, hydromorphone and buprenorphine are administered via intravenous administration.

In certain embodiments of the invention, the fentanyl or hydromorphone and buprenorphine are administered in a dosage form independently selected from an intravenous composition, an intramuscular composition, a subcutaneous composition, a sublingual composition, a buccal composition, a subdermal implantable system, or a transdermal therapeutic system. A preferred dosage form for fentanyl is a transdermal therapeutic system and for hydromorphone is an intravenous composition. In certain embodiments of the invention, the fentanyl and buprenorphine are administered in one transdermal therapeutic system comprising fentanyl and buprenorphine. The administration period is from 1 day to 7 days, such as 1 day, 3 days, 3.5 days and 7 days. In certain other embodiments of the invention, the hydromorphone and the buprenorphine are administered in one intravenous composition comprising buprenorphine and hydromorphone. The administration period is from about 5 minutes to 24 hours, or from about 15 minutes to 24 hours, or from about 15 minutes to 12 hours, or from about 30 minutes to 6 hours, or from about 30 minutes to 3 hours, or from about 30 minutes to 2 hours, in particular about 1 hour.

In certain embodiments of the invention, only the buprenorphine is administered by transdermal administration and the administration period 2 is from 1 day to 7 days, such as 1 day, 3 days, 3.5 days and 7 days.

In certain embodiments of the invention, the buprenorphine is administered by subdermal administration, and the administration period is from about 1 month to 1 year, or from about 1 months to 4 months, or from about 1 months to 3 months, such as, is selected from 1 month, 2 months, 3 months, 4 months, and 6 months.

Blood Levels

In certain embodiments, the method of the invention comprising administering hydromorphone and buprenorphine is characterized in that after a single dose administration, buprenorphine and hydromorphone each provide a mean $C_{max}$ or a mean $C_{av}$ and the ratio of the mean $C_{max}$ or the mean $C_{av}$ of buprenorphine to the mean $C_{max}$ or the mean $C_{av}$ of hydromorphone is from about 0.001 to about 0.006.

In certain embodiments, the method of the invention comprising administering fentanyl and buprenorphine is characterized in that after a single dose administration, buprenorphine and fentanyl each provide a mean $C_{max}$ or a mean $C_{av}$, and the ratio of the mean $C_{max}$ or the mean $C_{av}$ of buprenorphine to the mean $C_{max}$ or the mean $C_{av}$ of fentanyl is from about 0.02 to about 0.3. In certain embodiment, the ratio of the mean $C_{max}$ or $C_{av}$ of buprenorphine to the mean $C_{max}$ or $C_{av}$ of fentanyl is from about 0.02 to about 0.2.

In certain embodiments, the method of treatment of the present invention comprising a concurrent administration to a patient in need thereof of (i) an amount of oxycodone, and (ii) an amount of buprenorphine, is characterized in that after a single dose concurrent administration of oxycodone and buprenorphine in one group of subjects, a ratio of the mean $C_{max}$ of buprenorphine to the mean $C_{max}$ of oxycodone of at least about 1:280 is obtained, preferably under fasted conditions. In certain embodiments, the ratio of the mean $C_{max}$ of buprenorphine to the mean $C_{max}$ of oxycodone is at least about 1:250, or at least about 1:230 or at least about 1:200 or at least about 1:180. In certain embodiments, the ratio of the mean $C_{max}$ of buprenorphine to the mean $C_{max}$ of oxycodone is from about 1:50 to about 1:280, or from about 1:50 to about 1:250, or from about 1:80 to about 1:230, or from about 1:100 to about 1:200, or from about 1:100 to about 1:180, preferably under fasted conditions.

According to certain such embodiments, the oxycodone is administered in the form of oxycodone hydrochloride. In other such embodiments, the oxycodone is administered in the form of oxycodone myristate. According to certain such embodiments, the buprenorphine is administered in the form of buprenorphine hydrochloride. According to certain embodiments, said amount of buprenorphine is administered in immediate release form. According to certain embodiments, said amount of oxycodone is administered in immediate release form and said amount of buprenorphine is administered in immediate release form.

In certain such embodiments, the method of treatment is characterized in that after a single dose concurrent administration of oxycodone and buprenorphine in one group of subjects, a ratio of the mean $T_{max}$ of buprenorphine to the mean $T_{max}$ of oxycodone of equal to or less than about 1.5:1, or of equal to or less than about 1.3:1, or of equal to or less than about 1.1:1, or of equal to or less than about 1:1, is obtained, preferably under fasted conditions. In certain embodiments, the method of treatment is characterized in that after a single dose concurrent administration of oxycodone and buprenorphine in one group of subjects said concurrent administration provides in said group of subjects a mean $T_{max}$ of buprenorphine that is earlier than the mean $T_{max}$ of oxycodone, preferably under fasted conditions. In certain embodiments, the method of treatment is characterized in that after a single dose concurrent administration of oxycodone and buprenorphine in one group of subjects, said concurrent administration provides in said group of subjects a ratio of the mean $T_{max}$ of buprenorphine to the mean $T_{max}$ of oxycodone of from about 0.1:1 to about 1.5:1, or from about 0.1:1 to about 1.3:1, or from about 0.1:1 to about 1.1:1, or from about 0.1:1 to about 1:1 or from about 0.1:1 to about 0.9:1, preferably under fasted conditions. According to certain such embodiments, the oxycodone is administered in the form of oxycodone hydrochloride. In other such embodiments, the oxycodone is administered in the form of oxycodone myristate. According to certain such embodiments, the buprenorphine is administered in the form of buprenorphine hydrochloride. According to certain embodiments, said amount of buprenorphine is administered in immediate release form. According to certain embodiments, said amount of oxycodone is administered in immediate release form and said amount of buprenorphine is administered in immediate release form.

In certain embodiments, the method of treatment of the present invention as described herein which comprises a concurrent administration to a patient in need thereof of (i) an amount of oxycodone, and (ii) an amount of buprenorphine, is characterized in that the concurrent administration is an oral administration. In certain embodiments, the concurrent administration is the administration of an oral dosage form comprising both said amount of buprenorphine and said amount of oxycodone, as described herein.

In certain embodiments, the method of treatment of the present invention as described herein which comprises a concurrent administration to a patient in need thereof of (i) an amount of oxycodone, and (ii) an amount of buprenorphine, is characterized in that said amount of oxycodone is administered orally, i.e., by an oral dosage form comprising said amount of oxycodone, and said amount of buprenorphine is administered transdermally, i.e., by a transdermal dosage form comprising said amount of buprenorphine (such as, e.g., a transdermal patch). An example of a transdermal dosage form comprising buprenorphine is the Butrans® patch available in the dose strengths 5, 10 and 20 microgram/hour which delivers buprenorphine for a dosing period of up to seven days.

In certain embodiments wherein said amount of oxycodone is administered orally and said amount of buprenorphine is administered transdermally, the oral dosage form comprising said amount of oxycodone is a liquid dosage form, such as, e.g., a solution, a suspension or an emulsion. In certain embodiments wherein said amount of oxycodone is administered orally and said amount of buprenorphine is administered transdermally, the oral dosage form comprising said amount of oxycodone is a solid dosage form, such as, e.g., a tablet or a capsule. In certain embodiments, the oral dosage form comprises an amount of oxycodone which is equimolar to from about 5 mg to about 50 mg of oxycodone hydrochloride (Mw=351.82 g/mol), preferably from about 5 mg to about 40 mg of oxycodone hydrochloride (Mw=351.82 g/mol). In certain such embodiments, the oral dosage form comprises said amount of oxycodone in immediate release form.

In certain embodiments, the method of treatment of the present invention as described herein, which comprises a concurrent administration to a patient in need thereof of (i) an amount of oxycodone, and (ii) an amount of buprenorphine, is characterized in that said amount of oxycodone is administered orally, i.e., by an oral dosage form comprising said amount of oxycodone, and said amount of buprenorphine is administered subdermally, i.e., by a subdermal dosage form comprising said amount of buprenorphine (such as, a subdermal implant comprising said amount of buprenorphine). In certain such embodiments, the ratio of the mean $C_{max}$ of buprenorphine to the mean $C_{max}$ of oxycodone is defined to be the ratio of the mean steady state plasma concentration of buprenorphine to the mean $C_{max}$ of oxycodone.

An example of a subdermal dosage form for use in a method of treatment of the present invention is an implant for subdermal administration marketed in the United States under the tradename Probuphine®. According to the prescribing information (version February 2018), Probuphine® is indicated for the maintenance treatment of opioid dependence. The Probuphine® implant contains buprenorphine hydrochloride as the active pharmaceutical ingredient. It is a sterile, single, off-white, soft, flexible rod-shaped drug product. Each rod is 26 mm in length and 2.5 mm in diameter and contains 80 mg buprenorphine hydrochloride (corresponding to 74.2 mg buprenorphine base) and ethylene vinyl acetate. Probuphine® is designed to be implanted subdermally by a trained medical professional and to provide sustained delivery of buprenorphine for up to six months. According to the prescribing information, for the maintenance treatment of opioid dependence, each dose consists of four Probuphine® implants, which are inserted subdermally in the inner side of the upper arm for six months of treatment and are removed by the end of the sixth month. In pharmacokinetic trials, the median time to maximum plasma concentration of buprenorphine occurred at 12 hours after Probuphine® insertion. After the initial buprenorphine peak, plasma buprenorphine concentrations decreased slowly, and steady-state plasma buprenorphine concentrations were reached by approximately week 4. Mean steady-state plasma buprenorphine concentrations were approximately 0.5 ng/mL to 1.0 ng/mL and were maintained for approximately 20 weeks (week 4 through week 24) in a 24-week treatment period (see prescribing information of February 2018, or Smith et al., Probuphine (Buprenorphine) Subdermal Implants for the Treatment Of Opioid-Dependent Patients, Pharmacy and Therapeutics 2017 August; 42(8): 505-508). In order to achieve buprenorphine plasma concentrations suitable for the method of treatment of the present invention, for example the number and/or size of implants can be adjusted.

In certain embodiments wherein said amount of oxycodone is administered orally and said amount of buprenorphine is administered subdermally, the oral dosage form comprising said amount of oxycodone is a liquid dosage form, such as, a solution, a suspension or an emulsion. In certain embodiments wherein said amount of oxycodone is administered orally and said amount of buprenorphine is administered subdermally, the oral dosage form comprising said amount of oxycodone is a solid dosage form, such as, a tablet or a capsule. In certain embodiments, the oral dosage form comprises an amount of oxycodone which is equimolar to from about 5 mg to about 50 mg of oxycodone hydrochloride (Mw=351.82 g/mol), preferably from about 5 mg to about 40 mg of oxycodone hydrochloride (Mw=351.82 g/mol). In certain such embodiments, the oral dosage form comprises said amount of oxycodone in immediate release form.

Weight Ratios and Amounts in Oral Dosage Forms

In certain embodiments, the method of treatment is characterized by administering to a patient in need thereof an oral dosage form comprising:
  (i) an amount of oxycodone, and
  (ii) an amount of buprenorphine,
wherein the weight ratio of the amount of buprenorphine to the amount of oxycodone is greater than 1:40 calculated with the amount of buprenorphine in the dosage form expressed as the equimolar amount of buprenorphine base (Mw=467.64 g/mol) in mg, and the amount of oxycodone in the dosage form expressed as the equimolar amount of oxycodone hydrochloride (Mw=351.82 g/mol) in mg. In certain embodiments, said weight ratio of the amount of buprenorphine to the amount of oxycodone is from about 1:3 to greater than 1:40, or equal to or greater than about 1:38, or or from about 1:3 to about 1:38, or from about 1:4 to greater than 1:40, or from about 1:4 to about 1:38, or from about 1:5 to greater than 1:40, or from about 1:5 to about 1:38, or from about 1:5 to about 1:35, or from about 1:5 to about 1:30, or from about 1:6 to greater than 1:40, or from about 1:6 to about 1:38, or from about 1:6 to about 1:35, or from about 1:6 to about 1:30, or from about 1:6 to about 1:28 or from about 1:6 to about 1:20, or from about 1:8 to about 1:30, or from about 1:8 to about 1:28, or from about 1:8 to about 1:20, or from about 1:8 to about 1:15, or from about 1:10 to about 1:20, or from about 1:10 to about 1:15. According to certain such embodiments, the oxycodone is present in the form of oxycodone hydrochloride. In other such embodiments, the oxycodone is present in the form of oxycodone myristate. According to certain such embodiments, the buprenorphine is present in the form of buprenorphine hydrochloride. According to certain embodiments, the dosage form comprises said amount of buprenorphine in immediate release form. According to certain embodiments, the dosage form comprises said amount of oxycodone in immediate release form and said amount of buprenorphine in immediate release form.

In certain such embodiments, the method of treatment is characterized in that the dosage form comprises an amount of oxycodone which is equimolar to from about 5 mg to about 50 mg of oxycodone hydrochloride (Mw=351.82 g/mol), or which is equimolar to from about 5 mg to about 40 mg of oxycodone hydrochloride (Mw=351.82 g/mol), or which is equimolar to about 10 mg, about 15 mg, about 20 mg, about 30 mg, or about 40 mg of oxycodone hydrochloride (Mw=351.82 g/mol). According to certain such embodiments, the oxycodone is present in the form of oxycodone hydrochloride. In other such embodiments, the oxycodone is present in the form of oxycodone myristate. According to certain such embodiments, the buprenorphine is present in the form of buprenorphine hydrochloride. According to certain embodiments, the dosage form comprises said amount of buprenorphine in immediate release form. According to certain embodiments, the dosage form comprises said amount of oxycodone in immediate release form and said amount of buprenorphine in immediate release form.

In certain such embodiments, the method of treatment is characterized in that the dosage form comprises an amount of oxycodone which is equimolar to about 40 mg of oxycodone hydrochloride (Mw=351.82 g/mol), and an amount of buprenorphine which is equimolar to from about 1 mg to about 6 mg of buprenorphine base (Mw=467.64 g/mol), or wherein the dosage form comprises an amount of oxycodone which is equimolar to about 40 mg of oxycodone hydrochloride (Mw=351.82 g/mol), and an amount of buprenorphine which is equimolar to from about 2 mg to about 5 mg of buprenorphine base (Mw=467.64 g/mol). According to certain such embodiments, the oxycodone is present in the form of oxycodone hydrochloride. In other such embodiments the oxycodone is present in the form of oxycodone myristate. According to certain such embodiments, the buprenorphine is present in the form of buprenorphine hydrochloride. According to certain embodiments, the dosage form comprises said amount of buprenorphine in immediate release form. According to certain embodiments, the dosage form comprises said amount of oxycodone in immediate release form and said amount of buprenorphine in immediate release form.

In certain embodiments, the method of treatment is characterized by administering to a patient in need thereof an oral immediate release (IR) dosage form comprising:
(i) an amount of oxycodone in immediate release form, and
(ii) an amount of buprenorphine in immediate release form,
wherein the weight ratio of the amount of buprenorphine to the amount of oxycodone is equal to or greater than about 1:100 calculated with the amount of buprenorphine in the dosage form expressed as the equimolar amount of buprenorphine base (Mw=467.64 g/mol) in mg, and the amount of oxycodone in the dosage form expressed as the equimolar amount of oxycodone hydrochloride (Mw=351.82 g/mol) in mg. In certain embodiments, said weight ratio of the amount of buprenorphine to the amount of oxycodone is equal to or greater than about 1:80, or is equal to or greater than about 1:60, or is equal to or greater than about 1:50, or is equal to or greater than about 1:40, or is from about 1:6 to about 1:100, or from about 1:6 to about 1:80, or from about 1:6 to about 1:60, or from about 1:6 to about 1:50, or from about 1:6 to about 1:40, or from about 1:8 to about 1:100, or from about 1:8 to about 1:80, or from about 1:8 to about 1:60 or from about 1:8 to about 1:50, or from 1:8 to about 1:40, or from about 1:10 to about 1:100, or from about 1:10 to about 1:80, or from about 1:10 to about 1:60 or from about 1:10 to about 1:50; or from about 1:10 to about 1:40, or from about 1:20 to about 1:100, or from about 1:20 to about 1:80, or from about 1:20 to about 1:60, or from about 1:20 to about 1:50, or from about 1:20 to about 1:40, or is from about 1:20 to about 1:30. According to certain such embodiments, the oxycodone is present in the form of oxycodone hydrochloride. In other such embodiments, the oxycodone is present in the form of oxycodone myristate. According to certain such embodiments, the buprenorphine is present in the form of buprenorphine hydrochloride.

In certain such embodiments, the method of treatment is characterized in that the dosage form comprises an amount of oxycodone which is equimolar to from about 5 mg to about 50 mg of oxycodone hydrochloride (Mw=351.82 g/mol), or which is equimolar to from about 5 mg to about 40 mg of oxycodone hydrochloride (Mw=351.82 g/mol), or which is equimolar to about 10 mg, about 15 mg, about 20 mg, about 30 mg, or about 40 mg of oxycodone hydrochloride (Mw=351.82 g/mol). According to certain such embodiments, the oxycodone is present in the form of oxycodone hydrochloride. In other such embodiments, the oxycodone is present in the form of oxycodone myristate. According to certain such embodiments, the buprenorphine is present in the form of buprenorphine hydrochloride.

In certain such embodiments, the method of treatment is characterized in that the dosage form comprises an amount of oxycodone which is equimolar to about 40 mg of oxycodone hydrochloride (Mw=351.82 g/mol), and an amount of buprenorphine which is equimolar to from about 1 mg to about 5 mg of buprenorphine base (Mw=467.64 g/mol), or wherein the dosage form comprises an amount of oxycodone which is equimolar to about 40 mg of oxycodone hydrochloride (Mw=351.82 g/mol), and an amount of buprenorphine which is equimolar to from about 1 mg to about 4 mg of buprenorphine base (Mw=467.64 g/mol). According to certain such embodiments, the oxycodone is present in the form of oxycodone hydrochloride. In other such embodiments, the oxycodone is present in the form of oxycodone myristate. According to certain such embodiments, the buprenorphine is present in the form of buprenorphine hydrochloride.

Dosage Forms Comprising Oxycodone and Buprenorphine

According to certain embodiments, the dosage form is characterized in that after a single-dose administration in one group of subjects, a ratio of the mean $C_{max}$ of buprenorphine to the mean $C_{max}$ of oxycodone of at least about 1:280 is obtained. In certain embodiments, the ratio of the mean $C_{max}$ of buprenorphine to the mean $C_{max}$ of oxycodone is at least about 1:250, or at least about 1:230 or at least about 1:200 or at least about 1:180. In certain embodiments, the ratio of the mean $C_{max}$ of buprenorphine to the mean $C_{max}$ of oxycodone is from about 1:50 to about 1:280, or from about 1:50 to about 1:250, or from about 1:80 to about 1:230, or from about 1:100 to about 1:200, or from about 1:100 to about 1:180. According to certain such embodiments, the oxycodone is present in the form of oxycodone hydrochloride. In other such embodiments, the oxycodone is present in the form of oxycodone myristate. According to certain such embodiments, the buprenorphine is present in the form of buprenorphine hydrochloride. According to certain embodiments, the dosage form comprises said amount of buprenorphine in immediate release form. According to certain embodiments, the dosage form comprises said amount of oxycodone in immediate release form and said amount of buprenorphine in immediate release form.

According to certain embodiments, the dosage form is characterized by a weight ratio of the amount of buprenorphine to the amount of oxycodone that is greater than 1:40 calculated with the amount of buprenorphine in the dosage form expressed as the equimolar amount of buprenorphine base (Mw=467.64 g/mol) in mg, and the amount of oxycodone in the dosage form expressed as the equimolar amount of oxycodone hydrochloride (Mw=351.82 g/mol) in mg. In certain embodiments, said weight ratio of the amount of buprenorphine to the amount of oxycodone is from about 1:3 to greater than 1:40, or equal to or greater than about 1:38, or from about 1:3 to about 1:38, or from about 1:4 to greater than 1:40, or from about 1:4 to about 1:38, or from about 1:5 to greater than 1:40, or from about 1:5 to about 1:38, or from about 1:5 to about 1:35, or from about 1:5 to about 1:30, or from about 1:6 to greater than 1:40, or from about 1:6 to about 1:38, or from about 1:6 to about 1:35, or from about 1:6 to about 1:30, or from about 1:6 to about 1:28, or from about 1:6 to about 1:20, or from about 1:8 to about 1:30, or from about 1:8 to about 1:28, or from about 1:8 to about 1:20, or from about 1:8 to about 1:15, or from about 1:10 to about 1:20, or from about 1:10 to about 1:15. According to certain such embodiments, the oxycodone is present in the form of oxycodone hydrochloride. In other such embodiments, the oxycodone is present in the form of oxycodone myristate. According to certain such embodiments, the buprenorphine is present in the form of buprenorphine hydrochloride. According to certain embodiments, the dosage form comprises said amount of buprenorphine in immediate release form. According to certain embodiments, the dosage form comprises said amount of oxycodone in immediate release form and said amount of buprenorphine in immediate release form.

According to certain such embodiments, the dosage form is characterized in that the dosage form comprises an amount of oxycodone which is equimolar to about 40 mg of oxycodone hydrochloride (Mw=351.82 g/mol), and an amount of buprenorphine which is equimolar to from about 1 mg to about 6 mg of buprenorphine base (Mw=467.64 g/mol), or wherein the dosage form comprises an amount of oxycodone which is equimolar to about 40 mg of oxycodone hydrochloride (Mw=351.82 g/mol), and an amount of buprenorphine which is equimolar to from about 2 mg to about 5 mg of buprenorphine base (Mw=467.64 g/mol). According to certain such embodiments, the oxycodone is present in the form of oxycodone hydrochloride. In other such embodiments, the oxycodone is present in the form of oxycodone myristate. According to certain such embodiments, the buprenorphine is present in the form of buprenorphine hydrochloride. According to certain embodiments, the dosage form comprises said amount of buprenorphine in immediate release form. According to certain embodiments, the dosage form comprises said amount of oxycodone in immediate release form and said amount of buprenorphine in immediate release form.

According to certain embodiments, the dosage form is characterized in that it is an immediate release (IR) dosage form wherein the weight ratio of the amount of buprenorphine to the amount of oxycodone is equal to or greater than about 1:100 calculated with the amount of buprenorphine in the dosage form expressed as the equimolar amount of buprenorphine base (Mw=467.64 g/mol) in mg, and the amount of oxycodone in the dosage form expressed as the equimolar amount of oxycodone hydrochloride (Mw=351.82 g/mol) in mg. In certain such embodiments, said weight ratio of the amount of buprenorphine to the amount of oxycodone is equal to or greater than about 1:80, or is equal to or greater than about 1:60, or is equal to or greater than about 1:50, or is equal to or greater than about 1:40, or is from about 1:6 to about 1:100, or from about 1:6 to about 1:80, or from about 1:6 to about 1:60, or from about 1:6 to about 1:50, or from about 1:6 to about 1:40, or from about 1:8 to about 1:100, or from about 1:8 to about 1:80, or from about 1:8 to about 1:60 or from about 1:8 to about 1:50, or from 1:8 to about 1:40, or from about 1:10 to about 1:100, or from about 1:10 to about 1:80, or from about 1:10 to about 1:60 or from about 1:10 to about 1:50; or from about 1:10 to about 1:40, or from about 1:20 to about 1:100, or from about 1:20 to about 1:80, or from about 1:20 to about 1:60, or from about 1:20 to about 1:50, or from about 1:20 to about 1:40, or from about 1:20 to about 1:30.

According to certain such embodiments the oral immediate release dosage form is characterized in that it comprises an amount of oxycodone which is equimolar to from about 5 mg to about 50 mg of oxycodone hydrochloride (Mw=351.82 g/mol), or which is equimolar to from about 5 mg to about 40 mg of oxycodone hydrochloride (Mw=351.82 g/mol), or which is equimolar to about 10 mg, about 15 mg, about 20 mg, about 30 mg, or about 40 mg of oxycodone hydrochloride (Mw=351.82 g/mol). According to certain such embodiments, the oxycodone is present in the form of oxycodone hydrochloride. In other such embodiments, the oxycodone is present in the form of oxycodone myristate. According to certain such embodiments, the buprenorphine is present in the form of buprenorphine hydrochloride.

In certain such embodiments, the oral immediate release dosage form is characterized in that the dosage form comprises an amount of oxycodone which is equimolar to about 40 mg of oxycodone hydrochloride (Mw=351.82 g/mol), and an amount of buprenorphine which is equimolar to from about 1 mg to about 5 mg of buprenorphine base (Mw=467.64 g/mol), or wherein the dosage form comprises an amount of oxycodone which is equimolar to about 40 mg of oxycodone hydrochloride (Mw=351.82 g/mol), and an amount of buprenorphine which is equimolar to from about 1 mg to about 4 mg of buprenorphine base (Mw=467.64 g/mol). According to certain such embodiments, the oxycodone is present in the form of oxycodone hydrochloride. In other such embodiments, the oxycodone is present in the form of oxycodone myristate. According to certain such embodiments, the buprenorphine is present in the form of buprenorphine hydrochloride.

In the above embodiments, said dosage form may be liquid in the form of a solution, a suspension, an emulsion, such as e.g., a syrup.

In the above embodiments, said dosage form may be in the form of a solid dosage form, such as a tablet, or multiparticulates, or a capsule.

Pharmacodynamic Responses

According to certain embodiments the method and/or dosage form, in particular the co-administration of the amount of buprenorphine in the dosage form provides a prevention or reduction of an adverse pharmacodynamic response of oxycodone, fentanyl or hydromorphone observed for said amount of oxycodone, fentanyl or hydromorphone in the dosage form when administered alone.

The adverse pharmacodynamic response is selected from the group consisting of euphoria, feeling high, bowel dysfunction, nausea, vomiting, somnolence, dizziness, respiratory depression, headache, dry mouth, sedation, sweats, asthenia, hypotension, dysphoria, delirium, miosis, pruritus, urticaria, urinary retention, hyperalgesia, allodynia, physical dependence and tolerance. In certain embodiments, the adverse pharmacodynamic response is selected from the group consisting of respiratory depression, euphoria, feeling high, and bowel dysfunction. In other embodiments, the adverse pharmacodynamic response is euphoria and/or feeling high. In other embodiments, the adverse pharmacodynamic response is feeling high. In other embodiments, the adverse pharmacodynamic response is bowel dysfunction. In other embodiments, the adverse pharmacodynamic response is respiratory depression.

In other embodiments, the pharmacodynamic response is toxicity (or lethality).

Figure 8:
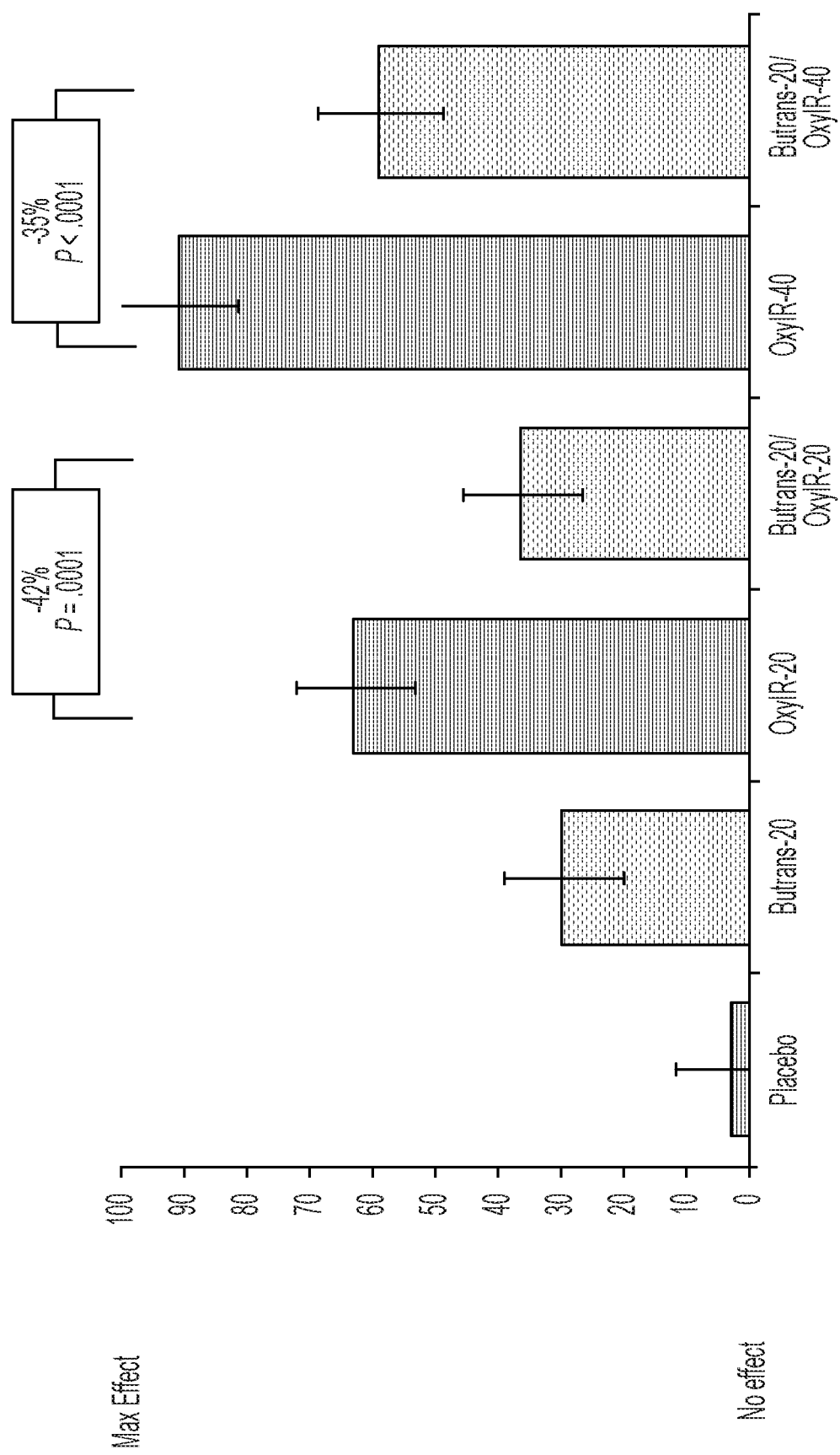
FIG. 8 depicts the results of Example 1 including the result of both iterations and all 6 treatments (mean feeling high VAS, $E_{max}$).

According to certain embodiments the method and/or dosage form provides a mean $E_{max}$ of "feeling high VAS" which, when measured in a comparison study, is reduced by at least 15%, or by at least 20%, or by at least 25%, or by at least 30%, or by at least 35%, or by at least 40%. Reference is made to FIG. 8.

According to certain embodiments, the method and/or dosage form, in particular the co-administration of the amount of buprenorphine in the dosage form provides a prevention or reduction of drug liking of oxycodone observed for said amount of oxycodone in the dosage form when administered alone.

Figure 6:
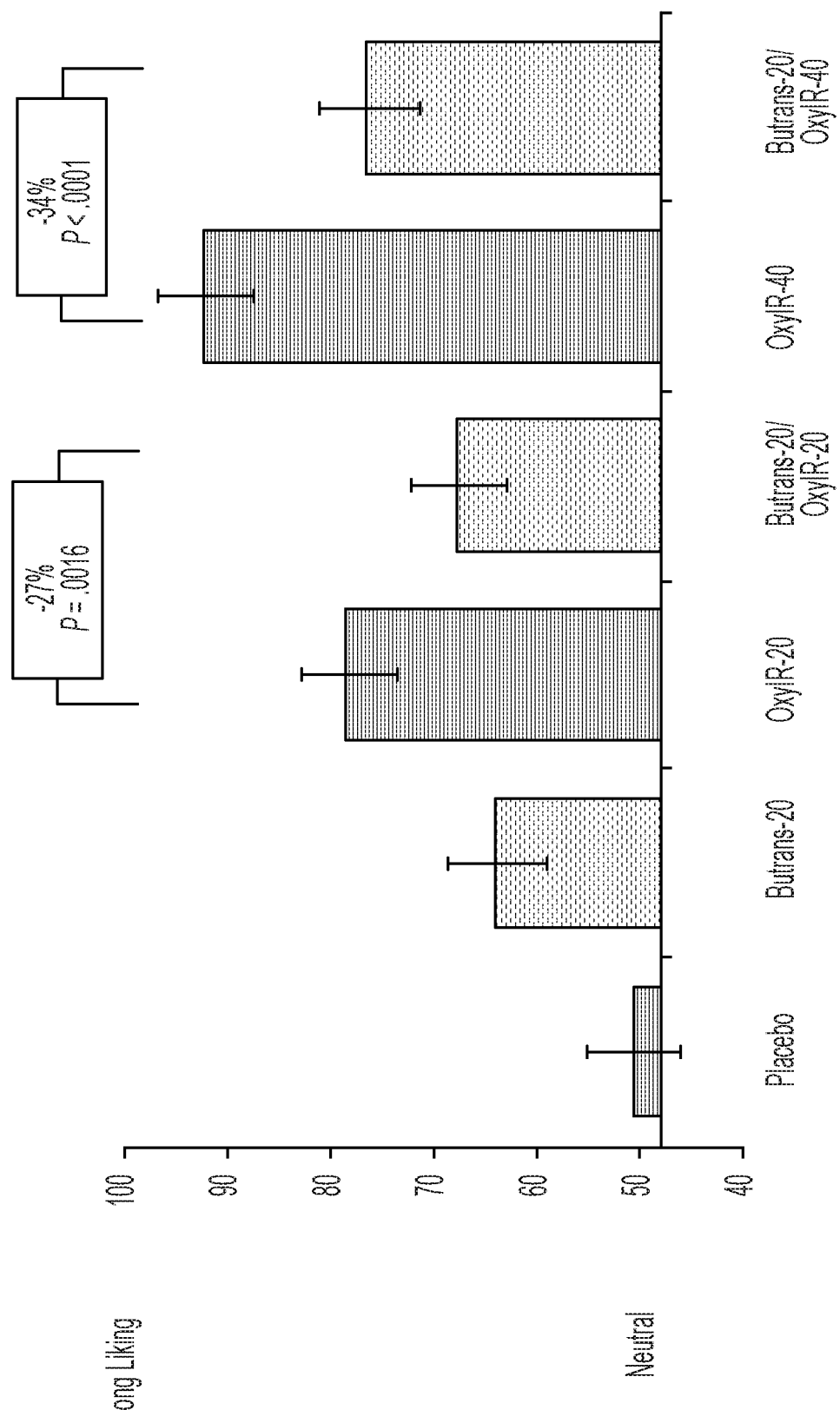
FIG. 6 depicts the results of Example 1 including the result of both iterations and all 6 treatments (mean 'at the moment' drug liking VAS, $E_{max}$).

According to certain embodiments, the method and/or dosage form provides a mean $E_{max}$ of "at the moment drug liking VAS" which, when measured in a comparison study, is reduced by at least 15%, or by at least 20%, or by at least 25%, or by at least 30. Reference is made to FIG. 6.

Figure 9:
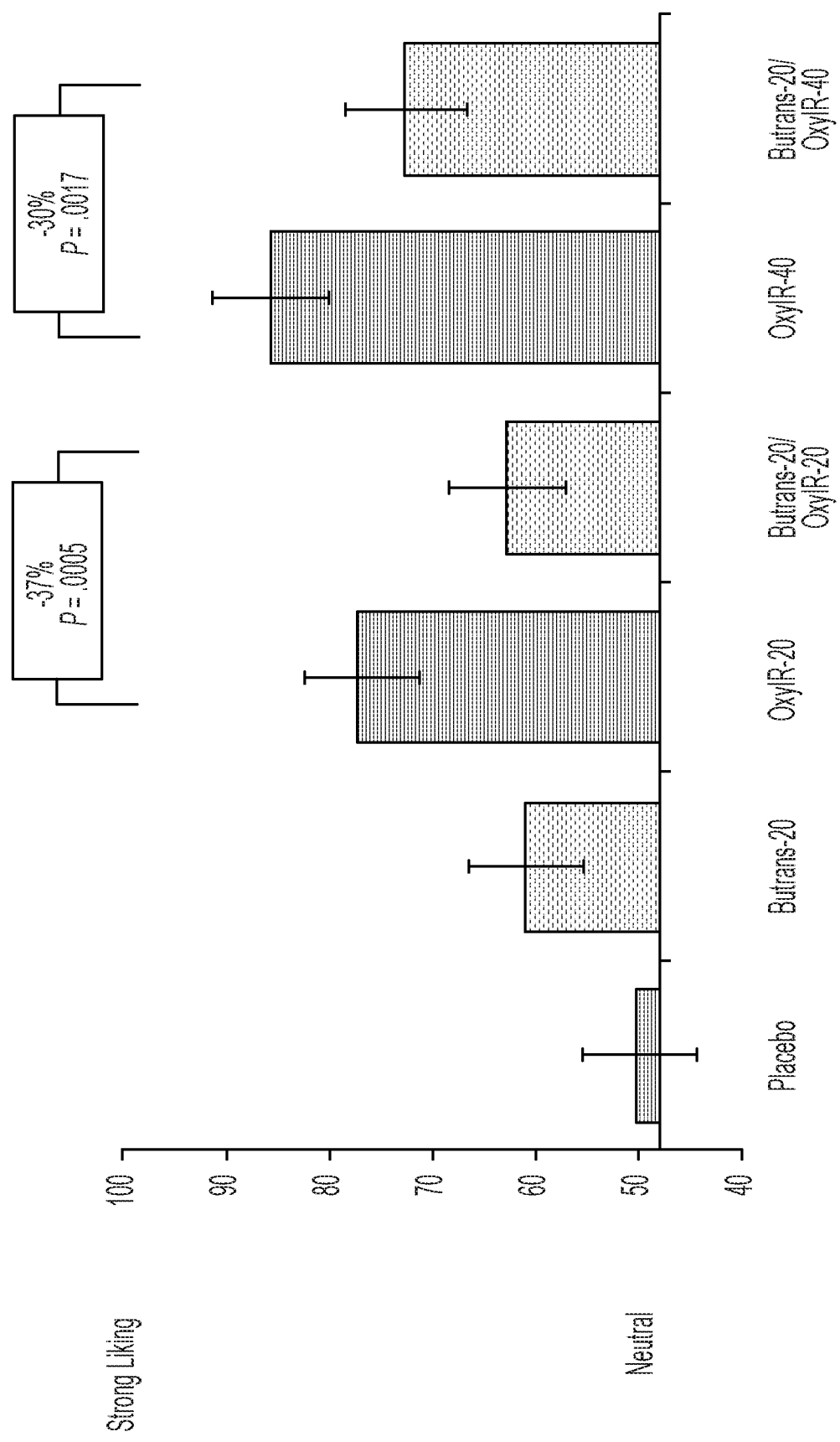
FIG. 9 depicts the results of Example 1 including the result of both iterations and all 6 treatments (overall drug liking VAS, $E_{max}$).

According to certain embodiments, the method and/or dosage form provides a mean $E_{max}$ of "overall drug liking VAS" which, when measured in a comparison study, is reduced by at least 15%, or by at least 20%, or by at least 25%, or by at least 30%, or by at least 35%. Reference is made to FIG. 9.

Figure 10:
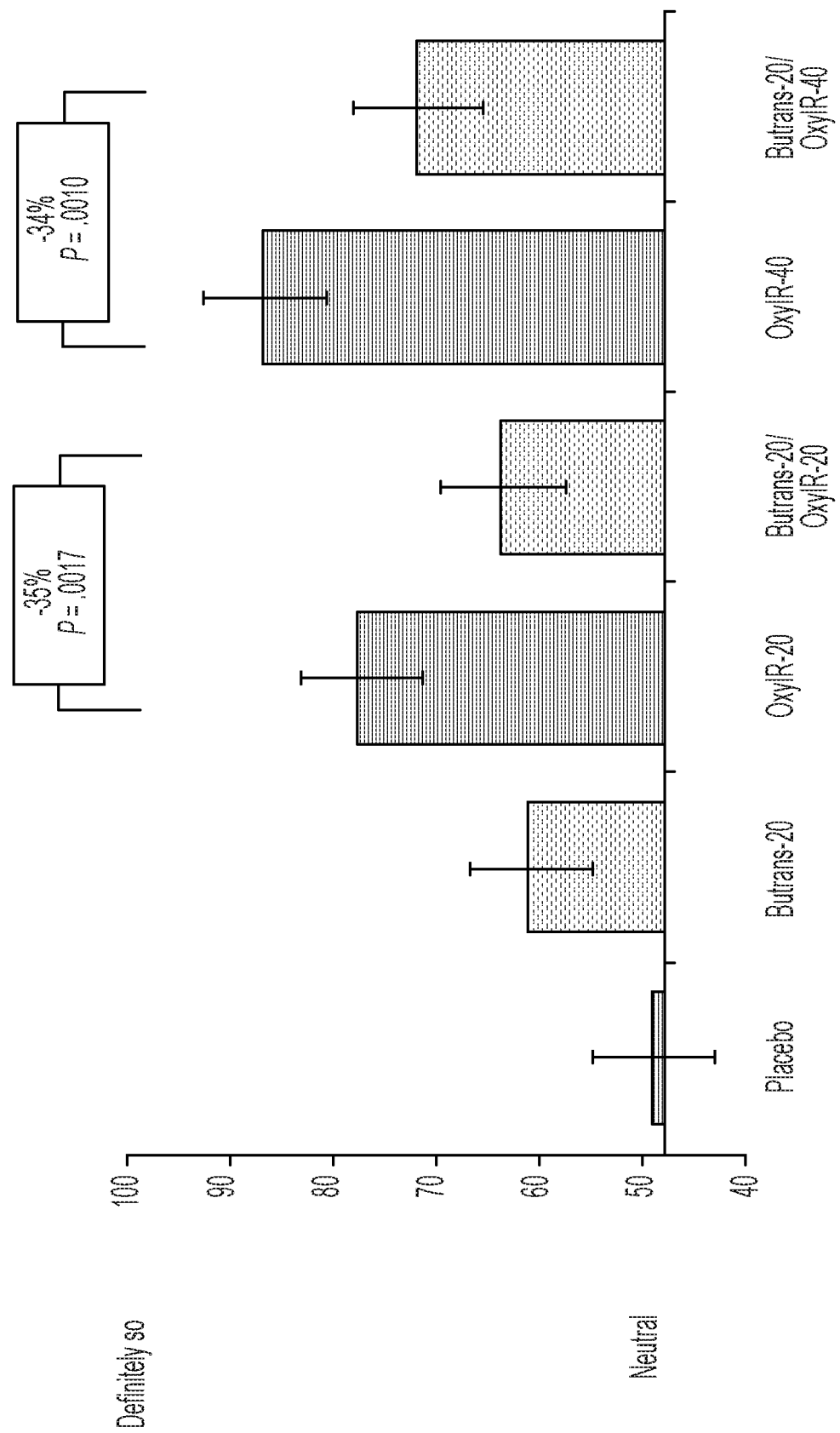
FIG. 10 depicts the results of Example 1 including the result of both iterations and all 6 treatments (take drug again VAS, $E_{max}$).

According to certain embodiments, the method and/or dosage form provides a mean $E_{max}$ of "take drug again VAS" which, when measured in a comparison study, is reduced by at least 15%, or by at least 20%, or by at least 25%, or by at least 30%, or by at least 35%. Reference is made to FIG. 10.

According to certain such embodiments, the analgesic effect is not substantially reduced when measured in a comparison study. According to certain such embodiments, the mean "cold pain score VAS" measured in a cold pressor test at 1, 2, 3 and 4 hours after administration does not increase more than 10% as compared to a comparative method of treatment when measured in a comparison study. Reference is made to FIGS. 11 to 15.

According to certain embodiments, the method and/or dosage form prevents or reduces the formation of addiction, the occurrence of drug abuse, or the occurrence of recreational drug use.

According to certain other embodiments, the method and/or dosage form of the invention reduces opioid-induced respiratory depression, compared with the use of a stand-alone opioid therapy.

In other embodiments, the method and/or dosage form of the invention provides much improved safety profiles, such as, prevents or significantly reduces opioid-induced lethality due to overdose.

According to certain embodiments, a method is provided which prevents or reduces an adverse pharmacodynamic response of oxycodone observed in the treatment of pain with an amount of oxycodone alone, by instead administering the oral dosage form according to the invention including both oxycodone and buprenorphine, and comprising the same amount of oxycodone. The method comprises reducing drug liking of oxycodone observed in the treatment of pain with said amount of oxycodone alone.

According to certain embodiments, a method is provided which reduces the formation of addiction, the occurrence of drug abuse, or the occurrence of recreational drug use by providing a dosage form according to the invention for the treatment of pain.

Buprenorphine Mono Oral Dosage Forms

Buprenorphine has been considered ineffective via oral administration because of the extensive first pass metabolism. Example 2, however, now shows that a dosage form comprising buprenorphine HCl in IR form in an amount equimolar to 5 mg buprenorphine base (Mw=467.64 g/mol) provides analgesic blood levels on the level of Butrans® 20 mcg/h for a period of at least 12 hours. Reference is made to FIG. 3.

According to certain embodiments, the invention is thus directed to a method of treating pain, comprising administering to a patient in need thereof an oral dosage form comprising an amount of buprenorphine, preferably buprenorphine HCl, as the sole opioid analgesic.

According to certain embodiments, the invention is directed to an oral dosage form comprising an amount of buprenorphine, preferably buprenorphine HCl, as the sole opioid analgesic.

According to certain embodiments the buprenorphine is present in the dosage form in an amount equimolar to 1 to 40 mg of buprenorphine base (Mw=467.64 g/mol) or in an amount equimolar to 2.5, 5, 10, 15, 20, 30 and 40 mg of buprenorphine base (Mw=467.64 g/mol). According to such embodiment, the daily dose is an amount equimolar to 1 to 40 mg of buprenorphine base (Mw=467.64 g/mol). In certain embodiments, the dosage form comprises buprenorphine in IR form, and in certain embodiment, buprenorphine is in the form of buprenorphine HCl.

According to certain embodiments, the dosage form is liquid or solid such as in a solution, a suspension, an emulsion (such as, a syrup), a tablet, or a capsule.

Further Embodiments

In view of the above, certain embodiments of the invention relate to:

Item 1: An oral dosage form comprising
(i) an amount of oxycodone and
(ii) an amount of buprenorphine,
wherein the weight ratio of the amount of buprenorphine to the amount of oxycodone is greater than 1:40 calculated with the amount of buprenorphine in the dosage form expressed as the equimolar amount of buprenorphine base (Mw=467.64 g/mol) in mg, and the amount of oxycodone in the dosage form expressed as the equimolar amount of oxycodone hydrochloride (Mw=351.82 g/mol) in mg.

Item 2. The oral dosage form of item 1, wherein the weight ratio of the amount of buprenorphine to the amount of oxycodone is equal to or greater than about 1:38.

Item 3. The oral dosage form of item 1, wherein the weight ratio of the amount of buprenorphine to the amount of oxycodone is from about 1:3 to greater than 1:40, or from about 1:3 to about 1:38.

Item 4. The oral dosage form of item 1, wherein the weight ratio of the amount of buprenorphine to the amount of oxycodone is from about 1:4 to greater than 1:40, or from about 1:4 to about 1:38.

Item 5. The oral dosage form of item 1, wherein the weight ratio of the amount of buprenorphine to the amount of oxycodone is from about 1:5 to greater than 1:40, or from about 1:5 to about 1:38.

Item 6. The oral dosage form of item 1, wherein the weight ratio of the amount of buprenorphine to the amount of oxycodone is from about 1:5 to about 1:35, preferably from about 1:5 to about 1:30.

Item 7: The oral dosage form of item 1, wherein the weight ratio of the amount of buprenorphine to the amount of oxycodone is from about 1:6 to greater than 1:40, or from about 1:6 to about 1:38.

Item 8: The oral dosage form of item 1, wherein the weight ratio of the amount of buprenorphine to the amount of oxycodone is from about 1:6 to about 1:35, preferably from about 1:6 to about 1:30, more preferably from about 1:6 to about 1:28 or from about 1:6 to about 1:20.

Item 9: The oral dosage form of item 1, wherein the weight ratio of the amount of buprenorphine to the amount of oxycodone is from about 1:8 to about 1:30.

Item 10: The oral dosage form of item 1, wherein the weight ratio of the amount of buprenorphine to the amount of oxycodone is from about 1:8 to about 1:28.

Item 11: The oral dosage form of item 1, wherein the weight ratio of the amount of buprenorphine to the amount of oxycodone is from about 1:8 to about 1:20.

Item 12: The oral dosage form of item 1, wherein the weight ratio of the amount of buprenorphine to the amount of oxycodone is from about 1:8 to about 1:15.

Item 13: The oral dosage form of item 1, wherein the weight ratio of the amount of buprenorphine to the amount of oxycodone is from about 1:10 to about 1:20.

Item 14: The oral dosage form of item 1, wherein the weight ratio of the amount of buprenorphine to the amount of oxycodone is from about 1:10 to about 1:15.

Item 15: The oral dosage form of any one of items 1 to 14, wherein the dosage form comprises an amount of oxycodone which is equimolar to from about 5 mg to about 50 mg of oxycodone hydrochloride (Mw=351.82 g/mol), preferably from about 5 mg to about 40 mg of oxycodone hydrochloride (Mw=351.82 g/mol).

Item 16: The oral dosage form of any one of items 1 to 14, wherein the dosage form comprises an amount of oxycodone which is equimolar to about 10 mg, about 15 mg, about 20 mg, about 30 mg, or about 40 mg of oxycodone hydrochloride (Mw=351.82 g/mol).

Item 17: The oral dosage form of item 16, wherein the dosage form comprises an amount of oxycodone hydrochloride which is equimolar to about 10 mg, about 15 mg, about 20 mg, about 30 mg, or about 40 mg of oxycodone hydrochloride (Mw=351.82 g/mol).

Item 18: The oral dosage form of item 16, wherein the dosage form comprises an amount of oxycodone myristate which is equimolar to about 10 mg, about 15 mg, about 20 mg, about 30 mg, or about 40 mg of oxycodone hydrochloride (Mw=351.82 g/mol).

Item 19: The oral dosage form of any one of items 1 to 14, wherein the dosage form comprises an amount of oxycodone which is equimolar to about 40 mg of oxycodone hydrochloride (Mw=351.82 g/mol), and an amount of buprenorphine which is equimolar to from about 1 mg to about 6 mg of buprenorphine base (Mw=467.64 g/mol).

Item 20: The oral dosage form of any one of items 1 to 14, wherein the dosage form comprises an amount of oxycodone which is equimolar to about 40 mg of oxycodone hydrochloride (Mw=351.82 g/mol), and an amount of buprenorphine which is equimolar to from about 2 mg to about 5 mg of buprenorphine base (Mw=467.64 g/mol).

Item 21: The oral dosage form of any one of items 1 to 16, 19 and 20, wherein the oxycodone is oxycodone hydrochloride and the buprenorphine is buprenorphine hydrochloride.

Item 22: The oral dosage form of any one of items 1 to 21, wherein the dosage form comprises said amount of buprenorphine in immediate release form.

Item 23: The oral dosage form of any one of items 1 to 22, wherein the dosage form comprises said amount of oxycodone in immediate release form and said amount of buprenorphine in immediate release form.

Item 24: The oral dosage form of any one of items 1 to 23, wherein said dosage form is a liquid dosage form.

Item 25: The oral dosage form of item 24, wherein said dosage form is a solution, a suspension, or an emulsion, preferably a solution.

Item 26: The oral dosage form of any one of items 1 to 23, wherein said dosage form is a solid dosage form.

Item 27: The oral dosage form of item 26, wherein said dosage form is a tablet or a capsule.

Item 28: The oral dosage form of any one of items 1 to 27, wherein after single-dose administration, the dosage form provides in one group of subjects a ratio of the mean $C_{max}$ of buprenorphine to the mean $C_{max}$ of oxycodone of at least about 1:280.

Item 29: The oral dosage form of item 28, wherein the ratio of the mean $C_{max}$ of buprenorphine to the mean $C_{max}$ of oxycodone is at least about 1:250.

Item 30: The oral dosage form of item 28, wherein the ratio of the mean $C_{max}$ of buprenorphine to the mean $C_{max}$ of oxycodone is at least about 1:230.

Item 31: The oral dosage form of item 28, wherein the ratio of the mean $C_{max}$ of buprenorphine to the mean $C_{max}$ of oxycodone is at least about 1:200.

Item 32: The oral dosage form of item 28, wherein the ratio of the mean $C_{max}$ of buprenorphine to the mean $C_{max}$ of oxycodone is at least about 1:180.

Item 33: The oral dosage form of item 28, wherein the ratio of the mean $C_{max}$ of buprenorphine to the mean $C_{max}$ of oxycodone is from about 1:50 to about 1:280.

Item 34: The oral dosage form of item 28, wherein the ratio of the mean $C_{max}$ of buprenorphine to the mean $C_{max}$ of oxycodone is from about 1:50 to about 1:250.

Item 35: The oral dosage form of item 28, wherein the ratio of the mean $C_{max}$ of buprenorphine to the mean $C_{max}$ of oxycodone is from about 1:80 to about 1:230.

Item 36: The oral dosage form of item 28, wherein the ratio of the mean $C_{max}$ of buprenorphine to the mean $C_{max}$ of oxycodone is from about 1:100 to about 1:200.

Item 37: The oral dosage form of item 28, wherein the ratio of the mean $C_{max}$ of buprenorphine to the mean $C_{max}$ of oxycodone is from about 1:100 to about 1:180.

Item 38: The oral dosage form of any one of items 28 to 37, wherein after single-dose administration, the dosage form further provides in said group of subjects a ratio of the mean $T_{max}$ of buprenorphine to the mean $T_{max}$ of oxycodone of equal to or less than about 1.5:1.

Item 39: The oral dosage form of item 38, wherein the ratio of the mean $T_{max}$ of buprenorphine to the mean $T_{max}$ of oxycodone is equal to or less than about 1.3:1.

Item 40: The oral dosage form of item 38, wherein the ratio of the mean $T_{max}$ of buprenorphine to the mean $T_{max}$ of oxycodone is equal to or less than about 1.1:1.

Item 41: The oral dosage form of item 38, wherein the ratio of the mean $T_{max}$ of buprenorphine to the mean $T_{max}$ of oxycodone is equal to or less than about 1:1.

Item 42: The oral dosage form of any one of items 28 to 37, wherein after single-dose administration, the dosage form further provides in said group of subjects a mean $T_{max}$ of buprenorphine that is earlier than the mean $T_{max}$ of oxycodone.

Item 43: The oral dosage form of any one of items 28 to 42, wherein after single-dose administration, the dosage form further provides in said group of subjects a ratio of the mean $T_{max}$ of buprenorphine to the mean $T_{max}$ of oxycodone of from about 0.1:1 to about 1.5:1, preferably from about 0.1:1 to about 1.3:1, more preferably from about 0.1:1 to about 1.1:1, most preferably from about 0.1:1 to about 1:1 or from about 0.1:1 to about 0.9:1.

Item 44: A method of treating pain comprising administering to a patient in need thereof an oral dosage form comprising
(i) an amount of oxycodone and
(ii) an amount of buprenorphine,
wherein the weight ratio of the amount of buprenorphine to the amount of oxycodone is greater than 1:40 calculated with the amount of buprenorphine in the dosage form expressed as the equimolar amount of buprenorphine base (Mw=467.64 g/mol) in mg, and the amount of oxycodone in the dosage form expressed as the equimolar amount of oxycodone hydrochloride (Mw=351.82 g/mol) in mg.

Item 45. The method of item 44, wherein the weight ratio of the amount of buprenorphine to the amount of oxycodone is equal to or greater than about 1:38.

Item 46. The method of item 44, wherein the weight ratio of the amount of buprenorphine to the amount of oxycodone is from about 1:3 to greater than 1:40, or from about 1:3 to about 1:38.

Item 47. The method of item 44, wherein the weight ratio of the amount of buprenorphine to the amount of oxycodone is from about 1:4 to greater than 1:40, or from about 1:4 to about 1:38.

Item 48. The method of item 44, wherein the weight ratio of the amount of buprenorphine to the amount of oxycodone is from about 1:5 to greater than 1:40, or from about 1:5 to about 1:38.

Item 49. The method of item 44, wherein the weight ratio of the amount of buprenorphine to the amount of oxycodone is from about 1:5 to about 1:35, preferably from about 1:5 to about 1:30.

Item 50. The method of item 44, wherein the weight ratio of the amount of buprenorphine to the amount of oxycodone is from about 1:6 to greater than 1:40, or from about 1:6 to about 1:38.

Item 51. The method of item 44, wherein the weight ratio of the amount of buprenorphine to the amount of oxycodone is from about 1:6 to about 1:35, preferably from about 1:6 to about 1:30, more preferably from about 1:6 to about 1:28 or from about 1:6 to about 1:20.

Item 52. The method of item 44, wherein the weight ratio of the amount of buprenorphine to the amount of oxycodone is from about 1:8 to about 1:30.

Item 53. The method of item 44, wherein the weight ratio of the amount of buprenorphine to the amount of oxycodone is from about 1:8 to about 1:28.

Item 54. The method of item 44, wherein the weight ratio of the amount of buprenorphine to the amount of oxycodone is from about 1:8 to about 1:20.

Item 55. The method of item 44, wherein the weight ratio of the amount of buprenorphine to the amount of oxycodone is from about 1:8 to about 1:15.

Item 56. The method of item 44, wherein the weight ratio of the amount of buprenorphine to the amount of oxycodone is from about 1:10 to about 1:20.

Item 57. The method of item 44, wherein the weight ratio of the amount of buprenorphine to the amount of oxycodone is from about 1:10 to about 1:15.

Item 58. The method of any one of items 44 to 57, wherein the dosage form comprises an amount of oxycodone which is equimolar to from about 5 mg to about 50 mg of oxycodone hydrochloride (Mw=351.82 g/mol), preferably from about 5 mg to about 40 mg of oxycodone hydrochloride (Mw=351.82 g/mol).

Item 59. The method of any one of items 44 to 57, wherein the dosage form comprises an amount of oxycodone which is equimolar to about 10 mg, about 15 mg, about 20 mg, about 30 mg, or about 40 mg of oxycodone hydrochloride (Mw=351.82 g/mol).

Item 60. The method of item 59, wherein the dosage form comprises an amount of oxycodone hydrochloride which is equimolar to about 10 mg, about 15 mg, about 20 mg, about 30 mg, or about 40 mg of oxycodone hydrochloride (Mw=351.82 g/mol).

Item 61. The method of item 59, wherein the dosage form comprises an amount of oxycodone myristate which is equimolar to about 10 mg, about 15 mg, about 20 mg, about 30 mg, or about 40 mg of oxycodone hydrochloride (Mw=351.82 g/mol).

Item 62. The method of any one of items 44 to 57, wherein the dosage form comprises an amount of oxycodone which is equimolar to about 40 mg of oxycodone hydrochloride (Mw=351.82 g/mol), and an amount of buprenorphine which is equimolar to from about 1 mg to about 6 mg of buprenorphine base (Mw=467.64 g/mol).

Item 63. The method of any one of items 44 to 57, wherein the dosage form comprises an amount of oxycodone which is equimolar to about 40 mg of oxycodone hydrochloride (Mw=351.82 g/mol), and an amount of buprenorphine which is equimolar to from about 2 mg to about 5 mg of buprenorphine base (Mw=467.64 g/mol).

Item 64. The method of any one of items 44 to 59, 62 and 63, wherein the oxycodone is oxycodone hydrochloride and the buprenorphine is buprenorphine hydrochloride.

Item 65. The method of any one of items 44 to 64, wherein the dosage form comprises said amount of buprenorphine in immediate release form.

Item 66. The method of any one of items 44 to 65, wherein the dosage form comprises said amount of oxycodone in immediate release form and said amount of buprenorphine in immediate release form.

Item 67. The method of any one of items 44 to 66, wherein said dosage form is a liquid dosage form.

Item 68. The method of item 67, wherein said dosage form is a solution, a suspension, or an emulsion, preferably a solution.

Item 69. The method of any one of items 44 to 66, wherein said dosage form is a solid dosage form.

Item 70. The method of item 69, wherein said dosage form is a tablet or a capsule.

Item 71. The method of any one of items 44 to 70, wherein after single-dose administration, the dosage form provides in one group of subjects a ratio of the mean $C_{max}$ of buprenorphine to the mean $C_{max}$ of oxycodone of at least about 1:280.

Item 72. The method of item 71, wherein the ratio of the mean $C_{max}$ of buprenorphine to the mean $C_{max}$ of oxycodone is at least about 1:250.

Item 73. The method of item 71, wherein the ratio of the mean $C_{max}$ of buprenorphine to the mean $C_{max}$ of oxycodone is at least about 1:230.

Item 74. The method of item 71, wherein the ratio of the mean $C_{max}$ of buprenorphine to the mean $C_{max}$ of oxycodone is at least about 1:200.

Item 75. The method of item 71, wherein the ratio of the mean $C_{max}$ of buprenorphine to the mean $C_{max}$ of oxycodone is at least about 1:180.

Item 76. The method of item 71, wherein the ratio of the mean $C_{max}$ of buprenorphine to the mean $C_{max}$ of oxycodone is from about 1:50 to about 1:280.

Item 77. The method of item 71, wherein the ratio of the mean $C_{max}$ of buprenorphine to the mean $C_{max}$ of oxycodone is from about 1:50 to about 1:250.

Item 78. The method of item 71, wherein the ratio of the mean $C_{max}$ of buprenorphine to the mean $C_{max}$ of oxycodone is from about 1:80 to about 1:230.

Item 79. The method of item 71, wherein the ratio of the mean $C_{max}$ of buprenorphine to the mean $C_{max}$ of oxycodone is from about 1:100 to about 1:200.

Item 80. The method of item 71, wherein the ratio of the mean $C_{max}$ of buprenorphine to the mean $C_{max}$ of oxycodone is from about 1:100 to about 1:180.

Item 81. The method of any one of items 71 to 80, wherein after single-dose administration, the dosage form further provides in said group of subjects a ratio of the mean $T_{max}$ of buprenorphine to the mean $T_{max}$ of oxycodone of equal to or less than about 1.5:1.

Item 82. The method of item 81, wherein the ratio of the mean $T_{max}$ of buprenorphine to the mean $T_{max}$ of oxycodone is equal to or less than about 1.3:1.

Item 83. The method of item 81, wherein the ratio of the mean $T_{max}$ of buprenorphine to the mean $T_{max}$ of oxycodone is equal to or less than about 1.1:1.

Item 84. The method of item 81, wherein the ratio of the mean $T_{max}$ of buprenorphine to the mean $T_{max}$ of oxycodone is equal to or less than about 1:1.

Item 85. The method of any one of items 71 to 80, wherein after single-dose administration, the dosage form further provides in said group of subjects a mean $T_{max}$ of buprenorphine that is earlier than the mean $T_{max}$ of oxycodone.

Item 86. The method of any one of items 71 to 85, wherein after single-dose administration, the dosage form further provides in said group of subjects a ratio of the mean $T_{max}$ of buprenorphine to the mean $T_{max}$ of oxycodone of from about 0.1:1 to about 1.5:1, preferably from about 0.1:1 to about 1.3:1, more preferably from about 0.1:1 to about 1.1:1, most preferably from about 0.1:1 to about 1:1 or from about 0.1:1 to about 0.9:1.

Item 87. The method of any one of items 44 to 86, wherein the method provides a prevention or reduction of an adverse pharmacodynamic response of oxycodone.

Item 88. The method of any one of items 44 to 86, wherein the co-administration of the amount of buprenorphine in the dosage form prevents or reduces an adverse pharmacodynamic response observed for said amount of oxycodone in the dosage form when administered alone.

Item 89. The method of item 87 or 88, wherein the adverse pharmacodynamic response is selected from the group consisting of euphoria, feeling high, bowel dysfunction, nausea, vomiting, somnolence, dizziness, respiratory depression, headache, dry mouth, sedation, sweats, asthenia, hypotension, dysphoria, delirium, miosis, pruritis, urticaria, urinary retention, hyperalgesia, allodynia, physical dependence and tolerance, preferably wherein the adverse pharmacodynamic response is selected from the group consisting of respiratory depression, euphoria, feeling high, and bowel dysfunction.

Item 90. The method of item 87 or 88, wherein the adverse pharmacodynamic response is euphoria.

Item 91. The method of item 87 or 88, wherein the adverse pharmacodynamic response is feeling high.

Item 92. The method of item 91, wherein the mean $E_{max}$ of "feeling high VAS" is reduced by at least 15%, when measured in a comparison study.

Item 93. The method of item 92, wherein the mean $E_{max}$ of "feeling high VAS" is reduced by at least 20%, preferably at least 25%, more preferably at least 30%, most preferably at least 35% or even 40%.

Item 94. The method of any one of items 44 to 93, wherein the method provides a prevention or reduction of drug liking of oxycodone.

Item 95. The method of any one of items 44 to 93, wherein the co-administration of the amount of buprenorphine in the dosage form prevents or reduces drug liking of oxycodone compared to drug liking observed for said amount of oxycodone in the dosage form when administered alone.

Item 96. The method of item 94 or 95, wherein the mean $E_{max}$ of "at the moment drug liking VAS" is reduced by at least 15%, when measured in a comparison study.

Item 97. The method of item 96, wherein the mean $E_{max}$ of "at the moment drug liking VAS" is reduced by at least 20%, preferably at least 25%, more preferably at least 30%.

Item 98. The method of item 94 or 95, wherein the mean $E_{max}$ of "overall drug liking VAS" is reduced by at least 15%, when measured in a comparison study.

Item 99. The method of item 98, wherein the mean $E_{max}$ of "overall drug liking VAS" is reduced by at least 20%, preferably at least 25%, more preferably at least 30%, most preferably at least 35%.

Item 100. The method of item 94 or 95, wherein the mean $E_{max}$ of "take drug again VAS" is reduced by at least 15%, when measured in a comparison study.

Item 101. The method of item 100, wherein the mean $E_{max}$ of "take drug again VAS" is reduced by at least 20%, preferably at least 25%, more preferably at least 30%, most preferably at least 35%.

Item 102. The method of any one of items 44 to 101, wherein the method provides an analgesic effect which is not substantially reduced when measured in a comparison study.

Item 103. The method of item 102, wherein the mean "cold pain score VAS" measured in a cold pressor test at 1, 2, 3 and 4 hours after administration, does not increase more than 10% as compared to a comparative method of treatment when measured in a comparison study.

Item 104. The method of any one of items 44 to 103, wherein the method prevents or reduces the formation of addiction, the occurrence of drug abuse, or the occurrence of recreational drug use.

Item 105. The oral dosage form of any one of items 1 to 43 for use in a method of treating pain.

Item 106. The oral dosage form of item 105 for use in a method of treating pain, wherein the method provides a prevention or reduction of an adverse pharmacodynamic response of oxycodone.

Item 107. The oral dosage form of item 105 for use in a method of treating pain, wherein the co-administration of the amount of buprenorphine in the dosage form prevents or reduces an adverse pharmacodynamic response observed for said amount of oxycodone in the dosage form when administered alone.

Item 108. The oral dosage form of item 106 or 107 for use in a method of treating pain, wherein the adverse pharmacodynamic response is selected from the group consisting of euphoria, feeling high, bowel dysfunction, nausea, vomiting, somnolence, dizziness, respiratory depression, headache, dry mouth, sedation, sweats, asthenia, hypotension, dysphoria, delirium, miosis, pruritis, urticaria, urinary retention, hyperalgesia, allodynia, physical dependence and tolerance, preferably wherein the adverse pharmacodynamic response is selected from the group consisting of respiratory depression, euphoria, feeling high, and bowel dysfunction.

Item 109. The oral dosage form of item 106 or 107 for use in a method of treating pain, wherein the adverse pharmacodynamic response is euphoria.

Item 110. The oral dosage form of item 106 or 107 for use in a method of treating pain, wherein the adverse pharmacodynamic response is feeling high.

Item 111. The oral dosage form of item 110 for use in a method of treating pain, wherein the mean $E_{max}$ of "feeling high VAS" is reduced by at least 15%, when measured in a comparison study.

Item 112. The oral dosage form of item 111 for use in a method of treating pain, wherein the mean $E_{max}$ of "feeling high VAS" is reduced by at least 20%, preferably at least 25%, more preferably at least 30%, most preferably at least 35% or even 40%.

Item 113. The oral dosage form of any one of items 105 to 112 for use in a method of treating pain, wherein the method provides a prevention or reduction of drug liking of oxycodone.

Item 114. The oral dosage form of any one of items 105 to 112 for use in a method of treating pain, wherein the co-administration of the amount of buprenorphine in the dosage form prevents or reduces drug liking of oxycodone compared to drug liking observed for said amount of oxycodone in the dosage form when administered alone.

Item 115. The oral dosage form of item 113 or 114 for use in a method of treating pain, wherein the mean $E_{max}$ of "at the moment drug liking VAS" is reduced by at least 15%, when measured in a comparison study.

Item 116. The oral dosage form of item 115 for use in a method of treating pain, wherein the mean $E_{max}$ of "at the moment drug liking VAS" is reduced by at least 20%, preferably at least 25%, more preferably at least 30%.

Item 117. The oral dosage form of item 113 or 114 for use in a method of treating pain, wherein the mean $E_{max}$ of "overall drug liking VAS" is reduced by at least 15%, when measured in a comparison study.

Item 118. The oral dosage form of item 117 for use in a method of treating pain, wherein the mean $E_{max}$ of "overall drug liking VAS" is reduced by at least 20%, preferably at least 25%, more preferably at least 30%, most preferably at least 35%.

Item 119. The oral dosage form of item 113 or 114 for use in a method of treating pain, wherein the mean $E_{max}$ of "take drug again VAS" is reduced by at least 15%, when measured in a comparison study.

Item 120. The oral dosage form of item 119 for use in a method of treating pain, wherein the mean $E_{max}$ of "take drug again VAS" is reduced by at least 20%, preferably at least 25%, more preferably at least 30%, most preferably at least 35%.

Item 121. The oral dosage form of any one of items 105 to 120 for use in a method of treating pain, wherein the method provides an analgesic effect which is not substantially reduced when measured in a comparison study.

Item 122. The oral dosage form of item 121 for use in a method of treating pain, wherein the mean "cold pain score VAS" measured in a cold pressor test at 1, 2, 3 and 4 hours after administration, does not increase more than 10% as compared to a comparative method of treatment when measured in a comparison study.

Item 123. The oral dosage form of any one of items 105 to 122 for use in a method of treating pain, wherein the method prevents or reduces the formation of addiction, the occurrence of drug abuse, or the occurrence of recreational drug use.

Item 124. A method of preventing or reducing an adverse pharmacodynamic response of oxycodone observed in the treatment of pain with an amount of oxycodone alone, by instead administering the oral dosage form of any one of items 1 to 43 comprising the same amount of oxycodone.

Item 125. The method of item 124, wherein the adverse pharmacodynamic response is selected from the group consisting of euphoria, feeling high, bowel dysfunction, nausea, vomiting, somnolence, dizziness, respiratory depression, headache, dry mouth, sedation, sweats, asthenia, hypotension, dysphoria, delirium, miosis, pruritis, urticaria, urinary retention, hyperalgesia, allodynia, physical dependence and tolerance, preferably wherein the adverse pharmacodynamic response is selected from the group consisting of respiratory depression, euphoria, feeling high, and bowel dysfunction.

Item 126. The method of item 124, wherein the adverse pharmacodynamic response is euphoria.

Item 127. The method of item 124, wherein the adverse pharmacodynamic response is feeling high.

Item 128. A method of preventing or reducing drug liking of oxycodone observed in the treatment of pain with an amount of oxycodone alone, by instead administering the oral dosage form of any one of items 1 to 43 comprising the same amount of oxycodone.

Item 129. A method of preventing or reducing the formation of addiction, the occurrence of drug abuse, or the occurrence of recreational drug use by providing a dosage form of any one of items 1 to 43.

Item 130. Use of a dosage form of any one of items 1 to 43 in the prevention or reduction of the formation of addiction, the occurrence of drug abuse, or the occurrence of recreational drug use.

Item 131. An oral dosage form comprising
(i) an amount of oxycodone in immediate release form, and
(ii) an amount of buprenorphine in immediate release form,
wherein the weight ratio of the amount of buprenorphine to the amount of oxycodone is equal to or greater than about 1:100 calculated with the amount of buprenorphine in the dosage form expressed as the equimolar amount of buprenorphine base (Mw=467.64 g/mol) in mg, and the amount of oxycodone in the dosage form expressed as the equimolar amount of oxycodone hydrochloride (Mw=351.82 g/mol) in mg.

Item 132. The oral dosage form of item 131, wherein the weight ratio of the amount of buprenorphine to the amount of oxycodone is equal to or greater than about 1:80.

Item 133. The oral dosage form of item 131, wherein the weight ratio of the amount of buprenorphine to the amount of oxycodone is equal to or greater than about 1:60.

Item 134. The oral dosage form of item 131, wherein the weight ratio of the amount of buprenorphine to the amount of oxycodone is equal to or greater than about 1:50.

Item 135. The oral dosage form of item 131, wherein the weight ratio of the amount of buprenorphine to the amount of oxycodone is equal to or greater than about 1:40.

Item 136. The oral dosage form of item 131, wherein the weight ratio of the amount of buprenorphine to the amount of oxycodone is from about 1:6 to about 1:100, preferably from about 1:6 to about 1:80, more preferably from about 1:6 to about 1:60 or from about 1:6 to about 1:50.

Item 137. The oral dosage form of item 131, wherein the weight ratio of the amount of buprenorphine to the amount of oxycodone is from about 1:6 to about 1:40.

Item 138. The oral dosage form of item 131, wherein the weight ratio of the amount of buprenorphine to the amount of oxycodone is from about 1:8 to about 1:100, preferably from about 1:8 to about 1:80, more preferably from about 1:8 to about 1:60 or from about 1:8 to about 1:50.

Item 139. The oral dosage form of item 131, wherein the weight ratio of the amount of buprenorphine to the amount of oxycodone is from about 1:8 to about 1:40.

Item 140. The oral dosage form of item 131, wherein the weight ratio of the amount of buprenorphine to the amount of oxycodone is from about 1:10 to about 1:100, preferably from about 1:10 to about 1:80, more preferably from about 1:10 to about 1:60 or from about 1:10 to about 1:50.

Item 141. The oral dosage form of item 131, wherein the weight ratio of the amount of buprenorphine to the amount of oxycodone is from about 1:10 to about 1:40.

Item 142. The oral dosage form of item 131, wherein the weight ratio of the amount of buprenorphine to the amount of oxycodone is from about 1:20 to about 1:100, preferably from about 1:20 to about 1:80, more preferably from about 1:20 to about 1:60 or from about 1:20 to about 1:50.

Item 143. The oral dosage form of item 131, wherein the weight ratio of the amount of buprenorphine to the amount of oxycodone is from about 1:20 to about 1:40.

Item 144. The oral dosage form of item 131, wherein the weight ratio of the amount of buprenorphine to the amount of oxycodone is from about 1:20 to about 1:30.

Item 145. The oral dosage form of any one of items 131 to 144, wherein the dosage form comprises an amount of oxycodone which is equimolar to from about 5 mg to about 50 mg of oxycodone hydrochloride (Mw=351.82 g/mol), preferably from about 5 mg to about 40 mg of oxycodone hydrochloride (Mw=351.82 g/mol).

Item 146. The oral dosage form of any one of items 131 to 144, wherein the dosage form comprises an amount of oxycodone which is equimolar to about 10 mg, about 15 mg, about 20 mg, about 30 mg, or about 40 mg of oxycodone hydrochloride (Mw=351.82 g/mol).

Item 147. The oral dosage form of items 146, wherein the dosage form comprises an amount of oxycodone hydrochloride which is equimolar to about 10 mg, about 15 mg, about 20 mg, about 30 mg, or about 40 mg of oxycodone hydrochloride (Mw=351.82 g/mol).

Item 148. The oral dosage form of item 146, wherein the dosage form comprises an amount of oxycodone myristate which is equimolar to about 10 mg, about 15 mg, about 20 mg, about 30 mg, or about 40 mg of oxycodone hydrochloride (Mw=351.82 g/mol).

Item 149. The oral dosage form of any one of items 131 to 144, wherein the dosage form comprises an amount of oxycodone which is equimolar to about 40 mg of oxycodone hydrochloride (Mw=351.82 g/mol), and an amount of buprenorphine which is equimolar to from about 1 mg to about 5 mg of buprenorphine base (Mw=467.64 g/mol).

Item 150. The oral dosage form of any one of items 131 to 144, wherein the dosage form comprises an amount of oxycodone which is equimolar to about 40 mg of oxycodone hydrochloride (Mw=351.82 g/mol), and an amount of buprenorphine which is equimolar to from about 1 mg to about 4 mg of buprenorphine base (Mw=467.64 g/mol).

Item 151. The oral dosage form of any one of items 131 to 144, wherein the dosage form comprises an amount of oxycodone which is equimolar to about 40 mg of oxycodone hydrochloride (Mw=351.82 g/mol), and an amount of buprenorphine which is equimolar to from about 2 mg to about 4 mg of buprenorphine base (Mw=467.64 g/mol).

Item 152. The oral dosage form of any one of items 131 to 144, wherein the dosage form comprises an amount of oxycodone which is equimolar to about 40 mg of oxycodone hydrochloride (Mw=351.82 g/mol), and an amount of buprenorphine which is equimolar to from about 1 mg to about 2 mg of buprenorphine base (Mw=467.64 g/mol).

Item 153. The oral dosage form of any one of items 131 to 146, and 149 to 152, wherein the oxycodone is oxycodone hydrochloride and the buprenorphine is buprenorphine hydrochloride.

Item 154. The oral dosage form of any one of items 131 to 153, wherein said dosage form is a liquid dosage form.

Item 155. The oral dosage form of item 154, wherein said dosage form is a solution, a suspension, or an emulsion, preferably a solution.

Item 156. The oral dosage form of any one of items 131 to 153, wherein said dosage form is a solid dosage form.

Item 157. The oral dosage form of item 156, wherein said dosage form is a tablet or a capsule.

Item 158. The oral dosage form of any one of items 131 to 157, wherein after single-dose administration, the dosage form provides in one group of subjects a ratio of the mean $C_{max}$ of buprenorphine to the mean $C_{max}$ of oxycodone of at least about 1:280.

Item 159. The oral dosage form of item 158, wherein the ratio of the mean $C_{max}$ of buprenorphine to the mean $C_{max}$ of oxycodone is at least about 1:250.

Item 160. The oral dosage form of item 158, wherein the ratio of the mean $C_{max}$ of buprenorphine to the mean $C_{max}$ of oxycodone is at least about 1:230.

Item 161. The oral dosage form of item 158, wherein the ratio of the mean $C_{max}$ of buprenorphine to the mean $C_{max}$ of oxycodone is at least about 1:200.

Item 162. The oral dosage form of item 158, wherein the ratio of the mean $C_{max}$ of buprenorphine to the mean $C_{max}$ of oxycodone is at least about 1:180.

Item 163. The oral dosage form of item 158, wherein the ratio of the mean $C_{max}$ of buprenorphine to the mean $C_{max}$ of oxycodone is from about 1:50 to about 1:280.

Item 164. The oral dosage form of item 158, wherein the ratio of the mean $C_{max}$ of buprenorphine to the mean $C_{max}$ of oxycodone is from about 1:50 to about 1:250.

Item 165. The oral dosage form of item 158, wherein the ratio of the mean $C_{max}$ of buprenorphine to the mean $C_{max}$ of oxycodone is from about 1:80 to about 1:230.

Item 166. The oral dosage form of item 158, wherein the ratio of the mean $C_{max}$ of buprenorphine to the mean $C_{max}$ of oxycodone is from about 1:100 to about 1:200.

Item 167. The oral dosage form of item 158, wherein the ratio of the mean $C_{max}$ of buprenorphine to the mean $C_{max}$ of oxycodone is from about 1:100 to about 1:180.

Item 168. The oral dosage form of any one of items 158 to 167, wherein after single-dose administration, the dosage form further provides in said group of subjects a ratio of the mean $T_{max}$ of buprenorphine to the mean $T_{max}$ of oxycodone of equal to or less than about 1.5:1.

Item 169. The oral dosage form of item 168, wherein the ratio of the mean $T_{max}$ of buprenorphine to the mean $T_{max}$, of oxycodone is equal to or less than about 1.3:1.

Item 170. The oral dosage form of item 168, wherein the ratio of the mean $T_{max}$ of buprenorphine to the mean $T_{max}$ of oxycodone is equal to or less than about 1.1:1.

Item 171. The oral dosage form of item 168, wherein the ratio of the mean $T_{max}$ of buprenorphine to the mean $T_{max}$ of oxycodone is equal to or less than about 1:1.

Item 172. The oral dosage form of any one of items 158 to 167, wherein after single-dose administration, the dosage form further provides in said group of subjects a mean $T_{max}$ of buprenorphine that is earlier than the mean $T_{max}$ of oxycodone.

Item 173. The oral dosage form of any one of items 158 to 172, wherein after single-dose administration, the dosage form further provides in said group of subjects a ratio of the mean $T_{max}$ of buprenorphine to the mean $T_{max}$ of oxycodone of from about 0.1:1 to about 1.5:1, preferably from about 0.1:1 to about 1.3:1, more preferably from about 0.1:1 to about 1.1:1, most preferably from about 0.1:1 to about 1:1 or from about 0.1:1 to about 0.9:1.

Item 174. A method of treating pain comprising administering to a patient in need thereof an oral dosage form comprising
(i) an amount of oxycodone in immediate release form, and
(ii) an amount of buprenorphine in immediate release form,
wherein the weight ratio of the amount of buprenorphine to the amount of oxycodone is equal to or greater than about 1:100 calculated with the amount of buprenorphine in the dosage form expressed as the equimolar amount of buprenorphine base (Mw=467.64 g/mol) in mg, and the amount of oxycodone in the dosage form expressed as the equimolar amount of oxycodone hydrochloride (Mw=351.82 g/mol) in mg.

Item 175. The method of item 174, wherein the weight ratio of the amount of buprenorphine to the amount of oxycodone is equal to or greater than about 1:80.

Item 176. The method of item 174, wherein the weight ratio of the amount of buprenorphine to the amount of oxycodone is equal to or greater than about 1:60.

Item 177. The method of item 174, wherein the weight ratio of the amount of buprenorphine to the amount of oxycodone is equal to or greater than about 1:50.

Item 178. The method of item 174, wherein the weight ratio of the amount of buprenorphine to the amount of oxycodone is equal to or greater than about 1:40.

Item 179. The method of item 174, wherein the weight ratio of the amount of buprenorphine to the amount of oxycodone is from about 1:6 to about 1:100, preferably from about 1:6 to about 1:80, more preferably from about 1:6 to about 1:60 or from about 1:6 to about 1:50.

Item 180. The method of item 174, wherein the weight ratio of the amount of buprenorphine to the amount of oxycodone is from about 1:6 to about 1:40.

Item 181. The method of item 174, wherein the weight ratio of the amount of buprenorphine to the amount of oxycodone is from about 1:8 to about 1:100, preferably from about 1:8 to about 1:80, more preferably from about 1:8 to about 1:60 or from about 1:8 to about 1:50.

Item 182. The method of item 174, wherein the weight ratio of the amount of buprenorphine to the amount of oxycodone is from about 1:8 to about 1:40.

Item 183. The method of item 174, wherein the weight ratio of the amount of buprenorphine to the amount of oxycodone is from about 1:10 to about 1:100, preferably from about 1:10 to about 1:80, more preferably from about 1:10 to about 1:60 or from about 1:10 to about 1:50.

Item 184. The method of item 174, wherein the weight ratio of the amount of buprenorphine to the amount of oxycodone is from about 1:10 to about 1:40.

Item 185. The method of item 174, wherein the weight ratio of the amount of buprenorphine to the amount of oxycodone is from about 1:20 to about 1:100, preferably from about 1:20 to about 1:80, more preferably from about 1:20 to about 1:60 or from about 1:20 to about 1:50.

Item 186. The method of item 174, wherein the weight ratio of the amount of buprenorphine to the amount of oxycodone is from about 1:20 to about 1:40.

Item 187. The method of item 174, wherein the weight ratio of the amount of buprenorphine to the amount of oxycodone is from about 1:20 to about 1:30.

Item 188. The method of any one of items 174 to 187, wherein the dosage form comprises an amount of oxycodone which is equimolar to from about 5 mg to about 50 mg of oxycodone hydrochloride (Mw=351.82 g/mol), preferably from about 5 mg to about 40 mg of oxycodone hydrochloride (Mw=351.82 g/mol).

Item 189. The method of any one of items 174 to 187, wherein the dosage form comprises an amount of oxycodone which is equimolar to about 10 mg, about 15 mg, about 20 mg, about 30 mg, or about 40 mg of oxycodone hydrochloride (Mw=351.82 g/mol).

Item 190. The method of item 189, wherein the dosage form comprises an amount of oxycodone hydrochloride which is equimolar to about 10 mg, about 15 mg, about 20 mg, about 30 mg, or about 40 mg of oxycodone hydrochloride (Mw=351.82 g/mol).

Item 191. The method of item 189, wherein the dosage form comprises an amount of oxycodone myristate which is equimolar to about 10 mg, about 15 mg, about 20 mg, about 30 mg, or about 40 mg of oxycodone hydrochloride (Mw=351.82 g/mol).

Item 192. The method of any one of items 174 to 187, wherein the dosage form comprises an amount of oxycodone which is equimolar to about 40 mg of oxycodone hydrochloride (Mw=351.82 g/mol), and an amount of buprenorphine which is equimolar to from about 1 mg to about 5 mg of buprenorphine base (Mw=467.64 g/mol).

Item 193. The method of any one of items 174 to 187, wherein the dosage form comprises an amount of oxycodone which is equimolar to about 40 mg of oxycodone hydrochloride (Mw=351.82 g/mol), and an amount of buprenorphine which is equimolar to from about 1 mg to about 4 mg of buprenorphine base (Mw=467.64 g/mol).

Item 194. The method of any one of items 174 to 187, wherein the dosage form comprises an amount of oxycodone which is equimolar to about 40 mg of oxycodone hydrochloride (Mw=351.82 g/mol), and an amount of buprenorphine which is equimolar to from about 2 mg to about 4 mg of buprenorphine base (Mw=467.64 g/mol).

Item 195. The method of any one of items 174 to 187, wherein the dosage form comprises an amount of oxycodone which is equimolar to about 40 mg of oxycodone hydrochloride (Mw=351.82 g/mol), and an amount of buprenorphine which is equimolar to from about 1 mg to about 2 mg of buprenorphine base (Mw=467.64 g/mol).

Item 196. The method of any one of items 174 to 189, and 192 to 195, wherein the oxycodone is oxycodone hydrochloride and the buprenorphine is buprenorphine hydrochloride.

Item 197. The method of any one of items 174 to 196, wherein said dosage form is a liquid dosage form.

Item 198. The method of item 197, wherein said dosage form is a solution, a suspension, or an emulsion, preferably a solution.

Item 199. The method of any one of items 174 to 196, wherein said dosage form is a solid dosage form.

Item 200. The method of item 199, wherein said dosage form is a tablet or a capsule.

Item 201. The method of any one of items 174 to 200, wherein after single-dose administration, the dosage form provides in one group of subjects a ratio of the mean $C_{max}$ of buprenorphine to the mean $C_{max}$ of oxycodone of at least about 1:280.

Item 202. The method of item 201, wherein the ratio of the mean $C_{max}$ of buprenorphine to the mean $C_{max}$ of oxycodone is at least about 1:250.

Item 203. The method of item 201, wherein the ratio of the mean $C_{max}$ of buprenorphine to the mean $C_{max}$ of oxycodone is at least about 1:230.

Item 204. The method of item 201, wherein the ratio of the mean $C_{max}$ of buprenorphine to the mean $C_{max}$ of oxycodone is at least about 1:200.

Item 205. The method of item 201, wherein the ratio of the mean $C_{max}$ of buprenorphine to the mean $C_{max}$ of oxycodone is at least about 1:180.

Item 206. The method of item 201, wherein the ratio of the mean $C_{max}$ of buprenorphine to the mean $C_{max}$ of oxycodone is from about 1:50 to about 1:280.

Item 207. The method of item 201, wherein the ratio of the mean $C_{max}$ of buprenorphine to the mean $C_{max}$ of oxycodone is from about 1:50 to about 1:250.

Item 208. The method of item 201, wherein the ratio of the mean $C_{max}$ of buprenorphine to the mean $C_{max}$ of oxycodone is from about 1:80 to about 1:230.

Item 209. The method of item 201, wherein the ratio of the mean $C_{max}$ of buprenorphine to the mean $C_{max}$ of oxycodone is from about 1:100 to about 1:200.

Item 210. The method of item 201, wherein the ratio of the mean $C_{max}$ of buprenorphine to the mean $C_{max}$ of oxycodone is from about 1:100 to about 1:180.

Item 211. The method of any one of items 201 to 210, wherein after single-dose administration, the dosage form further provides in said group of subjects a ratio of the mean $T_{max}$ of buprenorphine to the mean $T_{max}$ of oxycodone of equal to or less than about 1.5:1.

Item 212. The method of item 211, wherein the ratio of the mean $T_{max}$ of buprenorphine to the mean $T_{max}$ of oxycodone is equal to or less than about 1.3:1.

Item 213. The method of item 211, wherein the ratio of the mean $T_{max}$ of buprenorphine to the mean $T_{max}$ of oxycodone is equal to or less than about 1.1:1.

Item 214. The method of item 211, wherein the ratio of the mean $T_{max}$ of buprenorphine to the mean $T_{max}$ of oxycodone is equal to or less than about 1:1.

Item 215. The method of any one of items 201 to 210, wherein after single-dose administration, the dosage form further provides in said group of subjects a mean $T_{max}$ of buprenorphine that is earlier than the mean $T_{max}$ of oxycodone.

Item 216. The method of any one of items 201 to 215, wherein after single-dose administration, the dosage form further provides in said group of subjects a ratio of the mean $T_{max}$ of buprenorphine to the mean $T_{max}$ of oxycodone of from about 0.1:1 to about 1.5:1, preferably from about 0.1:1 to about 1.3:1, more preferably from about 0.1:1 to about 1.1:1, most preferably from about 0.1:1 to about 1:1 or from about 0.1:1 to about 0.9:1.

Item 217. The method of any one of items 174 to 216, wherein the method provides a prevention or reduction of an adverse pharmacodynamic response of oxycodone.

Item 218. The method of any one of items 174 to 216, wherein the co-administration of the amount of buprenorphine in the dosage form prevents or reduces an adverse pharmacodynamic response observed for said amount of oxycodone in the dosage form when administered alone.

Item 219. The method of item 217 or 218, wherein the adverse pharmacodynamic response is selected from the group consisting of euphoria, feeling high, bowel dysfunction, nausea, vomiting, somnolence, dizziness, respiratory depression, headache, dry mouth, sedation, sweats, asthenia, hypotension, dysphoria, delirium, miosis, pruritus, urticaria, urinary retention, hyperalgesia, allodynia, physical dependence and tolerance, preferably wherein the adverse pharmacodynamic response is selected from the group consisting of respiratory depression, euphoria, feeling high, and bowel dysfunction.

Item 220. The method of item 217 or 218, wherein the adverse pharmacodynamic response is euphoria.

Item 221. The method of item 217 or 218, wherein the adverse pharmacodynamic response is feeling high.

Item 222. The method of item 221, wherein the mean $E_{max}$ of "feeling high VAS" is reduced by at least 15%, when measured in a comparison study.

Item 223. The method of item 222, wherein the mean $E_{max}$ of "feeling high VAS" is reduced by at least 20%, preferably at least 25%, more preferably at least 30%, most preferably at least 35% or even 40%.

Item 224. The method of any one of items 174 to 223, wherein the method provides a prevention or reduction of drug liking of oxycodone.

Item 225. The method of any one of items 174 to 223, wherein the co-administration of the amount of buprenorphine in the dosage form prevents or reduces drug liking of oxycodone compared to drug liking observed for said amount of oxycodone in the dosage form when administered alone.

Item 226. The method of item 224 or 225, wherein the mean $E_{max}$ of "at the moment drug liking VAS" is reduced by at least 15%, when measured in a comparison study.

Item 227. The method of item 226, wherein the mean $E_{max}$ of "at the moment drug liking VAS" is reduced by at least 20%, preferably at least 25%, more preferably at least 30%.

Item 228. The method of item 224 or 225, wherein the mean $E_{max}$ of "overall drug liking VAS" is reduced by at least 15%, when measured in a comparison study.

Item 229. The method of item 228, wherein the mean $E_{max}$ of "overall drug liking VAS" is reduced by at least 20%, preferably at least 25%, more preferably at least 30%, most preferably at least 35%.

Item 230. The method of item 224 or 225, wherein the mean $E_{max}$ of "take drug again VAS" is reduced by at least 15%, when measured in a comparison study.

Item 231. The method of item 230, wherein the mean $E_{max}$ of "take drug again VAS" is reduced by at least 20%, preferably at least 25%, more preferably at least 30%, most preferably at least 35%.

Item 232. The method of any one of items 174 to 231, wherein the method provides an analgesic effect which is not substantially reduced when measured in a comparison study.

Item 233. The method of item 232, wherein the mean "cold pain score VAS" measured in a cold pressor test at 1, 2, 3 and 4 hours after administration, does not increase more than 10% as compared to a comparative method of treatment when measured in a comparison study.

Item 234. The method of any one of items 174 to 233, wherein the method prevents or reduces the formation of addiction, the occurrence of drug abuse, or the occurrence of recreational drug use.

Item 235. The oral dosage form of any one of items 131 to 173 for use in a method of treating pain.

Item 236. The oral dosage form of item 235 for use in a method of treating pain, wherein the method provides a prevention or reduction of an adverse pharmacodynamic response of oxycodone.

Item 237. The oral dosage form of item 235 for use in a method of treating pain, wherein the co-administration of the amount of buprenorphine in the dosage form prevents or reduces an adverse pharmacodynamic response observed for said amount of oxycodone in the dosage form when administered alone.

Item 238. The oral dosage form of item 236 or 237 for use in a method of treating pain, wherein the adverse pharmacodynamic response is selected from the group consisting of euphoria, feeling high, bowel dysfunction, nausea, vomiting, somnolence, dizziness, respiratory depression, headache, dry mouth, sedation, sweats, asthenia, hypotension, dysphoria, delirium, miosis, pruritis, urticaria, urinary retention, hyperalgesia, allodynia, physical dependence and tolerance, preferably wherein the adverse pharmacodynamic response is selected from the group consisting of respiratory depression, euphoria, feeling high, and bowel dysfunction.

Item 239. The oral dosage form of item 236 or 237 for use in a method of treating pain, wherein the adverse pharmacodynamic response is euphoria.

Item 240. The oral dosage form of item 236 or 237 for use in a method of treating pain, wherein the adverse pharmacodynamic response is feeling high.

Item 241. The oral dosage form of item 240 for use in a method of treating pain, wherein the mean $E_{max}$ of "feeling high VAS" is reduced by at least 15%, when measured in a comparison study.

Item 242. The oral dosage form of item 241 for use in a method of treating pain, wherein the mean $E_{max}$ of "feeling high VAS" is reduced by at least 20%, preferably at least 25%, more preferably at least 30%, most preferably at least 35% or even 40%.

Item 243. The oral dosage form of any one of items 235 to 242 for use in a method of treating pain, wherein the method provides a prevention or reduction of drug liking of oxycodone.

Item 244. The oral dosage form of any one of items 235 to 242 for use in a method of treating pain, wherein the co-administration of the amount of buprenorphine in the dosage form prevents or reduces drug liking of oxycodone compared to drug liking observed for said amount of oxycodone in the dosage form when administered alone.

Item 245. The oral dosage form of item 243 or 244 for use in a method of treating pain, wherein the mean $E_{max}$ of "at the moment drug liking VAS" is reduced by at least 15%, when measured in a comparison study.

Item 246. The oral dosage form of item 245 for use in a method of treating pain, wherein the mean $E_{max}$ of "at the moment drug liking VAS" is reduced by at least 20%, preferably at least 25%, more preferably at least 30%.

Item 247. The oral dosage form of item 243 or 244 for use in a method of treating pain, wherein the mean $E_{max}$ of "overall drug liking VAS" is reduced by at least 15%, when measured in a comparison study.

Item 248. The oral dosage form of item 247 for use in a method of treating pain, wherein the mean $E_{max}$ of "overall drug liking VAS" is reduced by at least 20%, preferably at least 25%, more preferably at least 30%, most preferably at least 35%.

Item 249. The oral dosage form of item 243 or 244 for use in a method of treating pain, wherein the mean $E_{max}$ of "take drug again VAS" is reduced by at least 15%, when measured in a comparison study.

Item 250. The oral dosage form of item 249 for use in a method of treating pain, wherein the mean En, of "take drug again VAS" is reduced by at least 20%, preferably at least 25%, more preferably at least 30%, most preferably at least 35%.

Item 251. The oral dosage form of any one of items 235 to 250 for use in a method of treating pain, wherein the method provides an analgesic effect which is not substantially reduced when measured in a comparison study.

Item 252. The oral dosage form of item 251 for use in a method of treating pain, wherein the mean "cold pain score VAS" measured in a cold pressor test at 1, 2, 3 and 4 hours after administration, does not increase more than 10% as compared to a comparative method of treatment when measured in a comparison study.

Item 253. The oral dosage form of any one of items 235 to 252 for use in a method of treating pain, wherein the method prevents or reduces the formation of addiction, the occurrence of drug abuse, or the occurrence of recreational drug use.

Item 254. A method of preventing or reducing an adverse pharmacodynamic response of oxycodone observed in the treatment of pain with an amount of oxycodone alone, by instead administering the oral dosage form of any one of items 131 to 173 comprising the same amount of oxycodone.

Item 255. The method of item 254, wherein the adverse pharmacodynamic response is selected from the group consisting of euphoria, feeling high, bowel dysfunction, nausea, vomiting, somnolence, dizziness, respiratory depression, headache, dry mouth, sedation, sweats, asthenia, hypotension, dysphoria, delirium, miosis, pruritis, urticaria, urinary retention, hyperalgesia, allodynia, physical dependence and tolerance, preferably wherein the adverse pharmacodynamic response is selected from the group consisting of respiratory depression, euphoria, feeling high, and bowel dysfunction.

Item 256. The method of item 254, wherein the adverse pharmacodynamic response is euphoria.

Item 257. The method of item 254, wherein the adverse pharmacodynamic response is feeling high.

Item 258. A method of preventing or reducing drug liking of oxycodone observed in the treatment of pain with an amount of oxycodone alone, by instead administering the oral dosage form of any one of items 131 to 173 comprising the same amount of oxycodone.

Item 259. A method of preventing or reducing the formation of addiction, the occurrence of drug abuse, or the occurrence of recreational drug use by providing a dosage form of any one of items 131 to 173.

Item 260. Use of a dosage form of any one of items 131 to 173 in the prevention or reduction of the formation of addiction, the occurrence of drug abuse, or the occurrence of recreational drug use.

Item 261. A dosage form comprising
(i) an amount of oxycodone, and
(ii) an amount of buprenorphine, wherein after single-dose administration, the dosage form provides in one group of subjects a ratio of the mean $C_{max}$ of buprenorphine to the mean $C_{max}$ of oxycodone of at least about 1:280.

Item 262. The dosage form of item 261, wherein the ratio of the mean $C_{max}$ of buprenorphine to the mean $C_{max}$ of oxycodone is at least about 1:250.

Item 263. The dosage form of item 261, wherein the ratio of the mean $C_{max}$ of buprenorphine to the mean $C_{max}$ of oxycodone is at least about 1:230.

Item 264. The dosage form of item 261, wherein the ratio of the mean $C_{max}$ of buprenorphine to the mean $C_{max}$ of oxycodone is at least about 1:200.

Item 265. The dosage form of item 261, wherein the ratio of the mean $C_{max}$ of buprenorphine to the mean $C_{max}$ of oxycodone is at least about 1:180.

Item 266. The dosage form of item 261, wherein the ratio of the mean $C_{max}$ of buprenorphine to the mean $C_{max}$ of oxycodone is from about 1:50 to about 1:280.

Item 267. The dosage form of item 261, wherein the ratio of the mean $C_{max}$ of buprenorphine to the mean $C_{max}$ of oxycodone is from about 1:50 to about 1:250.

Item 268. The dosage form of item 261, wherein the ratio of the mean $C_{max}$ of buprenorphine to the mean $C_{max}$ of oxycodone is from about 1:80 to about 1:230.

Item 269. The dosage form of item 261, wherein the ratio of the mean $C_{max}$ of buprenorphine to the mean $C_{max}$ of oxycodone is from about 1:100 to about 1:200.

Item 270. The dosage form of item 261, wherein the ratio of the mean $C_{max}$ of buprenorphine to the mean $C_{max}$ of oxycodone is from about 1:100 to about 1:180.

Item 271. The dosage form of any one of items 261 to 270, wherein after single-dose administration, the dosage form further provides in said group of subjects a ratio of the mean $T_{max}$ of buprenorphine to the mean $T_{max}$ of oxycodone of equal to or less than about 1.5:1.

Item 272. The dosage form of item 271, wherein the ratio of the mean $T_{max}$ of buprenorphine to the mean $T_{max}$ of oxycodone is equal to or less than about 1.3:1.

Item 273. The dosage form of item 271, wherein the ratio of the mean $T_{max}$ of buprenorphine to the mean $T_{max}$ of oxycodone is equal to or less than about 1.1:1.

Item 274. The dosage form of item 271, wherein the ratio of the mean $T_{max}$ of buprenorphine to the mean $T_{max}$ of oxycodone is equal to or less than about 1:1.

Item 275. The dosage form of any one of items 261 to 270, wherein after single-dose administration, the dosage form further provides in said group of subjects a mean $T_{max}$ of buprenorphine that is earlier than the mean $T_{max}$ of oxycodone.

Item 276. The dosage form of any one of items 261 to 275, wherein after single-dose administration, the dosage form further provides in said group of subjects a ratio of the mean $T_{max}$ of buprenorphine to the mean $T_{max}$ of oxycodone of from about 0.1:1 to about 1.5:1, preferably from about 0.1:1 to about 1.3:1, more preferably from about 0.1:1 to about 1.1:1, most preferably from about 0.1:1 to about 1:1 or from about 0.1:1 to about 0.9:1.

Item 277. The dosage form of any one of items 261 to 276, wherein the dosage form is an oral dosage form.

Item 278. The oral dosage form of item 277, wherein the dosage form comprises an amount of oxycodone which is equimolar to from about 5 mg to about 50 mg of oxycodone hydrochloride (Mw=351.82 g/mol), preferably from about 5 mg to about 40 mg of oxycodone hydrochloride (Mw=351.82 g/mol).

Item 279. The oral dosage form of item 277, wherein the dosage form comprises an amount of oxycodone which is equimolar to about 10 mg, about 15 mg, about 20 mg, about 30 mg, or about 40 mg of oxycodone hydrochloride (Mw=351.82 g/mol).

Item 280. The oral dosage form of item 279, wherein the dosage form comprises an amount of oxycodone hydrochloride which is equimolar to about 10 mg, about 15 mg, about 20 mg, about 30 mg, or about 40 mg of oxycodone hydrochloride (Mw=351.82 g/mol).

Item 281. The oral dosage form of item 279, wherein the dosage form comprises an amount of oxycodone myristate which is equimolar to about 10 mg, about 15 mg, about 20 mg, about 30 mg, or about 40 mg of oxycodone hydrochloride (Mw=351.82 g/mol).

Item 282. The oral dosage form of item 277, wherein the dosage form comprises an amount of oxycodone which is equimolar to about 40 mg of oxycodone hydrochloride (Mw=351.82 g/mol), and an amount of buprenorphine which is equimolar to from about 1 mg to about 6 mg of buprenorphine base (Mw=467.64 g/mol).

Item 283. The oral dosage form of item 277, wherein the dosage form comprises an amount of oxycodone which is equimolar to about 40 mg of oxycodone hydrochloride (Mw=351.82 g/mol), and an amount of buprenorphine which is equimolar to from about 2 mg to about 5 mg of buprenorphine base (Mw=467.64 g/mol) or from about 2 mg to about 4 mg of buprenorphine base (Mw=467.64 g/mol).

Item 284. The dosage form of any one of items 261-279, 282 and 283, wherein the oxycodone is oxycodone hydrochloride and the buprenorphine is buprenorphine hydrochloride.

Item 285. The dosage form of any one of items 261 to 284, wherein the dosage form comprises said amount of buprenorphine in immediate release form.

Item 286. The dosage form of any one of items 261 to 285, wherein the dosage form comprises said amount of oxycodone in immediate release form and said amount of buprenorphine in immediate release form.

Item 287. The dosage form of any one of items 261 to 286, wherein said dosage form is a liquid dosage form.

Item 288. The dosage form of item 287, wherein said dosage form is a solution, a suspension, or an emulsion, preferably a solution.

Item 289. The dosage form of any one of items 261 to 286, wherein said dosage form is a solid dosage form.

Item 290. The dosage form of item 289, wherein said dosage form is a tablet or a capsule.

Item 291. A method of treating pain comprising a concurrent administration to a patient in need thereof of:
(i) an amount of oxycodone, and
(ii) an amount of buprenorphine,
wherein said concurrent administration provides in one group of subjects a ratio of the mean $C_{max}$ of buprenorphine to the mean $C_{max}$ of oxycodone of at least about 1:280 after single-dose administration.

Item 292. The method of item 291, wherein the ratio of the mean $C_{max}$ of buprenorphine to the mean $C_{max}$ of oxycodone is at least about 1:250.

Item 293. The method of item 291, wherein the ratio of the mean $C_{max}$ of buprenorphine to the mean $C_{max}$ of oxycodone is at least about 1:230.

Item 294. The method of item 291, wherein the ratio of the mean $C_{max}$ of buprenorphine to the mean $C_{max}$ of oxycodone is at least about 1:200.

Item 295. The method of item 291, wherein the ratio of the mean $C_{max}$ of buprenorphine to the mean $C_{max}$ of oxycodone is at least about 1:180.

Item 296. The method of item 291, wherein the ratio of the mean $C_{max}$ of buprenorphine to the mean $C_{max}$ of oxycodone is from about 1:50 to about 1:280.

Item 297. The method of item 291, wherein the ratio of the mean $C_{max}$ of buprenorphine to the mean $C_{max}$ of oxycodone is from about 1:50 to about 1:250.

Item 298. The method of item 291, wherein the ratio of the mean $C_{max}$ of buprenorphine to the mean $C_{max}$ of oxycodone is from about 1:80 to about 1:230.

Item 299. The method of item 291, wherein the ratio of the mean $C_{max}$ of buprenorphine to the mean $C_{max}$ of oxycodone is from about 1:100 to about 1:200.

Item 300. The method of item 291, wherein the ratio of the mean $C_{max}$ of buprenorphine to the mean $C_{max}$ of oxycodone is from about 1:100 to about 1:180.

Item 301. The method of any one of items 291 to 300, wherein said concurrent administration further provides in said group of subjects a ratio of the mean $T_{max}$ of buprenorphine to the mean $T_{max}$ of oxycodone of equal to or less than about 1.5:1 after single-dose administration.

Item 302. The method of item 301, wherein the ratio of the mean $T_{max}$ of buprenorphine to the mean $T_{max}$ of oxycodone is equal to or less than about 1.3:1.

Item 303. The method of item 301, wherein the ratio of the mean $T_{max}$ of buprenorphine to the mean $T_{max}$ of oxycodone is equal to or less than about 1.1:1.

Item 304. The method of item 301, wherein the ratio of the mean $T_{max}$ of buprenorphine to the mean $T_{max}$ of oxycodone is equal to or less than about 1:1.

Item 305. The method of any one of items 291 to 300, wherein said concurrent administration further provides in said group of subjects a mean $T_{max}$ of buprenorphine that is earlier than the mean $T_{max}$ of oxycodone after single-dose administration.

Item 306. The method of any one of items 291 to 305, wherein said concurrent administration further provides in said group of subjects a ratio of the mean $T_{max}$ of buprenorphine to the mean $T_{max}$ of oxycodone of from about 0.1:1 to about 1.5:1, preferably from about 0.1:1 to about 1.3:1, more preferably from about 0.1:1 to about 1.1:1, most preferably from about 0.1:1 to about 1:1 or from about 0.1:1 to about 0.9:1 after single-dose administration.

Item 307. The method of any one of items 291 to 306, wherein the concurrent administration is an oral administration.

Item 308. The method of any one of items 291 to 307, wherein said amount of buprenorphine and said amount of oxycodone are administered within 30 minutes, within 20 minutes, within 10 minutes, within 5 minutes, or within 1 minute of each other, wherein preferably the buprenorphine is administered not later than the oxycodone.

Item 309. The method of any one of items 291 to 307, wherein the concurrent administration is the administration of an oral dosage form comprising both said amount of buprenorphine and said amount of oxycodone.

Item 310. The method of any one of items 307 to 309, wherein said amount of oxycodone is equimolar to from about 5 mg to about 50 mg of oxycodone hydrochloride (Mw=351.82 g/mol), preferably from about 5 mg to about 40 mg of oxycodone hydrochloride (Mw=351.82 g/mol).

Item 311. The method of any one of items 307 to 309, wherein said amount of oxycodone is equimolar to about 10 mg, about 15 mg, about 20 mg, about 30 mg, or about 40 mg of oxycodone hydrochloride (Mw=351.82 g/mol).

Item 312. The method of item 311, wherein said amount of oxycodone is an amount of oxycodone hydrochloride which is equimolar to about 10 mg, about 15 mg, about 20 mg, about 30 mg, or about 40 mg of oxycodone hydrochloride (Mw=351.82 g/mol).

Item 313. The method of item 311, wherein said amount of oxycodone is an amount of oxycodone myristate which is equimolar to about 10 mg, about 15 mg, about 20 mg, about 30 mg, or about 40 mg of oxycodone hydrochloride (Mw=351.82 g/mol).

Item 314. The method of any one of items 307 to 309, wherein said amount of oxycodone is equimolar to about 40 mg of oxycodone hydrochloride (Mw=351.82 g/mol), and said amount of buprenorphine is equimolar to from about 1 mg to about 6 mg of buprenorphine base (Mw=467.64 g/mol).

Item 315. The method of any one of items 307 to 309, wherein said amount of oxycodone is equimolar to about 40 mg of oxycodone hydrochloride (Mw=351.82 g/mol), and said amount of buprenorphine is equimolar to from about 2 mg to about 5 mg of buprenorphine base (Mw=467.64 g/mol) or from about 2 mg to about 4 mg of buprenorphine base (Mw=467.64 g/mol).

Item 316. The method of any one of items 291 to 311, 314 and 315, wherein the oxycodone is oxycodone hydrochloride and the buprenorphine is buprenorphine hydrochloride.

Item 317. The method of any one of items 291 to 316, wherein said amount of buprenorphine is in immediate release form.

Item 318. The method of any one of items 291 to 317, wherein said amount of oxycodone is in immediate release form and said amount of buprenorphine is in immediate release form.

Item 319. The method of any one of items 291 to 318, wherein said dosage form is a liquid dosage form.

Item 320. The method of item 319, wherein said dosage form is a solution, a suspension, or an emulsion, preferably a solution.

Item 321. The method of any one of items 291 to 318, wherein said dosage form is a solid dosage form.

Item 322. The method of item 321, wherein said dosage form is a tablet or a capsule.

Item 323. The method of any one of items 291 to 322, wherein the method provides a prevention or reduction of an adverse pharmacodynamic response of oxycodone.

Item 324. The method of any one of items 291 to 322, wherein the co-administration of the amount of buprenorphine in the dosage form prevents or reduces an adverse pharmacodynamic response observed for said amount of oxycodone in the dosage form when administered alone.

Item 325. The method of item 323 or 324, wherein the adverse pharmacodynamic response is selected from the group consisting of euphoria, feeling high, bowel dysfunction, nausea, vomiting, somnolence, dizziness, respiratory depression, headache, dry mouth, sedation, sweats, asthenia, hypotension, dysphoria, delirium, miosis, pruritis, urticaria, urinary retention, hyperalgesia, allodynia, physical dependence and tolerance, preferably wherein the adverse pharmacodynamic response is selected from the group consisting of respiratory depression, euphoria, feeling high, and bowel dysfunction.

Item 326. The method of item 323 or 324, wherein the adverse pharmacodynamic response is euphoria.

Item 327. The method of item 323 or 324, wherein the adverse pharmacodynamic response is feeling high.

Item 328. The method of item 327, wherein the mean $E_{max}$ of "feeling high VAS" is reduced by at least 15%, when measured in a comparison study.

Item 329. The method of item 328, wherein the mean $E_{max}$ of "feeling high VAS" is reduced by at least 20%, preferably at least 25%, more preferably at least 30%, most preferably at least 35% or even 40%.

Item 330. The method of any one of items 291 to 329, wherein the method provides a prevention or reduction of drug liking of oxycodone.

Item 331. The method of any one of items 291 to 329, wherein the co-administration of the amount of buprenorphine in the dosage form prevents or reduces drug liking of oxycodone compared to drug liking observed for said amount of oxycodone in the dosage form when administered alone.

Item 332. The method of item 330 or 331, wherein the mean $E_{max}$ of "at the moment drug liking VAS" is reduced by at least 15%, when measured in a comparison study.

Item 333. The method of item 332, wherein the mean $E_{max}$ of "at the moment drug liking VAS" is reduced by at least 20%, preferably at least 25%, more preferably at least 30%.

Item 334. The method of item 330 or 331, wherein the mean $E_{max}$ of "overall drug liking VAS" is reduced by at least 15%, when measured in a comparison study.

Item 335. The method of item 334, wherein the mean $E_{max}$ of "overall drug liking VAS" is reduced by at least 20%, preferably at least 25%, more preferably at least 30%, most preferably at least 35%.

Item 336. The method of item 330 or 331, wherein the mean $E_{max}$ of "take drug again VAS" is reduced by at least 15%, when measured in a comparison study.

Item 337. The method of item 336, wherein the mean $E_{max}$ of "take drug again VAS" is reduced by at least 20%, preferably at least 25%, more preferably at least 30%, most preferably at least 35%.

Item 338. The method of any one of items 291 to 337, wherein the method provides an analgesic effect which is not substantially reduced when measured in a comparison study.

Item 339. The method of item 338, wherein the mean "cold pain score VAS" measured in a cold pressor test at 1, 2, 3 and 4 hours after administration, does not increase more than 10% as compared to a comparative method of treatment when measured in a comparison study.

Item 340. The method of any one of items 291 to 339, wherein the method prevents or reduces the formation of addiction, the occurrence of drug abuse, or the occurrence of recreational drug use.

Item 341. The oral dosage form of any one of items 261 to 290 for use in a method of treating pain.

Item 342. The oral dosage form of item 341 for use in a method of treating pain, wherein the method provides a prevention or reduction of an adverse pharmacodynamic response of oxycodone.

Item 343. The oral dosage form of item 341 for use in a method of treating pain, wherein the co-administration of the amount of buprenorphine in the dosage form prevents or reduces an adverse pharmacodynamic response observed for said amount of oxycodone in the dosage form when administered alone.

Item 344. The oral dosage form of item 342 or 343 for use in a method of treating pain, wherein the adverse pharmacodynamic response is selected from the group consisting of euphoria, feeling high, bowel dysfunction, nausea, vomiting, somnolence, dizziness, respiratory depression, headache, dry mouth, sedation, sweats, asthenia, hypotension, dysphoria, delirium, miosis, pruritis, urticaria, urinary retention, hyperalgesia, allodynia, physical dependence and tolerance, preferably wherein the adverse pharmacodynamic response is selected from the group consisting of respiratory depression, euphoria, feeling high, and bowel dysfunction.

Item 345. The oral dosage form of item 342 or 343 for use in a method of treating pain, wherein the adverse pharmacodynamic response is euphoria.

Item 346. The oral dosage form of item 342 or 343 for use in a method of treating pain, wherein the adverse pharmacodynamic response is feeling high.

Item 347. The oral dosage form of item 346 for use in a method of treating pain, wherein the mean $E_{max}$ of "feeling high VAS" is reduced by at least 15%, when measured in a comparison study.

Item 348. The oral dosage form of item 347 for use in a method of treating pain, wherein the mean $E_{max}$ of "feeling high VAS" is reduced by at least 20%, preferably at least 25%, more preferably at least 30%, most preferably at least 35% or even 40%.

Item 349. The oral dosage form of any one of items 341 to 348 for use in a method of treating pain, wherein the method provides a prevention or reduction of drug liking of oxycodone.

Item 350. The oral dosage form of any one of items 341 to 348 for use in a method of treating pain, wherein the co-administration of the amount of buprenorphine in the dosage form prevents or reduces drug liking of oxycodone compared to drug liking observed for said amount of oxycodone in the dosage form when administered alone.

Item 351. The oral dosage form of item 349 or 350 for use in a method of treating pain, wherein the mean $E_{max}$m of "at the moment drug liking VAS" is reduced by at least 15%, when measured in a comparison study.

Item 352. The oral dosage form of item 351 for use in a method of treating pain, wherein the mean $E_{max}$ of "at the moment drug liking VAS" is reduced by at least 20%, preferably at least 25%, more preferably at least 30%.

Item 353. The oral dosage form of item 349 or 350 for use in a method of treating pain, wherein the mean $E_{max}$ of "overall drug liking VAS" is reduced by at least 15%, when measured in a comparison study.

Item 354. The oral dosage form of item 353 for use in a method of treating pain, wherein the mean $E_{max}$ of "overall drug liking VAS" is reduced by at least 20%, preferably at least 25%, more preferably at least 30%, most preferably at least 35%.

Item 355. The oral dosage form of item 349 or 350 for use in a method of treating pain, wherein the mean $E_{max}$ of "take drug again VAS" is reduced by at least 15%, when measured in a comparison study.

Item 356. The oral dosage form of item 355 for use in a method of treating pain, wherein the mean $E_{max}$ of "take drug again VAS" is reduced by at least 20%, preferably at least 25%, more preferably at least 30%, most preferably at least 35%.

Item 357. The oral dosage form of any one of items 341 to 356 for use in a method of treating pain, wherein the method provides an analgesic effect which is not substantially reduced when measured in a comparison study.

Item 358. The oral dosage form of item 357 for use in a method of treating pain, wherein the mean "cold pain score VAS" measured in a cold pressor test at 1, 2, 3 and 4 hours after administration, does not increase more than 10% as compared to a comparative method of treatment when measured in a comparison study.

Item 359. The oral dosage form of any one of items 341 to 358 for use in a method of treating pain, wherein the method prevents or reduces the formation of addiction, the occurrence of drug abuse, or the occurrence of recreational drug use.

Item 360. A method of preventing or reducing an adverse pharmacodynamic response of oxycodone observed in the treatment of pain with an amount of oxycodone alone, by instead administering the oral dosage form of any one of items 203 to 232 comprising the same amount of oxycodone.

Item 361. The method of item 360, wherein the adverse pharmacodynamic response is selected from the group consisting of euphoria, feeling high, bowel dysfunction, nausea, vomiting, somnolence, dizziness, respiratory depression, headache, dry mouth, sedation, sweats, asthenia, hypotension, dysphoria, delirium, miosis, pruritis, urticaria, urinary retention, hyperalgesia, allodynia, physical dependence and tolerance, preferably wherein the adverse pharmacodynamic response is selected from the group consisting of respiratory depression, euphoria, feeling high, and bowel dysfunction.

Item 362. The method of item 360, wherein the adverse pharmacodynamic response is euphoria.

Item 363. The method of item 360, wherein the adverse pharmacodynamic response is feeling high.

Item 364. A method of preventing or reducing drug liking of oxycodone observed in the treatment of pain with an amount of oxycodone alone, by instead administering the oral dosage form of any one of items 261 to 290 comprising the same amount of oxycodone.

Item 365. A method of preventing or reducing the formation of addiction, the occurrence of drug abuse, or the occurrence of recreational drug use by providing a dosage form of any one of items 261 to 290.

Item 366. Use of a dosage form of any one of items 261 to 290 in the prevention or reduction of the formation of addiction, the occurrence of drug abuse, or the occurrence of recreational drug use.

Item 367. A set of at least two oral dosage forms comprising oxycodone in different dosage strengths, wherein each of the dosage forms comprises
(i) an amount of oxycodone which is equimolar to
  a. about 10 mg of oxycodone hydrochloride (Mw=351.82 g/mol),
  b. about 15 mg of oxycodone hydrochloride (Mw=351.82 g/mol),
  c. about 20 mg of oxycodone hydrochloride (Mw=351.82 g/mol),
  d. about 30 mg of oxycodone hydrochloride (Mw=351.82 g/mol), or
  e. about 40 mg of oxycodone hydrochloride (Mw=351.82 g/mol); and
(ii) an amount of buprenorphine,
  wherein the weight ratio of the amount of buprenorphine to the amount of oxycodone
  is greater than 1:40 calculated with the amount of buprenorphine in the dosage form expressed as the equimolar amount of buprenorphine base (Mw=467.64 g/mol) in mg, and the amount of oxycodone in the dosage form expressed as the equimolar amount of oxycodone hydrochloride (Mw=351.82 g/mol) in mg, and
  has the same value for each dosage form of the set.

Item 368. The set of at least two oral dosage forms of item 367, wherein the weight ratio of the amount of buprenorphine to the amount of oxycodone is equal to or greater than about 1:38.

Item 369. The set of at least two oral dosage forms of item 367, wherein the weight ratio of the amount of buprenorphine to the amount of oxycodone is from about 1:3 to greater than 1:40, or from about 1:3 to about 1:38.

Item 370. The set of at least two oral dosage forms of item 367, wherein the weight ratio of the amount of buprenorphine to the amount of oxycodone is from about 1:4 to greater than 1:40, or from about 1:4 to about 1:38.

Item 371. The set of at least two oral dosage forms of item 367, wherein the weight ratio of the amount of buprenorphine to the amount of oxycodone is from about 1:5 to greater than 1:40, or from about 1:5 to about 1:38.

Item 372. The set of at least two oral dosage forms of item 367, wherein the weight ratio of the amount of buprenorphine to the amount of oxycodone is from about 1:5 to about 1:35, preferably from about 1:5 to about 1:30.

Item 373. The set of at least two oral dosage forms of item 367, wherein the weight ratio of the amount of buprenorphine to the amount of oxycodone is from about 1:6 to greater than 1:40, or from about 1:6 to about 1:38.

Item 374. The set of at least two oral dosage forms of item 367, wherein the weight ratio of the amount of buprenorphine to the amount of oxycodone is from about 1:6 to about 1:35, preferably from about 1:6 to about 1:30, more preferably from about 1:6 to about 1:28 or from about 1:6 to about 1:20.

Item 375. The set of at least two oral dosage forms of item 367, wherein the weight ratio of the amount of buprenorphine to the amount of oxycodone is from about 1:8 to about 1:30.

Item 376. The set of at least two oral dosage forms of item 367, wherein the weight ratio of the amount of buprenorphine to the amount of oxycodone is from about 1:8 to about 1:28.

Item 377. The set of at least two oral dosage forms of item 367, wherein the weight ratio of the amount of buprenorphine to the amount of oxycodone is from about 1:8 to about 1:20.

Item 378. The set of at least two oral dosage forms of item 367, wherein the weight ratio of the amount of buprenorphine to the amount of oxycodone is from about 1:8 to about 1:15.

Item 379. The set of at least two oral dosage forms of item 367, wherein the weight ratio of the amount of buprenorphine to the amount of oxycodone is from about 1:10 to about 1:20.

Item 380. The set of at least two oral dosage forms of item 367, wherein the weight ratio of the amount of buprenorphine to the amount of oxycodone is from about 1:10 to about 1:15.

Item 381. The set of at least two oral dosage forms of any one of items 367 to 380, wherein each of the dosage forms comprises oxycodone hydrochloride in an amount which is equimolar to one of the following amounts:
  a. about 10 mg of oxycodone hydrochloride (Mw=351.82 g/mol),
  b. about 15 mg of oxycodone hydrochloride (Mw=351.82 g/mol),
  c. about 20 mg of oxycodone hydrochloride (Mw=351.82 g/mol),
  d. about 30 mg of oxycodone hydrochloride (Mw=351.82 g/mol), or
  e. about 40 mg of oxycodone hydrochloride (Mw=351.82 g/mol).

Item 382. The set of at least two oral dosage forms of any one of item 367 to 380, wherein each of the dosage forms comprises oxycodone myristate in an amount which is equimolar to one of the following amounts:

a. about 10 mg of oxycodone hydrochloride (Mw=351.82 g/mol),
b. about 15 mg of oxycodone hydrochloride (Mw=351.82 g/mol),
c. about 20 mg of oxycodone hydrochloride (Mw=351.82 g/mol),
d. about 30 mg of oxycodone hydrochloride (Mw=351.82 g/mol), or
e. about 40 mg of oxycodone hydrochloride (Mw=351.82 g/mol).

Item 383. The set of at least two oral dosage forms of any one of items 367 to 382, wherein the set comprises
(1) a first dosage form comprising an amount of oxycodone which is equimolar to about 40 mg of oxycodone hydrochloride (Mw=351.82 g/mol), and an amount of buprenorphine which is equimolar to from about 1 mg to about 6 mg of buprenorphine base (Mw=467.64 g/mol); and
(2) at least one further dosage form comprising an amount of oxycodone which is equimolar to about 10 mg, about 15 mg, about 20 mg, or about 30 mg of oxycodone hydrochloride (Mw=351.82 g/mol).

Item 384. The set of at least two oral dosage forms of any one of items 367 to 382, wherein the set comprises
(1) a first dosage form comprising an amount of oxycodone which is equimolar to about 40 mg of oxycodone hydrochloride (Mw=351.82 g/mol), and an amount of buprenorphine which is equimolar to from about 2 mg to about 5 mg of buprenorphine base (Mw=467.64 g/mol); and
(2) at least one further dosage form comprising an amount of oxycodone which is equimolar to about 10 mg, about 15 mg, about 20 mg, or about 30 mg of oxycodone hydrochloride (Mw=351.82 g/mol).

Item 385. The set of at least two oral dosage forms of any one of items 367 to 380, 383 and 384, wherein the oxycodone is oxycodone hydrochloride and the buprenorphine is buprenorphine hydrochloride.

Item 386. The set of at least two oral dosage forms of any one of items 367 to 385, wherein each of the dosage forms comprises said amount of buprenorphine in immediate release form.

Item 387. The set of at least two oral dosage forms of any one of items 367 to 386, wherein each of the dosage forms comprises said amount of oxycodone in immediate release form and said amount of buprenorphine in immediate release form.

Item 388. The set of at least two oral dosage forms of any one of items 367 to 387, wherein each of the dosage forms is a liquid dosage form.

Item 389. The set of at least two oral dosage forms of item 388, wherein each of the dosage forms is in the same form selected from the group consisting of a solution, a suspension, or an emulsion, preferably a solution.

Item 390. The set of at least two oral dosage forms of any one of items 367 to 387, wherein each of the dosage forms is a solid dosage form.

Item 391. The set of at least two oral dosage forms of item 390, wherein each of the dosage forms is in the same form selected from a tablet or a capsule.

Item 392. The set of at least two oral dosage forms of any one of items 367 to 391, wherein after single-dose administration, each of the dosage forms provides in one group of subjects a ratio of the mean $C_{max}$ of buprenorphine to the mean $C_{max}$ of oxycodone of at least about 1:280.

Item 393. The set of at least two oral dosage forms of item 392, wherein the ratio of the mean $C_{max}$ of buprenorphine to the mean $C_{max}$ of oxycodone is at least about 1:250.

Item 394. The set of at least two oral dosage forms of item 392, wherein the ratio of the mean $C_{max}$ of buprenorphine to the mean $C_{max}$ of oxycodone is at least about 1:230.

Item 395. The set of at least two oral dosage forms of item 392, wherein the ratio of the mean $C_{max}$ of buprenorphine to the mean $C_{max}$ of oxycodone is at least about 1:200.

Item 396. The set of at least two oral dosage forms of item 392, wherein the ratio of the mean $C_{max}$ of buprenorphine to the mean $C_{max}$ of oxycodone is at least about 1:180.

Item 397. The set of at least two oral dosage forms of item 392, wherein the ratio of the mean $C_{max}$ of buprenorphine to the mean $C_{max}$ of oxycodone is from about 1:50 to about 1:280.

Item 398. The set of at least two oral dosage forms of item 392, wherein the ratio of the mean $C_{max}$ of buprenorphine to the mean $C_{max}$ of oxycodone is from about 1:50 to about 1:250.

Item 399. The set of at least two oral dosage forms of item 392, wherein the ratio of the mean $C_{max}$ of buprenorphine to the mean $C_{max}$ of oxycodone is from about 1:80 to about 1:230.

Item 400. The set of at least two oral dosage forms of item 392, wherein the ratio of the mean $C_{max}$ of buprenorphine to the mean $C_{max}$ of oxycodone is from about 1:100 to about 1:200.

Item 401. The set of at least two oral dosage forms of item 392, wherein the ratio of the mean $C_{max}$ of buprenorphine to the mean $C_{max}$ of oxycodone is from about 1:100 to about 1:180.

Item 402. The set of at least two oral dosage forms of any one of items 392 to 401, wherein after single-dose administration, each of the dosage forms further provides in said group of subjects a ratio of the mean $T_{max}$ of buprenorphine to the mean $T_{max}$ of oxycodone of equal to or less than about 1.5:1.

Item 403. The set of at least two oral dosage forms of item 402, wherein the ratio of the mean $T_{max}$ of buprenorphine to the mean $T_{max}$ of oxycodone is equal to or less than about 1.3:1.

Item 404. The set of at least two oral dosage forms of item 402, wherein the ratio of the mean $T_{max}$ of buprenorphine to the mean $T_{max}$ of oxycodone is equal to or less than about 1.1:1.

Item 405. The set of at least two oral dosage forms of item 402, wherein the ratio of the mean $T_{max}$, of buprenorphine to the mean $T_{max}$ of oxycodone is equal to or less than about 1:1.

Item 406. The set of at least two oral dosage forms of any one of items 392 to 401, wherein after single-dose administration, each of the the dosage forms further provides in said group of subjects a mean $T_{max}$ of buprenorphine that is earlier than the mean $T_{max}$ of oxycodone.

Item 407. The set of at least two oral dosage forms of any one of items 392 to 406, wherein after single-dose administration, each of the dosage forms further provides in said group of subjects a ratio of the mean $T_{max}$ of buprenorphine to the mean $T_{max}$ of oxycodone of from about 0.1:1 to about 1.5:1, preferably from about 0.1:1 to about 1.3:1, more preferably from about 0.1:1 to about 1.1:1, most preferably from about 0.1:1 to about 1:1 or from about 0.1:1 to about 0.9:1.

Item 408. The set of at least two oral dosage forms of any one of items 367 to 407, wherein the set comprises at least three, preferably at least four dosage forms comprising oxycodone in different dosage strengths.

Item 409. A method of treating pain comprising administering to a patient in need thereof an oral dosage form comprising
(i) an amount of oxycodone, and
(ii) an amount of buprenorphine,
wherein the mean $E_{max}$ of "feeling high VAS" is reduced by at least 15%, when measured in a comparison study, and/or
wherein the mean $E_{max}$ of "at the moment drug liking VAS" is reduced by at least 15%, when measured in a comparison study, and/or
wherein the mean $E_{max}$ of "overall drug liking VAS" is reduced by at least 15%, when measured in a comparison study, and/or
wherein the mean $E_{max}$ of "take drug again VAS" is reduced by at least 15%, when measured in a comparison study, and/or
wherein the mean "cold pain score VAS" measured in a cold pressor test at 1, 2, 3 and 4 hours after administration, does not increase more than 10% as compared to a comparative method of treatment when measured in a comparison study.

Item 410. A method of treating pain comprising a concurrent administration to a patient in need thereof of
(i) an amount of oxycodone, and
(ii) an amount of buprenorphine,
wherein the mean $E_{max}$ of "feeling high VAS" is reduced by at least 15%, when measured in a comparison study, and/or
wherein the mean $E_{max}$ of "at the moment drug liking VAS" is reduced by at least 15%, when measured in a comparison study, and/or
wherein the mean $E_{max}$ of "overall drug liking VAS" is reduced by at least 15%, when measured in a comparison study, and/or
wherein the mean $E_{max}$ of "take drug again VAS" is reduced by at least 15%, when measured in a comparison study, and/or
wherein the mean "cold pain score VAS" measured in a cold pressor test at 1, 2, 3 and 4 hours after administration, does not increase more than 10% as compared to a comparative method of treatment when measured in a comparison study.

Item 411. A method of treating pain comprising administering to a patient in need thereof an oral dosage form comprising
(i) an amount of oxycodone, and
(ii) an amount of buprenorphine,
wherein the mean $E_{max}$ of "feeling high VAS" is reduced by at least 35%, when measured in a comparison study, and/or
wherein the mean $E_{max}$ of "at the moment drug liking VAS" is reduced by at least 30%, when measured in a comparison study, and/or
wherein the mean $E_{max}$ of "overall drug liking VAS" is reduced by at least 30%, when measured in a comparison study, and/or
wherein the mean $E_{max}$ of "take drug again VAS" is reduced by at least 30%, when measured in a comparison study, and/or
wherein the mean "cold pain score VAS" measured in a cold pressor test at 1, 2, 3 and 4 hours after administration, does not increase more than 10% as compared to a comparative method of treatment when measured in a comparison study.

Item 412. A method of treating pain comprising a concurrent administration to a patient in need thereof of
(i) an amount of oxycodone, and
(ii) an amount of buprenorphine,
wherein the mean $E_{max}$ of "feeling high VAS" is reduced by at least 35%, when measured in a comparison study, and/or
wherein the mean $E_{max}$ of "at the moment drug liking VAS" is reduced by at least 30%, when measured in a comparison study, and/or
wherein the mean $E_{max}$ of "overall drug liking VAS" is reduced by at least 30%, when measured in a comparison study, and/or
wherein the mean $E_{max}$ of "take drug again VAS" is reduced by at least 30%, when measured in a comparison study, and/or
wherein the mean "cold pain score VAS" measured in a cold pressor test at 1, 2, 3 and 4 hours after administration, does not increase more than 10% as compared to a comparative method of treatment when measured in a comparison study.

Item 413. A method of treating pain, comprising administering to a patient in need thereof an oral dosage form comprising an amount of buprenorphine, preferably buprenorphine HCl, as the sole opioid analgesic.

Item 414. The method of item 413, wherein the amount of buprenorphine present in the dosage form is equimolar to from about 1 mg to about 40 mg of buprenorphine base (Mw=467.64 g/mol).

Item 415. The method of item 413, wherein the daily dose is an amount equimolar to from about 1 mg to about 40 mg of buprenorphine base (Mw=467.64 g/mol).

Item 416. The method of item 414, wherein the amount of buprenorphine present in the dosage form is equimolar to about 2.5 mg, about 5 mg, about 10 mg, about 15 mg, about 20 mg, about 30 mg or about 40 mg of buprenorphine base (Mw=467.64 g/mol).

Item 417. An oral dosage form comprising an amount of buprenorphine, preferably buprenorphine HCl, as the sole opioid analgesic.

Item 418. The dosage form of item 417, wherein buprenorphine is present in the dosage form in an amount equimolar to about 1 to about 40 mg of buprenorphine base (Mw=467.64 g/mol).

Item 419. The dosage form of item 418, wherein buprenorphine is present in the dosage form in an amount equimolar to about 2.5, about 5, about 10, about 15, about 20, about 30 and about 40 mg of buprenorphine base (Mw=467.64 g/mol).

Item 420. The dosage form of any one of items 417 to 419, wherein the dosage form comprises said amount of buprenorphine in immediate release form.

Item 421. The dosage form of item 420, wherein said dosage form is liquid, such as a solution, a suspension, or an emulsion.

Item 422. The dosage form of item 420, wherein said dosage form is solid, such as a tablet or a capsule.

Item 423. The method of any one of items 291 to 306, 323 to 340, 410 and 412, wherein said amount of oxycodone is administered orally and said amount of buprenorphine is administered transdermally.

Item 424. The method of any one of items 291 to 306, 323 to 340, 410 and 412, wherein said amount of oxycodone is administered orally and said amount of buprenorphine is administered subdermally.

Item 425. The method of item 423 or 424, wherein said amount of oxycodone is equimolar to from about 5 mg to about 50 mg of oxycodone hydrochloride (Mw=351.82 g/mol), preferably from about 5 mg to about 40 mg of oxycodone hydrochloride (Mw=351.82 g/mol).

Item 426. The method of item 423 or 424, wherein said amount of oxycodone is equimolar to about 10 mg, about 15 mg, about 20 mg, about 30 mg, or about 40 mg of oxycodone hydrochloride (Mw=351.82 g/mol).

Item 427. The method of any one of items 423 to 426, wherein the oxycodone is oxycodone hydrochloride and the buprenorphine is buprenorphine hydrochloride.

DETAILED DESCRIPTION OF THE PREFERRED EMBODIMENTS

The present invention is now described with reference to the accompanying examples. It should be understood, however, that the following description is illustrative only and should not be taken in any way as a restriction of the invention.

Example 1

Example 1 was a single-center, double-blind, placebo- and positive-controlled randomized, crossover study in 32 healthy male and female recreational opioid users to evaluate the abuse potential, the pain control and the pharmacokinetics of co-administered oxycodone hydrochloride and buprenorphine. Subjects received oral and transdermal treatments in each period in a randomized, double-blind, crossover design. The study was conducted in two iterations 1 and 2, each including 16 subjects, wherein in iteration 1 only 15 subjects completed and 1 subject discontinued for reasons unrelated to the study drugs. In iterations 1 and 2 abuse potential and the pharmacokinetics of co-administered oxycodone hydrochloride and buprenorphine were evaluated, in iteration 2 additionally pain control was evaluated. For the results regarding abuse potential and the pharmacokinetics of co-administered oxycodone hydrochloride and buprenorphine, the results of iterations 1 and 2 were combined resulting in N=32, whereas for pain control N=16 resulting only from iteration 2.

The study treatments were as follows:
Buprenorphine doses:
  Butrans®, 20 mcg/h, 20 mg (buprenorphine base, Mw=467.64 g/mol), patch, transdermal
  Butrans®, 0 mcg/h, 0 mg (Placebo patch), transdermal
Each buprenorphine dose was given with 3 oxycodone doses administered in random sequence:
  Oxycodone HCl (351.82 g/mol) IR (0 mg), (lactose powder) capsule, oral
  Oxycodone HCl (351.82 g/mol) IR (20 mg), oral tablet manufactured by ZyGenerics and overencapsulated for blinding purposes
  Oxycodone HCl (351.82 g/mol) IR (2×20 mg), oral tablet manufactured by ZyGenerics and overencapsulated for blinding purposes
Total of 6 treatments:
Placebo
OxyIR-20
OxyIR-40
Butrans-20
Butrans-20/OxyIR-20
Butrans-20/OxyIR-40

Subjects had a buprenorphine (Butrans 20 mcg/hour) or placebo transdermal patch applied for 108 hours in each period and then removed. In each period, Oxycodone IR or placebo was orally administered in a randomized design at 48, 72 and 96 hours post patch application. The administration scheme is summarized in FIG. 1.

Subject Selection

Healthy male and female recreational opioid users with a history of oral use, age 18 to 55 years, inclusive, with no clinically significant medical history, who are deemed suitable to take part in this clinical study by the investigator.

Following the screening phase, eligible subjects had a naloxone challenge test to exclude subjects who were physically dependent on opioids.

To qualify for the treatment phase, it was ensured that subjects with self-reported recreational opioid experience were able to tolerate and discriminate oxycodone IR and placebo as well as to report positive subjective effects of the drug in a controlled laboratory setting. In this phase "placebo responders", i.e., subjects who report subjective effects of placebo, were excluded.

Subjects meeting all the inclusion criteria and none of the exclusion criteria were randomized into the study.

Inclusion Criteria
1. Provide written informed consent.
2. Male or female subjects 18 to 55 years of age, inclusive.
3. Body mass index (BMI) within the range of 18.0 to 34.0 $kg/m^2$, inclusive, and a minimum weight of at least 50.0 kg at screening.
4. Moderately experienced opioid users who meet the following criteria: 1) have used opioids for nontherapeutic purposes (i.e., for psychoactive effects) on at least 10 occasions in the past year and 2) have used opioids at least 3 times in the 12 weeks prior to Screening.
5. Must report having taken a dose of opioid equivalent to 30 mg Oxycodone IR or higher on at least one occasion in the past year.
6. Heterosexually active females of childbearing potential must be using an adequate and reliable method of contraception during the study and through to at least 30 days after the last study drug administration. Heterosexually active females who are post-menopausal and not using approved contraception must have been post-menopausal ≥1 year and have an elevated serum follicle stimulating hormone (FSH) level (i.e., ≥50 mIU/mL).
7. Female subjects must have a negative pregnancy test at screening and/or admission.
8. Able to speak, read, and understand English sufficiently to understand the nature of the study, to provide written informed consent, and to allow completion of all study assessments.
9. Must be willing and able to abide by all study requirements and restrictions.

Exclusion Criteria
1. Clinically significant abnormality on physical examination, medical history, 12-lead electrocardiogram (ECG), vital signs, or laboratory values, as judged by the investigator or designee at screening.
2. Self-reported drug or alcohol dependence history (in the past 2 years) or subjects who have ever been in a drug rehabilitation program (other than treatment for smoking cessation or on a case-by-case basis; e.g. as a requirement for reduced incarceration or in lieu of incarceration for the use of marijuana only) or current drug or alcohol dependence (within the last 12 months; except nicotine or caffeine), as defined by the Diagnostic and Statistical Manual of Mental Disorders (DSM-IV).

3. History or presence of any clinically significant illness (e.g., cardiovascular, pulmonary, hepatic, renal, hematologic, gastrointestinal, endocrine, immunologic, dermatologic, neurologic, oncologic, musculoskeletal, or psychiatric) or any other condition, which in the opinion of the investigator would jeopardize the safety of the subject or the validity of the study results.
4. Any personal or family history of prolonged QT interval or disorders of cardiac rhythm.
5. Abnormal cardiac conditions including any of the following:
   QTcF interval >450 msec at screening
   QTcF interval >480 msec at check-in or noted during any ECGs during the treatment period.
6. History or presence of hypotension, judged to be clinically significant based on investigator or designee judgment.
7. Use of prohibited medications (i.e., non-prescription, prescription medications, herbal or natural health products).
8. Female subjects who are currently pregnant or lactating or who are planning to become pregnant during the study or within 30 days after last study drug administration.
9. Evidence of clinically significant hepatic or renal impairment including alanine aminotransferase (ALT) or aspartate aminotransferase (AST) >1.5× the upper limit of normal (ULN) or serum total bilirubin >10% above ULN.
10. History of severe allergic reaction (including anaphylaxis) to any food, medication, or bee sting or previous status asthmaticus.
11. History of allergy or hypersensitivity to oxycodone, buprenorphine, naloxone or related drugs (e.g., other opioids or opioid antagonists), or any of the drug excipients or other drug product components.
12. History of allergy to lactose.
13. Positive for Hepatitis B, Hepatitis C.
14. Whole blood donated within 56 days prior to entry into the qualification phase or through the EOS visit and for 30 days after completion of EOS visit, except as required by this protocol.
15. Plasma donated within 14 days prior to entry into the qualification phase or through the end of study (EOS) visit, except as required by this protocol.
16. Difficulty with venous access or unsuitable for or unwilling to undergo catheter insertion.
17. Treatment with any investigational drug within 30 days prior to first drug administration of the Naloxone Challenge.
18. Consumption of greater than 20 cigarettes per day on average, in the month prior to screening, or inability to abstain from smoking (or use of any nicotine-containing substance) for at least 18 hours.
19. Positive urine drug screen at screening and/or admission. Positive results may be repeated and/or subjects rescheduled at the Investigator's discretion. On a case-by-case basis, at the discretion of the Investigator, positive tetrahydrocannabinol (THC) may be acceptable for subjects examined (full or brief physical examination) and interviewed by a licensed medical doctor to verify that they are not under the influence of cannabinoids.
20. Any medical condition that in the opinion of the investigator would interfere with the study procedures or data integrity or compromise the safety of the subject.
21. A subject who, in the opinion of the investigator or designee, is considered unsuitable or unlikely to comply with the study protocol for any other reason.
22. Subjects who have allergies or other contraindications to transdermal systems or patch adhesives.
23. Clinically significant history of allergic reaction to wound dressings or elastoplast.
24. Subjects with a dermatological disorder at any relevant patch application site that precludes proper placement and/or rotation of patch.
25. Taking antihistamines within 72 hours prior to dosing or systemic or topical corticosteroids within 3 weeks prior to dosing.
26. Subjects who will not allow hair to be removed at the proposed patch application sites which may prevent proper placement of the patch.
27. Subjects with a history of frostbite or with any current injury or abnormalities to the nondominant hand, including abnormalities of the skin, circulation, or nervous system, if applicable.
28. Subjects who are deemed unsuitable by the investigator for any reason not described above (e.g., a safety concern for the subject or a concern regarding the scientific integrity of the study).

Naloxone Challenge Criteria

Clinical assessment of withdrawal signs and symptoms were based on the Objective Opioid Withdrawal Scale (OOWS) during the Naloxone Challenge test (Handelsman, L., Cochrane, K. J., Aronson, M. J. et al. (1987) Two New Rating Scales for Opiate Withdrawal, American Journal of Alcohol Abuse, 13, 293-308). Subjects were excluded from further participation in this study if their OOWS score is ≥3, unless in the opinion of the medical investigator the symptoms present were not related to opioid withdrawal.

Qualification Criteria

The Pharmacodynamic assessments ensured appropriate placebo and baseline responses and screened out subjects who did not demonstrate a consistent discrimination between Oxycodone IR and placebo. In addition, the assessments did demonstrate that subjects were able to complete and feel comfortable with the procedures, follow directions, and be cooperative.

Subjects had to pass the following qualification criteria to be eligible to enter the Treatment Phase:

Peak score ($E_{max}$) in response to manipulated Oxycodone IR greater than that of placebo on 'at the moment' Drug Liking VAS (difference of at least 15 points on this bipolar scale), Take Drug Again VAS (difference of at least 15 points on this bipolar scale), and Overall Drug Liking VAS (difference of at least 10 points on this bipolar scale). A peak score of ≥65 must be indicated on 'at the moment' Drug Liking VAS and ≥65 on Overall Drug Liking VAS and Take Drug Again VAS in response to Oxycodone IR.

Acceptable placebo response on Drug Liking VAS, Overall Drug Liking VAS, and Take Drug Again VAS (i.e., scores between 40 to 60, inclusive) and on High VAS, defined as a peak score between 0 to 10, inclusive.

The ability to tolerate oxycodone, as judged by the investigator or designated sub-investigator based on available safety data.

General behavior suggestive that they could successfully complete the study, as judged by the clinic staff.

Eligible subjects who appeared to have difficulty differentiating between bipolar and unipolar scales (e.g., making errors such as selecting 50 as neutral for a unipolar scale) did undergo additional practice training on the difference between the two scale types.

A cold pressor test (Iteration 2) was administered 5 times on each dosing day, and subjects who did not show adequate reduced pain following active drug compared to placebo were excluded from the Treatment Phase.

Removal of Subject from Study Participation

Subjects were informed that they are free to discontinue from the study at any time and for any reason. The investigator was allowed to remove a subject from the study if, in the investigator's opinion, it was not in the best interest of the subject to continue in the study. Subjects could have discontinued due to a change in compliance with inclusion/exclusion criteria that is clinically relevant and affects subject safety, occurrence of adverse events (AEs), or ingestion of protocol prohibited concomitant medication that might affect subject safety or study assessments/objectives. Notification of discontinuation was made to the sponsor (or designee).

In case of premature discontinuation of study participation, every effort was made to perform all end-of-study assessments. All subjects who prematurely discontinued were followed for ongoing and newly occurring AEs as described in section 10.

For subjects who discontinued the study prematurely due to an AE, per the United States Food and Drug Administration's (FDA's) Guidance for Industry-Premarketing Risk Assessment (March 2005)8, copies of relevant hospital records, autopsy reports, biopsy reports, and radiological reports related to the event were obtained, when feasible.

Reasons for screen failure consisted of the following:
The subject does not meet all the inclusion or meets any exclusion criteria—the criteria will be recorded; or
Subject's choice (the subject chooses for personal reasons to withdraw from the study, eg, family emergency precluding the subject from continuing in the study, relocation of the subject, or a new work schedule which precludes the subject from further study participation); or
Lost-to-follow-up (the study site personnel lose contact with the subject); or
Adverse Event or Serious Adverse Event (if an AE or SAE causes a subject to withdraw from the study); or
Administrative reason (the subject discontinues from study early for any logistical, nonmedical reason that is associated with either the clinical site or sponsor, eg, the sponsor stops the study or the clinical site is no longer able or is no longer approved to conduct the study).

Reasons for discontinuation from the study consisted of the following:
Adverse event (if an adverse event causes a subject to withdraw from the study), or
Subject's choice (the subject chooses for personal reasons, to withdraw from the study, e.g., family emergency precluding the subject from continuing in the study, relocation of the subject, or a new work schedule which precludes the subject from further study participation), or
Lost-to-follow-up (the study site personnel lose contact with the subject). Once suspecting the subject is lost, the study site must attempt to contact the subject by phone, making at least 3 documented attempts, each at least 1 week apart. Additionally, 1 registered letter must have been sent with a copy on file. The study site should only deem the subject as lost-to-follow-up no less than 30 days following the first documented phone call attempt, unless circumstances preclude this (eg, phone service has been discontinued, or there is other evidence that contact is not feasible), or
Confirmed or suspected diversion, or
Administrative reason (the subject discontinues from study early for any logistical, nonmedical reason that is associated with either the clinical site or sponsor, eg, the sponsor stops the study or the clinical site is no longer able or no longer approved to conduct the study).

If the subject discontinued due to subject's choice, administrative, or lost to follow-up reasons, the specific circumstances surrounding the discontinuation had to be recorded.

Administration

In each treatment period, subjects received both oral and transdermal treatments.

In an oral treatment subjects were administered the study drug with 240 mL of water preceded by an overnight fast (ie, at least 10 hours) from food, and was followed by a 4-hour fast (not including water). A mouth check was performed to verify that the doses administered were swallowed.

In a transdermal treatment, subjects had transdermal patches applied to one of the following approved sites:
upper outer arm
upper chest
upper back
side of the chest These 4 sites (located on both sides of the body) provide 8 possible application sites. Specific instructions for patch preparation, application and removal were provided in the pharmacy manual and Site Operations Manual.

Collection and Analysis of Blood Samples

Blood samples for determining plasma concentrations of oxycodone and buprenorphine were obtained for each subject during each period at the following timepoints: Relative to each oral study drug administration: −1.0, and at 0 (10 min prior to dosing) 0.25, 0.5, 1, 1.5, 2, 2.5, 3, 4, 6, 8, and 12 hours.

Buprenorphine and Oxycodone concentrations were quantified from 200 µL of human plasma using Buprenorphine-d4 and oxycodone-d3 as the internal standards. Samples were extracted using a liquid-liquid extraction (LLE) method. Extracts were chromatographed under normal phase conditions on a Luna® Silica HPLC column (2×50 mm, 3 µm) using a gradient system with 0.2% formic acid in aqueous 20 mM ammonium formate and 0.1% formic acid in acetonitrile. Buprenorphine and Oxycodone were detected and quantified by tandem mass spectrometry in a positive ion mode on a MDS Sciex API 5000™ equipped with a Turbo Ionspray interface. The quantitation linear range for buprenorphine and oxycodone were from 25-12,500 µg/mL and 100-50,000 µg/mL, respectively.

Abuse Potential Test

The primary measures were "at the moment" Drug Liking visual analog scale (VAS, bipolar) anchored at "0=Strong Disliking", "50=Neither like nor dislike" and "100=Strong liking"), Overall Drug Liking VAS anchored at "0=Strong Disliking", "50=Neither like nor dislike" and "100=Strong liking", and Take Drug Again VAS anchored at "0=Definitely not", "50=Neutral" and "100=Definitely so". A Secondary measure was Feeling High VAS anchored at "0=Not at all" and "100=Extremely". All subjective measures were administered as 100-point VAS. Conclusions regarding relative abuse potential did take into account responses on all primary and secondary measures listed below:

Balance of effects:
- 'At the Moment' Drug Liking VAS (Emax)
- Overall Drug Liking VAS (Emax)
- Take Drug Again VAS (Emax)
- Positive/euphoric subjective effects
- Mean Feeling High VAS (Emax)

Pain Control Test, Cold Pressor Test

The cold pressor test (CPT) was performed using a circulating water bath capable of sustaining water temperatures between 0-2° C. and accommodating an adult's hand submerged to the wrist. The temperature was set to within the range of 0-2° C., ideally 1° C.

An excursion of more than 2° was avoided because that may affect the pain experienced by the subject.

The nondominant hand was preferred, however, the dominant hand may have been used if necessary. Using a skin marker or similar pen, staff members marked a line on the subject's wrist at the distal aspect of the radius and ulna. Subjects were sitting or standing for the test and were instructed to immerse their hand quickly into the water bath, up to the line marked on their wrist. Subjects were instructed to keep their hand open, relaxed, and immersed until the pain becomes excruciating. The maximum duration of hand immersion was 2 minutes. Subjects were instructed that they may remove their hand from the water at any time and that they should not keep their hand in the water if they find the pain intolerable. The duration of hand immersion was measured from the moment of complete immersion until the subject removed his or her hand from the water bath. The start time and the duration in seconds was recorded in the source documents.

The subject rated the level of pain every 15 seconds until the hand was withdrawn from the bath or maximum time for immersion was met on a 100-mm visual analog scale (VAS) anchored at "0=no pain" and "100=maximum pain". The VAS was used at all-time points.

Results

TABLE 1

Oxycodone mean plasma concentration versus time following single oral administration of 20 mg oxycodone IR from both iterations.
Oxy IR 20 mg n = 32

| Time (h) | Mean (ng/mL) | SD |
|---|---|---|
| −1 | 0.529 | 0.809 |
| 0 | 0.465 | 0.723 |
| 0.25 | 0.453 | 0.685 |
| 0.5 | 13.523 | 14.463 |
| 1 | 32.616 | 12.704 |
| 1.5 | 29.891 | 9.051 |
| 2 | 27.594 | 8.867 |
| 2.5 | 25.351 | 7.703 |
| 3 | 23.700 | 6.711 |
| 4 | 20.916 | 4.924 |
| 6 | 17.539 | 6.307 |
| 8 | 12.698 | 5.812 |
| 12 | 5.704 | 2.847 |

Figure 2:
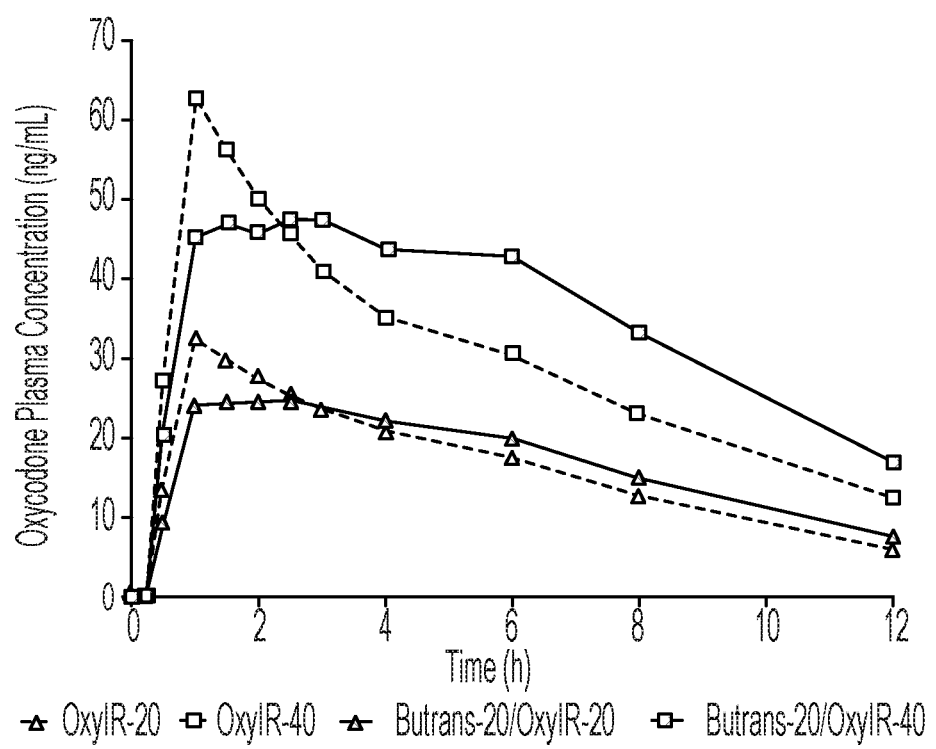
FIG. 2 depicts the results of Example 1 (oxycodone mean plasma concentration versus time following single oral administration of oxycodone and combined oral administration of oxycodone and transdermal administration of buprenorphine).

The result of table 1 is also presented in FIG. 2.

TABLE 2

Oxycodone mean plasma concentration versus time following single oral administration of 40 mg oxycodone IR from both iterations.
Oxy IR 40 mg n = 32

| Time (h) | Mean (ng/mL) | SD |
|---|---|---|
| −1 | 0.376 | 0.600 |
| 0 | 0.315 | 0.541 |
| 0.25 | 0.407 | 0.761 |
| 0.5 | 27.131 | 20.300 |
| 1 | 62.572 | 20.764 |
| 1.5 | 56.294 | 21.170 |
| 2 | 49.994 | 19.170 |
| 2.5 | 45.841 | 17.481 |
| 3 | 41.024 | 14.841 |
| 4 | 35.169 | 11.467 |
| 6 | 30.353 | 10.815 |
| 8 | 22.918 | 9.766 |
| 12 | 12.333 | 7.532 |

The result of table 2 is also presented in FIGS. 2 and 16.

TABLE 3

Oxycodone mean plasma concentration versus time following combined oral administration of 20 mg oxycodone IR and transdermal administration of buprenorphine (20 mg patch) from both iterations.
Butrans 20 mg/Oxy IR 20 mg n = 31

| Time (h) | Mean (ng/mL) | SD |
|---|---|---|
| −1 | 0.941 | 1.864 |
| 0 | 0.829 | 1.667 |
| 0.25 | 0.794 | 1.565 |
| 0.5 | 9.481 | 9.485 |
| 1 | 24.120 | 16.399 |
| 1.5 | 24.520 | 14.780 |
| 2 | 24.613 | 12.243 |
| 2.5 | 24.736 | 10.833 |
| 3 | 23.894 | 9.488 |
| 4 | 22.220 | 8.627 |
| 6 | 19.870 | 8.034 |
| 8 | 14.857 | 6.916 |
| 12 | 7.492 | 3.894 |

The result of table 3 is also presented in FIG. 2.

TABLE 4

Oxycodone mean plasma concentration versus time following combined oral administration of 40 mg oxycodone IR and transdermal administration of buprenorphine (20 mg patch) from both iterations.
Butrans 20 mg/Oxy IR 40 mg n = 29

| Time (h) | Mean (ng/mL) | SD |
|---|---|---|
| −1 | 0.526 | 0.852 |
| 0 | 0.460 | 0.769 |
| 0.25 | 0.476 | 0.763 |
| 0.5 | 20.505 | 22.606 |
| 1 | 45.301 | 27.348 |
| 1.5 | 46.996 | 24.052 |
| 2 | 45.693 | 20.030 |
| 2.5 | 47.438 | 17.809 |
| 3 | 47.531 | 15.172 |
| 4 | 43.600 | 14.624 |

TABLE 4-continued

Oxycodone mean plasma concentration versus time following combined oral administration of 40 mg oxycodone IR and transdermal administration of buprenorphine (20 mg patch) from both iterations.
Butrans 20 mg/Oxy IR 40 mg n = 29

| Time (h) | Mean (ng/mL) | SD |
|---|---|---|
| 6 | 42.928 | 14.782 |
| 8 | 33.169 | 12.560 |
| 12 | 16.862 | 7.303 |

The result of table 4 is also presented in FIG. 2.

TABLE 5

Buprenorphine mean plasma concentration versus time following single transdermal administration of buprenorphine (20 mg patch).
Butrans 20/Placebo IR n = 31

| Time (h) | Mean (ng/mL) | SD |
|---|---|---|
| −1 | 0.286 | 0.132 |
| 0 | 0.272 | 0.125 |
| 0.25 | 0.266 | 0.114 |
| 0.5 | 0.273 | 0.125 |
| 1 | 0.272 | 0.120 |
| 1.5 | 0.269 | 0.112 |
| 2 | 0.276 | 0.116 |
| 2.5 | 0.280 | 0.121 |
| 3 | 0.274 | 0.116 |
| 4 | 0.280 | 0.122 |
| 6 | 0.263 | 0.111 |
| 8 | 0.263 | 0.105 |
| 12 | 0.285 | 0.112 |

Figure 4:
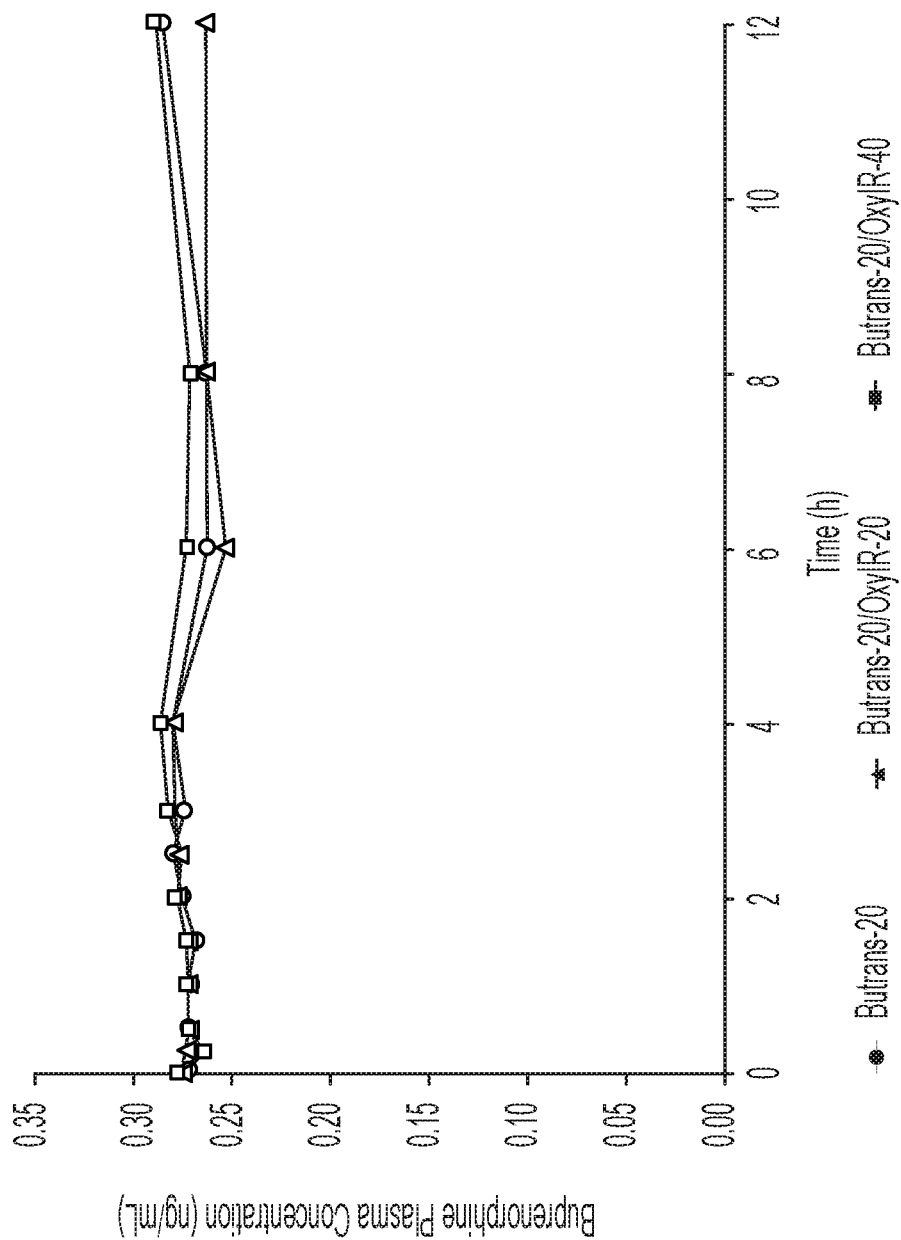
FIG. 4 depicts the results of Example 1 (buprenorphine mean plasma concentration versus time following single transdermal administration of buprenorphine and combined transdermal administration of buprenorphine and oral administration of oxycodone).

The result of table 5 is also presented in FIGS. 3, 4 and 16.

TABLE 6

Buprenorphine mean plasma concentration versus time combined transdermal administration of buprenorphine (20 mg patch) and oral administration of oxycodone (20 mg IR).
Butrans 20 mg/Oxy IR 20 mg n = 31

| Time (h) | Mean (ng/mL) | SD |
|---|---|---|
| −1 | 0.287 | 0.130 |
| 0 | 0.275 | 0.123 |
| 0.25 | 0.273 | 0.123 |
| 0.5 | 0.272 | 0.121 |
| 1 | 0.273 | 0.117 |
| 1.5 | 0.273 | 0.119 |
| 2 | 0.279 | 0.124 |
| 2.5 | 0.276 | 0.124 |
| 3 | 0.279 | 0.119 |
| 4 | 0.280 | 0.125 |
| 6 | 0.254 | 0.097 |
| 8 | 0.263 | 0.100 |
| 12 | 0.262 | 0.095 |

The result of table 6 is also presented in FIG. 4.

TABLE 7

Buprenorphine mean plasma concentration versus time combined transdermal administration of buprenorphine (20 mg patch) and oral administration of oxycodone (40 mg IR).
Butrans 20 mg/Oxy IR 40 mg n = 31

| Time (h) | Mean (ng/mL) | SD |
|---|---|---|
| −1 | 0.278 | 0.115 |
| 0 | 0.278 | 0.113 |
| 0.25 | 0.265 | 0.115 |
| 0.5 | 0.272 | 0.113 |
| 1 | 0.273 | 0.112 |
| 1.5 | 0.273 | 0.114 |
| 2 | 0.279 | 0.121 |
| 2.5 | 0.275 | 0.112 |
| 3 | 0.283 | 0.122 |
| 4 | 0.287 | 0.126 |
| 6 | 0.273 | 0.110 |
| 8 | 0.271 | 0.114 |
| 12 | 0.289 | 0.125 |

The result of table 7 is also presented in FIG. 4.

TABLE 8

Summary of oxycodone pharmacokinetic results.

| | Mean Cmax (ng/mL) | SD | Mean Tmax (h) | SD |
|---|---|---|---|---|
| OxyIR-20 (N = 32) | 35.403 | 13.299 | 1.797 | 1.570 |
| OxyIR-40 (N = 32) | 67.088 | 19.249 | 1.766 | 1.576 |
| Butrans-20/OxyIR-20 (N = 31) | 33.339 | 10.927 | 3.177 | 2.271 |
| Butrans-20/OxyIR-40 (N = 31) | 60.068 | 23.524 | 3.183 | 2.329 |

TABLE 9

Summary of buprenorphine pharmacokinetic results.

| | Mean Cmax (ng/mL) | SD | Mean Tmax (h) | SD |
|---|---|---|---|---|
| Butrans-20 | 0.319 | 0.133 | 5.532 | 4.959 |
| Butrans-20/OxyIR-20 | 0.317 | 0.125 | 5.129 | 4.485 |
| Butrans-20/OxyIR-40 | 0.324 | 0.134 | 5.661 | 4.383 |

Pain Control Result of Iteration 2

TABLE 10

Mean Cold Pain Score by Time: 0 hour (prior to oral dosing)
Mean cold pain score by time: 0 hour (prior to oral dosing)

| Time (sec) | Placebo N = 16 | SD | OxyIR-20 N = 16 | SD | OxyIR-40 N = 16 | SD |
|---|---|---|---|---|---|---|
| 15 | 30.375 | 25.796 | 28.750 | 24.797 | 29.000 | 24.339 |
| 30 | 48.188 | 26.898 | 49.000 | 28.083 | 49.688 | 25.829 |
| 45 | 64.500 | 27.166 | 65.063 | 28.748 | 66.688 | 25.578 |
| 60 | 80.438 | 23.978 | 75.813 | 27.694 | 79.750 | 23.606 |

TABLE 10-continued

Mean Cold Pain Score by Time: 0 hour (prior to oral dosing)
Mean cold pain score by time: 0 hour (prior to oral dosing)

| | | | | | |
|---|---|---|---|---|---|
| 75 | 89.000 | 18.250 | 88.375 | 18.966 | 89.438 | 17.682 |
| 90 | 98.938 | 2.909 | 96.875 | 9.831 | 98.250 | 4.837 |
| 105 | 99.938 | 0.250 | 98.750 | 5.000 | 99.500 | 2.000 |
| 120 | 100.000 | 0.000 | 99.375 | 2.500 | 100.000 | 0.000 |

| Time (sec) | Butrans-20 N = 16 | SD | Butrans-20/ OxyIR-20 N = 16 | SD | Butrans-20/ OxyIR-40 N = 14 | SD |
|---|---|---|---|---|---|---|
| 15 | 24.500 | 20.229 | 25.125 | 22.536 | 19.500 | 16.104 |
| 30 | 38.250 | 21.742 | 36.875 | 25.044 | 34.286 | 21.766 |
| 45 | 54.063 | 29.655 | 52.188 | 28.119 | 49.357 | 31.132 |
| 60 | 62.750 | 30.944 | 63.188 | 30.965 | 59.643 | 35.976 |
| 75 | 75.813 | 30.387 | 77.250 | 30.006 | 66.714 | 36.152 |
| 90 | 80.500 | 28.336 | 87.188 | 22.266 | 78.357 | 29.791 |
| 105 | 84.563 | 27.154 | 92.063 | 18.542 | 83.571 | 28.224 |
| 120 | 88.063 | 25.473 | 94.125 | 15.148 | 85.857 | 25.813 |

Figure 11:
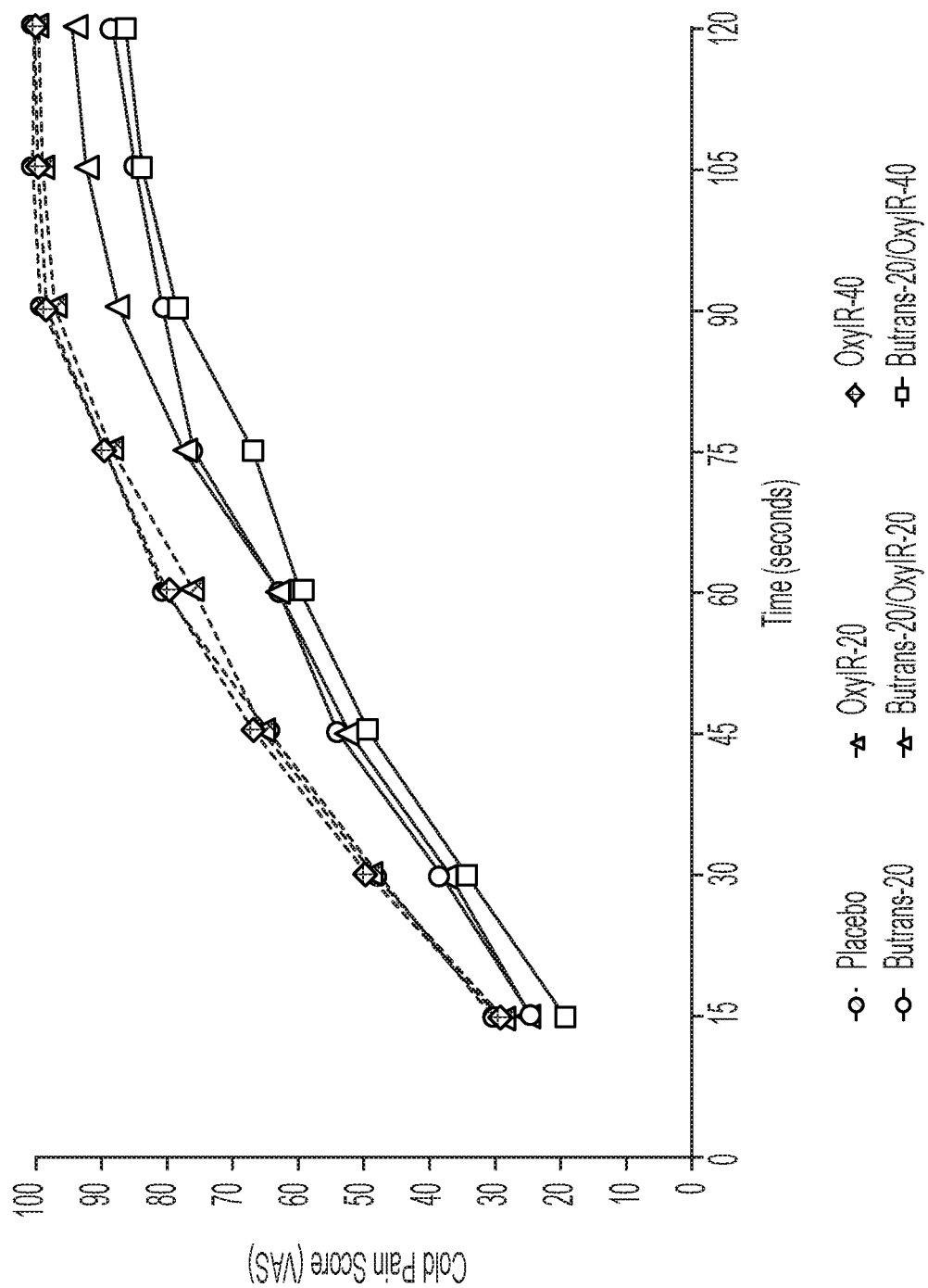
FIG. 11 depicts the results of Example 1 (iteration 2) and all 6 treatments (mean cold pain score by time: 0 hour—prior to oral dosing).

The result of table 10 is also presented in FIG. 11.

TABLE 11

Mean Cold Pain Score by Time: 1 hour.
Mean cold pain score by time: 1 hour

| Time (sec) | Placebo N = 16 | SD | OxyIR-20 N = 16 | SD | OxyIR-40 N = 16 | SD |
|---|---|---|---|---|---|---|
| 15 | 30.563 | 25.004 | 18.813 | 14.927 | 15.625 | 15.435 |
| 30 | 51.750 | 26.552 | 33.625 | 20.251 | 23.125 | 17.925 |
| 45 | 68.375 | 27.931 | 50.375 | 27.242 | 31.938 | 22.422 |
| 60 | 79.625 | 26.412 | 61.938 | 26.923 | 41.313 | 29.599 |
| 75 | 91.625 | 18.994 | 69.813 | 24.468 | 48.750 | 30.976 |
| 90 | 95.188 | 15.698 | 82.875 | 22.181 | 56.813 | 32.927 |
| 105 | 99.875 | 0.500 | 86.000 | 20.675 | 66.125 | 35.119 |
| 120 | 100.000 | 0.000 | 90.250 | 19.932 | 69.000 | 35.064 |

| Time (sec) | Butrans-20 N = 16 | SD | Butrans-20/ OxyIR-20 N = 16 | SD | Butrans-20/ OxyIR-40 N = 14 | SD |
|---|---|---|---|---|---|---|
| 15 | 25.000 | 22.636 | 21.875 | 22.175 | 16.071 | 17.336 |
| 30 | 36.563 | 23.082 | 32.438 | 21.655 | 21.714 | 19.420 |
| 45 | 50.188 | 26.116 | 45.500 | 24.345 | 29.786 | 22.029 |
| 60 | 61.875 | 29.154 | 57.500 | 28.946 | 37.714 | 25.778 |
| 75 | 70.563 | 28.057 | 67.188 | 29.530 | 45.714 | 31.190 |
| 90 | 82.500 | 24.350 | 81.500 | 29.947 | 52.714 | 35.582 |
| 105 | 86.250 | 22.296 | 84.625 | 28.345 | 57.357 | 37.749 |
| 120 | 88.813 | 19.654 | 86.500 | 27.122 | 60.357 | 38.973 |

Figure 12:
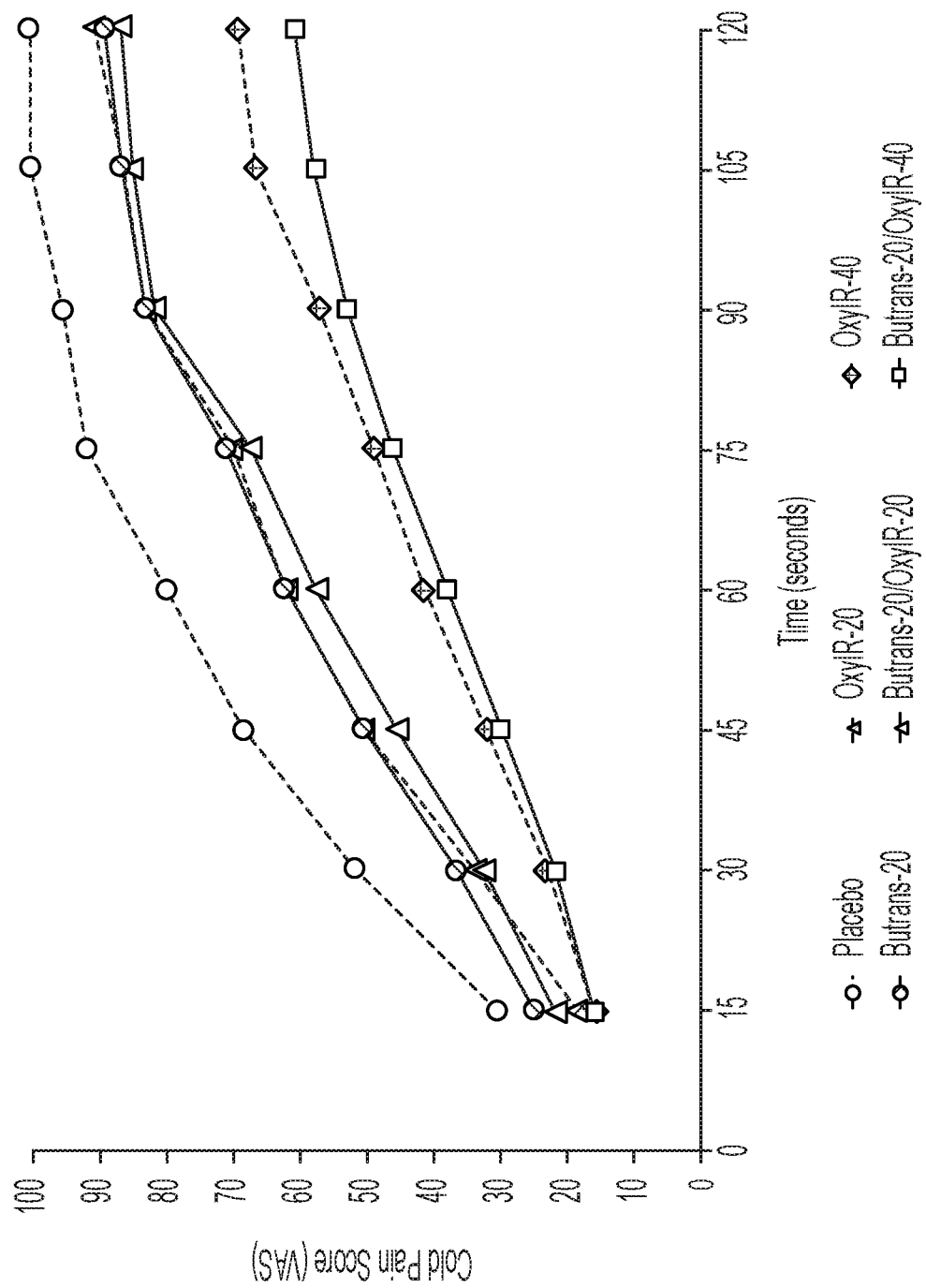
FIG. 12 depicts the results of Example 1 (iteration 2) and all 6 treatments (mean cold pain score by time: 1 hour).

The result of table 11 is also presented in FIG. 12.

TABLE 12

Mean Cold Pain Score by Time: 2 hours.
Mean cold pain score by time: 2 hours

| Time (sec) | Placebo N = 16 | SD | OxyIR-20 N = 16 | SD | OxyIR-40 N = 16 | SD |
|---|---|---|---|---|---|---|
| 15 | 33.250 | 24.659 | 19.563 | 16.801 | 12.938 | 12.266 |
| 30 | 54.313 | 28.439 | 30.688 | 18.460 | 22.063 | 15.190 |
| 45 | 68.750 | 27.312 | 43.500 | 22.583 | 32.688 | 22.691 |
| 60 | 81.125 | 22.727 | 56.500 | 27.679 | 41.875 | 26.976 |
| 75 | 96.188 | 7.494 | 65.188 | 26.334 | 49.188 | 28.566 |
| 90 | 98.938 | 2.909 | 73.125 | 27.205 | 57.375 | 31.644 |

TABLE 12-continued

Mean Cold Pain Score by Time: 2 hours.
Mean cold pain score by time: 2 hours

| | | | | | | |
|---|---|---|---|---|---|---|
| 105 | 99.938 | 0.250 | 78.125 | 26.648 | 69.375 | 32.964 |
| 120 | 99.938 | 0.250 | 82.188 | 27.605 | 72.938 | 33.065 |

| Time (sec) | Butrans-20 N = 16 | SD | Butrans-20/ OxyIR-20 N = 16 | SD | Butrans-20/ OxyIR-40 N = 14 | SD |
|---|---|---|---|---|---|---|
| 15 | 22.875 | 25.113 | 16.750 | 15.390 | 14.071 | 15.760 |
| 30 | 33.250 | 28.177 | 26.625 | 17.297 | 19.286 | 19.205 |
| 45 | 45.188 | 34.210 | 38.875 | 19.245 | 26.571 | 23.300 |
| 60 | 53.563 | 38.575 | 52.125 | 25.781 | 33.286 | 27.550 |
| 75 | 59.563 | 40.980 | 63.563 | 30.913 | 39.786 | 31.499 |
| 90 | 68.688 | 41.130 | 71.500 | 33.303 | 45.786 | 34.608 |
| 105 | 71.875 | 42.363 | 77.313 | 33.736 | 51.857 | 38.544 |
| 120 | 73.500 | 42.729 | 79.813 | 33.465 | 56.000 | 39.329 |

Figure 13:
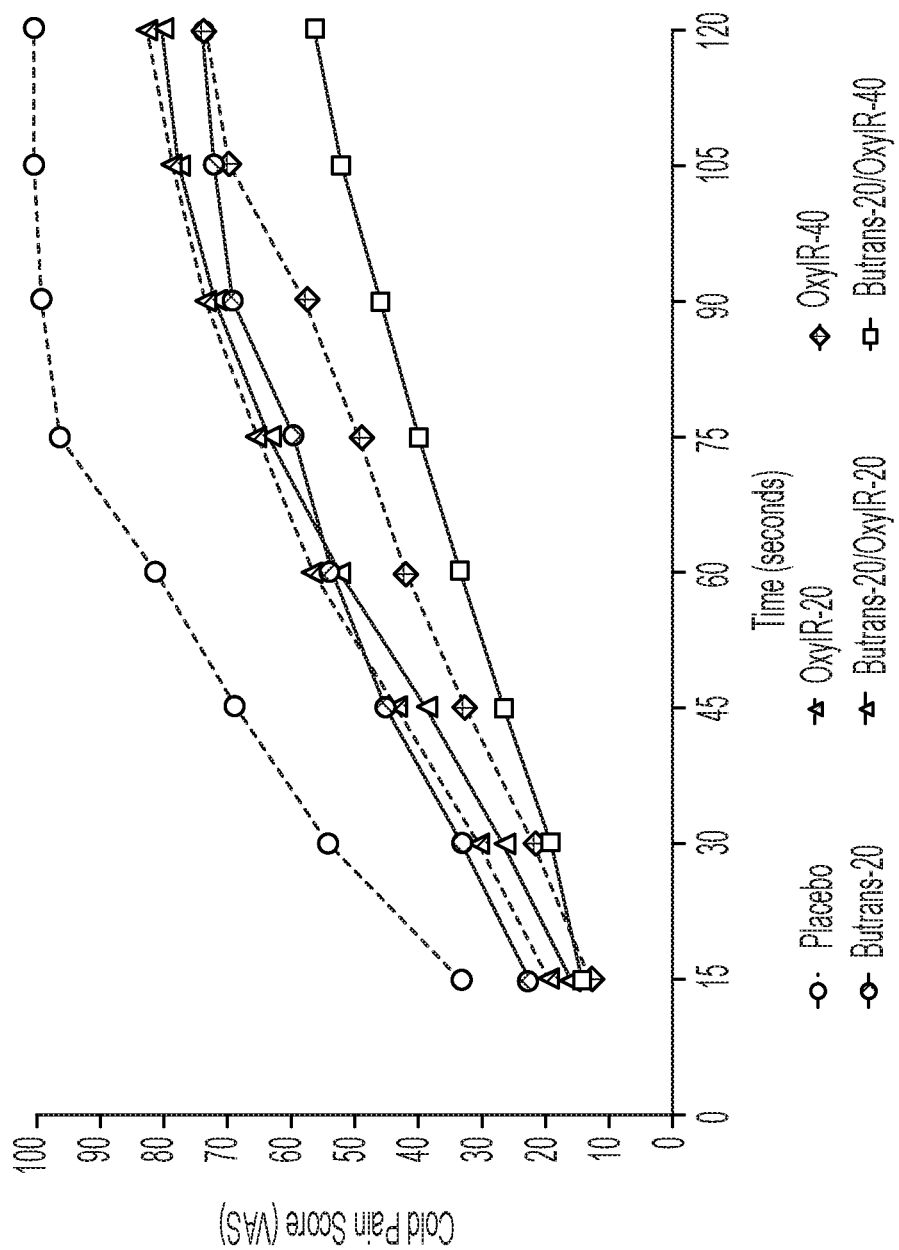
FIG. 13 depicts the results of Example 1 (iteration 2) and all 6 treatments (mean cold pain score by time: 2 hours).

The result of table 12 is also presented in FIG. 13.

TABLE 13

Mean Cold Pain Score by Time: 3 hours.
Mean cold pain score by time: 3 hours

| Time (sec) | Placebo N = 16 | SD | OxyIR-20 N = 16 | SD | OxyIR-40 N = 16 | SD |
|---|---|---|---|---|---|---|
| 15 | 32.313 | 23.329 | 20.563 | 17.359 | 16.750 | 12.646 |
| 30 | 54.625 | 27.592 | 34.250 | 22.317 | 25.625 | 15.995 |
| 45 | 69.313 | 25.458 | 50.125 | 26.904 | 37.688 | 20.908 |
| 60 | 82.813 | 20.299 | 60.875 | 25.610 | 48.125 | 24.055 |
| 75 | 92.250 | 15.914 | 70.188 | 22.382 | 60.938 | 26.639 |
| 90 | 98.625 | 3.775 | 81.563 | 22.827 | 74.875 | 26.800 |
| 105 | 99.813 | 0.750 | 88.813 | 21.173 | 81.938 | 25.339 |
| 120 | 99.813 | 0.750 | 90.500 | 20.255 | 87.813 | 22.477 |

| Time (sec) | Butrans-20 N = 16 | SD | Butrans-20/ OxyIR-20 N = 16 | SD | Butrans-20/ OxyIR-40 N = 14 | SD |
|---|---|---|---|---|---|---|
| 15 | 24.938 | 25.785 | 17.938 | 16.307 | 15.214 | 15.616 |
| 30 | 36.500 | 28.071 | 28.688 | 17.427 | 22.357 | 18.274 |
| 45 | 47.875 | 32.658 | 41.438 | 21.329 | 30.357 | 21.059 |
| 60 | 61.875 | 37.067 | 56.375 | 27.758 | 36.143 | 24.788 |
| 75 | 68.000 | 37.667 | 67.750 | 31.731 | 43.571 | 28.319 |
| 90 | 72.000 | 38.269 | 75.563 | 32.851 | 56.000 | 34.728 |
| 105 | 74.938 | 37.830 | 81.938 | 33.133 | 62.000 | 36.484 |
| 120 | 76.375 | 37.382 | 84.438 | 33.361 | 67.500 | 37.348 |

Figure 14:
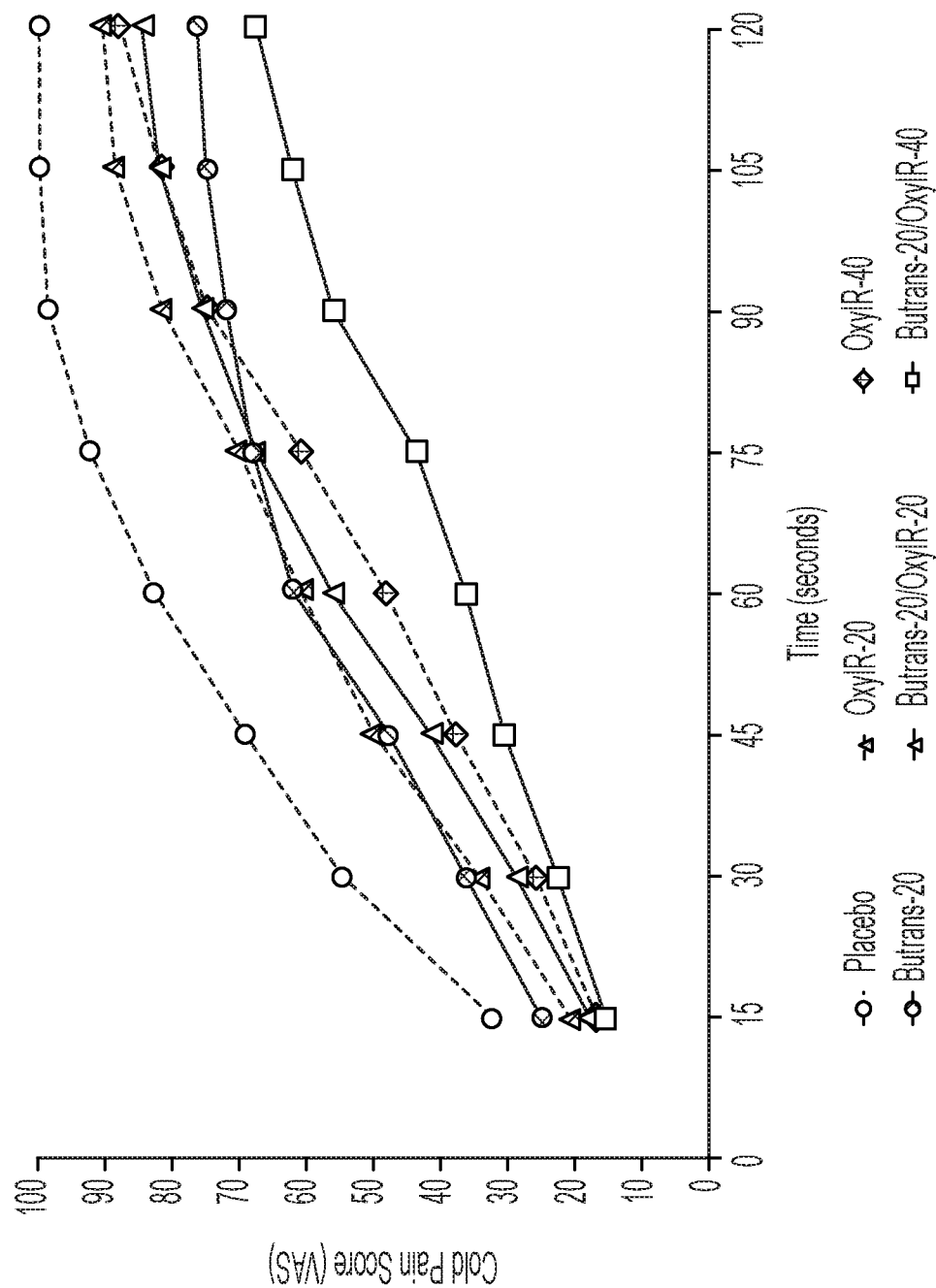
FIG. 14 depicts the results of Example 1 (iteration 2) and all 6 treatments (mean cold pain score by time: 3 hours).

The result of table 13 is also presented in FIG. 14.

TABLE 14

Mean Cold Pain Score by Time: 4 hours
Mean cold pain score by time: 4 hours

| Time (sec) | Placebo N = 16 | SD | OxyIR-20 N = 16 | SD | OxyIR-40 N = 16 | SD |
|---|---|---|---|---|---|---|
| 15 | 33.313 | 24.341 | 21.938 | 16.089 | 19.938 | 13.820 |
| 30 | 54.375 | 28.909 | 36.250 | 18.614 | 31.313 | 14.961 |
| 45 | 68.250 | 26.264 | 54.125 | 25.298 | 48.563 | 25.171 |
| 60 | 81.188 | 22.918 | 66.938 | 28.151 | 58.250 | 25.112 |
| 75 | 88.750 | 20.417 | 77.375 | 25.745 | 71.188 | 27.147 |
| 90 | 96.125 | 12.252 | 84.063 | 23.314 | 82.313 | 24.600 |

TABLE 14-continued

Mean Cold Pain Score by Time: 4 hours
Mean cold pain score by time: 4 hours

| | | | | | |
|---|---|---|---|---|---|
| 105 | 97.500 | 10.000 | 90.188 | 20.948 | 86.313 | 23.320 |
| 120 | 98.125 | 7.500 | 92.750 | 19.475 | 90.063 | 19.730 |

| Time (sec) | Butrans-20 N = 16 | SD | Butrans-20/ OxyIR-20 N = 16 | SD | Butrans-20/ OxyIR-40 N = 14 | SD |
|---|---|---|---|---|---|---|
| 15 | 23.688 | 24.918 | 18.625 | 16.116 | 17.214 | 17.747 |
| 30 | 37.875 | 26.818 | 27.750 | 19.372 | 24.929 | 20.477 |
| 45 | 49.688 | 31.313 | 38.563 | 24.862 | 33.286 | 23.669 |
| 60 | 62.375 | 35.035 | 48.250 | 30.220 | 41.000 | 27.746 |
| 75 | 68.375 | 34.314 | 58.375 | 35.659 | 48.929 | 31.222 |
| 90 | 77.375 | 33.894 | 65.563 | 38.356 | 57.143 | 36.249 |
| 105 | 81.375 | 33.248 | 73.875 | 38.147 | 64.143 | 37.461 |
| 120 | 83.125 | 31.991 | 77.125 | 38.392 | 69.643 | 39.244 |

Figure 15:
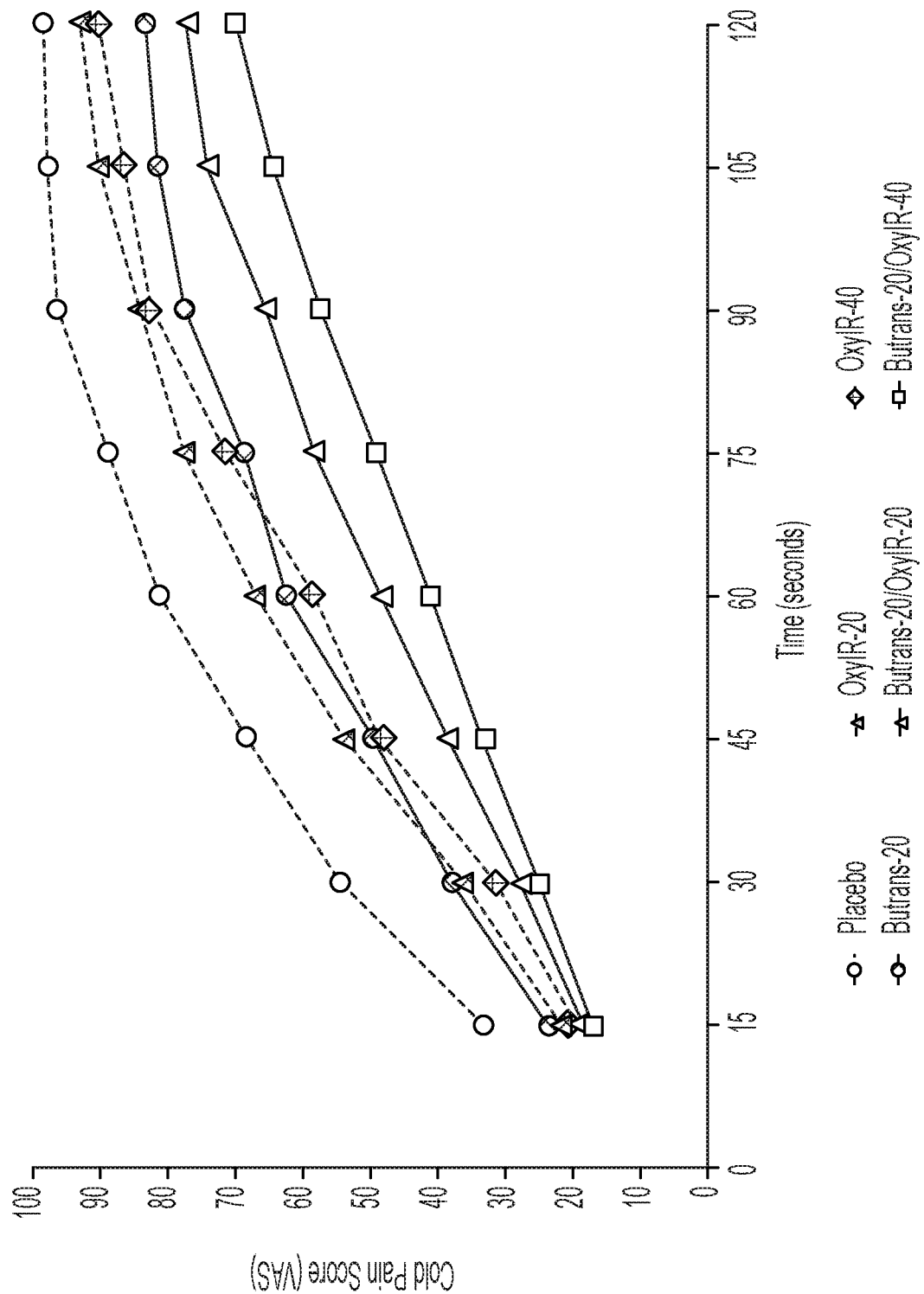
FIG. 15 depicts the results of Example 1 (iteration 2) and all 6 treatments (mean cold pain score by time: 4 hours).

The result of table 14 is also presented in FIG. 15.

TABLE 15

Mean "at the moment' drug liking, VAS, versus time.

| n = 32 Time (h) | Placebo Mean | SD | OxyIR-20 Mean | SD | OxyIR-40 Mean | SD |
|---|---|---|---|---|---|---|
| 0.25 | 50.281 | 1.611 | 50.031 | 0.177 | 49.581 | 2.335 |
| 0.5 | 50.219 | 1.070 | 51.625 | 7.832 | 57.938 | 14.655 |
| 1 | 50.188 | 1.256 | 69.344 | 18.654 | 88.438 | 13.833 |
| 1.5 | 50.219 | 1.263 | 75.469 | 18.286 | 87.219 | 14.298 |
| 2 | 49.750 | 1.796 | 74.375 | 19.265 | 83.688 | 14.875 |
| 2.5 | 49.563 | 2.475 | 72.250 | 19.827 | 79.688 | 15.507 |
| 3 | 49.750 | 1.606 | 69.344 | 19.221 | 74.563 | 16.317 |
| 4 | 49.813 | 1.256 | 65.281 | 18.908 | 65.406 | 21.596 |
| 6 | 49.750 | 1.796 | 60.875 | 17.529 | 62.727 | 17.445 |
| 8 | 49.688 | 1.768 | 58.188 | 14.248 | 58.000 | 14.731 |
| 12 | 49.500 | 3.016 | 53.094 | 9.379 | 53.871 | 8.578 |

| n = 31 Time (h) | Butrans-20 Mean | SD | Butrans20/OxyIR20 Mean | SD | Butrans20/OxyIR40 Mean | SD |
|---|---|---|---|---|---|---|
| 0.25 | 53.129 | 14.710 | 53.839 | 11.079 | 55.129 | 13.263 |
| 0.5 | 53.452 | 16.252 | 56.097 | 12.682 | 55.581 | 13.458 |
| 1 | 55.700 | 13.931 | 58.871 | 14.892 | 69.226 | 18.059 |
| 1.5 | 57.742 | 17.673 | 61.774 | 16.683 | 70.968 | 18.830 |
| 2 | 60.097 | 16.382 | 66.194 | 18.570 | 69.258 | 18.281 |
| 2.5 | 60.194 | 15.791 | 64.129 | 16.673 | 67.065 | 17.928 |
| 3 | 57.645 | 15.026 | 63.355 | 15.821 | 66.839 | 18.179 |
| 4 | 57.677 | 15.248 | 61.484 | 15.002 | 65.742 | 17.349 |
| 6 | 53.968 | 10.400 | 59.290 | 13.874 | 61.452 | 17.542 |
| 8 | 55.258 | 11.287 | 56.000 | 11.883 | 59.452 | 14.780 |
| 12 | 52.613 | 9.358 | 54.516 | 10.427 | 56.065 | 13.481 |

Figure 5:
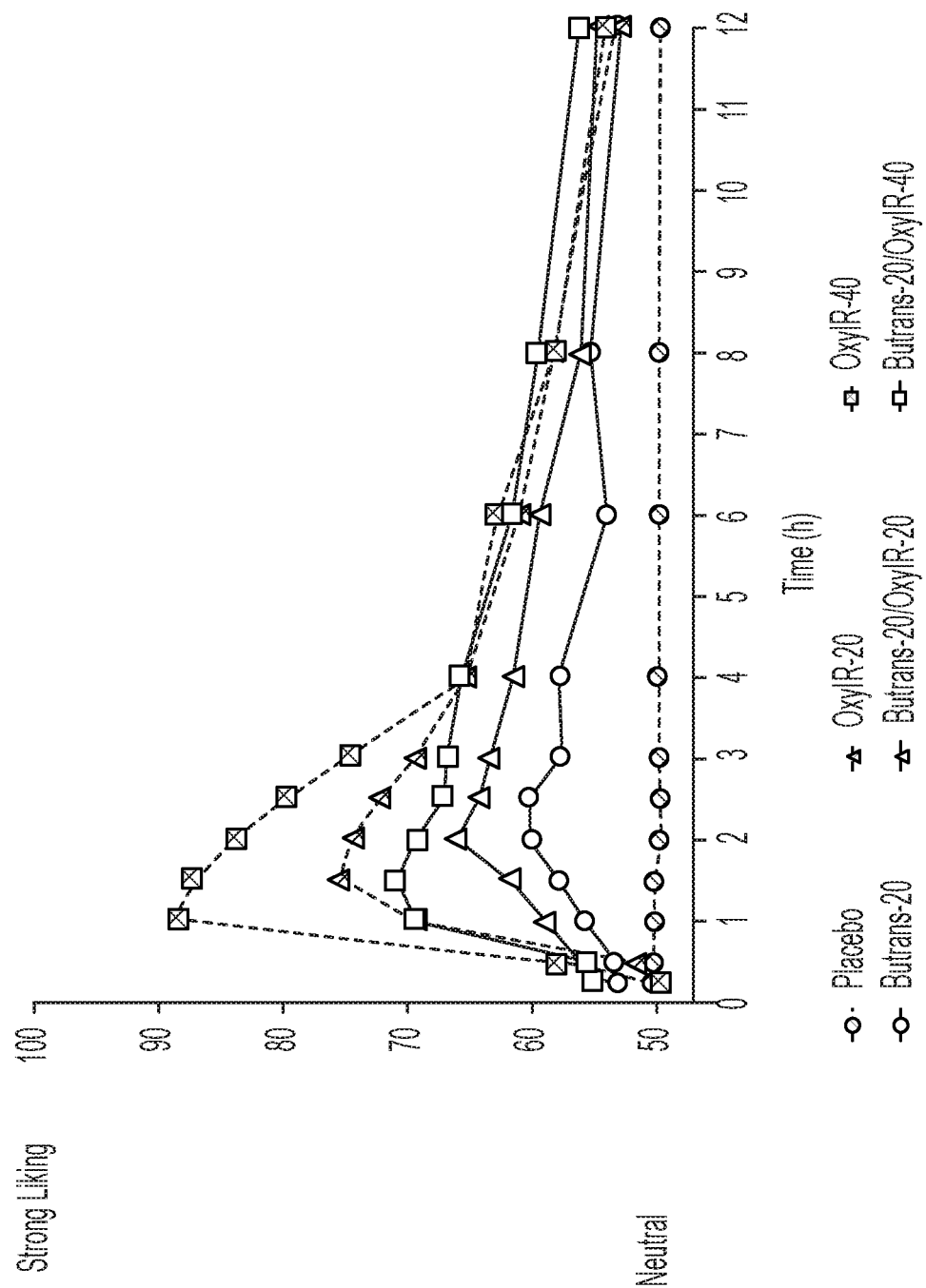
FIG. 5 depicts the results of Example 1 including the result of both iterations and all 6 treatments (mean 'at the moment' drug liking, VAS).

The result of table 15 is also presented in FIG. 5. The Emax comparison is presented in FIG. 6.

TABLE 16

Mean feeling high, VAS versus time.

| n = 32 Time (h) | Placebo Mean | SD | OxyIR-20 Mean | SD | OxyIR-40 Mean | SD |
|---|---|---|---|---|---|---|
| 0 | 2.281 | 12.723 | 0.031 | 0.177 | 1.515 | 8.704 |
| 0.25 | 1.813 | 10.253 | 0.000 | 0.000 | 0.000 | 0.000 |
| 0.5 | 1.938 | 10.960 | 3.406 | 17.698 | 18.469 | 32.513 |
| 1 | 1.875 | 10.607 | 43.938 | 39.934 | 84.188 | 25.332 |

TABLE 16-continued

Mean feeling high, VAS versus time.

| | | | | | | |
|---|---|---|---|---|---|---|
| 1.5 | 1.813 | 9.891 | 50.406 | 37.512 | 82.906 | 23.935 |
| 2 | 1.625 | 9.012 | 51.719 | 38.802 | 76.000 | 26.404 |
| 2.5 | 1.688 | 9.546 | 46.969 | 38.826 | 69.032 | 27.860 |
| 3 | 1.250 | 7.071 | 38.063 | 37.418 | 60.000 | 31.382 |
| 4 | 1.156 | 6.541 | 29.563 | 37.065 | 38.219 | 34.213 |
| 6 | 0.031 | 0.177 | 23.969 | 33.238 | 23.242 | 31.642 |
| 8 | 0.031 | 0.177 | 15.250 | 26.612 | 17.484 | 29.074 |
| 12 | 0.000 | 0.000 | 8.406 | 19.875 | 6.710 | 17.702 |

| n = 31 Time (h) | Butrans-20 Mean | SD | Butrans20/OxyIR20 Mean | SD | Butrans20/OxyIR40 Mean | SD |
|---|---|---|---|---|---|---|
| 0 | 16.032 | 27.218 | 6.688 | 16.225 | 8.613 | 21.730 |
| 0.25 | 13.548 | 26.514 | 8.871 | 19.679 | 9.968 | 24.243 |
| 0.5 | 15.516 | 26.761 | 10.387 | 21.363 | 12.194 | 25.379 |
| 1 | 18.452 | 28.258 | 21.677 | 31.173 | 40.419 | 37.486 |
| 1.5 | 23.000 | 31.638 | 30.645 | 34.876 | 48.677 | 38.326 |
| 2 | 23.194 | 31.846 | 32.548 | 36.099 | 43.548 | 37.260 |
| 2.5 | 23.194 | 30.979 | 30.290 | 33.944 | 41.194 | 37.236 |
| 3 | 18.452 | 30.285 | 29.258 | 32.915 | 37.935 | 39.629 |
| 4 | 15.194 | 27.844 | 24.419 | 31.314 | 36.645 | 39.665 |
| 6 | 11.161 | 22.026 | 18.645 | 25.643 | 29.419 | 36.674 |
| 8 | 8.742 | 20.062 | 12.516 | 22.212 | 23.032 | 30.417 |
| 12 | 5.097 | 14.084 | 6.226 | 15.601 | 14.613 | 25.106 |

Figure 7:
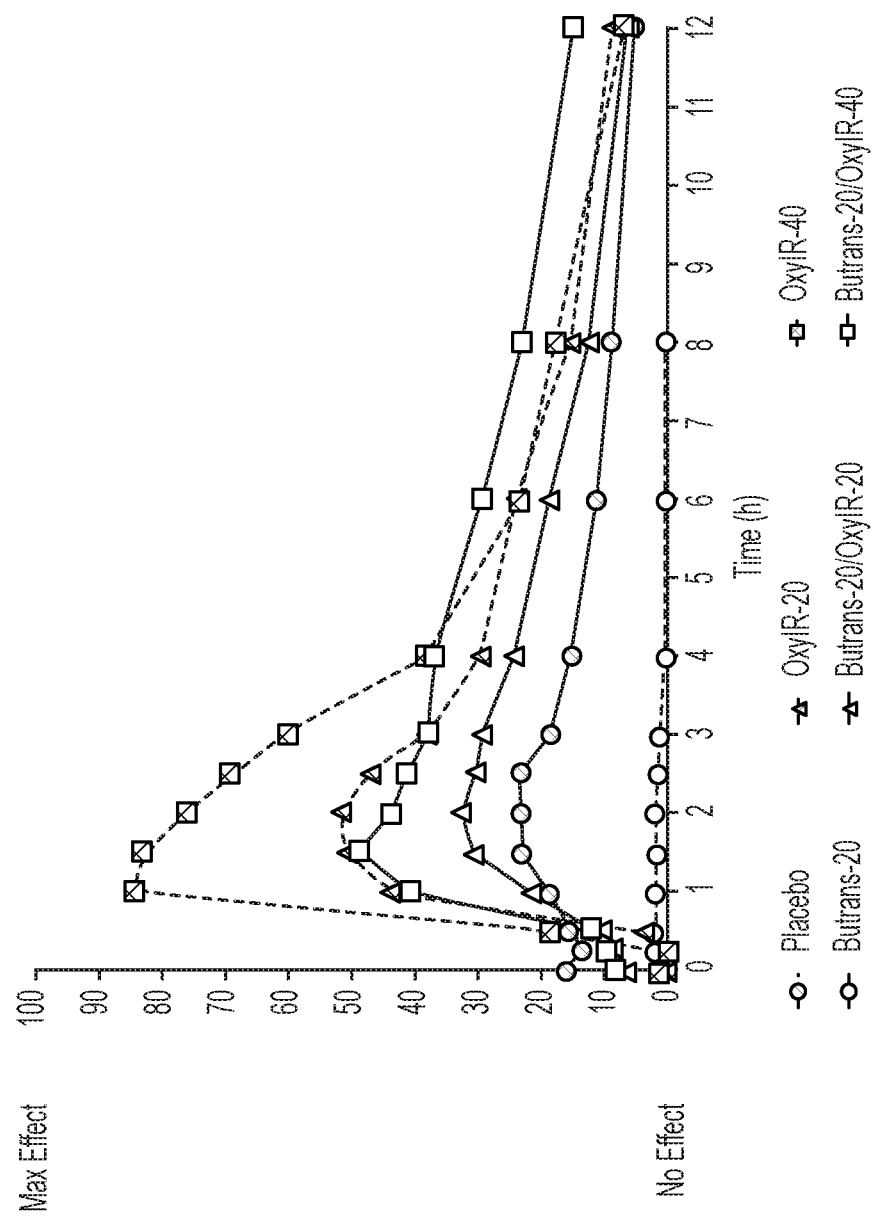
FIG. 7 depicts the results of Example 1 including the result of both iterations and all 6 treatments (mean feeling high, VAS).

The result of table 16 is also presented in FIG. 7. The $E_{max}$ comparison is presented in FIG. 8.

The $E_{max}$ comparison of "overall drug liking" and "take drug again" is also based on VAS and the result is presented in FIGS. 9 and 10, respectively.

Example 2

Example 2 was conducted as a non-randomized, open-labeled crossover single dose study in 8 healthy male and female subjects under naltrexone blockade to evaluate the pharmacokinetics of oral buprenorphine hydrochloride. The treatments are oral and intravenous buprenorphine hydrochloride and a 6-day washout period between study drug administrations.

The study treatments were as follows:
  Buprenorphine HCl oral solution (equimolar amount to 5 mg of buprenorphine base 467.64 g/mol).
  Buprenorphine HCl injection (equimolar amount to 0.3 mg of buprenorphine base 467.64 g/mol) administered intravenously over 15 minutes.

For each treatment, naltrexone HCl tablets (50 mg) were administered q12 h from 12 h predose through 36 h postdose in order to minimize opioid related adverse events (AEs). At the discretion of the investigator, a naltrexone HCl dose of 25 mg was administered to subjects reporting intolerance to the 50 mg dose. Subjects were administered the naltrexone HCl with 240 mL of water.

Subject Selection

Healthy male and female subjects age 18 to 55 years, inclusive, with no clinically significant medical history, were deemed suitable to take part in this clinical study by the investigator.

Subjects meeting all the inclusion criteria and none of the exclusion criteria were randomized into the study.

Inclusion Criteria

1. Provide written informed consent.
2. Male or female subjects 18 to 55 years of age, inclusive.
3. Body mass index (BMI) within the range of 18.0 to 34.0 kg/m², inclusive, and a minimum weight of at least 50.0 kg at screening.
4. Heterosexually active females of childbearing potential must be using an adequate and reliable method of contraception during the study and through to at least 30 days after the last study drug administration. Heterosexually active females who are post-menopausal and not using approved contraception must have been post-menopausal ≥1 year and have an elevated serum follicle stimulating hormone (FSH) level (i.e., ≥50 mIU/mL).
5. Female subjects must have a negative pregnancy test at screening and/or admission.
6. Able to speak, read, and understand English sufficiently to understand the nature of the study, to provide written informed consent, and to allow completion of all study assessments.
7. Must be willing and able to abide by all study requirements and restrictions.

Exclusion Criteria

1. Clinically significant abnormality on physical examination, medical history, 12-lead electrocardiogram (ECG), vital signs, or laboratory values, as judged by the investigator or designee at screening.
2. History or presence of any clinically significant illness (e.g., cardiovascular, pulmonary, hepatic, renal, hematologic, gastrointestinal, endocrine, immunologic, dermatologic, neurologic, oncologic, musculoskeletal, or psychiatric) or any other condition, which in the opinion of the investigator would jeopardize the safety of the subject or the validity of the study results.
3. Any personal or family history of prolonged QT interval or disorders of cardiac rhythm.
4. Abnormal cardiac conditions including any of the following:
   QTcF interval >450 msec at screening
   QTcF interval >480 msec at check-in or noted during any ECGs during the treatment period.
5. History or presence of hypotension, judged to be clinically significant based on investigator or designee judgment.
6. Use of prohibited medications (i.e., non-prescription, prescription medications, herbal or natural health products).
7. Female subjects who are currently pregnant or lactating or who are planning to become pregnant during the study or within 30 days after last study drug administration.
8. Evidence of clinically significant hepatic or renal impairment including alanine aminotransferase (ALT) or aspartate aminotransferase (AST) >1.5× the upper limit of normal (ULN) or serum total bilirubin >10% above ULN.
9. History of severe allergic reaction (including anaphylaxis) to any food, medication, or bee sting or previous status asthmaticus.
10. History of allergy or hypersensitivity to oxycodone, buprenorphine, naloxone or related drugs (e.g., other opioids or opioid antagonists), or any of the drug excipients or other drug product components.
11. History of allergy to lactose.
12. Positive for Hepatitis B, Hepatitis C.
13. Whole blood donated within 56 days prior to entry into the qualification phase or through the EOS visit and for 30 days after completion of EOS visit, except as required by this protocol.
14. Plasma donated within 14 days prior to entry into the qualification phase or through the end of study (EOS) visit, except as required by this protocol.
15. Difficulty with venous access or unsuitable for or unwilling to undergo catheter insertion.
16. Treatment with any investigational drug within 30 days prior to first drug administration of the Naloxone Challenge.
17. Positive urine cotinine results or frequent (>1× per week) smoking or use of nicotine products within 45 days of study drug administration.
18. Positive urine drug screen at screening and/or admission. Positive results may be repeated and/or subjects rescheduled at the Investigator's discretion.
19. Any medical condition that in the opinion of the investigator would interfere with the study procedures or data integrity or compromise the safety of the subject.
20. A subject who, in the opinion of the investigator or designee, is considered unsuitable or unlikely to comply with the study protocol for any other reason.
21. Subjects who are deemed unsuitable by the investigator for any reason not described above (e.g., a safety concern for the subject or a concern regarding the scientific integrity of the study).

Administration

Each subject received both oral and intravenous treatment.

In an oral treatment, subjects were administered the study drug solution. Followed by four 35-mL rinses with water. The total volume of water consumed was 240 mL (including water in the dose solution+4 rinses).

Oral solution treatment was preceded by an overnight fast (ie, at least 10 hours) from food, and was followed by a 4-hour fast (not including water).

Collection and Analysis of Blood Samples

Blood samples for determining plasma concentrations of buprenorphine were obtained for each subject during each period at the following timepoints:

IR oral solution: Predose and 0.25, 0.5, 1, 1.5, 2, 2.5, 3, 4, 5, 6, 8 and 12, hours post study drug administration.

IV: Predose, 2, 5, 10 and 15 minutes (stop infusion at 15 minutes) and 2, 5, 10, 15, 30 minutes, and 1, 1.5, 2, 4, 6, 8 and 12 hours after stopping the infusion.

Buprenorphine concentrations were quantified from 150 µL of human plasma using Buprenorphine-d4 as the internal standards. Samples were extracted using a protein precipitation extraction (PPE) method. Extracts were chromatographed under reversed phase conditions on an Xbridge C18 HPLC column (4.6×50 mm, 3.5 µm) using a gradient system with 0.1% formic acid in water and 0.1% formic acid in acetonitrile. Buprenorphine was detected and quantified by tandem mass spectrometry in a positive ion mode on a MDS Sciex API 5000™ equipped with a Turbo Ionspray interface. The quantitation linear range for Buprenorphine was from 25-2,500 µg/mL.

Result

TABLE 17

Buprenorphine mean plasma concentration versus time following oral administration of 5 mg buprenorphine IR.
Buprenorphine HCl IR oral
(equimolar amount to 5 mg of
buprenorphine base Mw = 467.64
g/mol), oral solution n = 8

| Time (h) | Mean (ng/mL) | SD |
|---|---|---|
| 0 | 0.016 | 0.025 |
| 0.25 | 0.218 | 0.241 |
| 0.5 | 0.424 | 0.315 |
| 1 | 0.579 | 0.429 |
| 1.5 | 0.501 | 0.268 |
| 2 | 0.444 | 0.244 |
| 2.5 | 0.401 | 0.171 |
| 3 | 0.337 | 0.125 |
| 4 | 0.298 | 0.156 |
| 5 | 0.344 | 0.262 |
| 6 | 0.321 | 0.230 |
| 8 | 0.260 | 0.124 |
| 12 | 0.283 | 0.137 |

The result of table 17 is also presented in FIGS. 3 and 16.

TABLE 18

Buprenorphine mean plasma concentration versus time following intravenous administration of 0.3 mg buprenorphine over 15 minutes.
Buprenorphine i.v. (equimolar amount
to 0.3 mg of buprenorphine base, Mw = 467.64 g/mol)
over 15 min n = 8

| Time (h) | Mean (ng/mL) | SD |
|---|---|---|
| 0 | 0.146 | 0.117 |
| 0.033 | 0.186 | 0.145 |
| 0.083 | 1.377 | 2.126 |
| 0.167 | 2.380 | 3.158 |
| 0.25 | 2.832 | 3.349 |
| 0.283 | 3.511 | 3.189 |
| 0.333 | 3.709 | 2.728 |
| 0.417 | 2.314 | 0.944 |
| 0.5 | 1.838 | 0.512 |
| 0.75 | 1.420 | 0.206 |
| 1.25 | 1.186 | 0.180 |
| 1.75 | 0.962 | 0.178 |
| 2.25 | 0.786 | 0.173 |
| 4.25 | 0.535 | 0.180 |
| 6.25 | 0.453 | 0.224 |
| 8.25 | 0.323 | 0.143 |
| 12.25 | 0.237 | 0.101 |

The result of table 18 is also presented in FIG. 3.

TABLE 19

Summary of buprenorphine pharmacokinetic results.

| n = 8 | Mean Cmax (ng/mL) | SD | Mean Tmax (h) | SD |
|---|---|---|---|---|
| Buprenorphine HCl IR (equimolar amount to 5 mg of buprenorphine base, Mw = 467.64 g/mol), oral | 0.628 | 0.392 | 2.500 | 3.891 |
| Buprenorphine HCl injection, (equimolar amount to 0.3 mg of buprenorphine base, Mw = 467.64 g/mol) administered over 15 min | 4.26 | 3.6043 | 0.337 | 0.073 |

Bioavailability Analysis:

Absolute bioavailability (F) was defined as AUCtoral/AUCtIV×DoseIV/Doseoral,

TABLE 20

Mean Absolute bioavailability.

| Buprenorphine | Buprenorphine HCl IR oral oral solution (equimolar amount to 5 mg of buprenorphine base Mw = 467.64 g/mol) (n = 8) Mean ± SD |
|---|---|
| Absolute Bioavailability (F %) | 5.18 ± 2.47 |

Example 3

Experimental Design

Animals are allowed to acclimate to a light—(12 hours on/12 hours off), humidity- and temperature-controlled environment for at least 6 days after arrival before they are tested. Animals are housed 2-3/cage for rats and 5/cage for mice. Food and water are available ad libitum prior to the beginning of any behavioral study. Animals are only food deprived over-night (max 16-24 hours) for the administration of test compounds that are to be administered by the oral route (PO).

Experiments include 8-12 animals per experimental group with each animal being identified with a number on its tail. Each study includes 4-6 experimental arms so that dose-response relationships and/or time course analyses for potential therapeutic agents can be conducted. This design also permits the inclusion of both negative and positive controls with each experiment. Individual experiments may vary with regard to test dose and time of assessment, but are consistent with the known characteristics of the test agent.

For most studies, a single dose of the test compound is administered 0.5-1 hour prior to behavioral assessment. Typically, behavior is assessed along a PK-designated time course for up to 24 hours post-dosing.

Recommended "good practice" dose volumes or these studies are as follows for rat:
PO (oral)=2 ml/kg;
SC (subcutaneous)=2 ml/kg;
IP (intraperitoneal)=2 ml/kg;
IV (intravenous)=1 ml/kg; and
IT (intrathecal)=50 µl.
Dose volumes for mouse include:
PO (oral)=10 ml/kg;
SC (subcutaneous)=10 ml/kg;
IP(intraperitoneal)=10 ml/kg; and
IV (intravenous)=5 ml/kg.

Vehicles include sterile water, 0.9% saline, 2% tween/0.5% methylcellulose and 25% 2-Hydroxypropyl-beta-cyclodextrin (HPBCD). A vehicle control group is run simultaneously with drug-treated groups in all assays defined. Similarly, a positive control compound is included in all assays as well.

All testings are done in a blinded manner, with all experimenters involved in the study being unaware of the group assignment of any animal they are testing. Animals are dosed in a blinded fashion after pre-treatment baseline assessment such that animals are assigned to treatment groups based on baseline response thresholds so that group means are approximately equal.

Animal Species

Animals used in the assays are supplied by Sage (Boyertown, PA), Jackson (Bar Harbor, Maine) or Harlan Labs (Indianapolis, IN) or alternately, bred in house from mating pairs (i.e. Barrestin 2 and GRK 5 KO rats):

Rats: Male or Female Sprague-Dawley or Hans Wistar

Mice: Male, CD-1, ICR or C57BL/6; and

Transgenic/knockout mice (129/C57BL/6 background)

Analysis of Results

To determine statistical significance of a compound compared to vehicle treatment a one-way or two-way ANOVA is performed on raw data (i.e. latency, time, distance traveled, temperature: using Graph Pad Prism™. The criterion for significance is set at P<0.05.

Example 3A Respiratory Depression

To evaluate respiratory depression, analysis of arterial PCO2 and PO2 levels were performed. Rats with indwelling arterial cathrters were purchased from Harlan.

Rats were co-dosed with the opioid and buprenorphine SC in the caudal part of the dorsum, or rats were administered a SC dose of an opioid or buprenorphine alone. Co-administration involves injecting compounds into alternate sites but in a conservative fashion.

Following compound dosing, an arterial blood sample (i.e. 180-200 microliters) was withdrawn from an indwelling catheter (Harlan Labs, IN) at baseline (time 0) and then 1, 3, and 5 hours after the SC dosing. The samples were collected using heparinized syringes (Innovative Med Tech) that were locked into the ABL machine. The samples were immediately analyzed for pH, pCO2, pO2 and sO2 (i.e., oxygen saturation) levels using a blood gas analyzer (ABL805, Radiometer America, Westlake, OH) according to the methods of Hoffman et al. (Effects of NMDA receptor antagonists on opioid-induced depression and acute antinociception in rats. *Pharmacol Biochem Behav* 74:933-941, 2003).

To assess, pH, pCO2, pO2 and sO2 in the animals, some rats are subjected to carotid artery catheterization surgery.

Results

The effects of each of buprenorphine, oxycodone, hydromorphone and fentanyl alone on blood gas parameters: A) $pCO_2$; and B) $sO_2$ (i.e., oxygen saturation), in rats were presented in FIG. 17 through FIGS. 20. As shown in the figures, buprenorphine has subtle but significant effects on arterial blood $pCO_2$ and oxygen saturation in rats (0.05-3 mg/kg, sc), oxycodone (3 & 8 mg/kg), hydromorphone (1-10 mg/kg) and fentanyl (0.5-1.5 mg/kg) have significant effects on arterial blood $pCO_2$ and oxygen saturation in rats.

FIGS. 21 A)-D) present the effect of buprenorphine on oxycodone-induced deficits in arterial blood gas (ABG) parameters: A) $sO_2\%$, B) $pO_2$, C) $pCO_2$, and D) arterial blood pH, in rats (male, Sprague-Dawley rats, weight=192-262 g; n=6-13/group), respectively. FIGS. 22 A)-B) depict the effect of buprenorphine on oxycodone-induced deficits in arterial blood gas (ABG) parameters: A) $pCO_2$, and B) $sO_2\%$, in rats, at 1 hour post-administration. As shown in the figures, 8 mg/kg sc Oxycodone caused a significant elevation in $pCO_2$ and a significant decrease in $sO_2\%$ that was normalized with 0.5-3 mg/kg sc Buprenorphine.

Figure 23:
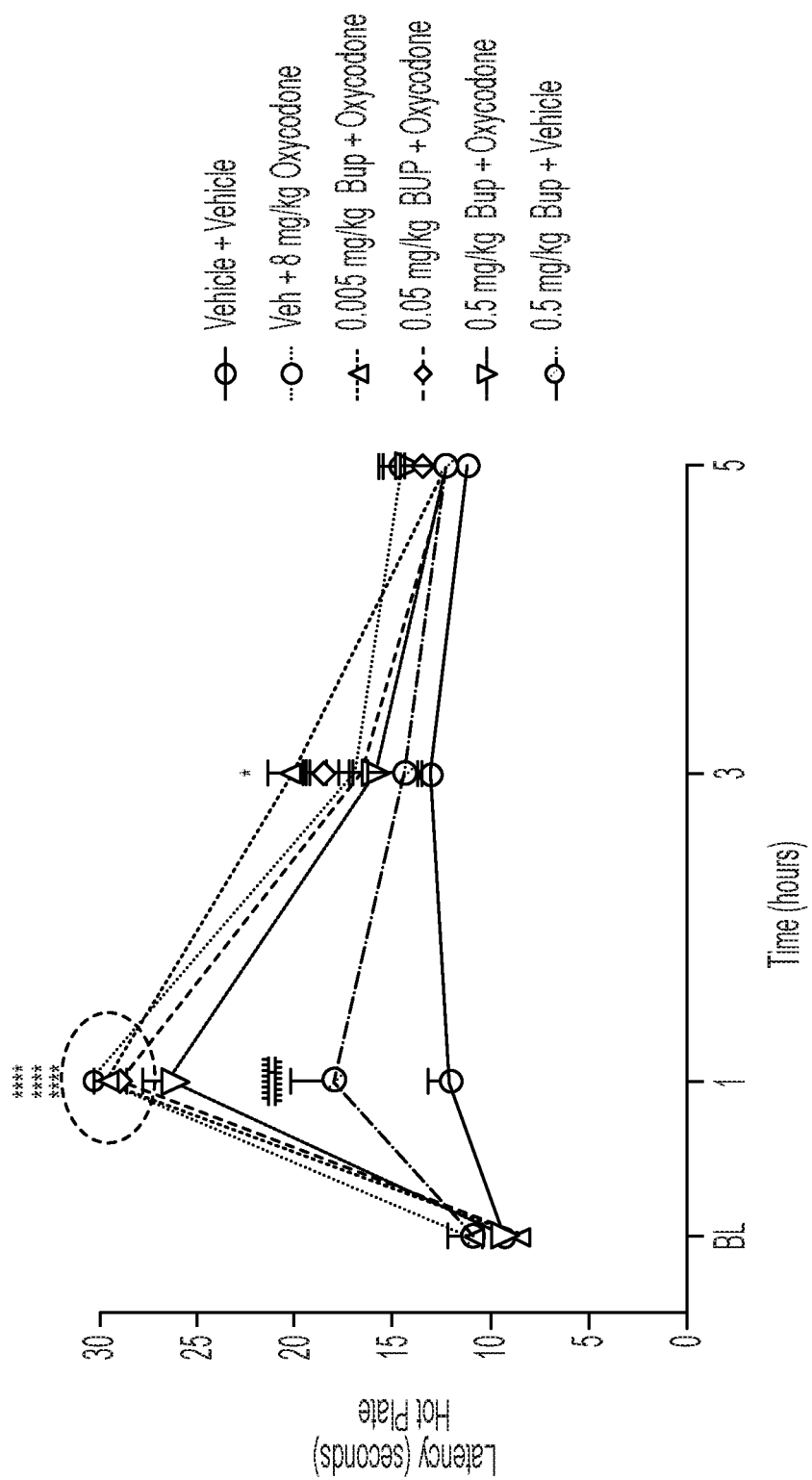
FIG. 23 depicts the analgesia effects of buprenorphine, oxycodone, and buprenorphine-oxycodone (8 mg/kg) combinations in rats.

Further, FIG. 23 shows that 8 mg/kg sc Oxycodone produced full analgesia in the rat that was not eroded by the same doses of buprenorphine that rescued aberrations in respiratory function.

Figure 26:
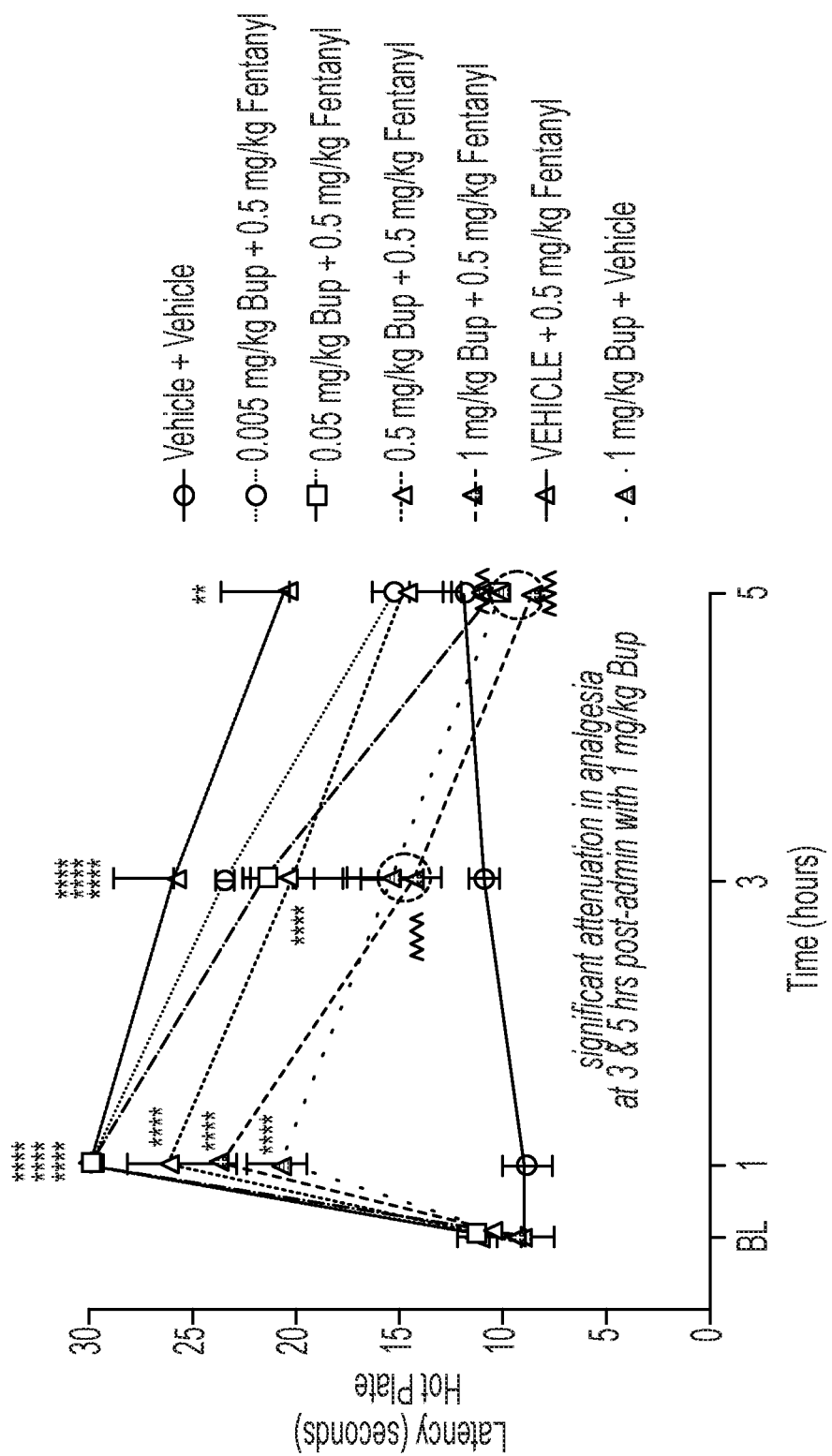
FIG. 26 depicts the analgesia effects of buprenorphine, fentanyl, and buprenorphine-fentanyl (0.5 mg/kg) combinations in rats.

FIGS. 24 A)-E) present the effect of buprenorphine on fentanyl-induced deficits in arterial blood gas (ABG) parameters: A) $sO_2\%$, B) $pO_2$, C) $pCO_2$, and D) arterial blood pH, and also on E) acid-base status in rats (male, Sprague-Dawley surgerized rats, weight=217-270 g; n=8-18/group; Harlan Surgery), respectively. FIGS. 25 A) and B) present the effect of buprenorphine on fentanyl-induced deficits in arterial blood gas (ABG) parameters: A) $pCO_2\%$; and B) $sO_2\%$ in rats at 1 hour post-administration. As shown in the figures, 0.5 mg/kg sc fentanyl caused a significant elevation in $pCO_2$ and a significant decrease in $sO_2\%$ that was normalized with 0.5 mg/kg sc buprenorphine. Further, FIG. 26 shows that 0.5 mg/kg sc fentanyl produced full analgesia in the rat that was not eroded by the same doses of buprenorphine that rescued aberrations in respiratory function.

Figure 29:
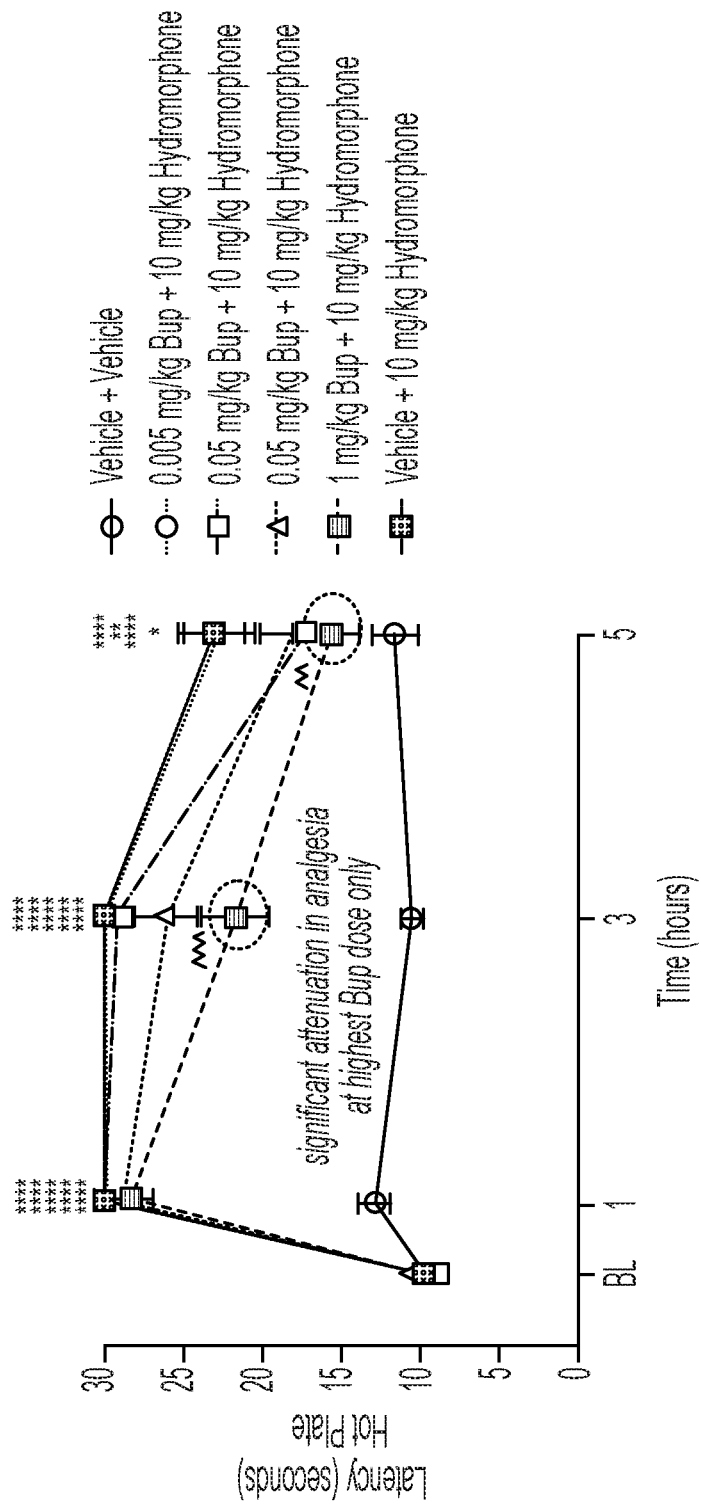
FIG. 29 depicts the analgesia effects of buprenorphine, hydromorphone, and buprenorphine-hydromorphone (10 mg/kg) combinations in rats.

FIGS. 27 A)-D) present the effect of buprenorphine on hydromorphone-induced deficits in arterial blood gas (ABG) parameters: A) $sO_2\%$, B) $pO_2$, C) $pCO_2$, and D) arterial blood pH, in rats (male, Sprague-Dawley surgerized rats, weight=217-270 g; n=8-18/group; Harlan Surgery), respectively. FIGS. 28 A) and B) present the effect of buprenorphine on hydromorphone-induced deficits in arterial blood gas (ABG) parameters: A) $pCO_2\%$; and B) $sO_2\%$ in rats at 1 hour post-administration. As shown in the figures, 10 mg/kg sc hydromorphone caused a significant elevation in $pCO_2$ and a significant decrease in $sO_2\%$ that was normalized with 0.5 mg/kg sc buprenorphine. Further, FIG. 29 shows that 10 mg/kg sc hydromorphone produced full analgesia in the rat that was not eroded by the same doses of buprenorphine that rescued aberrations in respiratory function.

The summary of the effects of various opioids in models, with or without burprenorphine, on arterial blood gas parameters in rats is presented in Table 21 and Table 22, respectively:

TABLE 21

| Opioid | Opioid dose (mg/kg) sc | Sampling time Post-dosing (hour) | MODEL | | | |
|---|---|---|---|---|---|---|
| | | | pH | $pCO_2$ | $pO_2$ | $sO_2\%$ |
| Hydromorphone HCl | 10 | 1 | 7.268 | 58.99 | 87.36 | 94.4 |
| Fentanyl Citrate | 0.5 | 1 | 7.1568 | 74.41 | 74.74 | 89.53 |
| Oxycodone HCl | 8 | 1 | 7.266 | 60.5 | 67.78 | 87.38 |
| Morphine Sulfate | 30 | 1 | 7.279 | 60.29 | 65.07 | 86.47 |

TABLE 22

| | MODEL + BUPRENORPHINE | | | | | | |
|---|---|---|---|---|---|---|---|
| Opioid | Opioid dose (mg/kg) sc | Sampling time post-dosing (hour) | Bup dose (mg/kg) sc | pH (7.27-7.4) | pCO$_2$ (37.9-56.4) | pO$_2$ (80-109) | sO$_2$% (90-100) |
| Hydromorphone HCl | 10 | 1 | 0.5 | 7.39 | 43.76 | 96.45 | 97.15 |
| Fentanyl Citrate | 0.5 | 1 | 0.5 | 7.408 | 39.46 | 108.65 | 97.94 |
| Oxycodone HCl | 8 | 1 | 0.5 | 7.437 | 38.408 | 79.93 | 94.65 |
| Morphine Sulfate | 30 | 1 | nd | | | | |

Example 3B Lethality Study

The purpose of the study is to assess lethality. Animals are expected to appear moribund. It is anticipated that such animals expire shortly after appearing moribund. Furthermore, the moribund state is not accompanied by pain or distress. This is due to the mechanism of opioid—induced lethality which involves rapid unconsciousness, escalation of depth of sedation with respiratory and ventilator depression.

Rats, male, Sprague-Dawley or Hans Wistar (supplied by Harlan Labs, Indianapolis, IN) are observed for overt side effects including rigidity, sedation and unresponsiveness to touch and/or startle. Occurrence of death is confirmed by lack of response to a tail pinch, lack of respiration and/or onset of rigor mortis.

For most studies, a single dose of the test compound or combination is administered. Recommended "good practice" dose volumes or these studies are as follows for the rat: IV (intravenous)=1-2 ml/kg.

The results of lethality studies in rats with combinations of opioid agonists (oxycodone, fentanyl, and hydromorphone) and buprenorphine are presented in FIGS. 30 through 32. Notably, buprenorphine at the IV doses of 0.46875 mg/kg, 0.9375 mg/kg, and 1.875 mg/kg provided full reversal of oxycodone (30 mg/kg, IV)-induced lethality (FIGS. 30 A & B). Buprenorphine at the IV dose of 0.5625 mg/kg provided full reversal of fentanyl (2.25 mg/kg, IV)-induced lethality (FIGS. 31 A & B).

And, buprenorphine at IV doses of 0.5 mg/kg, 3.125 mg/kg, and 12.5 mg/kg also significantly reduced hydropmorphone (100 mg/kg, IV)-induced death incidence (FIGS. 32 A & B).

Example 4

A single-center, randomized, double-blind, stepwise study in healthy subjects and/or healthy recreational opioid users, consisting of 2 parts is designed. Each part has several iterations. An iteration consists of up to 6 periods. A cohort includes healthy subjects only or healthy recreational opioid user subjects only.

Each part consists of 3 phases: Screening, Treatment, and Follow-up.

Each part may include a qualification phase to screen out subjects (e.g. who do not demonstrate appropriate tolerability, HCVR, PK, or other parameters). The qualification (if applicable) is not required if a subject has already qualified in a prior Part/Iteration. Each qualification cohort consists of up to 4 periods. Cohorts are dosed in parallel. A cohort includes healthy subjects only or healthy recreational opioid user subjects only. For each cohort, up to 2 opioids, each up to 2 dose strengths, is administered in order to determine a dose that induces respiratory depression. There is a minimum washout of approximately 24 hours between doses.

Study Design

Part 1 is to identify a safe opioid dosing regimen that produces readily quantifiable opioid-induced respiratory depression (OIRD). Each iteration consists of up to 4 cohorts with up to 20 subjects each. Each cohort consists of up to 4 periods. Cohorts are dosed in parallel. For each cohort, up to 2 opioids (IV fentanyl, IV hydromorphone, IV morphine, or oral oxycodone), each up to 2 dose strengths, is administered in order to determine a safe and tolerated dose that induce respiratory depression. With in a cohort, doses are escalated from low to high for each opioid. There is a minimum washout of approximately 24 hours between doses.

Part 2 evaluated the effect of transdermal buprenorphine co-administered with hydromorphone on opioid-induced respiratory depression.

In Part 2a), 16 healthy recreational opioid users received transdermal buprenorphine (Butrans® 20 mcg/hr) or placebo patch (applied for ~4.5 days) in a single-blind, non-randomized, 2-period crossover. In each period, 3 separate hydromorphone doses were administered at 48, 72 and 96 hours post patch application:

Hydromorphone 1.5 mg IV infusion (divided into 2 infusions)
    Hydromorphone 0.625 mg, administered over 10 minutes (loading dose)
    Hydromorphone 0.875 mg, administered over 30 minutes (maintenance dose)
Hydromorphone 3 mg IV infusion (divided into 2 infusions)
    Hydromorphone 1.25 mg, administered over 10 minutes (loading dose)
    Hydromorphone 1.75 mg, administered over 30 minutes (maintenance dose)
Hydromorphone 3 mg repeated as indicated above.

There was a minimum washout of approximately 24 hours between hydromorphone IV doses. There was a minimum washout of approximately 36 hours between patch applications. The administration scheme is summarized in FIGS. 33 A)-B).

In Part 2b, 16 healthy recreational opioid users received transdermal buprenorphine or placebo patches in a single-blind, nonrandomized design. A planned transdermal patch nominal dose escalation was performed 0(placebo), 5, 10 and 15 mcg/h. Placebo patch was applied for 2 days, Buprenorphine patches were applied for 4 days. This sequence was changed for the last dose of buprenorphine. Based on data review of previous doses, a lower dose of 2.5 mcg/h was administered. During each patch application, 2 IV Hydromorphone 3 mg doses were infused separated by 24 hours. Each IV Hydromorphone dose was divided into 2 infusions for a total of 3 mg:

Hydromorphone 1.25 mg, administered over 10 minutes (loading dose)

Hydromorphone 1.75 mg, administered over 30 minutes (maintenance dose)

Figure 37:
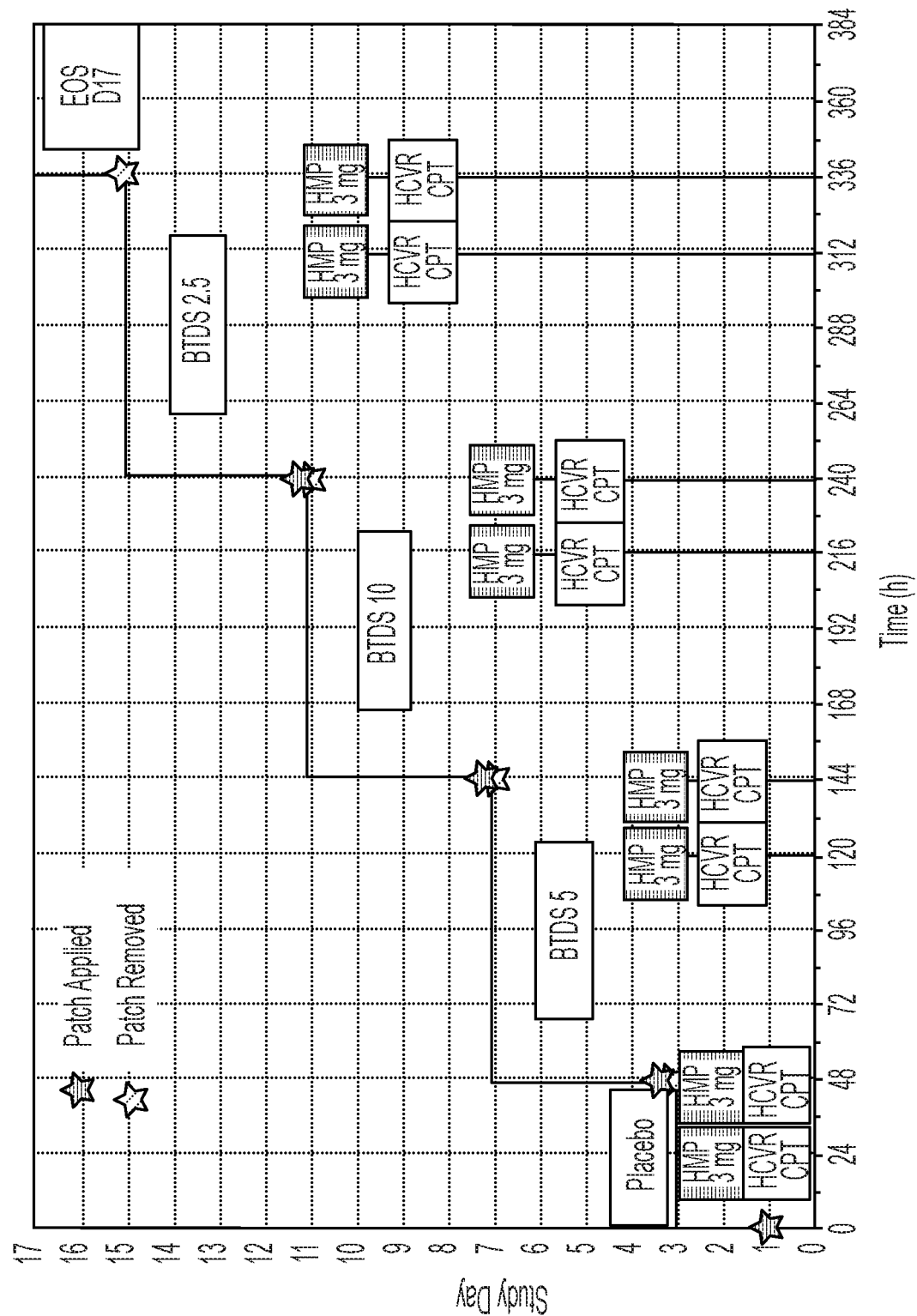
FIG. 37 presents the schematic view of part 2b) study design.

The administration scheme is summarized in FIG. 37.

Criteria for Inclusion/Exclusion

Healthy male and female recreational opioid users with a history of oral use, or otherwise healthy subjects, aged 18 to 55 years, inclusive, with no clinically significant medical history, who are deemed suitable to take part in this clinical study.

Test Treatment, Dose, and Mode of Administration
    Fentanyl citrate (up to 150 mcg), intravenously
    Hydromorphone hydrochloride (up to 3 mg), intravenously
    Oxycodone IR (up to 40 mg), oral
    Morphine sulfate (up to 20 mg), intravenously
    Butrans® (up to 20 mcg/hour), transdermal
Reference Treatment Dose, and Mode of Administration
    Placebo, intravenously
    Placebo patches, transdermal
    Placebo, oral
Concomitant Medication
    Naloxone HCl challenge test (at least approximately 12 hours prior to first study drug administration).
    The use of other concomitant medications during this trial is discouraged, unless necessary to treat adverse events (AEs).
Duration of Treatment and Study Duration Subjects are screened no more than 28 days prior to check-in of Period 1 or prior to qualification phase.

Qualification Phase

A study drug is administered in each period according to the study randomization schedule (if applicable). Subjects are confined to the unit the day prior to the first study drug until approximately 24 hours following the last dose of study drug or upon early discontinuation from the study. Subjects may be discharged after the Qualification Phase or remain confined in the unit until the Treatment Phase. Subjects who are discharged after the Qualification Phase undergo end-of-qualification procedures. A follow-up phone call is made to (or received from) each subject from 7 to 10 days post end-of-qualification for subjects not entered into treatment, or after early withdrawal from the study, to assess adverse events (AEs) and concomitant medications taken since the last study visit.

Treatment Phase

The study drug is administered in each period according to the study randomization schedule. Subjects are confined to the unit beginning the day prior to study drug administration (Check-in) in period 1 until EOS (or upon early discontinuation). Subjects may be discharged between periods but will have repeat check-in procedures when they return to the facility.

Subjects have EOS procedures conducted prior to discharge from the study at a time by which any meaningful pharmacologic effects have resolved or decreased to a clinically acceptable level in the view of the PI or designee or upon early discontinuation from the study.

A follow-up phone call is made to (or received from) each subject from 7 to 10 days post EOS or after early withdrawal from the study to assess AEs and concomitant medications taken since the last study visit.

Total study duration: Part 1—up to approximately 48 days. Part 2—up to approximately 54 days.

Study Procedures

Study procedures and time points are noted in the schedule of activities. AEs and concomitant medications are recorded from time of informed consent.

Screening Phase

Subjects are screened within 28 days of check-in, and this includes a training session with the hypercapnic ventilatory response (HCVR). This may be done as part of screening or part of admission procedures on day −1, or both.

Qualification Phase (if Applicable)

The qualification (if applicable) will not be required if a subject has already qualified in a prior Part/Iteration.

Check-in: Subjects check into the unit the day prior to period 1 dosing.

Subjects receive a naloxone HCl challenge test and an assessment using OOWS at least approximately 12 hours prior to first study drug administration to confirm that subjects are not opioid dependent.

Subjects are administered study drug according to the randomization schedule at specified times. At specified times, monitoring for respiratory depression (transcutaneous $CO_2$ and HCVR) are conducted with supplemental oxygen.

Treatment Phase

Check-In: Subjects check into the unit the day prior to period 1 dosing. If not already performed in Qualification Phase, a naloxone HCl challenge test and an assessment using OOWS are performed at least approximately 12 hours prior to first study drug administration to confirm that subjects are not opioid dependent.

Treatment: Subjects are administered study drug according to the randomization schedule at specified times. At specified times in the treatment period, monitoring for respiratory depression (transcutaneous $CO_2$ and HCVR) is conducted with supplemental oxygen.

End-of-study (EOS): Subjects have EOS procedures performed prior to discharge from the study at a time by which any meaningful pharmacologic effects have resolved or decreased to a clinically acceptable level in the view of the PI or designee or upon early discontinuation from the study.

Follow Up: A follow-up phone call is made to (or received from) each subject 7 to 10 days after EOS or after early withdrawal from the study to assess AEs and concomitant medications taken since the last study visit.

Criteria and Methods for Evaluation

Pharmacodynamic

Hypercapnic Ventilatory Response (HCVR)

The HCVR is calculated as the change in minute ventilation (inspiratory volume per breath times the breathing frequency, on a per kilogram basis) per mm Hg increase in $PCO_2$. These values are determined during a steady state in the baseline condition (no increase in $CO_2$, subject breathing normally) and during added CO$_2$ breathing. The HCVR is a direct measure of respiratory drive mediated by the central chemoreceptors.

Respiratory Drive

The evaluation of respiratory drive is done by comparing the ventilatory response to hypercapnia using minute ventilation and end-tidal CO$_2$ (ET CO$_2$) predose and after study drug treatment. The HCVR is calculated by the slope of the minute ventilation-P$_{ET}$CO$_2$ relationship (LPM/mm Hg CO$_2$). The HCVR is linear over the range of CO$_2$ studied with this protocol: hence the standard approach is to measure ventilation at 2 steady-state levels of CO$_2$ (one on room air or baseline CO$_2$ and one with added CO$_2$) and calculate the HCVR on that basis. Transcutaneous CO$_2$ (PCO$_2$)

The transcutaneous CO$_2$ is an important measure of respiratory drive and indicator of opioid-induced respiratory depression. Monitoring transcutaneous PCO$_2$ after drug administration is expected to be highly predictive of a blunting of the HCVR.

Subjective Sedative Effects
Drowsiness/Alertness VAS (Emin)
Subjective Shortness of Breath Effects
Dyspnea VAS (Emax)
Drug Concentration Measurements Blood samples for determining plasma concentrations of opioids and buprenorphine, as applicable, are obtained for each subject during each study drug administration as specified in the schedule of activities.

The timing of PK draws is adjusted if indicated.

Analysis Populations

Enrolled population: all subjects who provide informed consent.

Randomized safety population: all subjects who are randomized and receive study drug.

Full analysis population: all subjects who are randomized, receive study drug and have at least 1 valid pharmacodynamics (PD) measurement.

Bioanalytical Methodology

Plasma concentrations of opioids, and buprenorphine are quantified by a validated bioanalytical method.

Safety

Safety are assessed using recorded AEs, clinical laboratory test results, vital signs, SpO$_2$, physical examinations, and conventional 12-lead ECGs.

Respiratory Depression: CO$_2$ Challenge (Part 2a) Study

A part 2a) study using hydromorphone (IV HMP), and IV HMP combined with Buprenorphine TDS (transdermal delivery system) was conducted. The schematic views of the part 2a) designed are presented in FIGS. 33 A)-B), which showed constant HMP & Bup. concentrations during the HCVR measurements.

A sample minute ventilation (inspiratory volume per breath times the breathing frequency, on a per kilogram basis) per mm Hg increase in pCO$_2$ in a subject with no opioid was measured. A HCVR slope was calculated as follows:

$$HCVR\ Slope = \frac{\text{Change in Ventilation }(v)}{\text{Change in ET CO2 }(x)} = \frac{(24.5 - 8.0)}{(47 - 37)} = \boxed{1.65\ (L/\text{min/mmHg})}$$

A sample minute ventilation (inspiratory volume per breath times the breathing frequency, on a per kilogram basis) per mm Hg increase in pCO$_2$ in a subject with 3.0 mg IV hydromorphone (HMP) was measured. A HCVR slope was calculated as follows:

$$HCVR\ Slope = \frac{\text{Change in Ventilation }(v)}{\text{Change in ET CO2 }(x)} = \frac{(19 - 7.0)}{(53 - 40)} = \boxed{0.92\ (L/\text{min/mmHg})}$$

Figure 34:
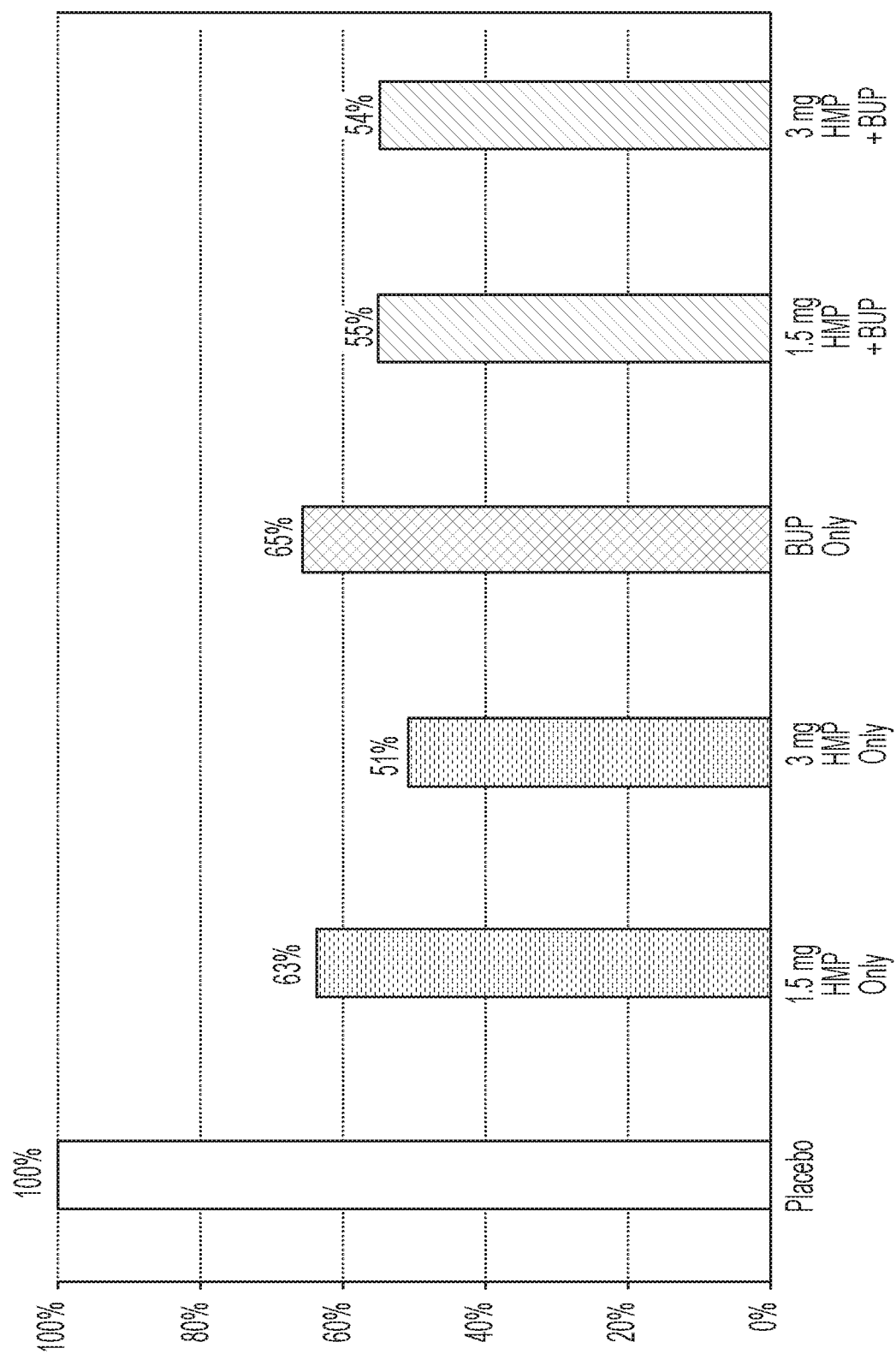
FIG. 34 depicts the mean HCVR slopes normalized to placebo, after administration of IV hydromorphone (HMP), buprenorphine (BUP, Butrans® patch), and HMP-BUP combinations in Study part 2a).

FIG. 34 shows that opioid-induced respiratory depression (OIRD) was demonstrated for positive control treatments (1.5 mg and 3.0 mg HMP infusions), compared to placebo:
  37% for 1.5 mg IV HMP only; and
  49% for 3.0 mg IV HMP only.

FIG. 34 also shows that OIRD was demonstrated for BUP (Butrans®, 20 mcg/hr) alone. The OIRD effects after the addition of BUP (20 mcg/hr) to 1.5 mg and 3.0 mg IV HMP were demonstrated in FIG. 34.

Figure 35:
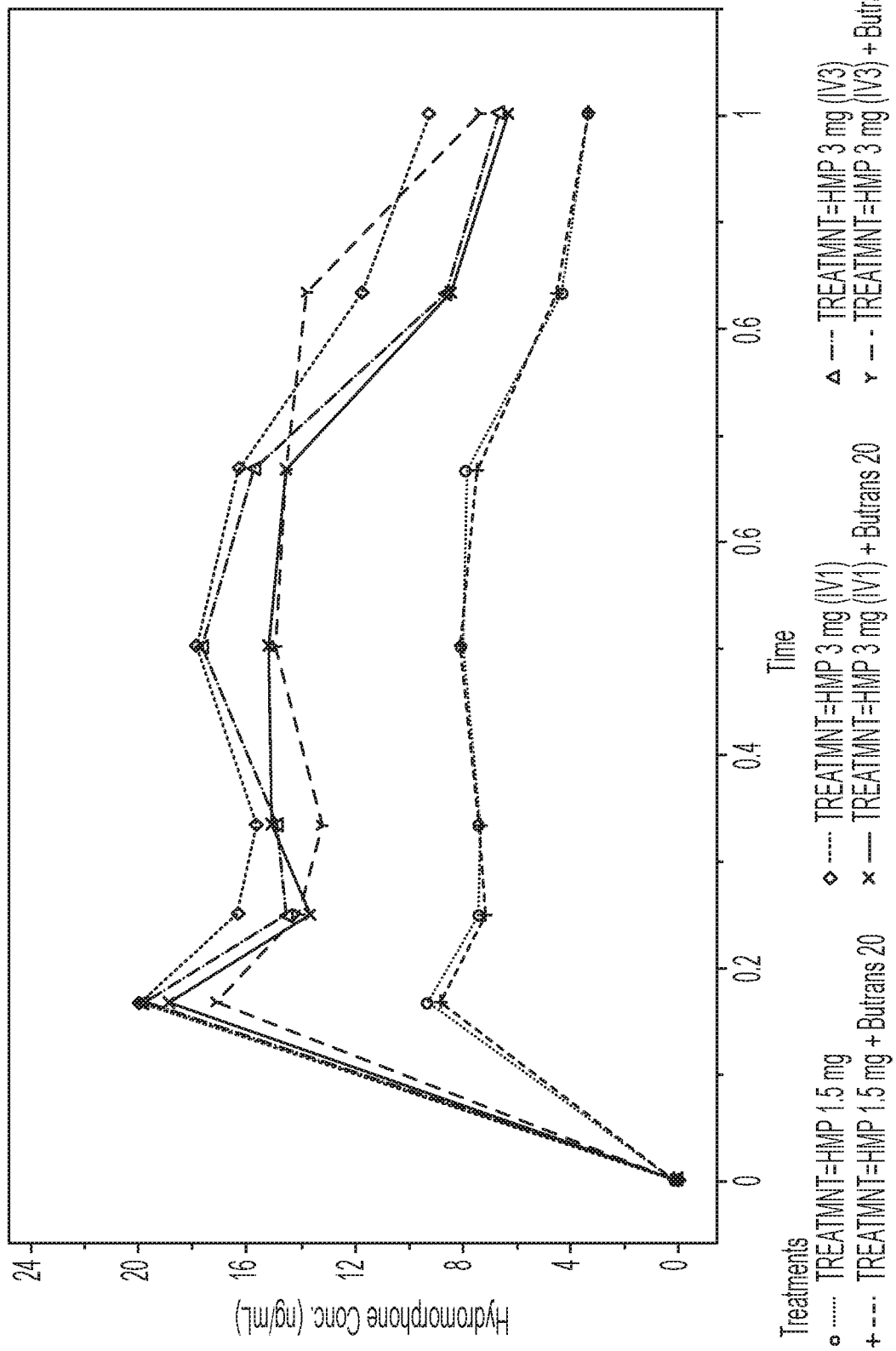
FIG. 35 depicts hydromorphone concentrations during HCVR measurements in Study part 2a).
Figure 36:
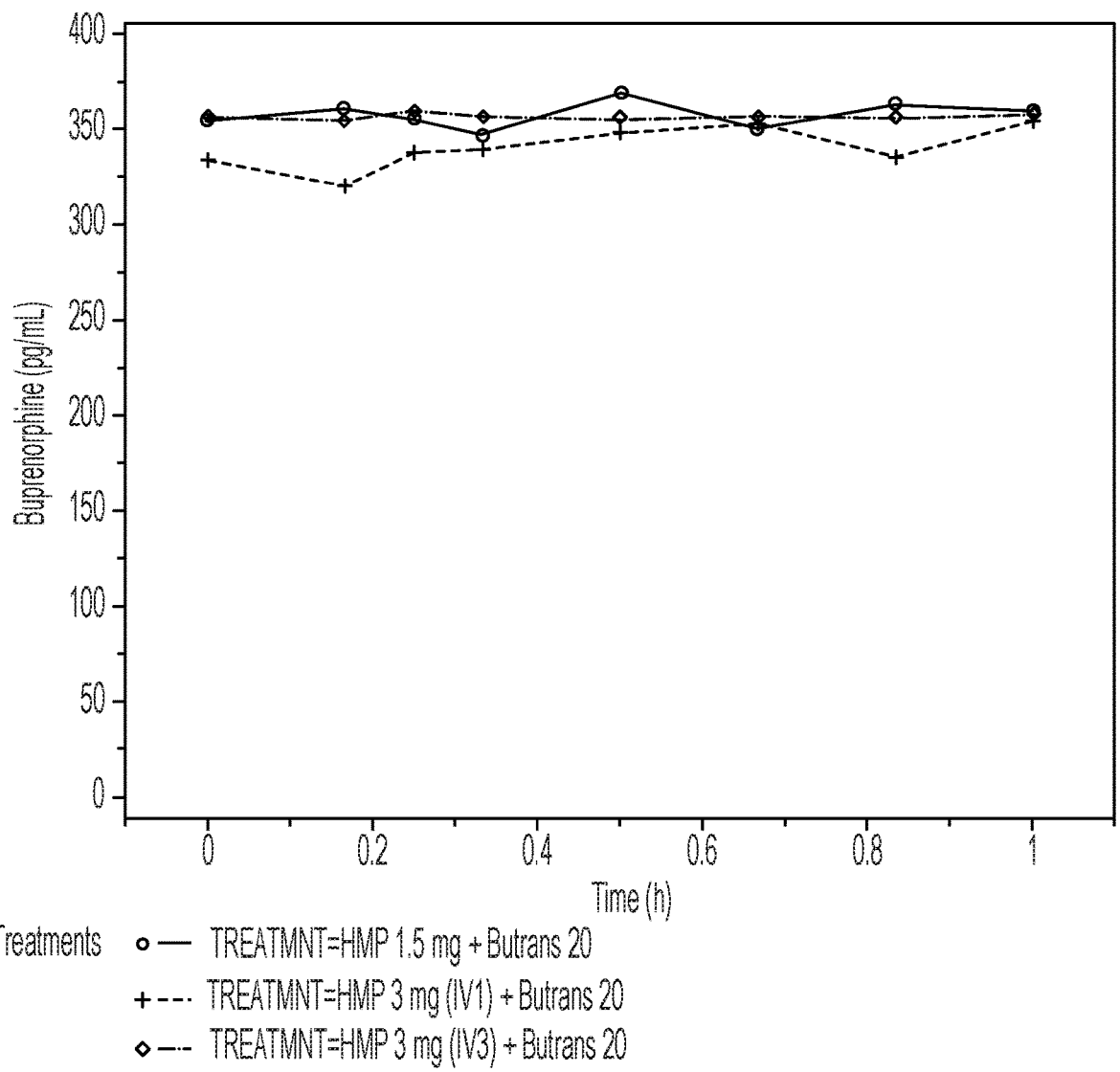
FIG. 36 depicts buprenorphine concentrations during HCVR measurements in Study part 2a).

FIGS. 35 and 36 present the hydromorphone (ng/mL) and buprenorphine (pg/mL) concentrations during the HCVR measurements in Study part 2a).

Study part 2b)

Study part 2b) using HMP infusions (3.0 mg, IV), and HMP (3.0 mg, IV) with escalated BUP doses (BTDS, 0, 5, 10, and 15 mcg/hr) was conducted. The schematic view of part 2b) study design was presented in FIG. 37, with HCVR measurements conducted pre- and during IV infusions and CPT as post-HCVR measurement.

Figure 38:
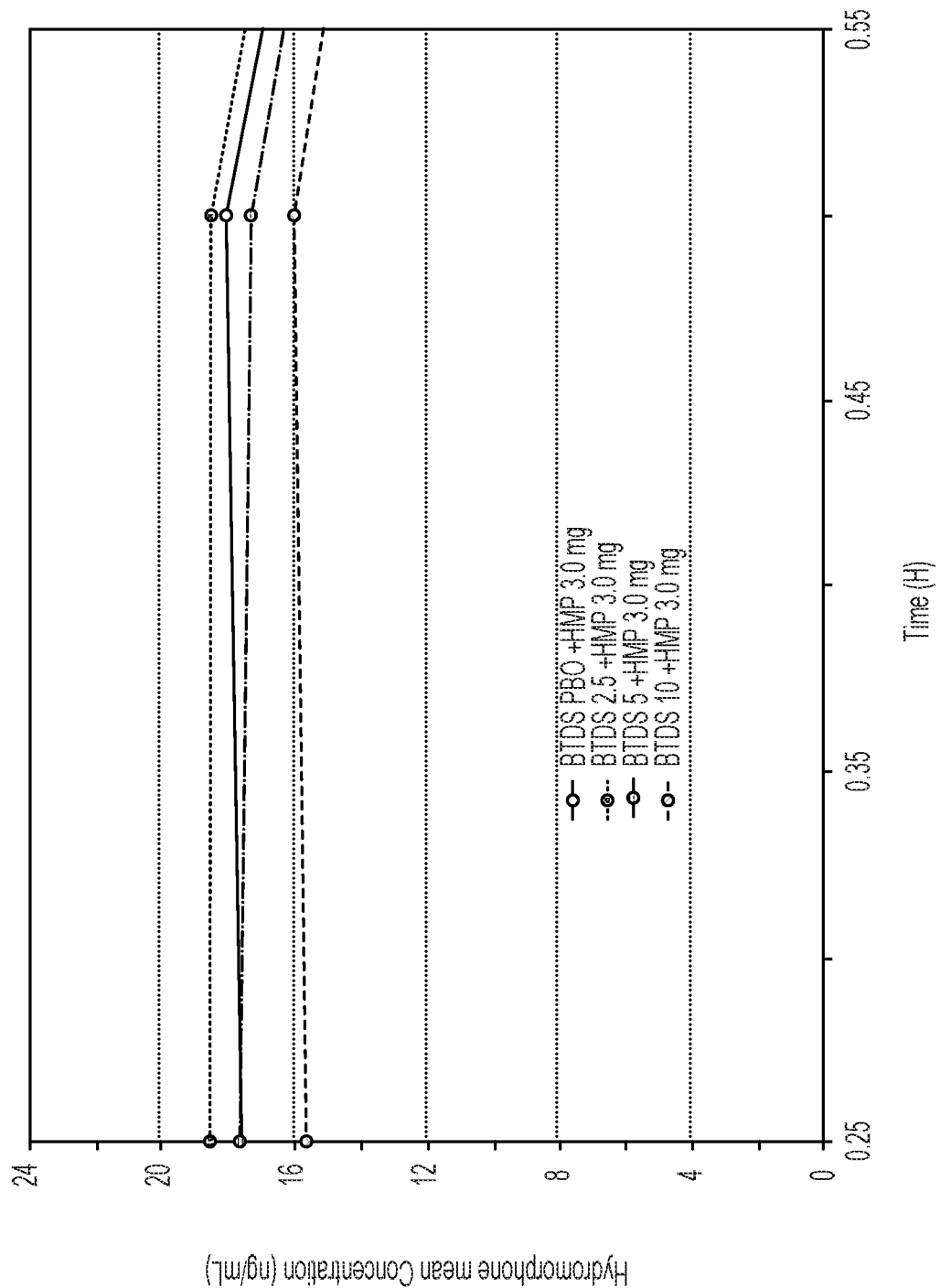
FIG. 38 depicts hydromorphone concentrations during HCVR measurements in Study part 2b).
Figure 39:
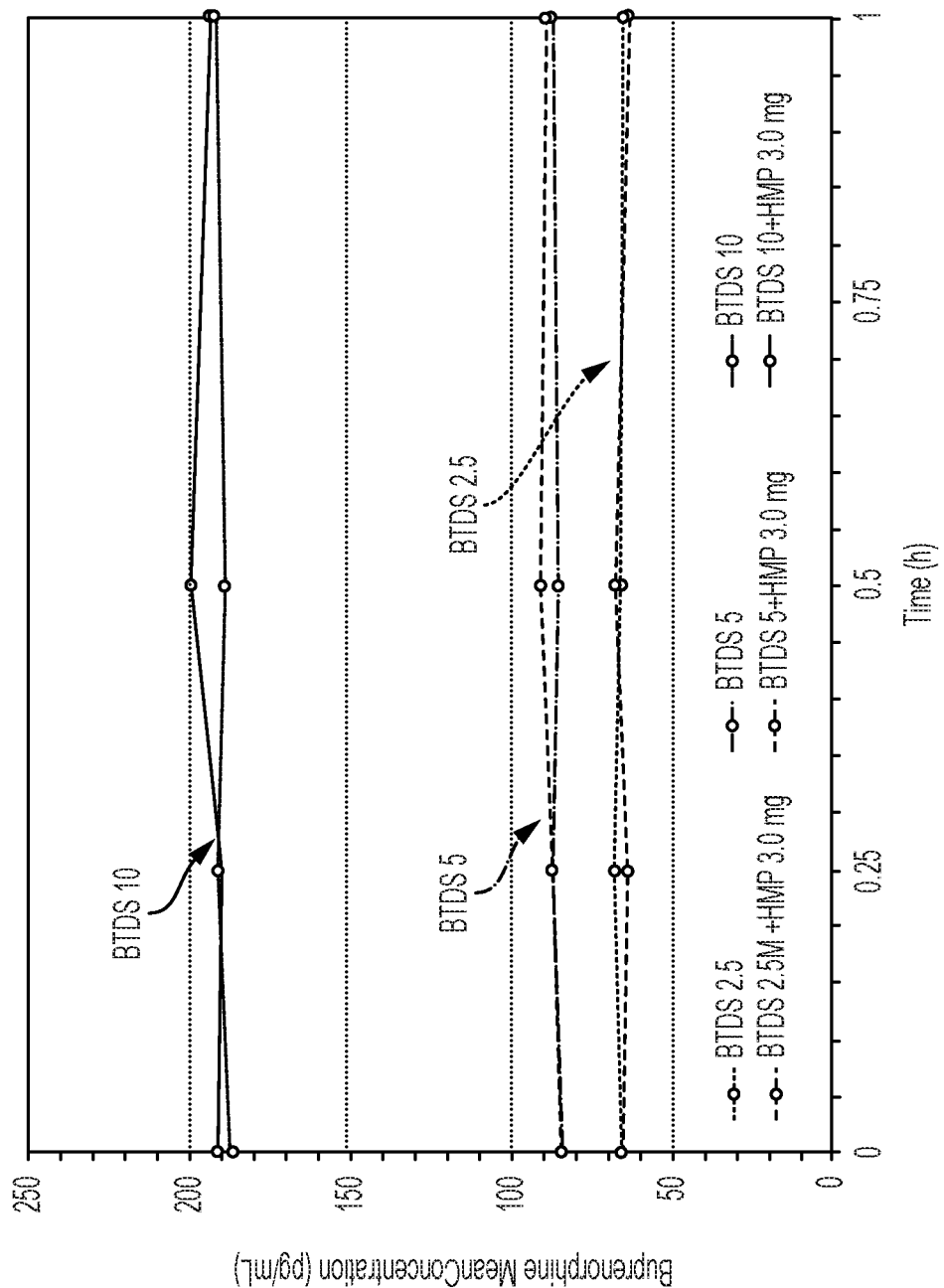
FIG. 39 depicts buprenorphine concentrations during HCVR measurements in Study part 2b).

FIGS. 38 and 39 show the mean HMP (ng/mL) and BUP (pg/mL) concentrations were maintained constant during the HCVR assessments in Study part 2b), respectively.

Figure 40:
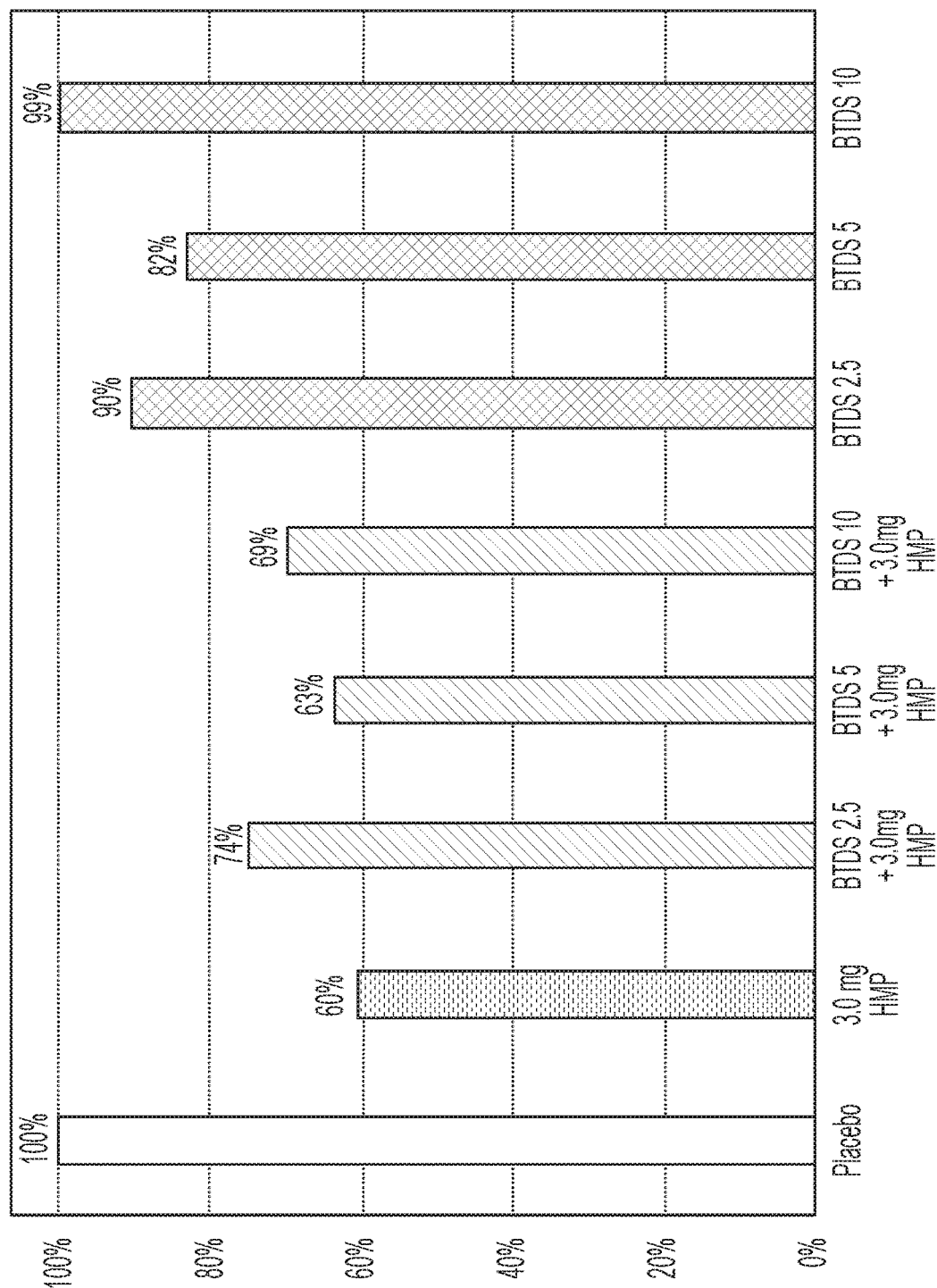
FIG. 40 depicts the mean HCVR slopes normalized to placebo, after administration of HMP (3.0 mg, IV), BTDS (at doses of 2.5 mcg/h, 5 mcg/h, and 10 mcg/h), and HMP-BTDS combinations in Study part 2b).

FIG. 40 depicts the mean HCVR slopes normalized to placebo, after administration of HMP (3.0 mg, IV), BTDS (at doses of 2.5 mcg/h, 5 mcg/h, and 10 mcg/h), and HMP-BTDS combinations in Study part 2b). The results show that BUP 2.5 mcg/h reversed HMP (3.0 mg, IV) OIRD effect by about ⅓.

Figure 41:
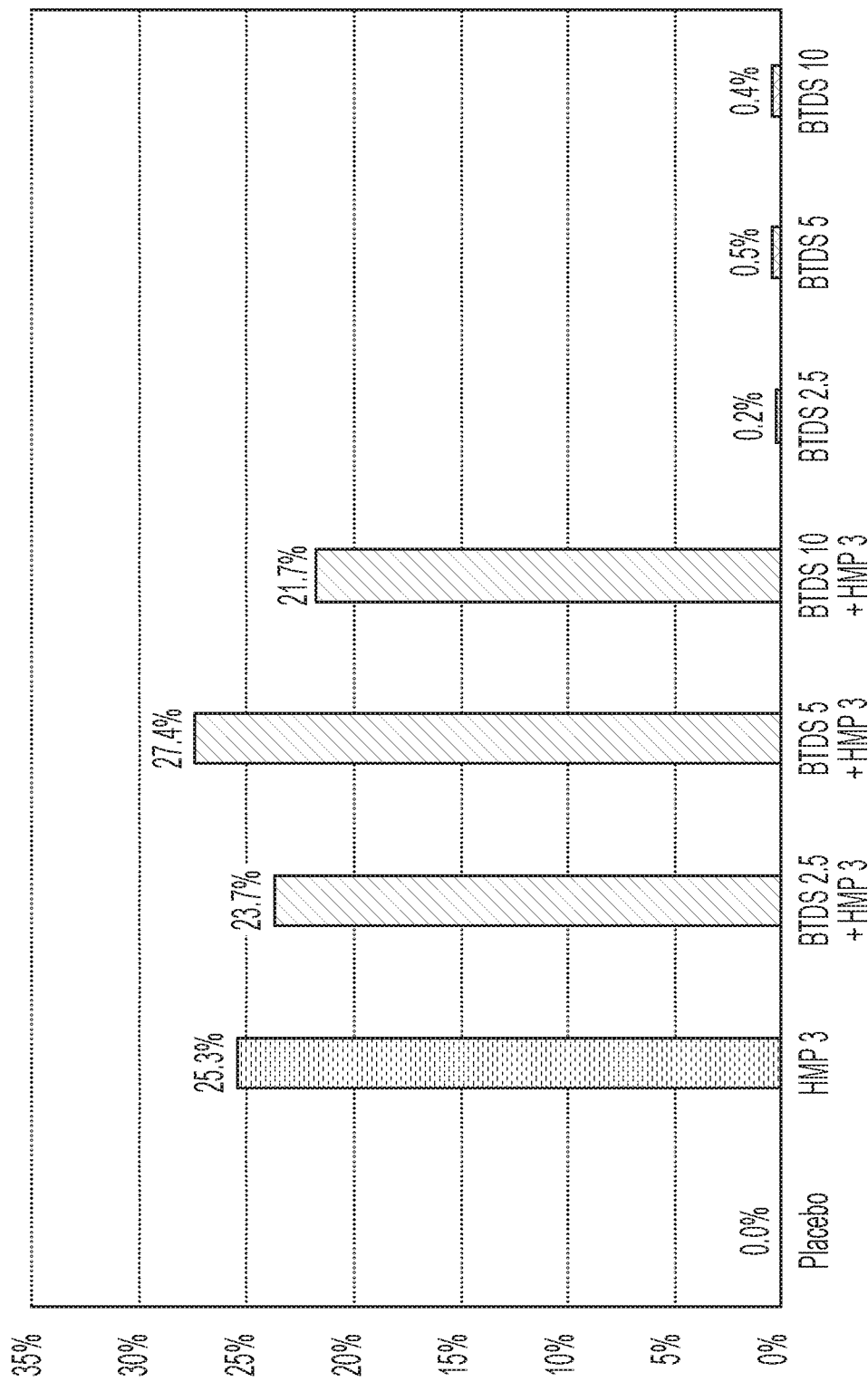
FIG. 41 depicts analgesic effects of HMP (3.0 mg, IV), BTDS (at doses of 2.5 mcg/h, 5 mcg/h, and 10 mcg/h), and HMP-BTDS combinations, compared to placebo, in Study part 2b).

The analgesic effects of HMP (3.0 mg, IV), BTDS (at doses of 2.5 mcg/h, 5 mcg/h, and 10 mcg/h), and HMP-BTDS combinations, compared to placebo in Study part 2b) were provided in FIG. 41. Pain, quantified as AUC of Pain VAS, was measured every 15 sec for 2 minutes in cold pressor test. FIG. 41 shows that HMP (3.0 mg, IV) reduced cold pressor pain, and the co-administration of BUP (at doses of 2.5, 5, & 10 mcg/hr) did not decrease (or increase) HMP analgesia effects.

The invention claimed is:
1. A method of treating pain comprising administering to a patient in need thereof
  (i) an effective amount of hydromorphone during an administration period 1 at a mean input rate (in mg/h) of hydromorphone during said administration period 1, wherein said mean input rate of hydromorphone is expressed as the equimolar amount of hydromorphone free base administered during said administration period 1 divided by the duration of said administration period 1,
  (ii) another effective amount of buprenorphine during an administration period 2 at a mean input rate (in mg/h) of buprenorphine during said administration period 2, wherein said mean input rate of buprenorphine is expressed as the equimolar amount of buprenorphine free base administered during said administration period 2 divided by the duration of said administration period 2, wherein the administration period 1 and the administration period 2 overlap by at least 75%, and wherein the ratio of said mean input rate of buprenorphine to said mean input rate of hydromorphone is from about 1:200 to about 1:8000;

wherein hydromorphone is formulated in a composition for intravenous infusion for treating pain, and buprenorphine is formulated in a transdermal patch or in a composition for intravenous infusion for treating pain;

wherein analgesia produced by the hydromorphone to the patient is not impacted by the buprenorphine.

2. The method of claim 1, wherein the administration period 1 and the administration period 2 overlap by at least 90%.

3. The method of claim 1, wherein the buprenorphine is formulated for intravenous administration.

4. The method of claim 1, wherein the buprenorphine is formulated for transdermal administration and the duration of said administration period 2 is from 1 day to 7 days.

5. The method of claim 1, wherein the hydromorphone is administered to the patient at a mean input rate of from about 1 mg/h to about 10 mg/h.

6. The method of claim 1, wherein the method reduces at least one side effect induced by hydromorphone, and said side effect is selected from the group consisting of respiratory depression, drug liking, sedation and bowel dysfunction.

7. The method of claim 1, wherein the method reduces hydromorphone-induced toxicity.

8. The method of claim 1, wherein the hydromorphone and the buprenorphine are administered in one composition for intravenous infusion.

9. The method of claim 8, wherein the administration period 1 and the administration period 2 are the same and are from about 30 minutes to 2 hours.

10. The method of claim 1, wherein the hydromorphone is administered at a mean input rate of about 1 mg/h, 3.5 mg/h, about 4 mg/h, about 4.5 mg/h, or about 10 mg/h.

11. The method of claim 1, wherein the method reduces hydromorphone-induced respiratory depression by ⅓ or higher.

12. A method of reducing opioid-induced death incidence in a subject identified in need thereof, comprising administering to the subject an effective amount of buprenorphine, wherein the opioid is administered intravenously to the subject during an administration period 1, and the opioid comprises hydromorphone, wherein the buprenorphine is administered to the subject during an administration period 2, and wherein the administration period 1 and the administration period 2 overlap by at least 75%, wherein analgesia produced by the opioid to the subject is not impacted by the administration of the said effective amount of buprenorphine.

13. The method of claim 12, wherein the method further prevents or reduces occurrence of opioid-induced addiction in the subject.

14. The method of claim 12, wherein the method further prevents or reduces occurrence of opioid-induced drug abuse in the subject.

* * * * *